US009067905B2

(12) United States Patent
Dyke et al.

(10) Patent No.: US 9,067,905 B2
(45) Date of Patent: Jun. 30, 2015

(54) SULPHONE COMPOUNDS AND METHODS OF MAKING AND USING SAME

(75) Inventors: Hazel J. Dyke, Harlow (GB); Susan M. Cramp, Harlow (GB); Thomas D. Pallin, Harlow (GB); Janusz J. Kulagowski, Harlow (GB); John G. Montana, Harlow (GB); Robert Zahler, Pennington, NJ (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 13/453,219

(22) Filed: Apr. 23, 2012

(65) Prior Publication Data
US 2013/0053364 A1 Feb. 28, 2013

Related U.S. Application Data

(63) Continuation of application No. PCT/US2010/052050, filed on Oct. 8, 2010.

(60) Provisional application No. 61/250,239, filed on Oct. 9, 2009, provisional application No. 61/250,193, filed on Oct. 9, 2009.

(51) Int. Cl.
C07D 307/54 (2006.01)
A61K 31/192 (2006.01)
C07C 317/46 (2006.01)
C07C 317/44 (2006.01)
C07D 213/55 (2006.01)
C07D 231/12 (2006.01)
C07D 263/32 (2006.01)
C07D 275/02 (2006.01)
C07D 277/30 (2006.01)
C07D 307/16 (2006.01)
C07D 333/24 (2006.01)
C07D 405/12 (2006.01)
C07D 451/02 (2006.01)
C07D 487/08 (2006.01)

(52) U.S. Cl.
CPC ............ *C07D 307/54* (2013.01); *C07C 317/44* (2013.01); *C07C 317/46* (2013.01); *C07C 2101/02* (2013.01); *C07D 213/55* (2013.01); *C07D 231/12* (2013.01); *C07D 263/32* (2013.01); *C07D 275/02* (2013.01); *C07D 277/30* (2013.01); *C07D 307/16* (2013.01); *C07D 333/24* (2013.01); *C07D 405/12* (2013.01); *C07D 451/02* (2013.01); *C07D 487/08* (2013.01)

(58) Field of Classification Search
USPC .................................................... 514/210.19
See application file for complete search history.

(56) References Cited

U.S. PATENT DOCUMENTS

| 5,164,410 | A | 11/1992 | Kishimoto et al. |
| 5,166,172 | A | 11/1992 | Kishimoto et al. |
| 5,180,735 | A | 1/1993 | Kishimoto et al. |
| 5,180,738 | A | 1/1993 | Kishimoto et al. |
| 5,196,406 | A | 3/1993 | Kamei et al. |
| 5,204,345 | A | 4/1993 | Kishimoto et al. |
| 5,238,950 | A | 8/1993 | Clader et al. |
| 5,288,722 | A | 2/1994 | Kishimoto et al. |
| 5,290,807 | A | 3/1994 | Folkman et al. |
| 5,422,363 | A | 6/1995 | Yanai et al. |
| 5,536,623 | A | 7/1996 | Ohmachi et al. |
| 5,698,586 | A | 12/1997 | Kishimoto et al. |
| 5,767,293 | A | 6/1998 | Oku et al. |
| 5,846,562 | A | 12/1998 | Yanai et al. |
| 5,900,431 | A | 5/1999 | Molina et al. |
| 6,017,949 | A | 1/2000 | D'Amato et al. |
| 6,017,954 | A | 1/2000 | Folkman et al. |
| 6,040,337 | A | 3/2000 | Hong, II et al. |
| 6,063,812 | A | 5/2000 | Hong et al. |
| 6,180,626 | B1 | 1/2001 | Shimomura et al. |
| 6,207,704 | B1 | 3/2001 | Liu et al. |
| 6,242,494 | B1 | 6/2001 | Craig et al. |
| 6,268,387 | B1 | 7/2001 | Connor et al. |
| 6,306,819 | B1 | 10/2001 | Rupnick et al. |
| 6,323,228 | B1 | 11/2001 | BaMaung et al. |
| 6,383,471 | B1 | 5/2002 | Chen et al. |
| 6,548,477 | B1 | 4/2003 | Olson et al. |
| 6,566,541 | B2 | 5/2003 | Liu et al. |
| 6,664,244 | B1 | 12/2003 | Furuse et al. |
| 6,803,382 | B2 | 10/2004 | Eustache et al. |

(Continued)

FOREIGN PATENT DOCUMENTS

| EP | 0682020 A1 | 11/1995 |
| WO | WO-98/38859 | 9/1998 |
| WO | WO-99/59986 A1 | 11/1999 |
| WO | WO-99/59987 A1 | 11/1999 |
| WO | WO-9957097 | 11/1999 |
| WO | WO-00/64876 A1 | 11/2000 |
| WO | WO-0064876 A1 | 11/2000 |
| WO | WO-01/24796 A1 | 4/2001 |
| WO | WO-0124796 A1 | 4/2001 |
| WO | WO-02/26782 A2 | 4/2002 |

(Continued)

OTHER PUBLICATIONS

Cos et al., Structure-Activity Relationship and Classification of Flavonoids as Inhibitors of Xanthine Oxidase and Superoxide Scavengers, J. Nat. Prod., 61:71-76, 1998.*

(Continued)

*Primary Examiner* — Jeffrey S Lundgren
*Assistant Examiner* — Zenab Olabowale
(74) *Attorney, Agent, or Firm* — Goodwin Procter LLP

(57) ABSTRACT

The invention provides sulphone compounds and their use in treating medical disorders, such as obesity. Pharmaceutical compositions and methods of making various sulphone compounds are provided. The compounds are contemplated to have activity against methionyl aminopeptidase 2.

24 Claims, No Drawings

(56) References Cited

U.S. PATENT DOCUMENTS

| | | | |
|---|---|---|---|
| 6,887,863 B2 | 5/2005 | Craig et al. | |
| 6,989,392 B2 | 1/2006 | Collins et al. | |
| 7,005,440 B1 * | 2/2006 | Jayyosi et al. | 514/375 |
| 7,030,262 B2 | 4/2006 | BaMaung et al. | |
| 7,084,108 B2 | 8/2006 | Olson et al. | |
| 7,115,632 B1 | 10/2006 | Bedell et al. | |
| 7,268,111 B2 | 9/2007 | Olson et al. | |
| 7,282,588 B2 | 10/2007 | Dhanak et al. | |
| 7,288,651 B2 | 10/2007 | Deng et al. | |
| 7,297,816 B2 | 11/2007 | Allison et al. | |
| 7,396,833 B2 | 7/2008 | Xie et al. | |
| 7,491,718 B2 | 2/2009 | Comess et al. | |
| 7,718,695 B2 | 5/2010 | Kim et al. | |
| 8,367,721 B2 | 2/2013 | Hughes et al. | |
| 2002/0002152 A1 | 1/2002 | Craig et al. | |
| 2004/0019113 A1 | 1/2004 | Jozefiak et al. | |
| 2004/0067266 A1 | 4/2004 | Toppo | |
| 2004/0068012 A1 | 4/2004 | Comess et al. | |
| 2004/0116495 A1 | 6/2004 | Marino Jr. et al. | |
| 2004/0157836 A1 | 8/2004 | Comess et al. | |
| 2004/0167128 A1 | 8/2004 | Comess et al. | |
| 2004/0204472 A1 | 10/2004 | Briggs et al. | |
| 2005/0037994 A1 | 2/2005 | Kim et al. | |
| 2005/0239878 A1 | 10/2005 | Thompson et al. | |
| 2006/0045865 A1 | 3/2006 | Jacob et al. | |
| 2006/0069161 A1 | 3/2006 | Lee et al. | |
| 2006/0276512 A1 | 12/2006 | Han et al. | |
| 2007/0078172 A1 | 4/2007 | McElroy et al. | |
| 2008/0200402 A1 | 8/2008 | Alvinerie et al. | |
| 2008/0312231 A1 | 12/2008 | Merla et al. | |
| 2009/0088437 A1 | 4/2009 | Xie et al. | |
| 2009/0148396 A1 | 6/2009 | Akullian et al. | |
| 2010/0016425 A1 | 1/2010 | Vath | |
| 2010/0111894 A1 | 5/2010 | Benny-Ratsaby et al. | |
| 2012/0004162 A1 | 1/2012 | Vath | |
| 2012/0010259 A1 | 1/2012 | Vath | |
| 2012/0010290 A1 | 1/2012 | Vath | |
| 2013/0123235 A1 | 5/2013 | Clark et al. | |
| 2013/0217759 A1 | 8/2013 | Zahler et al. | |
| 2013/0331420 A1 | 12/2013 | Dyke et al. | |
| 2014/0073623 A1 | 3/2014 | Cramp et al. | |
| 2014/0080822 A1 | 3/2014 | Cramp et al. | |
| 2014/0088078 A1 | 3/2014 | Cramp et al. | |

FOREIGN PATENT DOCUMENTS

| | | | | |
|---|---|---|---|---|
| WO | WO-0226782 A2 | 4/2002 | | |
| WO | WO-02/059124 A2 | 8/2002 | | |
| WO | WO-02059124 A2 | 8/2002 | | |
| WO | WO-02/083065 A2 | 10/2002 | | |
| WO | WO-02083065 A2 | 10/2002 | | |
| WO | WO-03/027104 A1 | 4/2003 | | |
| WO | WO-2004/033419 A1 | 4/2004 | | |
| WO | WO-2004033419 A1 | 4/2004 | | |
| WO | WO 2005/025554 * | 3/2005 | | A61K 31/00 |
| WO | WO-2005/025554 A2 | 3/2005 | | |
| WO | WO-2005/082349 A1 | 9/2005 | | |
| WO | WO-2005/113513 A2 | 12/2005 | | |
| WO | WO-2005113513 A2 | 12/2005 | | |
| WO | WO-2006/080591 A1 | 8/2006 | | |
| WO | WO-2008/008374 A2 | 1/2008 | | |
| WO | WO-2008008374 A2 | 1/2008 | | |
| WO | WO-2009/009501 A2 | 1/2009 | | |
| WO | WO-2009/073445 A2 | 6/2009 | | |
| WO | WO-2010/042163 A2 | 4/2010 | | |
| WO | WO-2010/048499 A1 | 4/2010 | | |
| WO | WO-2010/065877 A2 | 6/2010 | | |
| WO | WO-2010/065879 A2 | 6/2010 | | |
| WO | WO-2010/065881 A2 | 6/2010 | | |
| WO | WO-2010/065883 A2 | 6/2010 | | |
| WO | WO-2010065879 A2 | 6/2010 | | |
| WO | WO-2010065883 A2 | 6/2010 | | |
| WO | WO-2011/044506 A2 | 4/2011 | | |
| WO | WO-2011044506 A2 | 4/2011 | | |
| WO | WO-2011/085198 A1 | 7/2011 | | |
| WO | WO-2011/088055 A2 | 7/2011 | | |
| WO | WO-2011/127304 A2 | 10/2011 | | |
| WO | WO-2011/150338 A1 | 12/2011 | | |
| WO | WO-2012/012642 A1 | 1/2012 | | |
| WO | WO-2012012642 A1 | 1/2012 | | |
| WO | WO-2012/051318 A1 | 4/2012 | | |
| WO | WO-2012051318 A1 | 4/2012 | | |
| WO | WO-2012/064838 A1 | 5/2012 | | |
| WO | WO-2012/064928 A1 | 5/2012 | | |
| WO | WO-2012/074968 A1 | 6/2012 | | |
| WO | WO-2012/075020 A1 | 6/2012 | | |
| WO | WO-2012/075026 A1 | 6/2012 | | |
| WO | WO-2012/103333 A1 | 8/2012 | | |
| WO | WO-2012103333 A1 | 8/2012 | | |
| WO | WO-2012/154676 A1 | 11/2012 | | |
| WO | WO-2012/154678 A1 | 11/2012 | | |
| WO | WO-2012/154679 A1 | 11/2012 | | |
| WO | WO-2012154676 A1 | 11/2012 | | |
| WO | WO-2012154678 A1 | 11/2012 | | |
| WO | WO-2012154679 A1 | 11/2012 | | |
| WO | WO-2013/033430 A1 | 3/2013 | | |

OTHER PUBLICATIONS

Siddiqui et al., The Presence of Substituents on the Aryl Moiety of the Aryl Phosphoramidate Derivative of d4T Enhances Anti-HIV Efficacy in Cell Culture: A Structure-Activity Relationship, J. Med. Chem., 42, 393-399, 1999.*

Chan, Laval, et al. (2004) "Discovery of thiophene-2-carboxylic acids as potent inhibitors of HCV NS5B polymerase and HCV subgenomic RNA replication. Part 1: Sulfonamides", *Bioorganic & Medicinal Chemistry*, vol. 14, pp. 793-796.

Database Registry [Online] (Apr. 10, 2004), *Chemical Abstracts Service*, XP002664464.

Database Registry [Online] (Jan. 28, 2009), *Chemical Abstracts Service*, XP002664457.

Database Registry [Online] (Sep. 11, 2009), *Chemical Abstracts Service*, XP002664455.

Database Registry [Online] (Oct. 4, 2010), *Chemical Abstracts Service*, XP002664453.

Kawai, Megumi, et al. (2006) "Development of sulfonamide compounds as potent methionine aminopeptidase type II inhibiotrs with antiproliferative properties", *Biorganic & Medicinal Chemistry Letters*, vol. 16, pp. 3574-3577.

Patent Cooperation Treaty (PCT) International Search Report and Written Opinion; International Application No. PCT/US2011/044864, mailed on Oct. 7, 2011 (7 pages).

Patent Cooperation Treaty (PCT) International Search Report; International Application No. PCT/US2010/052050, mailed Mar. 25, 2011 (11 pages).

Patent Cooperation Treaty (PCT) International Search Report; International Application No. PCT/US2012/022721, mailed on Mar. 29, 2012 (3 pages).

Patent Cooperation Treaty (PCT) International Search Report; International Application No. PCT/US2012/036789, mailed Jul. 17, 2012 (4 pages).

Patent Cooperation Treaty (PCT) International Search Report; International Application No. PCT/US2012/036792, mailed on Jun. 27, 2012 (3 pages).

Patent Cooperation Treaty (PCT) International Search Report; International Application No. PCT/US2012/036793, mailed on Jun. 21, 2012 (4 pages).

Patent Cooperation Treaty (PCT) Written Opinion of the International Searching Authority; International Application No. PCT/US2009/066811, mailed on Sep. 1, 2010 (3 pages).

Patent Cooperation Treaty (PCT) International Search Report and Written Opinion; International Application No. PCT/US2011/055987, mailed Jan. 16, 2012 (24 pages).

Sheppard, George S., et al. (2004) "3-Amino-2-hydroxyamides and related compounds as inhibitors of methionine aminopeptidase-2" *Bioorganic & Medicinal Chemistry Letters*, vol. 14, pp. 865-868.

(56) References Cited

OTHER PUBLICATIONS

Sheppard, George S., et al. (2006) "Discovery and Optimization of Anthranilic Acid Sulfonamides as Inhibitors of Methionine Aminopeptidase-2: A Structural Basis for the Reduction of Albumin Binding," *J. Med. Chem.* vol. 49, pp. 3332-3849.
Shvedov, V. I, et al. (1977) "Functional Derivatives of Thiophene", *Chemistry of Heterocyclic Compounds*, vol. 13, pp. 163-165.
Wang, Gary T., et al. (2007) "Lead optimization of methionine aminopeptidase-2 (MetAP2) inhibitors containing sulfonamides of 5, 6-disubstituted anthranilic acids," Bioorganic & Medicinal Chemistry Letters vol. 17, pp. 2817-2822.
Wang, Jieyi, et al. (2003) "Tumor Suppression by a Rationally Designed Reversible Inhibitor of Methionine Aminopeptidase-2", *Cancer Research*, vol. 63, pp. 7861-7869.
Anderson, "The Use of Fumagillin in Amoebiasis" Ann NY Acad Sci. Dec. 30, 1952;55(6):1118-24.
Benny, et al., "An Orally Delivered Small-Molecule Formulation with Antiangiogenic and Anticancer Activity" Nat Biotechnol Jul. 2008;26(7):799-807. doi: 10.1038/nbt1415. Epub Jun. 29, 2008.
Bernier, et al., "Fumagillin class inhibitors of methionine aminopeptidase-2" Drugs of the Future 2005 30(5): 497-500.
Brakenhielm, et al., "Angiogenesis Inhibitor, TNP-470, Prevents Diet-Induced and Genetic Obesity in Mice" Circ Res. Jun. 25, 2004;94(12):1579-88. Epub May 20, 2004.
Braunwald, et al., "Obesity" in Harrison's Principles of Internal Medicine, 15th Ed., 479-86 2001.
Chan, et al. "Discovery of thiophene-2-carboxylic acids as potent inhibitors of HCV NS5B polymerase and HCV subgenomic RNA replication. Part 1: Sulfonamides" Bioorg Med Chem Lett. Feb. 9, 2004;14(3):793-6.
Chun et al. "Novel inhibitors targeted to methionine aminopeptidase 2 (MetAP2) strongly inhibit the growth of cancers in xenografted nude model" Int J Cancer. Mar. 10, 2005;114(1):124-30.
Database Registry [Online] (Apr. 18, 2001), Chemical Abstracts Service, XP002664465.
Database Registry [Online] (Nov. 10, 2004), Chemical Abstracts Service, XP002664464.
Database Registry [Online] (Apr. 13, 2007), Chemical Abstracts Service, XP002664462.
Database Registry [Online] (Aug. 24, 2008), Chemical Abstracts Service, XP002664461.
Database Registry [Online] (Jan. 20, 2009), Chemical Abstracts Service, XP002664460.
Database Registry [Online] (Jan. 23, 2009), Chemical Abstracts Service, XP002664459.
Database Registry [Online] (Jan. 27, 2009), Chemical Abstracts Service, XP002664458.
Database Registry [Online] (Sep. 15, 2009), Chemical Abstracts Service, XP002664454.
Database Registry [Online], (Sep. 11, 2009) Chemical Abstracts Service, XP002664455.
Database Registry [Online], (Oct. 4, 2010) Chemical Abstracts Service, XP002664453.
Database Registry [Online] (Jun. 7, 2009), Chemical Abstracts Service, XP002664456.
Database Registry [Online] (Mar. 13, 2007), Chemical Abstracts Service, XP002664463.
Didier, et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.
DiPaolo, et al. "Studies on the Carcinolytic Activity of Fumagillin and Some of its Derivatives" Antibiot Annu. 1958-1959;6:541-6.
Drevs, et al. "Antiangiogenic Potency of FK866/K22.175, a New Inhibitor of Intracellular NAD Biosynthesis, In Murine Renal Cell Carcinoma". Anticancer Res. Nov.-Dec. 2003;23(6C):4853-8.
Dumas, et al., "Synthesis and Structure Activity Relationships of Novel Small Molecule Cathepsin D Inhibitors" Bioorg Med Chem Lett. Sep. 6, 1999;9(17):2531-6.
Eder, et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics."), 2006.
European Search Report for EP 09798793 dated Oct. 11, 2011, 9 pages.
Everhart "Contributions of Obesity and Weight Loss to Gallstone Disease" Ann Intern Med. Nov. 15, 1993;119(10):1029-35.
Garrabrant, et al., "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.
Han, et al., "Design and Synthesis of Highly Potent Fumagillin Analogues from Homology Modeling for a Human MetAP-2" Bioorg Med Chem Lett. Jan. 3, 2000;10(1):39-43.
Ingber, et al., "Synthetic analogues of fumagillin that inhibit angiogenesis and suppress tumour growth" Nature. Dec. 6, 1990;348(6301):555-7.
Jeong, et al., "Total Synthesis and Antiangiogenic Activity of Cyclopentane Analogues of Fumagillol" *Bioorg Med Chem Lett.* Aug. 1, 2005;15(15):3580-3.
Kawai, et al., "Development of sulfonamide compounds as potent methionine aminopeptidase type II inhibitors with antiproliferative properties". Bioorg Med Chem Lett. Jul. 1, 2006;16(13):3574-7. Epub May 2, 2006.
Kim et al., "Development of parenteral formulation for a novel angiogenesis inhibitor, CKD-732 through complexation with hydroxypropyl-beta-cyclodextrin" Int J Pharm. Mar. 19, 2004;272(1-2):79-89.
Kim et al., "General pharmacology of CKD-732, a new anticancer agent: effects on central nervous, cardiovascular, and respiratory system," Biol Pharm Bull. Feb. 2005;28(2):217-23.
Kim, et al., "Assessment of the Anti-Obesity Effects of the TNP-470 Analog, CKD-732," J Mol Endocrinol. Apr. 2007;38(4):455-65.
Kruger "TNP-470: An Angiogenesis Inhibitor in Clinical Development for Cancer," Expert Opin Investig Drugs. Jun. 2000;9(6):1383-96.
Lee et al., "Absorption, distribution, metabolism, and excretion of CKD-732, a novel antiangiogenic fumagillin derivative, in rats, mice, and dogs," Arch Pharm Res. Feb. 2004;27(2):265-72.
Lee et al.,"Selective N-Demethylation of Tertiary Aminofumagillols with Selenium Dioxide via a Non-classical Polonovski Type Reaction" *Heterocycles* vol. 68, No. 5, 2006, pp. 915-932.
Lee et al., "Design, Synthesis, and Antiangiogenic Effects of a Series of Potent Novel Fumagillin Analogues" Chem Pharm Bull (Tokyo). Jul. 2007;55(7):1024-9.
Lijnen et al., "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Makosza et al. "Reaction of organic anions. 131. Vicarious nucleophilic substitution of hydrogen in nitrobenzoic acids" Makosza, M.; Ludwiczak, S. Dep. Chem.,Tech. Univ. Warsaw, Warsaw, Pol. Synthesis (1986), (1), 50-2. CODEN: SYNTBF ISSN: 0039-7881. Journal written in English. CAN 105:171971 AN 1986:571971 CAPLUS (Copyright (C) 2009 ACS on SciFinder (R)).
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowan, et al., "Fumagillin (H-3), a New Antibiotic with Amebicidal Properties" Science. Feb. 23, 1951;113(2930):202-3.
Milkowski, Deborah M., et al., Antiangiogenic Agents in Cancer Therapy, Chapter 22 "TNP-470," pp. 385-398, 2012.
Molina et al., "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al., "Fumagillin Treatment of Intestinal Microsporidiosis" N Engl J Med. Jun. 20, 2002;346(25):1963-9.
Molina, et al., "Trial of Oral Fumagillin for the Treatment of Intestinal Microsporidiosis in Patients with HIV Infection" AIDS. Jul. 7, 2000;14(10):1341-8.

(56) References Cited

OTHER PUBLICATIONS

Myung et al., "The identification of in vitro metabolites of CKD-732 by liquid chromatography/tandem mass spectrometry" Rapid Commun Mass spectrom. 2002;16(21):2048-53.
Naganuma et al., "Metronomic Doxifluridine Chemotherapy Combined with the Anti-Angiogenic Agent TNP=470 Inhibits the Growth of Human Uterine Carcinosarcoma Xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very Low-Calorie Diets," JAMA. Aug. 25, 1993;270(8):967-74.
Noel et al., "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.
Pagliarulo et al., "Gallstone disease and related risk factors in a large cohort of diabetic patients" Dig Liver Dis. Feb. 2004;36(2):130-4.
Patra et al., "Regiospecific Synthesis of Benzo[b]fluorenones via Ring Contraction by Benzil-Benzilic Acid Rearrangement of Benz[a]anthracene-5,6-diones" Synthesis 2006, (15), 2556-2562.
International Search Report and Written Opinion for International Application No. PCT/US2011/044864, mailed on Oct. 7, 2011, 7 pages.
International Search Report and Written Opinion for International Application No. PCT/US2010/052050, mailed Mar. 25, 2011, 11 pages.
International Search Report for International Application No. PCT/US2012/022721, mailed on Mar. 29, 2012, 3 pages.
International Search Report for International Application No. PCT/US2012/036789, mailed Jul. 17, 2012, 4 pages.
International Search Report for International Application No. PCT/US2012/036792, mailed on Jun. 27, 2012 (3 pages).
International Search Report for International Application No. PCT/US2012/036793, mailed on Jun. 21, 2012, 4 pages.
Written Opinion for International Application No. PCT/US2009/066811, mailed on Sep. 1, 2010, 3 pages.
International Search Report and Written Opinion for International Application No. PCT/US2011/055987, mailed Jan. 16, 2012, 24 pages.
Picoul et al., "Progress in fumagillin synthesis" Pure Appl. Chem., vol. 75, Nos. 2-3, pp. 235-249, 2003.
Rhee et al., "Angiogenesis inhibitor attenuates parathyroid hormone-induced anabolic effect" Biomed Pharmacother. Jan. 2009;63(1):63-8. doi: 10.1016/j.biopha.2007.10.013. Epub Nov. 20, 2007.
Rupnick "Adipose Tissue Mass Can be Regulated Through the Vasculature" Proc Natl Acad Sci U S A. Aug. 6, 2002;99(16):10730-5. Epub Jul. 29, 2002.
Sankar et al., "2-[1-(Phenylsulfonyl)ethyl]benzoic acid and 2-[1-(phenylsulfonyl)propyl]benzoic acid" Acta Crystallogr C. May 2002;58(Pt 5):o257-9. Epub Apr. 11, 2002.
Seneca et al., "Amebiasis: a review. II. Laboratory diagnosis, differential diagnosis and therapy" Am J Dig Dis. Jul. 1956;1(7):310-22.
Sheppard et al., "3-Amino-2-hydroxyamides and related compounds as inhibitors of methionine aminopeptidase-2" Bioorg Med Chem Lett. Feb. 23, 2004;14(4):865-8.
Sheppard et al., "Discovery and Optimization of Anthranilic Acid Sulfonamides as Inhibitors of Methionine Aminopeptidase-2: A Structural Basis for the Reduction of Albumin Binding" J Med Chem. Jun. 29, 2006;49(13):3832-49.
Shin et al., "A Phase Ib pharmacokinetic study of the anti-angiogenic agent CKD-732 used in combination with capecitabine and oxaliplatin (XELOX) in metastatic colorectal cancer patients who progressed on irinotecan-based chemotherapy" Invest New Drugs. Apr. 2012;30(2):672-80. doi: 10.1007/s10637-010-9625-x. Epub Dec. 29, 2010.
Shin "A phase I pharmacokinetic and pharmacodynamic study of CKD-732, an antiangiogenic agent, in patients with refractory solid cancer" Invest New Drugs. Oct. 2010;28(5):650-8. doi: 10.1007/s10637-009-9287-8. Epub Jul. 8, 2009.
Shvedov et al., "Functional Derivatives of Thiophene" Chemistry of Heterocyclic Compounds Feb. 1977, vol. 13, Issue 2, pp. 163-165.
Siddiqui et al., "The Presence of Substituents on the Aryl Moiety of the Aryl Phosphoramidate Derivative of d4T Enhances Anti-HIV Efficacy in Cell Culture: A Structure-Activity Relationship" *J Med Chem*. Feb. 11, 1999;42(3):393-9.
Srikumar et al., "Structural Insights On *Brugia malayi* Transglutaminase With Cinnamoyl Derivatives—A Molecular Docking Approach" Int J Pharm Bio Sci Jul. 2012; 3(3): (B) 998-1006.
Teicher, et al., "Antiangiogenic Agents in Cancer Therapy" pp. 385-398, 1999.
Thirumamagal, et al., "Formation of 2-arylindane-1,3-diones and 3-alkylphthalides from methyl o-[ -phenylsulfonyl]toluate" Tetrahedron Letters (2008), 49(3), 512-515.
Wang, et al., "Lead optimization of methionine aminopeptidase-2 (MetAP2) inhibitors containing sulfonamides of 5, 6-disubstituted anthranilic acids" Bioorg Med Chem Lett. May 15, 2007;17(10):2817-22. Epub Feb. 25, 2007.
Wang, et al., "Tumor Suppression by a Rationally Designed Reversible Inhibitor of Methionine Aminopeptidase-2" Cancer Res. Nov. 15, 2003;63(22):7861-9.
Weinsier et al., "Gallstone Formation and Weight Loss" Obes Res. Jan. 1993;1(1):51-6.
Weinsier, et al., "Medically Safe Rate of Weight Loss for the Treatment of Obesity: A Guideline Based on Risk of Gallstone Formation" Am J Med. Feb. 1995;98(2):115-7.
Winter et al., "Endothelial $\alpha_\nu\beta_3$ Integrin-Targeted Fumagillin Nanoparticles Inhibit Angiogenesis in Atherosclerosis," Arterioscler Thromb Vasc Biol. Sep. 2006;26(9):2103-9. Epub Jul. 6, 2006.
Yanai, et al., "Antitumor Effect of Arterial Administration of a Medium-Chain Triglyceride Solution of an Angiogenesis Inhibitor, TNP-470, in Rabbits Bearing VX-2 Carcinoma" Pharm Res. May 1995;12(5):653-7.
Yanai, et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

\* cited by examiner

SULPHONE COMPOUNDS AND METHODS OF MAKING AND USING SAME

RELATED APPLICATIONS

This application is a continuation of International (PCT) Patent Application Serial No. PCT/US2010/052050, filed Oct. 8, 2010, which claims priority to U.S. Ser. No. 61/250,193, filed Oct. 9, 2009, and U.S. Ser. No. 61/250,239, filed Oct. 9, 2009, each of which is incorporated by reference in its entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitor, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc. Natl. Acad. Sci. USA 99:10730).

Such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The invention provides, for example, compounds which may be modulators of MetAP2, and their use as medicinal agents, processes for their preparation, and pharmaceutical compositions containing them as an active ingredient both alone or in combination with other agents, as well as provides for their use as medicaments and/or in the manufacture of medicaments for the inhibition of MetAP2 activity in warm-blooded animals such as humans. In particular this invention relates to compounds useful for the treatment of obesity, type 2 diabetes, and other obesity-associated conditions. Also provided are pharmaceutical compositions comprising at least one disclosed compound and a pharmaceutically acceptable carrier.

In an embodiment, provided herein are compounds represented by Formula Ia:

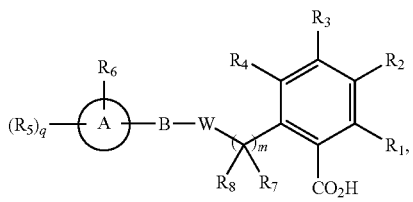

or pharmaceutically acceptable salts, stereoisomers, esters or prodrugs thereof, where $R_1$, $R_2$, W, A, B, $R_7$, $R_8$, $R_6$, $R_5$, B, q, and m are as defined herein.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_2$-$C_6$alkenyl, and $C_3$-$C_4$alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, alkoxys of 1-6 or 2-6 carbon atoms, referred to herein as $C_1$-$C_6$alkoxy, and $C_2$-$C_6$alkoxy, respectively. Exemplary alkoxy groups include, but are not limited to methoxy, ethoxy, isopropoxy, etc.

The term "alkenyloxy" used herein refers to a straight or branched alkenyl group attached to an oxygen (alkenyl-O). Exemplary alkenoxy groupd include, but are not limited to, groups with an alkenyl group of 3-6 carbon atoms, (also e.g. referred to as $C_3$-$C_6$alkenyloxy). Exemplary "alkenoxy" groups include, but are not limited to allyloxy, butenyloxy, etc.

The term "alkynyloxy" used herein refers to a straight or branched alkynyl group attached to an oxygen (alkynyl-O)).

Exemplary alkynyloxy groups include, but are not limited to, $C_3$-$C_6$alkynyloxy, e.g., propynyloxy.

The term "alkyl" as used herein refers to a saturated straight or branched hydrocarbon, such as a straight or branched group of 1-6, 1-4, or 1-3 carbon atoms, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$alkynyl, and $C_3$-$C_6$alkynyl, respectively. Exemplary alkynyl groups include, but are not limited to, ethynyl, propynyl, butynyl, pentynyl, hexynyl, methylpropynyl, etc.

The term "bridged cycloalkyl", as used herein, is defined as a monocyclic 4- to 7-membered cycloalkyl group in which two non-adjacent atoms are linked by a $CH_2$ or $CH_2CH_2$ group. A "bridged cycloalkyl" may be fused to one or more phenyl, partially unsaturated, or saturated rings. Examples of bridged carbocyclic groups include but are not limited to bicyclo[2.2.1]heptane, bicyclo[2.2.2]octane, bicyclo[2.2.2]octene etc.

The term "carbonyl" as used herein refers to the radical —C(O)—. The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or particlly unsaturated hydrocarbon group of for example 3-6, or 4-6 carbons, referred to herein, e.g., as "$C_{3-6}$cycloalkyl" or "$C_{4-6}$cycloalkyl," and derived from a cycloalkane. Exemplary cycloalkyl groups include, but are not limited to, cyclohexane, cyclohexene, cyclopentane, cyclobutane, cyclopropane or cyclopentane.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine, and pyrimidine.

The terms "heterocyclyl" or "heterocyclic group" are art-recognized and refer to saturated or partially unsaturated 4- to 7-membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited to pyrrolidine, piperidine, morpholine, thiomorpholine, and piperazine.

"Bridged heterocyclyl", as used herein, is defined as a saturated or partially unsaturated monocyclic 4- to 7-membered heterocyclyl group in which two non-adjacent atoms are linked by a $CH_2$ or $CH_2CH_2$ group. A "bridged heterocycle" may be fused to one or more phenyl, partially unsaturated, or saturated rings. Examples of bridged heterocyclic groups include but are not limited to 7-azabicyclo[2.2.1]heptane, 2-azabicyclo[2.2.1]heptane, 2-oxabicyclo[2.2.2]heptane, 2-oxabicyclo[2.2.2]heptene etc.

The term "heterocyclylalkoxy" as used herein refers to a heterocyclyl-alkyl-O— group.

The term "heterocyclyloxyalkyl" refers to a heterocyclyl-O-alkyl- group.

The term "heterocycloxy" refers to a heterocyclyl-O— group. The term "cycloalkyloxy" refers to a cycloalkyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the invention contains an alcohol functional group, a prodrug can be formed by the replacement of the hydrogen atom of the alcohol group with a group such as $(C_1-C_6)$alkanoyloxymethyl, 1-($(C_1-C_6)$alkanoyloxy)ethyl, 1-methyl-1-($(C_1-C_6)$alkanoyloxy)ethyl $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

I. Sulphone Compounds

In certain embodiments, the present invention provides compounds of Formula Ia and/or Formula Ib:

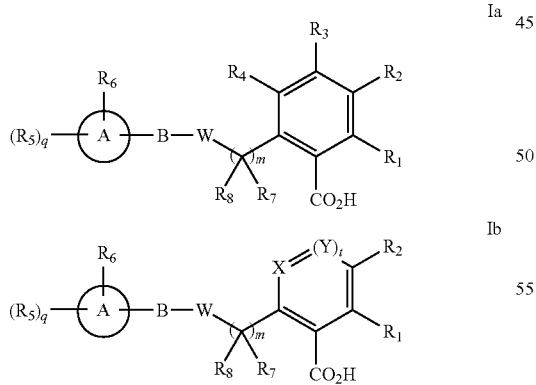

and pharmaceutically acceptable salts, stereoisomers, esters and prodrugs thereof, wherein
t is 0 or 1; wherein
when t is 1
X is $CR_4$ or N;
Y is $CR_3$ or N; or
when t is 0
X is S, O, or $NR_4'$;

B is selected from the group consisting of a bond or $(CR_9R_{10})_p$, wherein p is 1 or 2;
A is a ring selected from the group consisting of phenyl, a 5-6 membered heteroaryl having 1, 2 or 3 heteroatoms selected from S, N or O, a $C_{3-6}$cycloalkyl, a 4-7 membered heterocycle, a bridged 6-10 membered heterocycle, and a bridged 6-10 membered cycloalkyl;
$R_1$ is selected from the group consisting of:
hydrogen, halogen, cyano, hydroxyl, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— wherein w is 0, 1 or 2, $C_{1-6}$ alkyl-N($R^a$)-carbonyl, $R^fR^gN$—, $R^fR^gN$-carbonyl, $R^fR^gN$-carbonyl-N($R^a$)—, $R^fR^gNSO_2$—, $C_{1-6}$alkyl-carbonyl-N($R^a$)—, $C_{1-6}$ alkoxy-carbonyl-N($R^a$)—, phenyl, phenyloxy, phenyl-$C_{1-6}$alkyl-, phenyl-$C_{1-6}$alkoxy, heteroaryl, heteroaryloxy, heteroaryl-$C_{1-6}$alkyl, heteroaryl-$C_{1-6}$alkoxy, heterocyclyl, heterocyclyloxy, heterocyclyl-$C_{1-6}$alkyl, and heterocyclyl-$C_{1-6}$alkoxy, wherein said heteroaryl is a 5-6 membered ring having one, two or three heteroatoms selected from O, S, or N, and wherein said phenyl or heteroaryl is optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$; and wherein $C_{2-6}$alkenyl, $C_{2-6}$alkynyl, $C_{3-6}$alkenyloxy, and $C_{3-6}$alkynyloxy may be optionally substituted by one or more substituents selected from $R^p$, and wherein $C_{1-6}$alkyl and $C_{1-6}$alkoxy may be optionally substituted by one or more substituents selected from $R^{p'}$ and wherein $C_{3-6}$cycloalkyl and $C_{3-6}$cycloalkoxy may be optionally substituted by one or more substituents selected from $R^{p''}$;
$R_2$ is selected from the group consisting of:
hydrogen, halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkyloxy, $C_{1-6}$alkyl-S(O)$_2$—, $C_{3-6}$cycloalkylC$_{1-4}$alkyl-, $C_{3-6}$cycloalkylC$_{1-4}$alkoxy-, $R^fR^gN$-carbonyl, phenyl-$C_{1-6}$ alkyl-, phenyl, phenyoxy, phenyl-$C_{1-6}$alkoxy-, heteroaryl, heteroaryloxy, heteroaryl-$C_{1-6}$alkyl, heteroaryl-$C_{1-6}$alkoxy, heterocyclylC$_{1-6}$alkyl-, and heterocyclyl-$C_{1-6}$alkoxy, wherein said heteroaryl is a 5-6 membered monocyclic ring having one, two or three heteroatoms selected from O, S, or N, and optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$, and wherein $C_{1-6}$alkyl, $C_{2-6}$alkenyl, $C_{2-6}$alkynyl, $C_{1-6}$alkoxy, $C_{3-6}$alkenyloxy, or $C_{3-6}$alkynyloxy may be optionally substituted by one or more substituents selected from halogen, hydroxyl, $R^aR^aN$—, or cyano, and wherein $C_{3-6}$cycloalkyl and $C_{3-6}$cycloalkoxy may be optionally substituted by one or more substituents selected from halogen, hydroxyl, $R^aR^aN$—, cyano and $C_{1-6}$alkyl; or
$R_1$ and $R_2$ may be joined together with the carbons to which they are attached to form a 5-7 membered saturated, partially unsaturated, or unsaturated ring, optionally having 1, 2 or 3 heteroatoms selected from O, NR$^h$, or S(O)$_r$ where r is 0, 1, or 2, wherein the formed 5-7 membered ring is optionally substituted on a carbon by one or more groups R$^e$, and wherein the formed ring may be optionally bridged by a moiety selected from —O—, CH$_2$, —(CH$_2$)$_2$—, cis-CH=CH—, NR$^h$; or —CH$_2$NR$^h$—;

and wherein if R$_1$ is hydrogen, R$_2$ may not be hydrogen;

R$_3$ is selected from the group consisting of hydrogen, hydroxyl, cyano, halogen, C$_{1-6}$alkyl, or, C$_{1-6}$alkoxy, wherein C$_{1-6}$ alkyl, and C$_{1-6}$ alkoxy may be optionally substituted by one or more halogens;

R$_4$ is selected from the group consisting of hydrogen, halogen, hydroxyl, cyano, C$_{1-6}$alkyl, C$_{2-6}$alkenyl, C$_{2-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-S(O)$_w$, wherein w is 0, 1 or 2, R$^f$R$^g$N—, R$^f$R$^g$N-carbonyl, R$^f$R$^g$N-carbonyl-N(R$^a$)—, R$^f$R$^g$N—SO$_2$—, C$_{1-6}$alkyl-carbonyl-N(R$^a$)—, and C$_{1-6}$alkoxy-carbonyl-N(R$^a$)—, wherein C$_{2-6}$alkenyl, C$_{2-6}$alkynyl, C$_{1-6}$alkoxy, C$_{3-6}$alkenyloxy, or C$_{3-6}$alkynyloxy may be optionally substituted by one or more substituents selected from R$^p$; C$_{1-6}$alkyl and C$_{1-6}$alkoxy may be optionally substituted by one or more substituents selected from R$^{p'}$, and wherein C$_{3-6}$cycloalkyl and C$_{3-6}$cycloalkoxy may be optionally substituted by one or more substituents selected from R$^{p''}$;

R$_4$' is selected from the group consisting of hydrogen, C$_{1-6}$alkyl, C$_{3-6}$alkenyl (wherein the unsaturated bond is not directly attached to the nitrogen), C$_{3-6}$alkynyl (wherein the unsaturated bond is not directly attached to the nitrogen), C$_{3-6}$cycloalkyl, C$_{1-6}$ alkyl-S(O)$_2$—, C$_{1-6}$ alkyl-N(R$^a$)carbonyl, and C$_{1-6}$ alkyl-carbonyl-, wherein C$_{3-6}$alkenyl and C$_{3-6}$alkynyl may be optionally substituted by one or more substituents selected from R$^p$, and wherein C$_{1-6}$ alkyl may be optionally substituted by one or more substituents selected from R$^{p'}$, and wherein C$_{3-6}$cycloalkyl may be optionally substituted by one or more substituents selected from R$^{p''}$;

m is 1 or 2;

R$_5$ is selected, independently for each occurrence, from the group consisting of hydrogen, hydroxyl, cyano, halogen, C$_{1-6}$alkyl, C$_{2-6}$alkenyl, C$_{3-6}$alkynyl, C$_{3-6}$cycloalkyl, or C$_{1-6}$alkoxy, or R$^f$R$^g$N—, wherein C$_{1-6}$alkyl, C$_{2-6}$alkenyl, C$_{3-6}$alkynyl, C$_{3-6}$cycloalkyl, or C$_{1-6}$alkoxy may be optionally substituted with one or more halogens;

R$_6$ is selected from the group consisting of hydrogen, hydroxyl, cyano, halogen, C$_{1-6}$alkyl, C$_{2-6}$alkenyl, C$_{2-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-S(O)$_w$— wherein w is 0, 1 or 2, R$^f$R$^g$N—, R$^f$R$^g$N-carbonyl-, R$^f$R$^g$N-carbonyl-N(R$^a$)—, R$^f$R$^g$N—SO$_2$—, C$_{1-6}$alkyl-carbonyl-N(R$^a$)—, C$_{1-6}$alkylsulphonylN(R$^a$)—, C$_{1-6}$alkoxycarbonyl-N(R$^a$)—, phenyl, phenoxy, phenyl-C$_{1-6}$alkyl-, phenyl-C$_{1-6}$alkoxy, heteroaryl, heteroaryloxy, heterocycloxy, heteroaryl-C$_{1-6}$alkyl, heteroaryl-C$_{1-6}$alkoxy-, heterocyclyl-C$_{1-6}$alkyl-, and heterocyclyl-C$_{1-6}$alkoxy-, wherein said heteroaryl is a 5-6 membered monocyclic ring having one, two or three heteroatoms selected from O, S, or N, and optionally substituted with one or more substituents selected from R$^b$; wherein said heterocyclyl is a 4-7 membered ring optionally substituted by one or more substituents selected from R$^c$ and wherein if said heterocyclyl contains a —NH moiety that nitrogen may be optionally substituted by one or more groups R$^d$, and wherein C$_{1-6}$alkyl and C$_{1-6}$alkoxy may be optionally substituted by R$^{p'}$, and wherein C$_{2-6}$alkenyl, and C$_{2-6}$ alkynyl may be optionally substituted by one or more substituents selected from R$^p$; and C$_{3-6}$cycloalkyl or C$_{3-6}$cycloalkoxy may be optionally substituted by one or more substituents selected from R$^{p''}$;

R$_7$ and R$_8$ are independently selected from the group consisting of hydrogen, halogen, C$_{1-6}$alkoxy, C$_{1-6}$alkyl, C$_{2-6}$alkenyl, C$_{3-6}$alkynyl, and C$_{3-6}$cycloalkyl wherein C$_{2-6}$alkenyl, C$_{3-6}$alkynyl is optionally substituted by R$^p$, and wherein C$_{1-6}$alkyl is optionally substituted by R$^{p'}$; and C$_{3-6}$ cycloalkyl is optionally substituted by R$^{p''}$; or R$_7$ and R$_8$ taken together with the carbon to which they are attached form a cyclopropyl ring or 4-6 membered ring which may optionally have one group selected from N(R$^h$), O or S(O)$_r$ wherein r is 0, 1, or 2;

R$_9$ and R$_{10}$ are independently selected from the group consisting of hydrogen, C$_{1-6}$alkoxy, halogen, C$_{1-6}$alkyl, C$_{2-6}$alkenyl, C$_{3-6}$alkynyl, and C$_{3-6}$cycloalkyl wherein C$_{2-6}$alkenyl, C$_{3-6}$alkynyl is optionally substituted by R$^p$, and wherein C$_{1-6}$alkyl and C$_{1-6}$alkoxy is optionally substituted by R$^{p'}$; and C$_{3-6}$cycloalkyl is optionally substituted by R$^{p''}$; or R$_9$ and R$_{10}$ taken together with the carbon to which they are attached form a cyclopropyl ring or 4-6 membered ring which may optionally have one group selected from N(R$^h$), O or S(O)$_r$ wherein r is 0, 1, or 2;

W is —S(O)$_n$— or —S(=O)(=NR$_{11}$)—;

n is 1 or 2;

R$_{11}$ is selected from the group consisting of H, C$_{1-3}$alkyl, or CN;

q is 0, 1, 2, or 3;

R$^a$ and R$^{a'}$ are independently selected, for each occurrence, from the group consisting of hydrogen and C$_{1-6}$alkyl, or R$^a$ and R$^{a'}$ when they occur together may form a 4-6 membered heterocyclic ring, wherein C$_{1-6}$alkyl may be optionally substituted by one or more substituents selected from the group consisting of halogen, oxo and hydroxyl, and wherein the heterocyclic ring may be optionally substituted by one or more substituents selected from the group consisting of halogen, alkyl, oxo or hydroxyl;

R$^b$ is independently selected, for each occurrence, from the group consisting of halogen, hydroxyl, cyano, C$_{1-6}$alkyl, C$_{2-6}$alkenyl, C$_{3-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-S(O)$_w$— wherein w is 0, 1 or 2, C$_{1-6}$alkylN(R$^a$)—, C$_{1-6}$alkyl-N(R$^a$)carbonyl, R$^a$R$^{a'}$N—, R$^a$R$^{a'}$N-carbonyl-, R$^a$R$^{a'}$N-carbonyl-N(R$^a$)—; R$^a$R$^{a'}$N—SO$_2$—, and C$_{1-6}$alkyl-carbonyl-N(R$^a$)—, wherein C$_{2-6}$alkenyl, C$_{3-6}$alkynyl, or C$_{1-6}$alkoxy may be optionally substituted by one or more substituents selected from R$^p$; wherein C$_{3-6}$cycloalkyl and C$_{3-6}$cycloalkoxy may be optionally substituted by one or more substituents selected from R$^{p''}$, and wherein C$_{1-6}$alkyl may be optionally substituted by one or more substituents selected from R$^{p'}$;

R$^c$ for each occurrence is independently selected from the group consisting of, hydroxyl, cyano, oxo, halogen, C$_{1-6}$alkyl, C$_{2-6}$alkenyl, C$_{2-6}$alkynyl, C$_{3-6}$cycloalkyl, C$_{1-6}$alkoxy, C$_{1-6}$alkyl-S(O)$_w$—, wherein w is 0, 1 or 2, C$_{1-6}$alkyl-NR$^a$—, C$_{1-6}$alkylC$_{3-6}$cycloalkyl-, C$_{3-6}$cycloalkylC$_{1-6}$alkyl, R$^a$R$^{a'}$N—, C$_{1-6}$alkylcarbonyl-N(R$^a$)—; C$_{1-6}$alkoxycarbonyl-N(R$^a$)—, R$^a$R$^{a'}$N—SO$_2$—, R$^a$R$^{a'}$N-carbonyl-, R$^a$R$^{a'}$N-carbonyl-N(R$^a$), wherein C$_{1-6}$alkyl, C$_{2-6}$alkenyl, C$_{2-6}$alkynyl, C$_{3-6}$cycloalkyl, or C$_{1-6}$alkoxy may be optionally substituted by R$^t$;

$R^d$ is independently selected for each occurrence from the group consisting of $C_{1-6}$alkyl, $C_{1-6}$alkylcarbonyl or $C_{1-6}$alkylsulphonyl, wherein $C_{1-6}$alkyl is optionally substituted by one or more substituents selected from halogen, hydroxyl, and $R^aR^{a\prime}N$—;

$R^e$ is independently selected for each occurrence from the group consisting of hydroxyl, cyano, halogen, oxo, $C_{1-4}$alkyl, $C_{2-4}$alkenyl, $C_{2-4}$alkynyl, $C_{3-6}$cycloalkyl, $C_{1-4}$alkoxy, $C_{3-6}$alkenyloxy, $C_{3-6}$alkynyloxy, $C_{3-6}$cycloalkoxy, $C_{3-6}$cycloalkyl-$C_{1-4}$alkyloxy-, $C_{1-4}$alkyl-S(O)$_w$— wherein w is 0, 1 or 2, $R^aR^{a\prime}N$—, $R^aR^{a\prime}N$-carbonyl, $R^aR^{a\prime}N$-carbonyl-N($R^a$)—, $R^aR^{a\prime}N$—SO$_2$—, $C_{1-6}$alkyl-carbonyl-N($R^a$)—, $C_{1-6}$alkyl-SO$_2$—N($R^a$)—, $C_{1-6}$alkoxycarbonyl-, $C_{1-4}$alkoxycarbonyl-N($R^a$)—, wherein $C_{2-6}$alkenyl, and $C_{2-6}$alkynyl may be optionally substituted by one or more substituents selected from $R^p$; wherein $C_{1-6}$alkyl and $C_{1-6}$ alkoxy may optionally substituted by one or more substituents selected from $R^{p\prime}$; and wherein $C_{3-6}$cycloalkyl or $C_{3-6}$cycloalkoxy may be optionally substituted by $R^{p\prime\prime}$;

$R^f$ and $R^g$, independently for each occurrence, are selected from group consisting of hydrogen, $C_{1-4}$alkyl optionally substituted by one or more substituents selected from $R^{p\prime}$, and $C_{3-6}$cycloalkyl optionally substituted by one or more substituents selected from $R^{p\prime\prime}$, or $R^f$ and $R^g$ taken together with the nitrogen to which they are attached form a 4-7 membered heterocyclyl, optionally substituted by one or more substituents selected from the group consisting of halogen, hydroxyl, oxo, cyano, $C_{1-6}$alkyl, $C_{1-6}$alkoxy, $R^aR^{a\prime}N$—, $C_{1-6}$alkylcarbonyl-N($R^a$)—; $C_{1-6}$alkoxycarbonyl-N($R^a$)—, $R^aR^{a\prime}N$—SO$_2$—, $R^aR^{a\prime}N$-carbonyl-, $R^aR^{a\prime}N$-carbonyl-N($R^a$), and wherein $C_{1-6}$alkyl or $C_{1-4}$alkoxy may be optionally substituted by at least one or more substituent selected from the group consisting of $R^aR^{a\prime}N$—, halogen, hydroxy, cyano; $C_{1-4}$alkoxycarbonyl, $R^aR^{a\prime}N$-carbonyl, $R^aR^{a\prime}N$—SO$_2$—, $C_{1-4}$alkoxy, $C_{1-4}$alkylS(O)$_w$—, wherein w is 0, 1 or 2;

$R^p$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, and $C_{1-4}$alkylS(O)$_w$—, wherein w is 0, 1 or 2;

$R^{p\prime}$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, $C_{1-4}$alkylS(O)$_w$— and $C_{3-6}$cycloalkyl, wherein w is 0, 1 or 2 and wherein $C_{3-6}$cycloalkyl is optionally substituted with $R^{p\prime\prime}$;

$R^{p\prime\prime}$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, $C_{1-4}$alkylS(O)$_w$ and $C_{1-6}$alkyl, wherein w is 0, 1 or 2 and $C_{1-6}$alkyl is optionally substituted by one or more substituents selected from $R^p$;

$R^t$ is independently selected from the group consisting of $R^fR^gN$—, halogen, cyano, hydroxyl and $C_{1-6}$alkoxy $R^h$ is independently selected from the group consisting of hydrogen, $C_{1-6}$alkyl, $C_{3-6}$alkenyl (wherein any unsaturated bond is not directly attached to a nitrogen), $C_{3-6}$alkynyl(wherein any unsaturated bond is not directly attached to a nitrogen), $C_{3-6}$cycloalkyl, $C_{1-6}$alkyl-S(O)$_2$—, and $C_{1-6}$alkyl-N($R^a$)carbonyl, wherein $C_{1-6}$alkyl is optionally substituted by one or more substituents selected from $R^p$; wherein $C_{3-6}$alkenyl and $C_{3-6}$alkynyl are optionally substituted by at least one substituent selected from $R^p$, and wherein $C_{3-6}$cycloalkyl is optionally substituted by at least one substituent selected from $R^{p\prime\prime}$.

For example, A may be, in certain embodiments, phenyl or pyridinyl, a bridged cycloalkyl such as for example, bicyclo[2.2.1]heptanyl or a bicyclo[2.2.2]octanyl, a bridged heterocyclyl such as for example, bicyclo[2.2.1]heptane or a bicyclo[2.2.2]octane. In an embodiment, A may be piperidinyl or a pyrrolidinyl.

In certain embodiments, B is a bond. In another embodiment, m is 1 and/or W is —SO$_2$—. When B is a bond and W is —SO$_2$—, for example, A may be a nitrogen containing bridged heterocycle bonded to the —S(O)$_2$ of Formula Ia or Ib through the heterocycle nitrogen atom, for example, A may be 7-azabicyclo[2.2.1]heptane or 7-azabicyclo[2.2.1]heptene.

$R_2$ may be, in certain embodiments, selected from the group consisting of halogen, cyano, $C_1$-$C_4$alkyl, $C_3$-$C_6$cycloalkyl, a 5-6 membered monocyclic heteroaryl, or a $C_4$-$C_6$heterocyclyl. For example, $R_2$ may be selected from the group consisting of furyl, furazanyl, imidazolyl, thiazolyl; thienyl, pyrrolyl, pyrazolyl, isothiazolyl, isoxazolyl, triazolyl, or oxazolyl, e.g. $R_2$ may be selected from 3-furyl and 5-isothiazolyl.

In a different embodiment, $R_2$ may be selected from the group consisting of methyl, ethyl, propyl, or cyclopropyl.

$R_1$, in certain embodiments, may be H or $C_1$-$C_4$alkoxy, for example, $R_1$ may be methoxy or ethoxy optionally substituted by one, two or three substituents selected from the group consisting of Cl or F, or $R_1$ may be $C_1$-$C_4$alkoxy optionally substituted by hydroxyl, cyano, or —NH$_2$.

In some embodiments, $R_1$ and $R_2$ may be taken together with the ring to which they are attached form a moiety selected from the group consisting of:

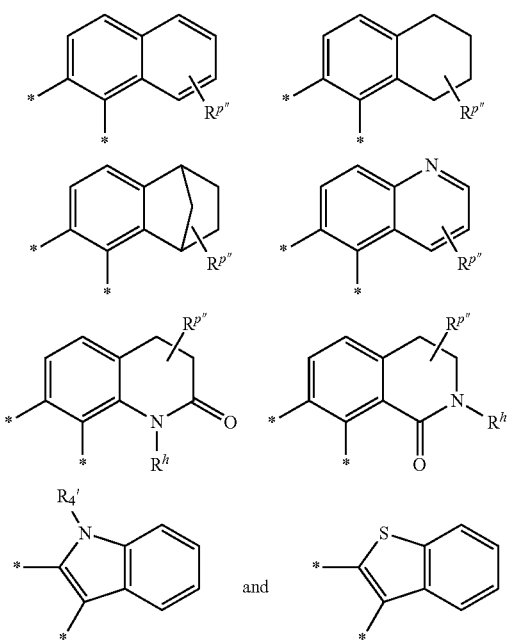

where the point of attachments relate to Formula I.

In a certain embodiment, compounds represented by the following are contemplated:

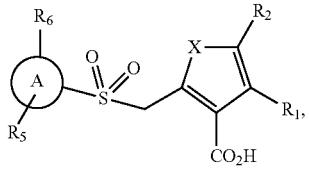

wherein X is S, O, or NR$^{4'}$, and R$_1$, R$_2$, R$_5$, and R$_6$ are defined above.

Contemplated herein are compounds represented by Formula II:

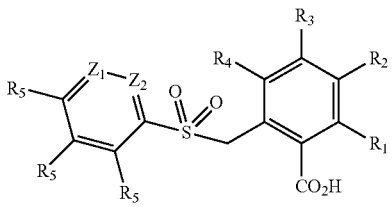

wherein $Z_1$ is CR$_5$ and $Z_2$ is CR$_6$, or $Z_1$ is N and $Z_2$ is CR$_6$, or $Z_2$ is N and $Z_1$ is CR$_5$;

R$_1$ is selected from the group consisting of hydrogen, halogen, hydroxyl, cyano, R$^f$R$^g$N—, C$_{1-4}$alkyl, C$_{1-4}$alkoxy and C$_{3-6}$cycloalkyl, wherein C$_{1-4}$alkyl and C$_{1-4}$alkoxy may be optionally substituted by one or more substituents selected from R$^{p'}$, and wherein C$_{3-6}$cycloalkyl may be optionally substituted by one or more substituents selected from R$^{p'''}$;

R$_2$ is selected from the group consisting of hydrogen, halogen, hydroxyl, cyano, R$^f$R$^g$N—, C$_{1-4}$alkyl, C$_{1-4}$alkoxy, C$_{3-6}$cycloalkyl, C$_{3-6}$cycloalkyl-C$_{1-4}$alkyl, a 5 membered monocyclic heteroaryl having one or two heteroatoms selected from O, S, or N, and a 4-5 membered heterocyclyl, wherein said heteroaryl is optionally substituted by one or more groups R$^b$; and wherein said heterocyclyl is optionally substituted by R$^c$;

R$_3$ is selected from H or halogen;

R$_4$ is selected from the group consisting of H, halogen, hydroxyl, or methyl; and R$_5$ is selected, independently for each occurrence, from the group consisting of hydrogen, hydroxyl, cyano, halogen, C$_{1-4}$ alkyl, C$_{3-6}$ cycloalkyl, or C$_{1-4}$ alkoxy, wherein C$_{1-4}$alkyl or C$_{1-4}$alkoxy may be optionally substituted by one or more substituents selected from R$^{p'}$, and C$_{3-6}$cycloalkyl may be optionally substituted by one or more substituents selected from R$^{p'''}$.

For example, R$_1$ may be selected from H, hydroxyl, or C$_{1-4}$alkoxy optionally substituted by NH$_2$ or hydroxyl, or R$_1$ may be methoxy or ethoxy, optionally substituted by one, two, or three substituents selected from Cl or F. R$_2$ is selected from cyclopropyl, halogen, or C$_{1-4}$ alkyl, or R$_2$ may be selected from the group consisting of furyl, thienyl, isothiazolyl, isoxazolyl, oxazolyl, and pyrrolyl, for example, selected from:

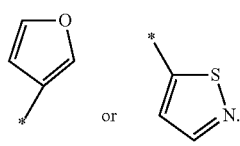

Z$_1$ of Formula II, e.g., may be CH, and Z$_2$ is CR$_6$.

R$_6$ of Formula I or II, or other Formulas, may be for example, C$_{1-4}$alkyl substituted by (N,N di-C$_{1-4}$alkyl)amino), or C$_{3-4}$alkenyl substituted by (N,N-di-C$_{2-4}$alkylamino), e.g., R$_6$ is cis-3-N,N-diethylamino-prop-1-en-1-yl. In other embodiments, R$_6$ may be selected from the group consisting of halogen, C$_{1-4}$alkyl and C$_{1-4}$alkoxy, for example, methoxy or ethoxy. R$_5$ may be independently selected for each occurrence from the group consisting of hydrogen, Cl, F, methyl, or methoxy.

Also provided herein are compounds represented by Formula III:

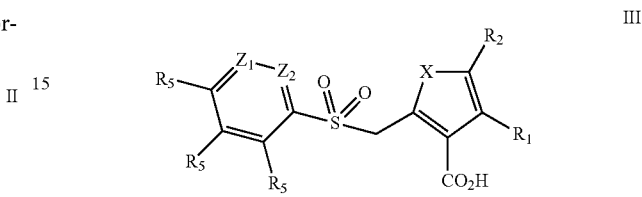

wherein $Z_1$ is CR$_5$ and $Z_2$ is CR$_6$, or $Z_1$ is N and $Z_2$ is CR$_6$, or $Z_2$ is N and $Z_1$ is CR$_5$; and X is S or NR$^a$, and R$_1$, R$_2$, R$_5$ and R$_6$ are defined above.

Also provided herein are compounds represented by Formula IV:

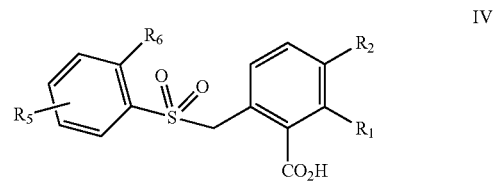

or pharmaceutically acceptable salts, esters, stereoisomers, or prodrugs thereof, wherein R$_1$ is selected from the group consisting of:

hydrogen, halogen, cyano, hydroxyl, C$_{1-6}$alkyl, C$_{2-6}$alkenyl, C$_{2-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-S(O)$_w$— wherein w is 0, 1 or 2, C$_{1-6}$alkyl-N(R$^a$)-carbonyl, R$^f$R$^g$N—, R$^f$R$^g$N-carbonyl, R$^f$R$^g$N-carbonyl-N(R$^a$)—, R$^f$R$^g$NSO$_2$—, C$_{1-6}$alkyl-carbonyl-N(R$^a$)—, C$_{1-6}$ alkoxy-carbonyl-N(R$^a$)—, phenyl, phenyloxy, phenyl-C$_{1-6}$alkyl-, phenyl-C$_{1-6}$alkoxy, heteroaryl, heteroaryloxy, heteroaryl-C$_{1-6}$alkyl, heteroaryl-C$_{1-6}$alkoxy, heterocyclyl, heterocyclyloxy, heterocyclyl-C$_{1-6}$alkyl, and heterocyclyl-C$_{1-6}$alkoxy, wherein said heteroaryl is a 5-6 membered ring having one, two or three heteroatoms selected from O, S, or N, and wherein said phenyl or heteroaryl is optionally substituted with one or more substituents selected from R$^b$; wherein said heterocyclyl is a 4-7 membered ring optionally substituted by one or more substituents selected from R$^c$ and wherein if said heterocyclyl contains a —NH moiety that nitrogen may be optionally substituted by one or more groups R$^d$; and wherein C$_{2-6}$alkenyl, C$_{2-6}$alkynyl, C$_{3-6}$alkenyloxy, and wherein C$_{3-6}$alkynyloxy may be optionally substituted by one or more substituents selected from R$^p$, C$_{1-6}$alkyl and C$_{1-6}$alkoxy may be optionally substituted by one or more substituents selected from R$^{p'}$ and wherein C$_{3-6}$cycloalkyl and C$_{3-6}$cycloalkoxy may be optionally substituted by one or more substituents selected from R$^{p'''}$;

R$_2$ is selected from the group consisting of:

halogen, hydroxyl, cyano, C$_{1-6}$alkyl, C$_{2-6}$alkenyl, C$_{2-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkyloxy, C$_{1-6}$alkyl-S(O)$_2$—, C$_{3-6}$cycloalkylC$_{1-4}$alkyl-, C$_{3-6}$cycloalkylC$_{1-4}$alkoxy-, R$^f$R$^g$N-carbonyl, phenyl-C$_{1-6}$alkyl-, phenyl, phenyoxy, phenyl- $C_{1-6}$alkoxy-, heteroaryl, heteroaryloxy, heteroaryl-$C_{1-6}$alkyl, heteroaryl-$C_{1-6}$alkoxy, heterocyclyl$C_{1-6}$alkyl-, and heterocyclyl-$C_{1-6}$alkoxy, wherein said heteroaryl is a 5-6 membered monocyclic ring having one, two or three heteroatoms selected from O, S, or N, and optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$, and wherein $C_{1-6}$alkyl, $C_{2-6}$alkenyl, $C_{2-6}$alkynyl, $C_{1-6}$alkoxy, $C_{3-6}$alkenyloxy, or $C_{3-6}$alkynyloxy may be optionally substituted by one or more substituents selected from halogen, hydroxyl, $R^aR^{a\prime}N$—, or cyano, and wherein $C_{3-6}$cycloalkyl and $C_{3-6}$cycloalkoxy may be optionally substituted by one or more substituents selected from halogen, hydroxyl, $R^aR^{a\prime}N$—, cyano and $C_{1-6}$alkyl; or $R_1$ and $R_2$ may be joined together with the carbons to which they are attached to form a 5-7 membered saturated, partially unsaturated, or unsaturated ring, optionally having 1, 2 or 3 atoms/groups selected from O, $NR^h$, or $S(O)_r$ where r is 0, 1, or 2, wherein the formed 5-7 membered ring is optionally substituted on a carbon by one or more groups $R^e$, and wherein the formed ring may be optionally bridged by a moiety selected from $CH_2$, —$(CH_2)_2$—, cis-CH=CH—, $NR^h$; or —$CH_2NR^h$—; and wherein if $R_1$ is hydrogen, $R_2$ may not be hydrogen;

$R_5$ is selected, independently for each occurrence, from the group consisting of hydrogen, hydroxyl, cyano, halogen, $C_{1-6}$alkyl, $C_{2-6}$alkenyl, $C_{3-6}$alkynyl, $C_{3-6}$cycloalkyl, or $C_{1-6}$alkoxy, or $R^fR^gN$—, wherein $C_{1-6}$alkyl, $C_{2-6}$alkenyl, $C_{3-6}$ alkynyl, $C_{3-6}$cycloalkyl, or $C_{1-6}$alkoxy may be optionally substituted with one or more halogens;

$R_6$ is selected from the group consisting of hydrogen, hydroxyl, cyano, halogen, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— wherein w is 0, 1 or 2, $R^fR^gN$—, $R^fR^gN$-carbonyl-, $R^fR^gN$-carbonyl-$N(R^a)$—, $R^fR^gN$—$SO_2$—, $C_{1-6}$alkyl-carbonyl-$N(R^a)$—, $C_{1-6}$alkylsulphonylN$(R^a)$—, $C_{1-6}$alkoxycarbonyl-$N(R^a)$—, phenyl, phenyloxy, phenyl-$C_{1-6}$alkyl-, phenyl-$C_{1-6}$alkyoxy, heteroaryl, heteroaryloxy, heterocycloxy, heteroaryl-$C_{1-6}$alkyl, heteroaryl-$C_{1-6}$alkoxy-, heterocyclyl-$C_{1-6}$alkyl-, and heterocyclyl-$C_{1-6}$alkoxy-, wherein said heteroaryl is a 5-6 membered monocyclic ring having one, two or three heteroatoms selected from O, S, or N, and optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$, and, wherein $C_{1-6}$alkyl and $C_{1-6}$alkoxy may be optionally substituted by $R^{p\prime}$, $C_{2-6}$alkenyl, and wherein $C_{2-6}$ alkynyl may be optionally substituted by one or more substituents selected from $R^p$; and wherein $C_{3-6}$cycloalkyl or $C_{3-6}$ cycloalkoxy may be optionally substituted by one or more substituents selected from $R^{p\prime\prime}$;

$R^a$ and $R^{a\prime}$ are independently selected, for each occurrence, from the group consisting of hydrogen and $C_{1-6}$alkyl, or $R^a$ and $R^{a\prime}$ when they occur together may form a 4-6 membered heterocyclic ring, wherein $C_{1-6}$alkyl may be optionally substituted by one or more substituents selected from the group consisting of halogen, oxo and hydroxyl, and wherein the heterocyclic ring may be optionally substituted by one or more substituents selected from the group consisting of halogen, alkyl, oxo or hydroxyl;

$R^b$ is independently selected, for each occurrence, from the group consisting of halogen, hydroxyl, cyano, $C_{1-6}$alkyl, $C_{2-6}$alkenyl, $C_{3-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkoxy, $C_{3-6}$cycloalkyl, $C_{1-6}$alkyl-$S(O)_w$— wherein w is 0, 1 or 2, $C_{1-6}$alkylN$(R^a)$—, $C_{1-6}$alkyl-$N(R^a)$carbonyl, $R^aR^{a\prime}N$—, $R^aR^{a\prime}N$-carbonyl-, $R^aR^{a\prime}N$-carbonyl-$N(R^a)$—; $R^aR^{a\prime}N$—$SO_2$—, and $C_{1-6}$alkyl-carbonyl-$N(R^a)$—, wherein $C_{2-6}$alkenyl, $C_{2-6}$alkynyl, or $C_{1-6}$alkoxy may be optionally substituted by one or more substituents selected from $R^p$; wherein $C_{3-6}$cycloalkyl and $C_{3-6}$cycloalkoxy may be optionally substituted by one or more substituents selected from $R^{p\prime\prime}$, and wherein $C_{1-6}$alkyl may be optionally substituted by one or more substituents selected from $R^{p\prime}$;

$R^c$ for each occurrence is independently selected from the group consisting of, hydroxyl, cyano, oxo, halogen, $C_{1-6}$alkyl, $C_{2-6}$alkenyl, $C_{2-6}$ alkynyl, $C_{3-6}$cycloalkyl, $C_{1-6}$alkoxy, $C_{1-6}$alkyl-$S(O)_w$—, wherein w is 0, 1 or 2, $C_{1-6}$alkyl-NR$^a$—, $C_{1-6}$alkylC$_{3-6}$cycloalkyl-, $C_{3-6}$cycloalkylC$_{1-6}$alkyl, $R^aR^{a\prime}N$—, $C_{1-6}$alkylcarbonyl-$N(R^a)$—; $C_{1-6}$alkoxycarbonyl-$N(R^a)$—, $R^aR^{a\prime}N$—$SO_2$—, $R^aR^{a\prime}N$-carbonyl-, $R^aR^{a\prime}N$-carbonyl-$N(R^a)$, wherein $C_{1-6}$alkyl, $C_{2-6}$alkenyl, $C_{3-6}$alkynyl, $C_{3-6}$cycloalkyl, or $C_{1-6}$alkoxy may be optionally substituted by $R^t$;

$R^d$ is independently selected for each occurrence from the group consisting of $C_{1-6}$alkyl, $C_{1-6}$alkylcarbonyl or $C_{1-6}$alkylsulphonyl, wherein $C_{1-6}$alkyl is optionally substituted by one or more substituents selected from halogen, hydroxyl, and $R^aR^{a\prime}N$—;

$R^e$ is independently selected for each occurrence from the group consisting of hydroxyl, cyano, halogen, oxo, $C_{1-4}$alkyl, $C_{2-4}$alkenyl, $C_{2-4}$alkynyl, $C_{3-6}$cycloalkyl, $C_{1-4}$alkoxy, $C_{2-6}$alkenyloxy, $C_{3-6}$alkynyloxy, $C_{3-6}$cycloalkoxy, $C_{3-6}$cycloalkyl-$C_{1-4}$alkoxy-, $C_{1-4}$alkyl-$S(O)_w$— wherein w is 0, 1 or 2, $R^aR^{a\prime}N$—, $R^aR^{a\prime}N$-carbonyl, $R^aR^{a\prime}N$-carbonyl-$N(R^a)$—, $R^aR^{a\prime}N$—$SO_2$—, $C_{1-6}$alkyl-carbonyl-$N(R^a)$—, $C_{1-6}$alkyl-$SO_2$—$N(R^a)$—, $C_{1-6}$alkoxycarbonyl-, $C_{1-4}$alkoxycarbonyl-$N(R^a)$—, wherein $C_{2-4}$alkenyl, and $C_{2-4}$alkynyl may be optionally substituted by one or more substituents selected from $R^p$; wherein $C_{1-4}$alkyl and $C_{1-4}$alkoxy may optionally substituted by one or more substituents selected from $R^{p\prime}$; and $C_{3-6}$cycloalkyl or $C_{3-6}$cycloalkoxy may be optionally substituted by $R^{p\prime\prime}$;

$R^f$ and $R^g$, independently for each occurrence, are selected from group consisting of hydrogen, $C_{1-4}$alkyl optionally substituted by one or more substituents selected from $R^{p\prime}$, and $C_{3-7}$cycloalkyl optionally substituted by one or more substituents selected from $R^{p\prime\prime}$, or $R^f$ and $R^g$ taken together with the nitrogen to which they are attached form a 4-7 membered heterocyclyl, optionally substituted by one or more substituents selected from the group consisting of halogen, hydroxyl, oxo, cyano, $C_{1-6}$alkyl, $C_{1-6}$alkoxy, $R^aR^{a\prime}N$—, $C_{1-6}$alkylcarbonyl-$N(R^a)$—; $C_{1-6}$alkoxycarbonyl-$N(R^a)$—, $R^aR^{a\prime}N$—$SO_2$—, $R^aR^{a\prime}N$-carbonyl-, $R^aR^{a\prime}N$-carbonyl-$N(R^a)$, and wherein $C_{1-6}$alkyl or $C_{1-6}$alkoxy may be optionally substituted by at least one or more substituent selected from the group consisting of $R^aR^{a\prime}N$, halogen, hydroxy, cyano; $C_{1-4}$alkoxycarbonyl, $R^aR^{a\prime}N$-carbonyl, $R^aR^{a\prime}N$—$SO_2$—, $C_{1-4}$alkoxy, $C_{1-4}$alkylS$(O)_w$—, wherein w is 0, 1 or 2;

$R^p$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—$SO_2$—, $C_{1-4}$alkoxy, and $C_{1-4}$alkylS$(O)_w$—, wherein w is 0, 1 or 2;

$R^{p\prime}$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—$SO_2$—, $C_{1-4}$alkoxy, $C_{1-4}$alkylS$(O)_w$—and $C_{3-6}$cycloalkyl, wherein w is 0, 1 or 2 and wherein $C_{3-6}$cycloalkyl is optionally substituted with $R^{p\prime\prime}$;

$R^{p\prime\prime}$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—$SO_2$—, $C_{1-4}$alkoxy, $C_{1-4}$alkylS(O)$_w$ and $C_{1-6}$alkyl, wherein w is 0, 1 or 2 and $C_{1-6}$alkyl is optionally substituted by one or more substituents selected from $R^p$;

$R^t$ is independently selected from the group consisting of $R^a R^{a'} N$—, halogen, cyano, hydroxyl and $C_{1-6}$alkoxy;

$R^h$ is independently selected from the group consisting of hydrogen, $C_{1-6}$alkyl, $C_{3-6}$alkenyl (wherein any unsaturated bond is not directly attached to a nitrogen), $C_{3-6}$alkynyl (wherein any unsaturated bond is not directly attached to a nitrogen), $C_{3-6}$cycloalkyl, $C_{1-6}$alkyl-S(O)$_2$—, and $C_{1-6}$alkyl-N($R^a$)carbonyl, wherein $C_{1-6}$alkyl is optionally substituted by one or more substituents selected from $R^{p'}$; $C_{3-6}$alkenyl and $C_{3-6}$alkynyl are optionally substituted by at least one substituent selected from $R^p$, and $C_{3-6}$cycloalkyl is optionally substituted by at least one substituent selected from $R^{p''}$.

For example, $R_1$ may be selected from the group consisting of hydrogen, methoxy, ethoxy, —O—(CH$_2$)$_2$—NH$_2$, —O—CH$_2$—CN, or —O—(CH$_2$)$_2$—OH. In certain embodiments, $R_2$ may be selected from the group consisting of halogen, cyano, methyl, ethyl, propyl, $C_{3-5}$cycloalkyl, $C_{3-6}$cycloalkyloxy, $C_{3-5}$cycloalkyl-$C_{1-2}$alkyl-, or a 5 membered heteraryl having one or two heteroatoms selected from O, N, and S, for example, $R_2$ may be selected from the group consisting of furyl, thienyl, isothiazolyl, isoxazolyl, oxazolyl and pyrrolyl, e.g. may be 3-furyl or 5-isoxazolyl.

Provided herein are compounds that may be selected from the group consisting of: 2-(Benzenesulphonylmethyl)-5-ethylbenzoic acid; 6-(Benzenesulphonylmethyl)-3-ethyl-2-methoxy-benzoic acid; 6-(Benzenesulphonylmethyl)-2-methoxy-3-propyl-benzoic acid; 6-(Benzenesulphinylmethyl)-3-ethyl-2-methoxy-benzoic acid; 6-(Benzenesulphonylmethyl)-3-cyclopropyl-2-methoxy-benzoic acid; 6-(4-Chlorobenzenesulphonylmethyl)-3-ethyl-2-methoxy-benzoic acid; 6-(Benzenesulphonylmethyl)-3-bromo-2-methoxy-benzoic acid; 6-(Benzenesulphonylmethyl)-2-methoxy-3-methyl-benzoic acid; 3-Ethyl-2-methoxy-6-(2-methylbenzenesulphonylmethyl)benzoic acid; 6-(Benzenesulphonylmethyl)-3-(furan-3-yl)-2-methoxy-benzoic acid; 6-(1-Benzenesulphonylethyl)-3-ethyl-2-methoxy-benzoic acid; 6-(Benzenesulphonylmethyl)-2-methoxy-3-(oxazol-5-yl)benzoic acid; 6-(Benzenesulphonylmethyl-3-(isothiazol-5-yl)-2-methoxy-benzoic acid; 2-(Benzenesulphonylmethyl)-5-(furan-3-yl)benzoic acid; 2-(Benzenesulphonylmethyl)-5-(oxazol-5-yl)benzoic acid; 3-(Furan-3-yl)-2-methoxy-6-(2-methyl-benzenesulphonylmethyl)benzoic acid; 6-(3-Chlorobenzenesulphonylmethyl)-3-(furan-3-yl)-2-methoxybenzoic acid; 6-(Benzenesulphonylmethyl)-3-(oxazol-4-yl)-2-methoxybenzoic acid; 6-(Benzenesulphonylmethyl)-3-(isothiazol-4-yl)-2-methoxybenzoic acid; (Z)-6-((2-(3-(Diethylamino)prop-1-enyl)benzenesulfonyl)methyl)-3-(furan-3-yl)-2-methoxybenzoic acid; (E)-6-((2-(3-(Diethylamino)prop-1-enyl)benzenesulfonyl)methyl)-3-(furan-3-yl)-2-methoxybenzoic acid; 6-(Benzenesulphonylmethyl)-2-ethoxy-3-(furan-3-yl)benzoic acid; 6-(Benzenesulphonylmethyl)-3-(furan-3-yl)-2-hydroxy-benzoic acid; 6-(Benzenesulphonylmethyl)-3-(furan-3-yl)-2-(2-hydroxyethoxy)benzoic acid; 6-(2-(3-diethylaminopropyl)benzenesulphonylmethyl)-3-(furan-3-yl)-2-methoxybenzoic acid; 3-(Furan-3-yl)-2-methoxy-6-(pyridin-3-ylsulphonylmethyl)benzoic acid; 6-(Benzenesulphonylmethyl)-3-(isoxazol-3-yl)-2-methoxybenzoic acid; 3-(Furan-3-yl)-2-methoxy-6-(2-methoxybenzenesulphonylmethyl)-benzoic acid; 3-(Furan-3-yl)-2-methoxy-6-(pyridin-2-ylsulphonylmethyl)benzoic acid; 3-Ethyl-6-(4-fluorobenzenesulphonylmethyl)-2-methoxybenzoic acid; 6-(Benzenesulphonylmethyl)-3-cyano-2-methoxybenzoic acid; 6-(Benzenesulphonylmethyl)-3-(furan-2-yl)-2-methoxy-benzoic acid; 2-(2-Aminoethoxy)-6-(benzenesulphonylmethyl)-3-(furan-3-yl)benzoic acid hydrochloride; 2-(2-Aminoethoxy)-6-(3-chlorobenzenesulphonylmethyl)-3-(furan-3-yl)benzoic acid hydrochloride; 2-(2-Aminoethoxy)-6-(4-fluorobenzenesulphonylmethyl)-3-(furan-3-yl)benzoic acid hydrochloride; 2-(2-Aminoethoxy)-3-(furan-3-yl)-6-(2-methoxybenzenesulphonylmethyl)benzoic acid hydrochloride; 6-(2-Chlorobenzenesulphonylmethyl)-3-(furan-3-yl)-2-methoxybenzoic acid; 6-(3-Fluorobenzenesulphonylmethyl)-3-(furan-3-yl)-2-methoxybenzoic acid; 6-(2-Fluorobenzenesulphonylmethyl)-3-(furan-3-yl)-2-methoxybenzoic acid; 3-(Furan-3-yl)-6-(3-methoxybenzenesulphonylmethyl)-2-methoxybenzoic acid; 2-(2-Aminoethoxy)-3-ethyl-6-benzenesulphonylmethylbenzoic acid hydrochloride; 2-(3-Aminopropoxy)-6-(benzenesulphonylmethyl)-3-(furan-3-yl)benzoic acid hydrochloride; 6-(Benzenesulphonylmethyl)-2-methoxy-3-(thien-2-yl)benzoic acid; 6-(4-Fluorobenzenesulphonylmethyl)-3-(furan-3-yl)-2-methoxybenzoic acid; 6-(Benzenesulphonylmethyl)-2-methoxy-3-phenylbenzoic acid; 6-(Benzenesulphonylmethyl)-2-methoxy-3-(3-pyridyl)benzoic acid; 6-(Benzenesulphonylmethyl)-2-methoxy-3-(pyrazol-3-yl)benzoic acid; 2-Methoxy-6-(2-methylbenzenesulphonylmethyl)benzoic acid; 6-(Benzenesulphonylmethyl)-2-methoxy-3-(thiazol-2-yl)benzoic acid; 6-(Benzenesulphonylmethyl)-3-(furan-3-yl)-2-(2-methoxyethoxy)-benzoic acid; 6-(Benzenesulphonylmethyl)-2-(2-dimethylaminoethoxy)-3-(furan-3-yl)benzoic acid hydrochloride; 6-(Benzenesulphonylmethyl)-2-methyoxy-3-(thien-3-yl)benzoic acid; 6-(Benzenesulphonylmethyl)-2-(cyanomethoxy)-3-(furan-3-yl)benzoic acid; 2-(2-Aminoethylamino)-6-benzenesulphonylmethyl-3-(furan-3-yl)-benzoic acid hydrochloride; 6-(Benzenesulphonylmethyl)-3-(furan-3-yl)-2-[2-[(methylamino)-ethoxy]benzoic acid hydrochloride; 6-(Benzenesulphonylmethyl)-3-ethyl-2-(2-methyl-2H-pyrazol-3-yl)-benzoic acid; 2-(2-Aminopropoxy)-6-(benzenesulphonylmethyl)-3-(furan-3-yl)-benzoic acid hydrochloride; 6-Benzenesulphonylmethyl-3-ethyl-2-(1-methyl-1H-pyrazol-3-yl)-benzoic acid; 2-(3-Aminopropyl)-6-(benzenesulphonylmethyl)-3-(furan-3-yl)-benzoic acid hydrochloride; 6-(Benzenesulphonylmethyl)-2-methoxy-3-(pyrazol-1-yl)benzoic acid; 2-(Benzenesulphonylmethyl)-5-(2-methyl-2H-pyrazol-3-yl)benzoic acid; 2-(Benzenesulphonylmethyl)naphthalene-1-carboxylic acid; 3-(Furan-3-yl)-6-(2-hydroxybenzenesulphonylmethyl)-2-methoxybenzoic acid; 3-(Furan-3-yl)-6-(3-hydroxybenzenesulphonylmethyl)-2-methoxy-benzoic acid; 2-(Benzenesulphonylmethyl)-5-(2-methylfuran-3-yl)benzoic acid; 6-(Benzenesulphonylmethyl)-3-ethyl-2-(1H-pyrazol-3-yl)benzoic acid; 3-(Furan-3-yl)-2-methoxy-6-(piperidine-1-ylsulphonylmethyl)benzoic acid; 3-(Furan-3-yl)-2-methoxy-6-(pyrrolidin-1-ylsulphonylmethyl)-benzoic acid; 6-[2-(2-Diethylaminoethylamino)benzenesulphonylmethyl]-3-(furan-3-yl)-2-methoxybenzoic acid; 6-(Benzenesulphonylmethyl)-2-ethyl-3-(furan-3-yl)benzoic acid; 6-[2-(2-Diethylaminoethoxy)benzenesulphonylmethyl]-3-(furan-3-yl)-2-methoxybenzoic acid; 6-(Benzenesulphonylmethyl)-3-(furan-3-yl)-2-(prop-1-yn-1-yl)benzoic acid; 2-(Benzenesulphonylmethyl)-6-methoxybenzoic acid; 6-(Cyclohexanesulphonylmethyl)-3-(furan-3-yl)-2-methoxybenzoic acid; 6-(Benzenesulphonylmethyl)-2-(carbamoylmethoxy)-3-(furan-3-yl)-benzoic acid; (Z)-6-((2-(3-(Diethylamino)prop-1-enyl)-4-fluorobenzenesulfonyl)methyl)-3-(furan-3-yl)-2-methoxybenzoic acid; 3-(Furan-3-yl)-6-(3-hydroxypyrrolidine-1-ylsulphonylmethyl)-2-methoxybenzoic acid; 2-(Azetidin-3-yloxy)-6-(benzenesulphonylmethyl)-3-(furan-3-yl)-benzoic acid hydrochloride; 6-(Bicyclo[2.2.2]octane-2-ylsulphonylmethyl)-3-(furan-3-yl)-2-methoxybenzoic acid; 6-(Bicyclo[2.2.2]octane-2-ylsulphonylmethyl)-2-methoxy-3-(tetrahydrofuran-3-yl)benzoic acid; 6-(7-Azabicyclo[2.2.1]heptane- 7-ylsulphonylmethyl)-3-(furan-3-yl)-2-methoxybenzoic acid; 6-(4,4-Difluoropiperidine-1-ylsulphonylmethyl)-3-(furan-3-yl)-2-methoxybenzoic acid; 6-(Bicyclo[2.2.1]heptane-7-ylsulphonylmethyl)-3-(furan-3-yl)-2-methoxybenzoic acid; 6-(Benzenesulphonylmethyl)-3-(furan-3-yl)-2-methylamino benzoic acid; 6-(8-Azabicyclo[3.2.1]octane-8-ylsulphonylmethyl)-3-(furan-3-yl)-2-methoxybenzoic acid; 2-(Benzenesulphonylmethyl)-8-methoxynaphthalene-1-carboxylic acid; 6-[2-(3-Diethylaminopropylamino)benzenesulphonylmethyl]-3-(furan-3-yl)-2-methoxybenzoic acid; (Z)-2-(2-Cyanomethoxy)-6-((2-(3-(diethylamino)prop-1-enyl)-4-fluorobenzenesulfonyl)methyl)-3-(furan-3-yl)benzoic acid; (Z)-3-(Furan-3-yl)-2-methoxy-6-((2-(3-(piperidin-1-yl)prop-1-enyl)benzenesulfonyl)methyl)benzoic acid; 6-(Benzenesulphonylmethyl)-3-(furan-3-yl)-2,4-dimethoxybenzoic acid; 6-[2-(2-Diethylaminomethylazetidin-1-yl)-benzenesulphonylmethyl]-3-(furan-3-yl)-2-methoxybenzoic acid; 6-(Benzenesulphonylmethyl)-2-(cyanomethylamino)-3-(furan-3-yl)benzoic acid; 6-(Benzenesulphonylmethyl)-3-(imidazol-1-yl)-2-methoxybenzoic acid; 6-(Benzenesulphonylmethyl)-2-methoxy-3-(thiazol-5-yl)benzoic acid; 3-(Furan-3-yl)-2-methoxy-6-[(S-phenylsulphonimidoyl)methyl]benzoic acid; 3-(Furan-3-yl)-2-methoxy-6-[(N-methyl-S-phenylsulphonimidoyl)methyl]benzoic acid; 6-[(N-cyano-S-phenylsulphonimidoyl)methyl]-3-(furan-3-yl)-2-methoxybenzoic acid; and pharmaceutically acceptable salts and stereoisomers thereof.

Procedures for making compounds described herein are provided below with reference to Schemes 1-12. In the reactions described below, it may be necessary to protect reactive functional groups (such as hydroxy, amino, thio or carboxy groups) to avoid their unwanted participation in the reactions. The incorporation of such groups, and the methods required to introduce and remove them are known to those skilled in the art. (for example, see Greene, Wuts, *Protective Groups in Organic Synthesis*. 2nd Ed. (1999). The deprotection step may be the final step in the synthesis such that the removal of protecting groups affords compounds of Formulas I, II, III, or IV, as disclosed herein, or as exemplified in for example, General Formula I, below. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

The synthetic strategy, as depicted in Scheme 1, generally involves forming intermediate 1F, which can be achieved in a variety of ways as exemplified below. Then, compounds of General Formula I can be prepared from intermediate 1F by removal of any protecting groups. Specific steps in the synthetic process are described in more detail below.

SCHEME 1

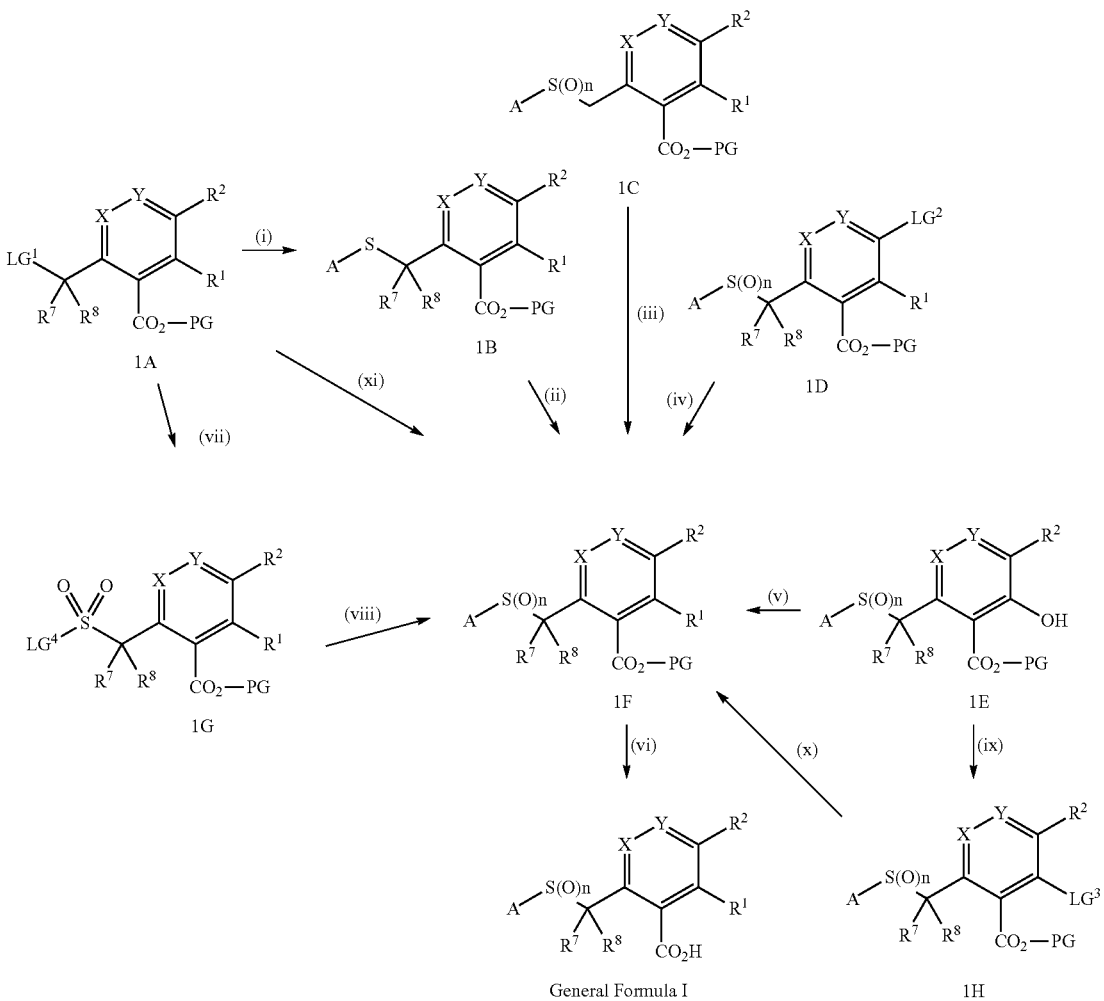

LG$^1$ is a suitable leaving group (such as a halide, triflate or tosylate) in Step 1(i). Structure 1A can be treated with an appropriate thiol (such as an arylthiol, heteroaryl thiol, arylalkylthiol, heteroarylalkyl thiol, cycloalkylthiol or heterocycloalkyl thiol) in the presence of a base (such as potassium carbonate, or sodium hydride) in an appropriate solvent (such as DMF or ethanol) and under appropriate conditions (such as heating, for example to 80-120° C. for 1-6 hours, or at room temperature) to give the thioether 1B. A wide range of appropriate reagents and conditions are known to those skilled in the art to convert 1A to the thioether 1B. [for example, see Peach in Patai *The Chemistry of the Thiol Group, pt2*; Wiley: New York, 1974, pp. 721]

In Step 1(ii) structure 1B can be treated with an oxidising agent (such as 3-chloroperbenzoic acid) in a suitable solvent (such as dichloromethane) under suitable conditions (for example at room temperature or below) to give the sulphinyl derivative 1F, n=1. Alternatively, 1B can be treated with an oxidising agent (such as hydrogen peroxide) in a suitable solvent (such as acetic acid) and under appropriate conditions (such as heating, for example to 50-100° C. for 1-6 hours) to afford the sulphonyl derivative 1F, n=2. A wide range of appropriate reagents and conditions are known to those skilled in the art to oxidise 1B to 1F. [for example, see Drabowicz, Kielbasinski, Mikolajczyk in Patai, Rappoport, Stirling *The Chemistry of Sulphones and Sulphoxides*; Wiley: New York, 1988, pp. 233-378, pp 235-255. Madesclaire *Tetrahedron* 1986, 42, 549-5495. Oae *The Organic Chemistry of Sulfur*; Plenum: New York 1977, pp. 385-390. Smith, March, *March's Advanced Organic Chemistry, 5$^{th}$ Edition*, Wiley: New York, 2001, pp. 1541-1542].

Structure 1C of alternative Step 1(iii) can be treated with an alkylating agent (such as an alkyl halide, alkyltriflate or alkylsulphate which may, or may not be further substituted) in the presence of a base (such as sodium hydride or lithium hexamethyldisilazide), in an appropriate solvent (such as dimethylformamide or tetrahydrofuran) and under appropriate conditions (such as room temperature or below, for example 0° C.) to afford 1F. A wide range of appropriate reagents and conditions are known to those skilled in the art to monoalkylate 1C to afford 1F (R$^7$ or R$^8$=H), or to dialkylate 1C to afford 1F (R$^7$ and R$^8$≠H). [Smith, March, *March's Advanced Organic Chemistry, 5$^{th}$ Edition*, Wiley: New York, 2001, pp. 548-551]

Structure 1D of alternative Step 1(iv) may be treated under a range of conditions to afford 1F and to introduce different substituents at R$^2$. The conversion of LG$^2$ to R$^2$ may require a number of steps and the preparation of a number of intermediates. Protecting groups may also be required. If LG$^2$ is a suitable functional group (such as a halide or triflate), a substituent can be introduced by the formation of a carbon-carbon bond to afford 1F. The carbon-carbon bond can be formed by using an aryl, or heteroaryl, or alkyl borane, boronate or boronic acid (such as a substituted phenylboronate or a trialkylborane) in the presence of a palladium catalyst (such as palladium chloride dppf adduct), in the presence of a base (such as cesium carbonate) in an appropriate solvent (such as dichloromethane or tetrahydrofuran) and under appropriate conditions (such as heating, for example heating at 80-120° C. for 1-2 hours or microwave irradiation at 120-10° C. for 10 minutes to 1 hour) to afford 1F. A wide range of appropriate reagents and conditions are known to those skilled in the art to couple organoboranes, boronates and boronic acids to 1D. [for example, see Miyaura, Suzuki, *Chem. Rev.* 1995, 95, 2457; Suzuki, *Modern Arene Chemistry* (2002), 53-106.].

Alternatively the carbon-carbon bond can be formed by using an aryl, or heteroaryl, or vinyl stannane in the presence of a palladium catalyst (such as palladium chloride dppf adduct), in an appropriate solvent (such as dimethoxyethane or tetrahydrofuran) and under appropriate conditions (such as heating, at 80-120° C. for 1-2 hours or by microwave irradiation at 120-160° C. for 10 minutes to 1 hour) to afford 1F. A wide range of appropriate reagents and conditions are known to those skilled in the art to couple stannanes to 1D. [for example, see Smith, March, *March's Advanced Organic Chemistry, 5$^{th}$ Edition*, Wiley: New York, 2001, pp. 931-932; De Souza, *Current Organic Synthesis* (2006), 3(3), 313-326.].

In an alternative embodiment, the carbon-carbon bond can be formed by using an alkene (such as a substituted acrylate) in the presence of a catalyst (such as a palladium catalyst, for example tetrakis-(triphenylphosphine) palladium) and a base or salt (such as tributylamine or potassium acetate) and under appropriate conditions (such as heating, at 80-120° C. for 1-2 hours or by microwave irradiation at 120-160° C. for 10 minutes to 1 hour) to afford 1F. A wide range of appropriate reagents and conditions are known to those skilled in the art to couple alkenes to 1D. [for example, see Smith, March, *March's Advanced Organic Chemistry, 5$^{th}$ Edition*, Wiley: New York, 2001, pp. 930-931]. The carbon-carbon bond can be formed, alternatively, by using an organozinc reagent (such as an alkyl zinc halide) in the presence of catalysts (such as a palladium catalyst, for example tetrakis-(triphenylphosphine) palladium and/or a copper catalyst, such as a copper (I) halide) and a base or salt (such as tributylamine or potassium acetate) and under appropriate conditions (such as heating at 80-120° C. for 1-2 hours or by microwave irradiation at 120-160° C. for 10 minutes to 1 hour) to afford 1F. A wide range of appropriate reagents and conditions are known to those skilled in the art to couple organozinc reagents to 1D. [for example, see Smith, March, *March's Advanced Organic Chemistry, 5$^{th}$ Edition*, Wiley: New York, 2001, pp. 540-541]. The carbon-carbon bond can also be formed by using an alkyne (such as a substituted acetylene) in the presence of a catalyst (such as a palladium catalyst, for example tetrakis-(triphenylphosphine) palladium and/or a copper catalyst, such as a copper (I) halide) and a base or salt (such as tributylamine or potassium acetate) and under appropriate conditions (such as heating at 80-120° C., for 1-2 hours or by microwave irradiation at 120-160° C. for 10 minutes to 1 hour) to afford 1F. A wide range of appropriate reagents and conditions are known to those skilled in the art to couple alkynes to 1D [for example, see Chinchilla, Najera, *Chemical Reviews* (2007), 107(3), 874-922].

If LG$^2$ is a suitable functional group (such as a halide or triflate) a substituent can be introduced by the formation of a carbon-nitrogen bond to afford 1F. The carbon-nitrogen bond can be formed by using a primary or secondary amine, or a heterocycle containing an NH moiety (such as a piperidine, pyrazole or pyrrolidinone) under appropriate conditions (such as heating in the presence of a palladium or copper catalyst) to afford 1F. A wide range of appropriate reagents and conditions are known to those skilled in the art to couple such moieties to 1D. [Mauger, Mignani *Aldrichimica Acta* (2006), 39(1), 17]. If LG$^2$ is a suitable functional group (such as a halide or triflate), it may be converted to another functional group (such as a boronic acid or boronate ester, or a trialkylstannane) and the R$^2$ substituent introduced by coupling to an aryl (or heteroaryl) triflate or halide as described above, or treatment with zinc cyanide in the presence of a catalyst (such as a palladium catalyst, for example, tetrakis-(triphenylphosphine) palladium) can be used to introduce a nitrile. When LG$^2$ is the same or different suitable functional group (such as a carboxylic acid, aldehyde, ketone, or amine) further chemical reactions may be performed to convert said group into a 5-, or 6-membered heterocycle. Such transformations are well known to those skilled in the art [for example, see Joule, Mills and Smith, *Heterocyclic Chemistry* 3rd Ed., Chapman &Hall, London 1995].

1E can be alkylated to give 1F, in which R¹ is a substituted alkoxy group. 1E can be treated with an alkyl halide (such as ethylbromide, 2-bromoethanol or 2-[N-(t-butoxycarbonyl) amino]ethyl bromide) or an alkylsulphonate (such as an alkyl triflate or alkyltosylate) in the presence of a base (such as caesium carbonate or diisopropylethylamine) to afford 1F. Alternatively, 1E can be treated with an alcohol in the presence of a phosphine (such as triphenylphosphine) and a dehydrating agent (such as diethyl azodicarboxylate) to afford 1F. A wide range of appropriate reagents and conditions are known to those skilled in the art to convert 1E to 1F [for example, see Mitsunobu, *Synthesis* (1981) 1].

Step 1(vi) indicates that compounds of General Formula I can be prepared from 1F by the removal of any protecting groups. For example, the carboxylic acid present in all compounds of General Formula I can be protected as a carboxylic acid ester. Methods to cleave the protecting group include but are not limited to using a strong nucleophile in an appropriate solvent (such as potassium trimethylsilanoate/tetrahydrofuran, or lithium hydroxide/tetrahydrofuran/water), or a strong acid (such as heating in aqueous hydrochloric acid).

In exemplary Step 1(vii) compound 1A can be treated with sodium sulphite in an appropriate solvent (such as water, tetrahydrofuran) to afford an alkylsulphonic acid which can be treated with a chlorinating agent (such as phosphorous pentachloride or thionyl chloride) to afford 1G (LG⁴=Cl). 1G can then be treated with a cyclic amine (such as piperidine or morpholine) in an appropriate solvent (such as pyridine or dimethylformamide) in the presence of a base (such as diisopropylamine or cesium carbonate) to afford 1F, in which A is an N-linked heterocycle, as depicted in Step 1(viii).

In an alternative step, 1E can be treated with a sulphonylating agent (such as trifluoromethane sulphonyl chloride) to afford 1H, in which LG³ is an appropriate leaving group (such as a triflate) as depicted in Step 1(ix). 1H can be then treated under a range of conditions to introduce different substituents at R² and afford 1F. The methods described in Step 1(iv) to introduce substituents by the formation of carbon-carbon, and carbon-nitrogen bonds can be used to convert 1H to 1F, as depicted in Step 1(x).

As depicted in alternative Step 1(xi), 1A can be treated with an appropriate sulphinate (such as an arylsulphinate, heteroaryl sulphinate, arylalkylsulphinate, cycloalkylsulphinate or heterocycloalkyl sulphinate) in the presence of a base (such as sodium bicarbonate, potassium carbonate, or diisopropylethylamine) in an appropriate solvent (such as dimethylacetamide/water) and under appropriate conditions (such as heating, for example to 80-120° C. for 1-6 hours), to give the sulphone 1F.

More specifically, compounds of the General Formula II can be prepared from an appropriately substituted 2-methylbenzoic acid using the general synthetic route outlined in Scheme 2.

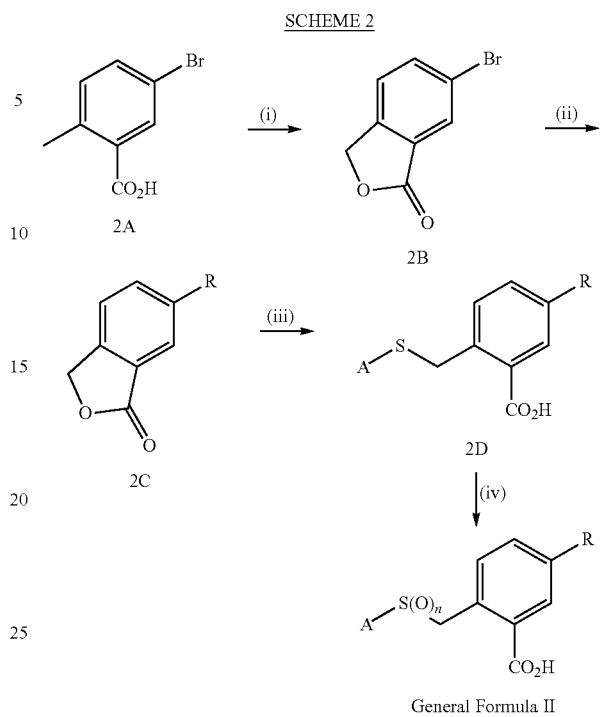

Compound 2A included in Step 2(i) can be treated with an oxidising agent (such as (diacetoxyiodo)benzene/potassium bromide or peroxydisulphuric acid, or sodium bromate) in an appropriate solvent (such as dichloromethane), to afford the lactone, 2B. The aryl halide 2B can be treated with various reagents such as those described in Step 1(iv), to derivatise the phenyl ring and afford 2C, as depicted in Step 2(ii).

2C can be treated with an appropriate thiol (such as an arylthiol or a heteroaryl thiol, or an arylalkylthiol) in the presence of a base (such as potassium carbonate, or sodium hydride) in an appropriate solvent (such as DMF or ethanol) and under appropriate conditions (such as heating, for example to 80-120° C. for 1-6 hours), to give the thioether 2D. as in Step 2(iii). In Step 2(iv), compound 2D can be treated with an oxidising agent (such as 3-chloroperbenzoic acid) as described in Step 1(ii) to afford the sulphinyl derivative of General Formula II. Alternatively, 2D can be treated with an oxidising agent (such as hydrogen peroxide) as described in Step 1(ii) to afford the sulphonyl derivative of General Formula II.

Alternatively, compounds of the General Formula II can be prepared from an appropriately substituted 2-carboxybenzyl halide such as 3A using the general synthetic method outlined in Scheme 3.

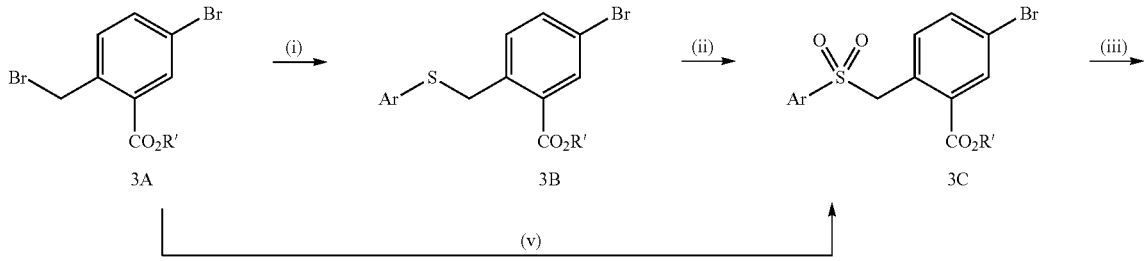

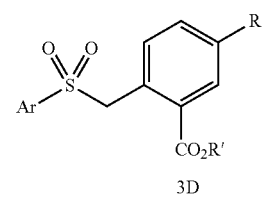

3D

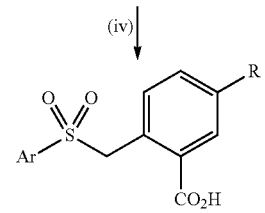

General Formula II

Compound 3A can be treated with an appropriate thiol (such as an aryl thiol) using the methods described in Step 1(i) to afford the thioether 3B (Step 3(i)). 3B can be treated with an oxidising agent (such as hydrogen peroxide) using the methods described above in Step 1(ii) to afford 3C: Step 3(ii). In Step 3(iii), 3C can be derivatised further to give 3D, using the methods described above in Step 1(iv). Compound 3D can be converted (Step 3(iv)) to give a compound of General Formula II by the removal of any remaining protecting groups (for example, by hydrolysis of an ester to a carboxylic acid) as described in Step 1(vi). Alternatively, 3A can be treated with an appropriate sulphinate (such as an arylsulphinate) as described in Step 1(xi) to afford the sulphone 3C. Step 3(v))

Compounds of the General Formula II can be prepared from an appropriately substituted 2-hydroxy-6-methylbenzoic acid such as 4B using the synthetic route outlined in Scheme 4.

SCHEME 4

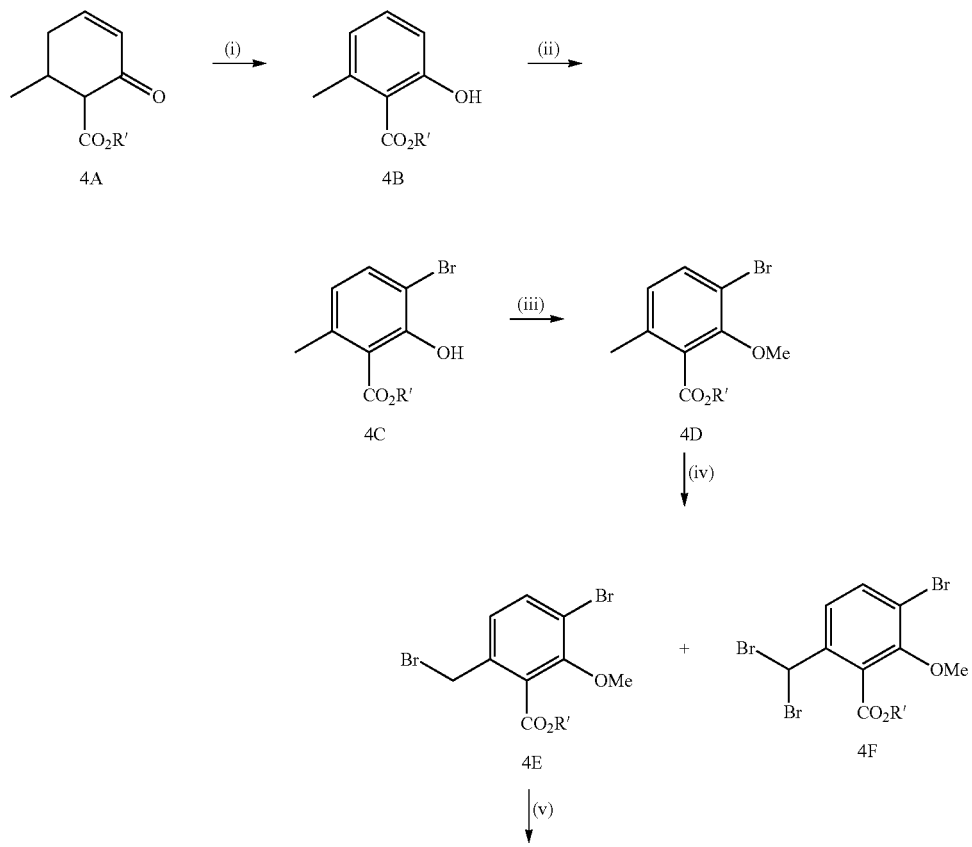

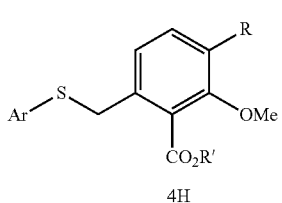

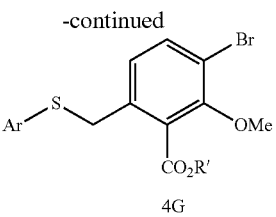

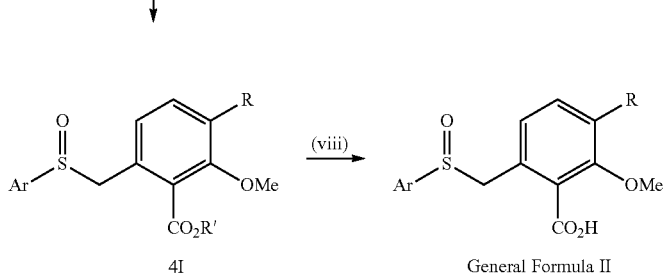

For example, compound 4A can be treated with bromine in an appropriate solvent (such as acetic acid) and under appropriate conditions (such as cooling below room temperature, for example to 0° C.) to afford 4B, as outlined in Step 4(i). 4B can be treated with a brominating agent (such as N-bromosuccinimide) in an appropriate solvent (such as dichloromethane), in the presence of a catalytic amine (such as di-isopropyl amine) under appropriate conditions (such as cooling below room temperature, for example to 0° C.) to afford the arylbromide 4C (Step 4(ii)). 4C can be treated with an alkylating agent (such as dimethylsulphate) in the presence of a base (such as potassium carbonate or sodium hydride) in an appropriate solvent (such as dry acetone or tetrahydrofuran) and under appropriate conditions (such as heating, for example at reflux) to afford the methyl ether 4D (Step 4(iii)). Alternative methods to prepare 4D from 4C that are well known in the art can involve the treatment of 4C with an alkyl halide (such as iodomethane) in the presence of a base (such as cesium carbonate or diisopropylethylamine) [for example, see Feuer and Hooz in Patai *The chemistry of the ether linkage*; Wiley: New York, 1967, pp. 446-460], or with an alcohol, (such as methanol) in the presence of triphenylphosphine and a dehydrating agent (such as diethylazodicarboxylate) [for example, see Mitsunobu, *Synthesis* 1981, 1]. 4D can be treated with a brominating agent (such as 1,3-dibromo-5,5-dimethylhydantoin or N-bromosuccinimde) in an appropriate solvent (such as 1,2-dichloroethane) in the presence of a free radical initiator (such as AIBN) and under appropriate conditions (such as heating under a strong light source) to afford a mixture of 4E and 4F, as in Step 4(iv). 4E and 4F can be separated by chromatographic or other methods. Alternative halogenation conditions are known in the art and can be used to prepare 4E and 4F [for example, see Huyser in Patai *The Chemistry of the Carbon-Halogen Bond*; Wiley: New York, 1973, pp. 549].

Compound 4E can be treated with an appropriate thiol (such as an arylthiol) to give the thioether 4G using the methods described in Step 1(i). 4G can be derivatised to give 4H by using the methods described in Step 1(iv). Compound 4H can then be treated with an oxidising agent to give the sulphoxide 4I using the methods described in Step 1(ii). In Step 4(viii), 4I can be converted to give a compound of General Formula II by the removal of any protecting groups (for example, by hydrolysis of an ester to a carboxylic acid) as described in Step 1(vi).

In another scheme, compounds of the General Formula II can be prepared from 4E or 4F using the synthetic route as described in Scheme 5.

SCHEME 5

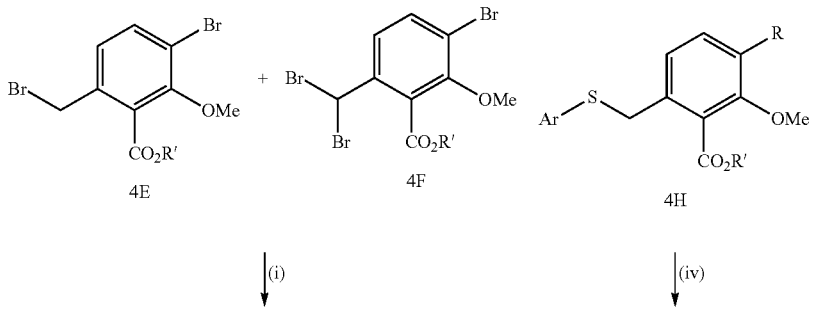

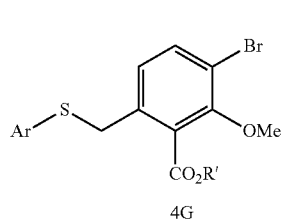 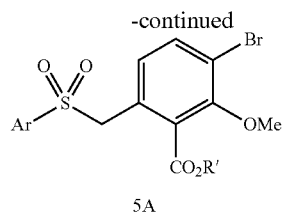 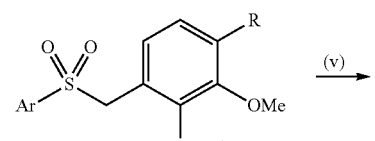

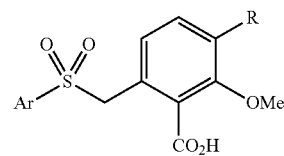

General Formula II

In Step 5(i), compounds 4E or 4F, or a mixture of 4E and 4F, can be treated with an aryl (or heteroaryl) sulphinate (such as a substituted benzenesulphinate) in an appropriate solvent (such as dimethylacetamide/water) and in the presence of a base (such as sodium bicarbonate) under appropriate conditions (such as stirring at room temperature or heating for example at 50-120° C. for 1-5 hours) to afford the sulphone 5A. Alternatively, compound 4G (Step 5(ii)) can be treated with an oxidising agent to afford the sulphone 5A using the methods described in Step 1(ii). Compound 5A can be derivatised to give 5B by using the methods described in Step 1(iv), as shown in Step 5(iii).

Alternatively, 4H can be treated with an oxidising agent to afford the sulphone 5B using the methods described in Step 1(ii). Compound 5B can then be converted to give a compound of General Formula II by the removal of any protecting groups (for example, by hydrolysis of an ester to a carboxylic acid) as described in Step 1(vi).

In another embodiment, compounds of the General Formula II can be prepared from 5A using the synthetic route described in Scheme 6.

SCHEME 6

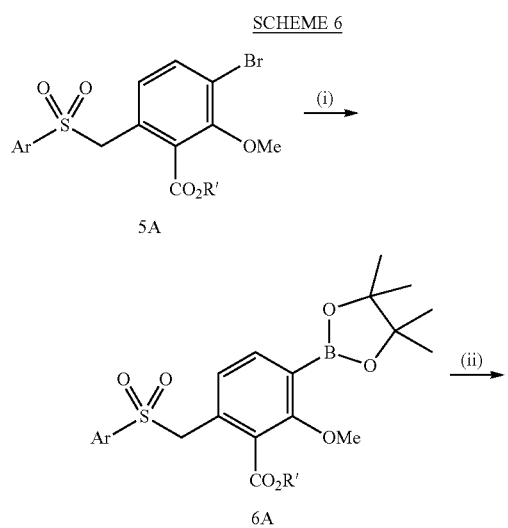

-continued

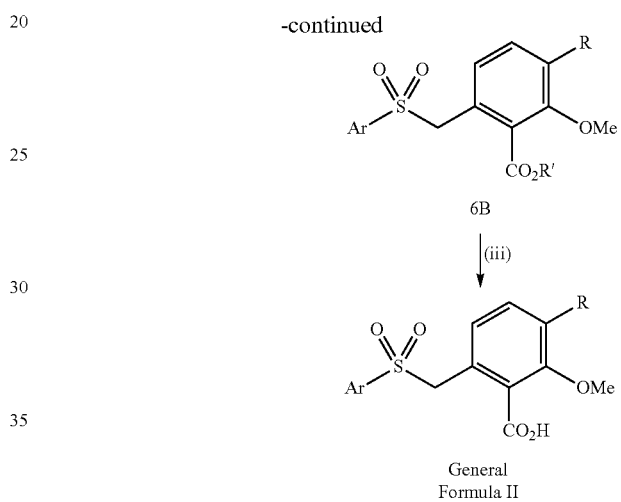

General Formula II

Compound 5A can be treated with a diboronate (such as bis-pinacolatodiboron) in the presence of a palladium catalyst (such as palladium chloride dppf adduct) and a base (such as potassium acetate or diisopropylamine) in an appropriate solvent (such as dioxane/water) and under appropriate conditions (such as heating for example at 80-120° C. for 1-2 hours or by microwave irradiation at 120-160° C. for 10 minutes to 1 hour) to afford 6A, as shown in Step 6(i). A wide range of appropriate reagents and conditions are known to those skilled in the art to convert an arylhalide to an arylborane (or arylboronate) [for example, see Marshall *Chemtracts* (2000), 13(4), 219-222]. Compound 6A can be then treated with an aryl halide, or heteroaryl halide in the presence of suitable reagents such as a phosphine (such as tri-tert-butyl-phosphonium tetrafluoroborate), a base (such as cesium carbonate) and a catalyst (such as tris-(dibenzylideneacetone)-dipalladium) in an appropriate solvent (such as water/dioxane) under appropriate conditions (such as heating at 80-120° C. for 1-2 hours or by microwave irradiation at 80-120° C. for 10 minutes to 1 hour) to afford 6B. A wide range of appropriate reagents and conditions are known to those skilled in the art to couple an arylborane or arylboronate such as 6A, to an aryl halide, or heteroaryl halide to give 6B [for example, see Miyaura, Suzuki, *Chem. Rev.* 1995, 95, 2457]. Compound 6B can be converted to give a compound of General Formula II by the removal of any protecting groups (for example, by hydrolysis of an ester to a carboxylic acid) as described in Step 1(vi).

In another scheme, compounds of the General Formula II can be prepared from 5B by the route described in Scheme 7.

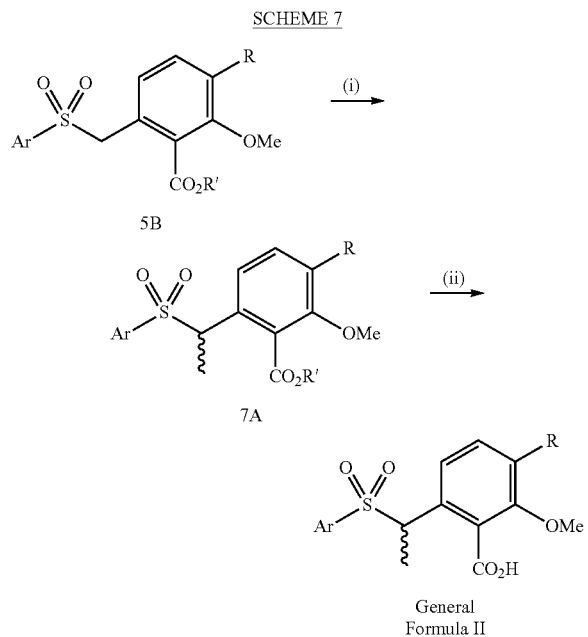

Compound 5B can be treated with a methylating agent (such as methyl halide, methyl triflate or methylsulphate) using the method described in Step 1(iii) to afford 7A. Compound 7A can then be converted to give a compound of General Formula II by the removal of any protecting groups (for example, by hydrolysis of an ester to a carboxylic acid) as described in Step 1(vi).

Alternatively, compounds of the General Formula II can be prepared from 5A by the synthetic route described in Scheme 8.

For example, compound 5A can be treated with a stannane (such as 1-ethoxyvinyl tributyl stannane) in the presence of a palladium catalyst (such as tetrakis-(triphenylphosphine)palladium) and an adduct (such as lithium chloride, potassium acetate or diisopropylethylamine), in a suitable solvent (such as dioxane), and under suitable conditions (such as heating at 80-120° C. for 1-2 hours or by microwave irradiation at 120-170° C. for 10-45 minutes) followed by stirring with an aqueous acid (such as 1M hydrochloric acid) to afford the ketone 8A (Step 8(i)). In Step 8(ii), compound 8A can be treated with Brederick's reagent in a suitable solvent (such as dioxane) and under appropriate conditions (such as heating at 60-100° C. for 1-2 hours or by microwave irradiation at 120-170° C. for 10-45 minutes) to afford 8B. 8B can be treated with hydroxylamine hydrochloride in a suitable solvent (such as ethanol/pyridine) and under the appropriate conditions (such as heating at reflux for up to 12 hours) to afford 8C (Step 8(iii)). Compound 8C can be dissolved in an appropriate solvent (such as ethanol) and heated (for example at reflux, or above in a sealed vessel for several hours) to afford 8D, as in Step 8(iv).) Then, compound 8D can be converted to give a compound of General Formula II by the removal of any protecting groups (for example, by hydrolysis of an ester to a carboxylic acid) as described in Step 1(vi).

Compounds of the General Formula II may also be prepared from 8A by the synthetic route described in Scheme 9.

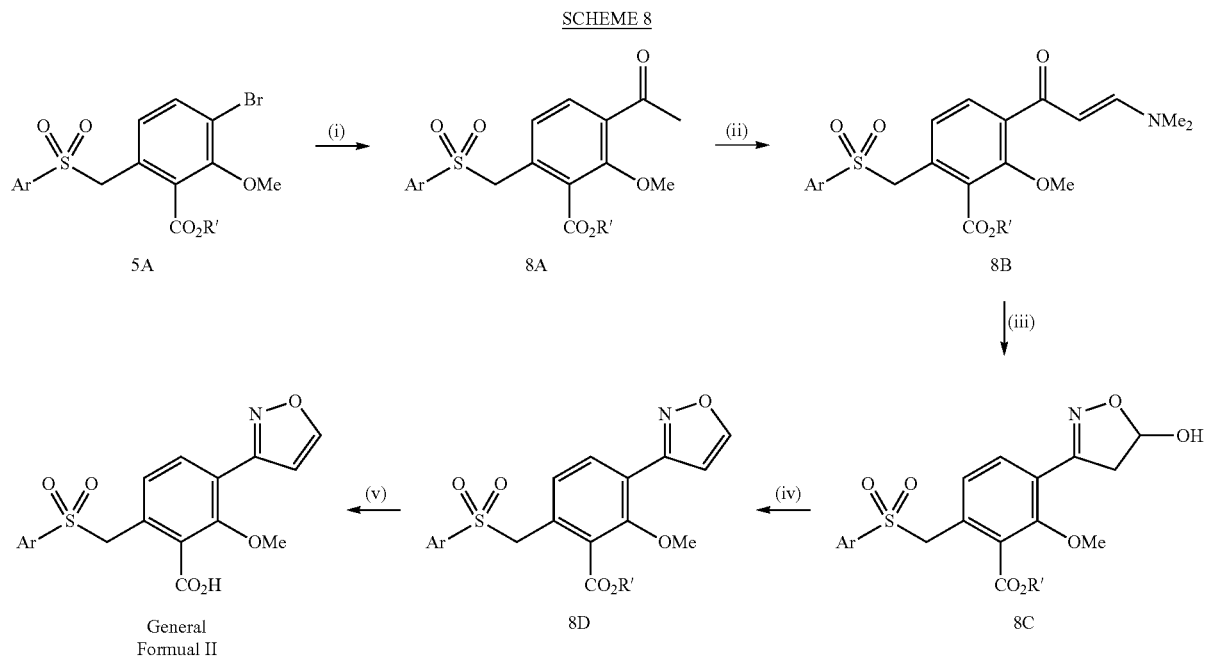

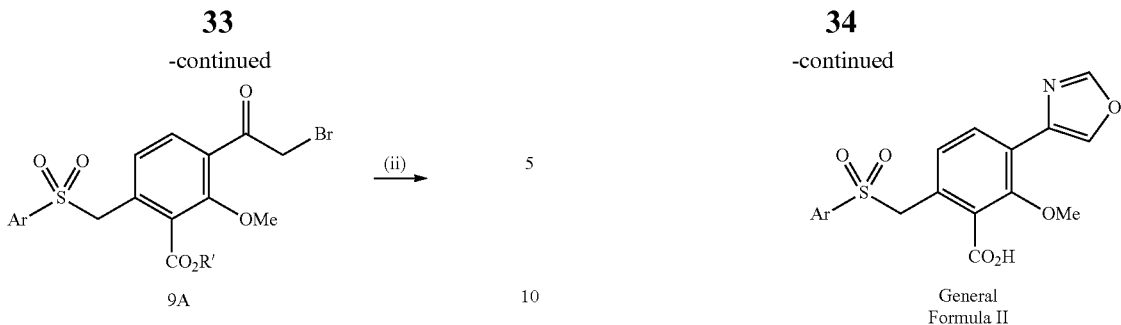

For example, compound 8A can be brominated (for example with bromine/acetic acid) to give the bromoketone 9A. Other methods can be used to halogenate 8A using modified conditions that are well known in the art. [for example, see Huyser in Patai *The Chemistry of the Carbon-Halogen Bond*; Wiley: New York, 1973, pp. 549], as in Step 9(i). In Step 9(ii), compound 9A can be treated with ammonium formate in formic acid under appropriate conditions (such as heating, for example at 40-100° C. for 1-12 hours) to afford 9B. 9B can be converted to give a compound of General Formula II by the removal of any protecting groups (for example, by hydrolysis of an ester to a carboxylic acid) as described in Step 1(vi).

In another embodiment, compounds of General Formula III can be prepared from 10A by the synthetic route described in Scheme 10. Compound 10A can be prepared by the method described in Scheme 5 to synthesise 5A.

SCHEME 10

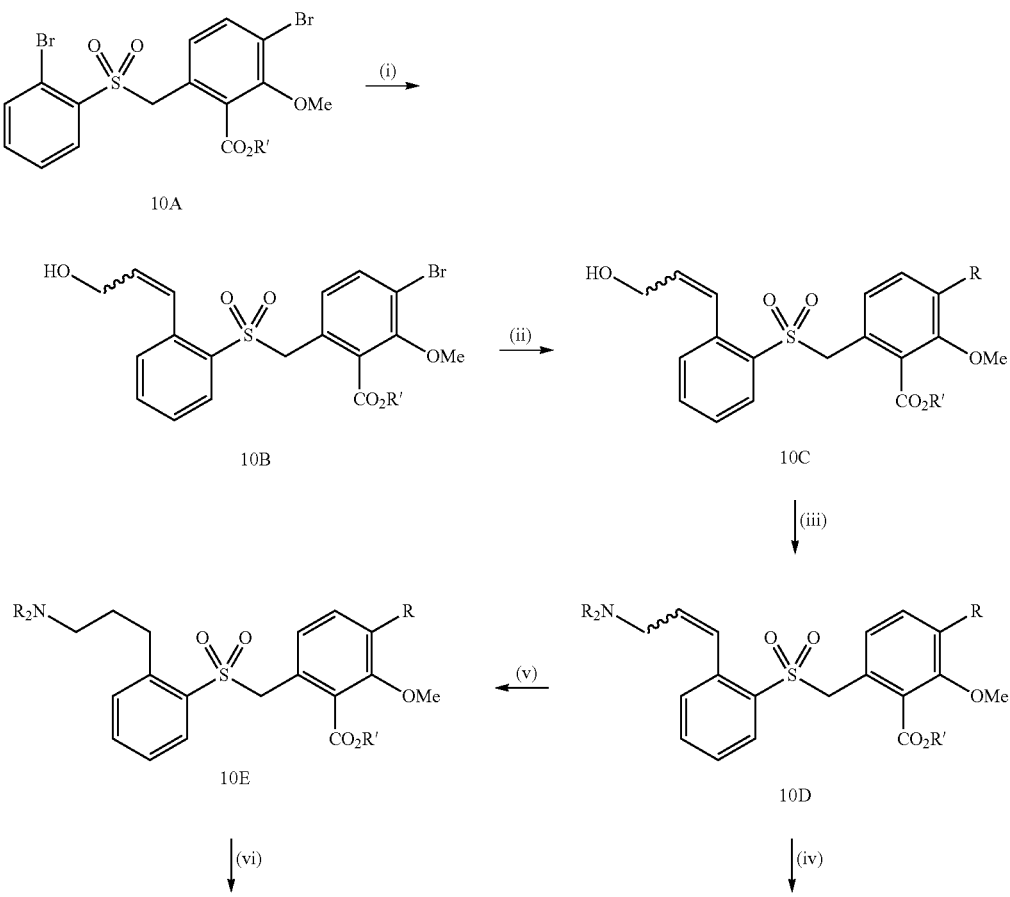

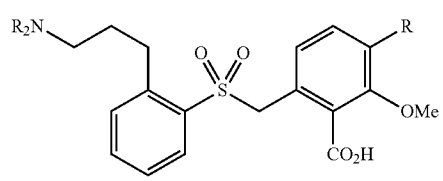

General Formula III

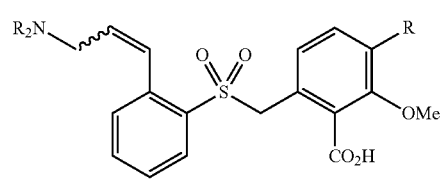

In Step 10(i), compound 10A can be treated with a stannane (such as 3-tributylstannyl-(Z)-prop-2-en-1-ol) in a suitable solvent (such as toluene) and in the presence of a palladium catalyst (such as bis-(tributylphosphine)palladium) and under appropriate conditions (such as stirring at room temperature or heating at a temperature up to 80° C.) to afford 10B. Derivatisation of 10B to give 10C can be achieved by using the methods described in Step 1(iv). (Step 10(ii)). The allylic alcohol present in 10C can then be modified to introduce a leaving group in Step 10(iii). For example, 10C can be treated with a halogenating agent (such as carbon tetrabromide/triphenylphosphine in an appropriate solvent (such as dichloromethane) to give an alkylhalide. 10C can be converted into the corresponding alkylhalide using alternative methods known in the art [for example, see Larock *Comprehensive Organic Transformations*; VCH: New York 1989, p. 353.]. Alternatively, 10C could be modified to introduce an alternative leaving group (such mesylate, tosylate or trifluoromethylsulphonate) by treatment of the alcohol with a sulphonyl chloride (such as methane sulphonyl chloride, toluene sulphonyl chloride or trifluoromethane sulphonyl chloride) in the presence of a base (such as diisopropylethylamine) and in a solvent such as dichloromethane. After evaporation, the residue can be dissolved in an appropriate solvent (such as tetrahydrofuran) and treated with an amine (such as diethylamine) and the mixture stirred to afford 10D.

Compound 10D can be converted, as in Step 10(iv), to give a compound of General Formula II by the removal of any protecting groups (for example, by hydrolysis of an ester to a carboxylic acid) as described in Step 1(vi). Alternatively, compound 10D can be dissolved in an appropriate solvent (such as methanol or ethyl acetate) and a catalyst added (such as palladium on carbon) and the mixture stirred under an atmosphere of hydrogen to afford 10E. Step 10(v). Numerous methods known in the art can be used to convert 10D to 10E [for example, see Rylander *Hydrogenation methods*; Academic Press New York, 1985]. Compound 10E can be converted to give a compound of General Formula II by the removal of any protecting groups (for example, by hydrolysis of an ester to a carboxylic acid) as described in Step 1(vi).

In another embodiment, compounds of the General Formula II can be prepared from 4E using the synthetic route described in Scheme 11.

SCHEME 11

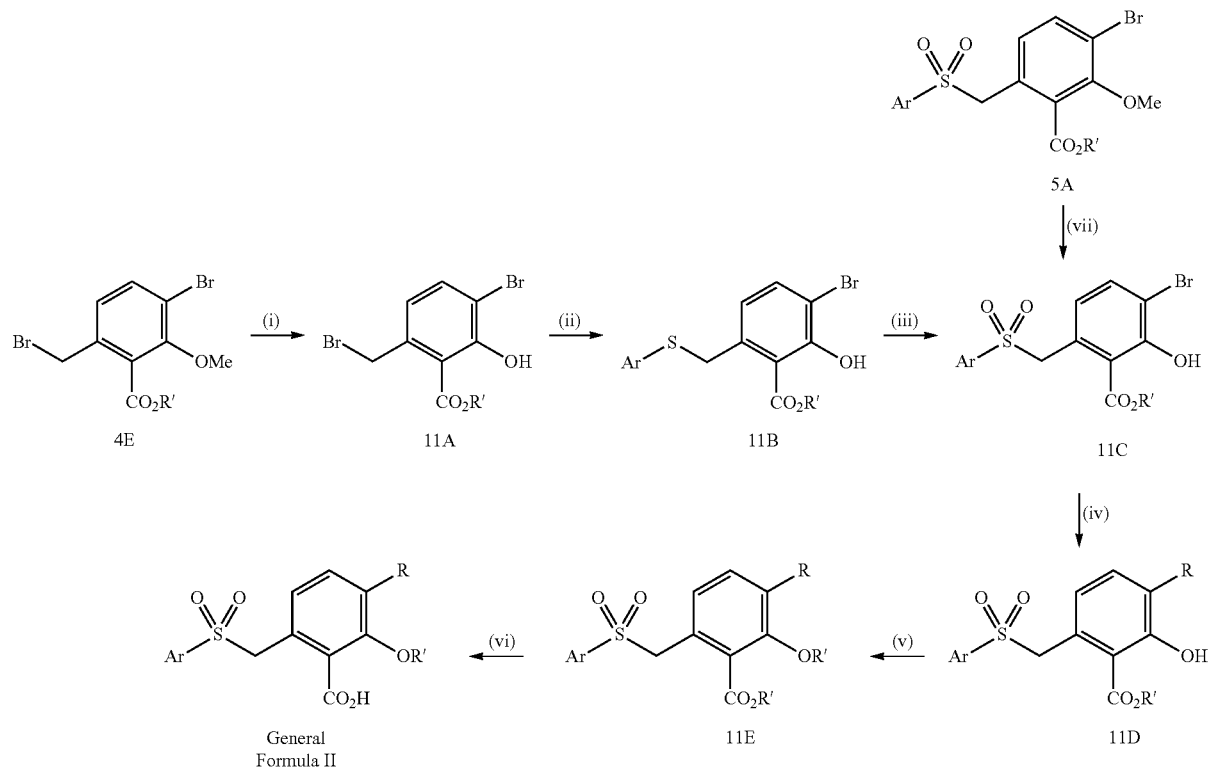

Compound 4E can be treated, as in Step 11(i), with a Lewis acid under appropriate reaction conditions (such as boron tribromide in dichloromethane with cooling, for example at −70° C. or aluminium chloride and dimethylaniline in dichloromethane at room temperature) to afford 11A. Compound 4E can be demethylated by other methods known to those skilled in the art [for example, see Greene, Wuts *Protective Groups in Organic Synthesis. 2nd Ed.* (1991), pp. 146-149]. Compound 11A can be then treated with a thiol (such as an aryl thiol) to give the thioether 11B using the methods described in Step 1(i). 11B can then be treated with an oxidising agent (such as hydrogen peroxide) to afford the sulphone 11C using the methods described in Step 1(ii). 11C can be derivatised to give 11D by using the methods described in Step 1(iv). 11D can be treated with an alkyl halide (such as ethylbromide, 2-bromoethanol or 2-[N-(t-butoxycarbonyl)amino]ethyl bromide) in the presence of a base (such as cesium carbonate or diisopropylethylamine) to afford 11E. Alternatively, 11D can be treated with an alcohol in the presence of a phosphine (such as triphenylphosphine) and a dehydrating agent (such as diethylazodicarboxylate) to afford 11E. A wide range of appropriate reagents and conditions are known to those skilled in the art to convert 11D to 11E [for example, see Larock *Comprehensive Organic Transformations*; VCH: New York 1989, p. 445].

11E can be converted to give a compound of General Formula II by the removal of any protecting groups (for example, by hydrolysis of an ester to a carboxylic acid) as described in Step 1(vi).

In an alternate embodiment, compound 5A can be demethylated via Step 11(vii) to afford 11C by using the methods described in Step 11(i).

In yet another embodiment, compounds of General Formula II having a bicyclic ring such as a naphthalene ring can be prepared from 12A using the synthetic route described in Scheme 12.

SCHEME 12

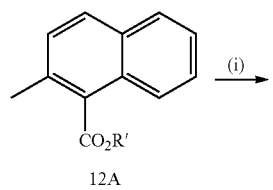

12A

In Step 12(i), for example, compound 12A can be treated with a brominating agent to give the bromide 12B using the methods described in Step 4(iv). 12B can then be treated with an appropriate thiol (such as an aryl thiol) to give the thioether 12C using the methods described in Step 1(iv). In turn, 12C can be treated with an oxidising agent (such as hydrogen peroxide) to give the sulphone 12D using the methods described in Step 1(ii). 12D can then be converted to give 12E by the removal of any protecting groups (for example by hydrolysis of an ester to a carboxylic acid) as described in Step 1(vi).

In yet another embodiment compounds of Formula Ia or Ib in which W represents $S(O)(NR^{11})$, such as the compound of General Formula IV, may be prepared using the synthetic route described in Scheme 13.

SCHEME 13

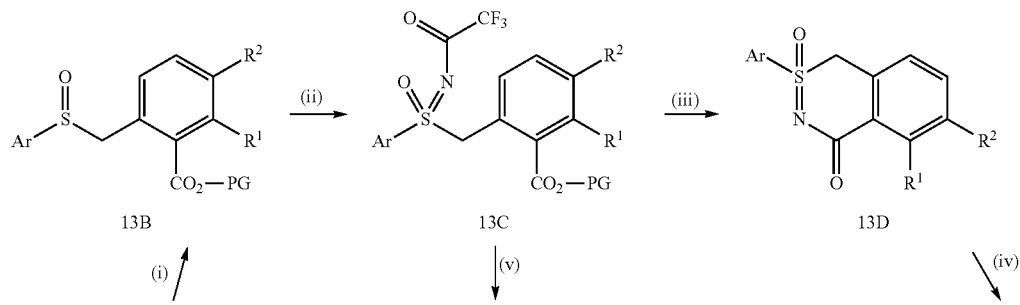

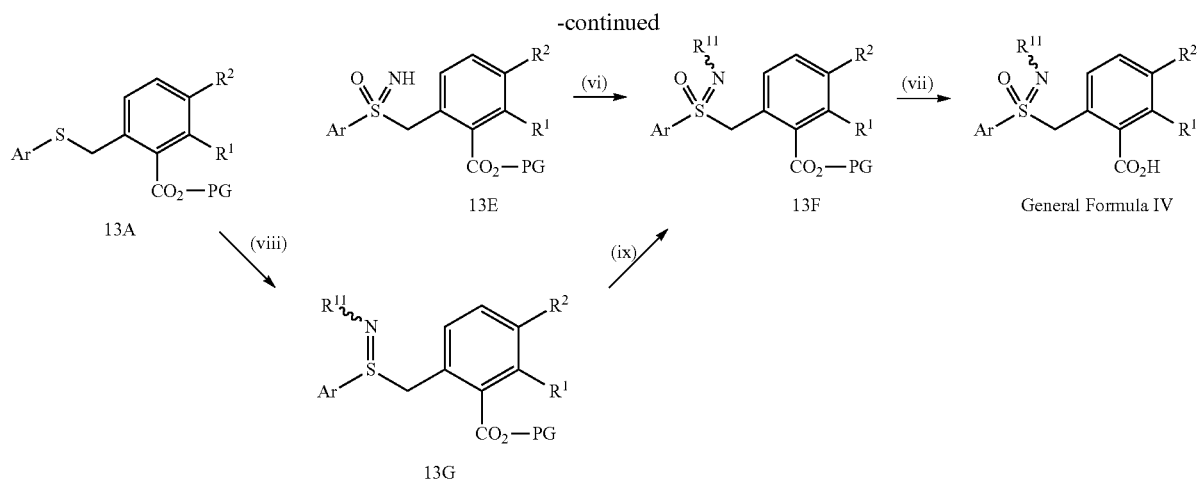

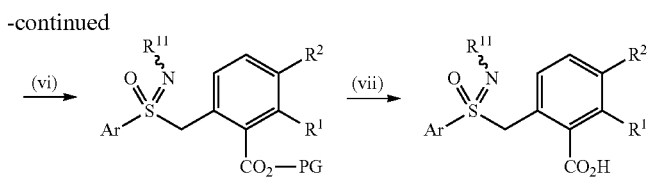

In Step 13(i), for example, 13A may be treated with an oxidizing agent (such as 3-chloroperbenzoic acid) in a suitable solvent (such as dichloromethane) under suitable conditions (for example at room temperature or below) to give the sulphinyl derivative 13B. A wide range of appropriate reagents and conditions are known to those skilled in the art to oxidise 13A to 13B. [for example, see Drabowicz, Kielbasinski, Mikolajczyk in Patai, Rappoport, Stirling *The Chemistry of Sulphones and Sulphoxides*; Wiley: New York, 1988, pp. 233-378, pp 235-255. Madesclaire *Tetrahedron* 1986, 42, 549-5495. Oae *The Organic Chemistry of Sulfur*; Plenum: New York 1977, pp. 385-390. Smith, March, *March's Advanced Organic Chemistry*, 5$^{th}$ Edition, Wiley: New York, 2001, pp. 1541-1542].

In Step 13(ii), 13B may be converted to 13C by treatment with trifluoroacetamide in the presence of magnesium oxide, iodobenzene diacetate and rhodium acetate dimer. Removal of the trifluoroacteate group in Step 13(iii) or Step 13(v) may be achieved by treatment with a base such as potassium carbonate in a solvent such as methanol. If the group PG in 13C is Me then the cyclised product 13D may be formed. Alternatively if the group PG is for example a tert-butyl group then 13E is generated. 13E may be alkylated to give 13F by treatment with an alkyloxonium fluoroborate to give 13F. 13D or 13F may be converted to a compound of General Formula IV using conditions described for Step 1(vi).

Alternatively compounds 13H in which $R^{11}$ is a CN group may be prepared from 13A by treatment with cyanamide in the presence of iodobenzene diacetate. Subsequent oxidation of 13G as described in Step 13(i) would give 13F which may be converted to a compound of General Formula IV using conditions described for Step 1(vi)

It is appreciated by one of skill in the art that, for example, the synthetic schemes disclosed and described herein can be used to arrive at compounds of Formula Ia or Ib:

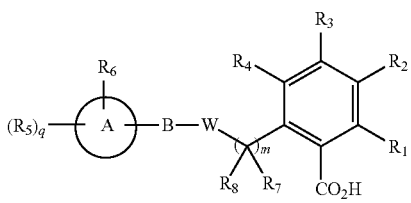

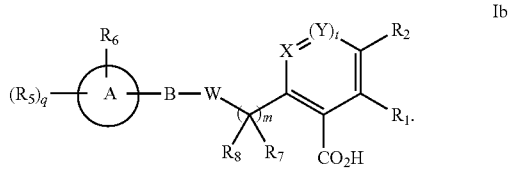

Compounds of any of Formulas Ia, Ib, II, III, or IV, or for example, General Formula I as depicted above, or any of the intermediates described in the schemes above, can be further derivatised by using one or more standard synthetic methods known to those skilled in the art. Such methods can involve substitution, oxidation or reduction reactions. These methods can also be used to obtain or modify compounds of General Formula I or any preceding intermediates by modifying, introducing or removing appropriate functional groups. Particular substitution approaches include alkylation, arylation, heteroarylation, acylation, thioacylation, halogenation, sulphonylation, nitration, formylation, hydrolysis and coupling procedures. These procedures can be used to introduce a functional group onto the parent molecule (such as the nitration or sulphonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent such as tetrahydrofuran in the presence of a phosphine (such as triphenylphosphine) and a dehydrating agent (such as diethyl, diisopropyl or dimethylazodicarboxylate). Alternatively, ether groups can be prepared by deprotonation of an alcohol, using a suitable base (such as sodium hydride) followed by the addition of an alkylating agent (such as an alkyl halide or an alkylsulphonate).

In another example, a primary or secondary amine can be alkylated using a reductive alkylation process. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups such as halogen atoms or sulphonyloxy groups (such as alkylsulphonyloxy, for example trifluoromethylsulphonyloxy, or arylsuphonyl, for example p-toluenesulphonyloxy) using conditions known to those skilled in the art. For example, an aliphatic alcohol can be reacted with thionyl chloride in a halogenated hydrocarbon (such as dichloromethane) to afford the corresponding alkylchloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxan). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyl lithium) optionally at a low temperature (such as −78° C.) in a solvent (such as tetrahydrofuran) and the mixture may then quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as the Dess-Martin reagent) in a solvent (such as a halogenated hydrocarbon, for example dichloromethane). Alternative oxidising conditions can be used, such as treatment with oxalyl chloride and an activating amount of dimethylsulphoxide and subsequent quenching by the addition of an amine (such as triethylamine). Such a reaction can be carried out in an appropriate solvent (such as a halogentaed hydrocarbon, for example dichloromethane) and under appropriate conditions (such as cooling below room temperature, for example to −78° C. followed by warming to room temperature). In another example, sulphur atoms can be oxidised to the corresponding sulphoxide or sulphone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups, saturation (or partial saturation) of unsaturated compounds including aromatic rings. For example, primary alcohols can be generated from the corresponding ester or aldehyde by reduction, using a metal hydride (such as lithium aluminium hydride or sodium borohydride in a solvent such as methanol). Alternatively, —OH groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as tin or iron) in the presence of an acid (such as hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of General Formula I and IV can be prepared by the reaction of a compound of General Formula I or IV with an appropriate acid or base in a suitable solvent, or mixture of solvents (such as an ether, for example, diethylether, or an alcohol, for example ethanol, or an aqueous solvent) using conventional procedures. Salts of compound of General Formula I or IV can be exchanged for other salts by treatment using conventional ion-exchange chromatography procedures.

Where it is desired to obtain a particular enantiomer of a compound of General Formula I or IV, this may be produced from a corresponding mixture of enantiomers by employing any suitable conventional procedure for resolving enantiomers. For example, diasteromeric derivatives (such as salts) can be produced by reaction of a mixture of enantiomers of a compound of General Formula I or IV (such a racemate) and an appropriate chiral compound (such as a chiral base). The diasteromers can then be separated by any conventional means such as crystallisation,) and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel *Steroselective Biocatalysts*, Marcel Decker; New York 2000).

In another resolution process a racemate of compounds of General Formula I or IV can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

II. Methods

Another aspect of the invention provides methods of modulating the activity of MetAP2. Such methods comprise exposing said receptor to a compound described herein. In some embodiments, the compound utilized by one or more of the foregoing methods is one of the generic, subgeneric, or specific compounds described herein, such as a compound of Formula Ia, Ib, II, III or IV. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to inhibit MetAP2 substrate cleavage in the patient and to induce multi organ stimulation of anti-obesity processes in the subject, for example, by administering a disclosed compound in an amount insufficient to reduce angiogenesis in the patient.

In certain embodiments, the invention provides a method of treating and or ameliorating obesity in a patient by administering an effective amount of a disclosed compound. Also provided herein are methods for inducing weight loss in a patient in need thereof.

Other contemplated methods of treatment include method of treating or amelioriating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

Also provided herein is a method of treating, or minimizing the risk of, cardiovascular disease (for example atherosclerosis, heart attack, stroke, or heart failure) in a patient in need thereof, comprising administering to said patient an therapeutically effective amount of disclosed compound. The patient being treated may be for example, obese, overweight, and/or suffering from diabetes, e.g. type 2 diabetes. A method of reducing triglycerides in the serum of a patient in need thereof (e.g. an obese and/or diabetic patient) is also provided, comprising administering to said patient a therapeutically effective amount of a disclosed compound, wherein said therapeutically effective amount does not substantially modulate or suppress angiogenesis. In a particular embodiment, a method is provided for improving, or increasing high density lipoprotein (HDL) in the serum of a patient, that includes administering to a patient a therapeutically effective amount of a disclosed compound.

Also provided herein is a method of treating a diabetic patient suffering from hypercholesterolemia including elevations of low density lipoprotein cholesterol, hyperlipidemia, and/or hypoalphalipoproteinemia, comprising administering to said patient a therapeutically effective amount of a disclosed compound. Such therapeutically effective amount may not, in some embodiments, substantially modulate or suppress angiogenesis. For example, a method of treating hyperlipidemia and/or hypercholesterolemia in a patient in need thereof is provided that comprises administering an effective amount of the following to said patient: a) one or more therapeutic agents each selected from the group consisting of: niacin, a statin, a fibrate, an angiotension-converting enzyme inhibitor, and a cholesterol absorption inhibitor (e.g., ezetimibe, simvastatin, atorvastatin, cerivastatin, fluvastatin, lovastatin, mevastatin, pitavastatin, rosuvastatin, bezafibrate, ciprofibrate, clofibrate, gemfibrozil, and fenofibrate); and b) a disclosed compound. Such a method may minimize flushing, an undesired vasodilatory effect of niacin administration.

In particular, in certain embodiments, the invention provides a method of treating the above medical indications comprising administering to a subject in need thereof a therapeutically effective amount of a compound described herein, such as a compound of Formula Ia, Ib, II, III, or IV.

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$(m$^2$) (SI) or 703× weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds of the present invention also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the invention provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of Formula Ia, Ib, II, III or IV.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. a lower dose sufficient to prevent weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may bemixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the invention also provides kits for use by a e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497):1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9): 978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (*Chest* (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7): 824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectra were recorded at ambient temperature using a Varian Unity Inova (400 MHz) spectrometer with a triple re$^s$onance 5 mm probe for example compounds, and either a Bruker Avance DRX (400 MHz) spectrometer or a Bruker Avance DPX (300 MHz) spectrometer for intermediate compounds. Chemical shifts are expressed in ppm relative to tetramethylsilane. The following abbreviations have been used: br=broad signal, s=singlet. d=doublet, dd=double doublet, ddd=double double doublet, dt=double triplet, tt=triple triplet, t=triplet, q=quartet, m=multiplet.

Mass Spectrometry (LCMS) experiments to determine retention times (r/t) and associated mass ions were performed using the following methods:

Method A: Experiments were performed on a Micromass Platform LCT spectrometer with positive ion electrospray and single wavelength UV 254 nm detection using a Higgins Clipeus C18 5 µm 100×3.0 mm column and a 2 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Method B: Experiments were performed on a Waters Micromass ZQ2000 quadrapole mass spectrometer with positive ion and negative ion mode electrospray and single wavelength UV 254 nm detection using a Higgins Clipeus C18 5 µm 100×3.0 mm column and a 1 mL/minute flow rate. The initial solvent system was 85% water containing 0.1% formic acid (solvent A) and 15% methanol containing 0.1% formic acid (solvent B) for the first minute followed by a gradient up to 5% solvent A and 95% solvent B over the next 12 minutes. The final solvent system was held constant for a further 7 minutes.

Method C: Experiments were performed on a Waters Micromass ZQ2000 quadrapole mass spectrometer linked to a Waters Acquity UPLC system with a PDA UV detector. The spectrometer has an electrospray source operating in positive and negative ion mode and single wavelength UV 254 nm detection using a Acquity BEH C18 1.7 um or Acquity BEH Shield RP18 1.7 um and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 6 minutes. The final solvent system was held constant for a further 0.8 minutes.

Method D: Experiments were performed on a Waters Micro triple quadrupole mass spectrometer linked to a Hewlett Packard HP1100 LC system with a DAD UV detector. The spectrometer has an electrospray source operating in positive and negative ion mode and DAD/ELS detection using a Higgins Clipeus C18 100×3.0 mm column and a 1 mL/minute flow rate. The solvent system was 85% water containing 0.1% formic acid (solvent A) and 15% methanol containing 0.1% formic acid (solvent B) for the first 1.0 minutes followed by a gradient up to 5% solvent A and 95% solvent B over the next 12 minutes. The final solvent system was held constant for a further 7 minutes.

Method E: Experiments were performed on a Micromass Platform LC spectrometer with positive and negative ion electrospray and ELS/Diode array detection using a Phenomenex Luna C18(2) 30×4.6 mm column and a 2 mL/minute flow rate. The solvent system was 95% water containing 0.1% formic acid (solvent A) and 5% methanol containing 0.1% formic acid (solvent B) for the first 0.50 minutes followed by a gradient up to 5% solvent A and 95% solvent B over the next 4 minutes. The final solvent system was held constant for a further 0.50 minutes.

Method F: Experiments were performed on a Waters ZMD quadrapole mass spectrometer with an electrospray source operating in positive and negative ion mode and ELS/Diode array detection using a Phenomenex Luna C18(2) 30×4.6 mm column and a 2 mL/minute flow rate or equivalent. The solvent system was 95% water containing 0.1% formic acid (solvent A) and 5% methanol containing 0.1% formic acid (solvent B) for the first 0.50 minutes followed by a gradient up to 5% solvent A and 95% solvent B over the next 4 minutes. The final solvent system was held constant for a further 1 minute.

Method G: Experiments were performed on a Finnigan AQA single quadrupole mass spectrometer linked to a Hewlett Packard 1050 LC system with a diode array detector. The spectrometer has an electrospray source operating in positive ion mode. Additional detection was achieved using a Sedex 65 evaporative light scattering detector. LC was carried out using a Luna 3 µm 30×4.6 mm C18 column and a 2 ml/minute flow rate. The initial solvent system was 95% water containing 0.1% formic acid (solvent A) and 5% methanol containing 0.1% formic acid (solvent B) for the first 0.5 minute followed by a gradient up to 5% solvent A and 95% solvent B over the next 4 minutes. The final solvent system was held constant for a further 1 minute.

Method H: Experiments were performed on a Waters platform LC quadrupole mass spectrometer linked to a Hewlett Packard HP1100 LC system with diode array detection. The spectrometer has an electrospray source operating in positive and negative ion mode. Additional detection was achieved using a Sedex 65 evaporative light scattering detector. LC was carried out using a Phenomenex Luna 3 µm 30×4.6 mm C18 column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. The final solvent system was held constant for a further 1 minute.

Microwave experiments were carried out using a Biotage Initiator™, which uses a single-mode resonator and dynamic field tuning, both of which give reproducibility and control. Temperatures from 40-250° C. can be achieved, and pressures of up to 20 bars can be reached. Three types of vial are available for this processor, 0.5-2.0 ml, 2.0-5.0 ml and 5.0-20 ml.

Preparative HPLC purification was carried out using either a C18-reverse-phase column from Genesis (C18) or a C6-phenyl column from Phenomenex (C6 phenyl) (100×22.5 mm i d with 7 µm particle size, UV detection at 230 or 254 nm, flow 5-15 ml/min), eluting with gradients from 100-0 to 0-100% water/acetonitrile or water/methanol containing 0.1% formic acid, with a flow rate of 18 ml per minute. Fractions containing the required product (identified by LCMS analysis) were pooled, the organic fraction removed by evaporation, and the remaining aqueous fraction lyophilised, to give the final product.

Compounds which required column chromatography were purified manually or fully automatically using either a Biotage SP1™ Flash Purification system with Touch Logic Control™ or a Combiflash Companion® with pre-packed silica gel Isolute® SPE cartridge, Biotage SNAP cartridge or Redisep® Rf cartridge respectively.

Abbreviations: THF: Tetrahydrofuran; DMF: N,N-Dimethylformamide; DCM: Dichloromethane; Dppf: diphenylphosphino ferrocene; AIBN: Azo-bis-(isobutyronitrile), DMA: dimethylacetamide, DIPEA: di-isopropylethylamine, BINAP: 1,1'-bi(2-naphthylamine), DCE: 1,2-dichloroethane, Boc: t-butoxycarbonyl, HATU: O-(7-azabenzotriazol-1-yl)-N,N,N',N'-tetramethyluronium hexafluorophosphate.

Example 1

2-(Benzenesulphonylmethyl)-5-ethylbenzoic acid

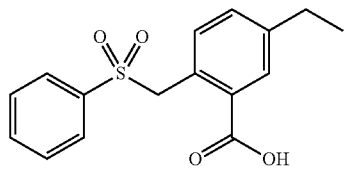 [SMILES: CCc1ccc(CS(=O)(=O)c2ccccc2)c(C(=O)O)c1]

Hydrogen peroxide (30% aqueous solution, 0.961 ml) was added dropwise to a solution of 2-(phenylthiomethyl)-5-ethylbenzoic acid (Intermediate 1, 0.231 g) in acetic acid (8.5 ml). The resultant mixture was stirred and heated at 60° C. for 2 hours. The mixture was cooled to room temperature and evaporated to dryness to give 2-(benzenesulphonylmethyl)-5-ethylbenzoic acid (0.186 g) as a white solid.

NMR (CDCl$_3$) δ 7.85 (s, 1H), 7.7 (d, 2H), 7.6 (t, 1H), 7.5 (t, 2H), 7.35 (dd, 1H), 7.3 (d, 1H), 5.05 (s, 2H), 2.7 (q, 2H), 1.3 (t, 3H).

LCMS (Method A) r/t 9.39 (M+Na) 327, (M−H) 303

Example 2

6-(Benzenesulphonylmethyl)-3-ethyl-2-methoxybenzoic acid

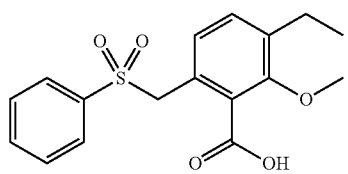

Hydrogen peroxide (30% aqueous solution, 0.117 ml) was added to a solution of ethyl 6-(phenylthiomethyl)-3-ethyl-2-methoxybenzoate (Intermediate 19, 0.057 g) in acetic acid (1.7 ml) and the resultant solution was stirred and heated at 60° C. for 2 hours. After cooling, the solution was evaporated to dryness to give the crude sulphone. The residue was dissolved in a mixture of dioxane (1 ml) and water (1 ml) and lithium hydroxide (0.072 g) was added. The mixture was stirred and heated in the microwave at 160° C. for 15 minutes. After cooling, the mixture was evaporated to dryness and the residue was acidified by addition of hydrochloric acid (1M) and then immediately purified by preparative HPLC (C18) eluting with a mixture of methanol and water containing 0.1% formic acid to give 6-(benzenesulphonylmethyl)-3-ethyl-2-methoxy-benzoic acid (0.022 g) as a white solid.

NMR (DMSO-d$_6$) δ 13.2 (br s, 1H), 7.7 (m, 3H), 7.6 (t, 2H), 7.3 (d, 1H), 6.9 (d, 1H), 4.7 (s, 2H), 3.7 (s, 3H), 2.6 (q, 2H), 1.15 (t, 3H).

LCMS (Method B) r/t 9.16 (M+Na) 357, (M−1) 333.

Example 3

6-(Benzenesulphonylmethyl)-2-methoxy-3-propylbenzoic acid

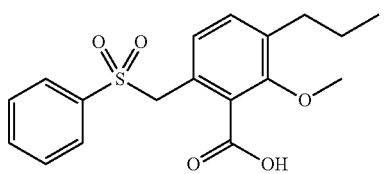 [SMILES: CCCc1ccc(CS(=O)(=O)c2ccccc2)c(C(=O)O)c1OC]

Lithium hydroxide (1M aqueous solution, 0.45 ml) was added to a solution of ethyl 6-(benzenesulphonylmethyl)-2-methoxy-3-propylbenzoate (Intermediate 24, 0.034 g) in dioxane and the solution was stirred and heated in the microwave at 160° C. for 15 minutes. The cooled solution was acidified by addition of formic acid and then purified by preparative HPLC (C18) eluting with a mixture of methanol and water containing 0.1% formic acid to give 6-(benzenesulphonylmethyl)-2-methoxy-3-propylbenzoic acid (0.024 g) as a white solid.

NMR (CDCl$_3$) δ 7.75 (d, 2H), 7.65 (t, 1H), 7.5 (t, 2H), 7.3 (d, 1H), 7.1 (d, 1H), 4.8 (s, 2H), 3.8 (s, 3H), 2.65 (t, 2H), 1.7 (m, 2H), 1.0 (t, 3H).

LCMS (Method B) r/t 10.08 (M+Na) 371, (M−H) 347.

Example 4

6-(Benzenesulphinylmethyl)-3-ethyl-2-methoxybenzoic acid

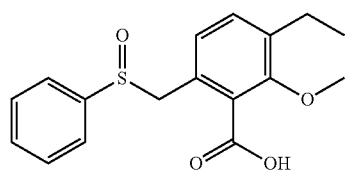 [SMILES: CCc1ccc(CS(=O)c2ccccc2)c(C(=O)O)c1OC]

Prepared by proceeding in a similar manner to Example 3, starting from ethyl 6-(benzenesulphinylmethyl)-3-ethyl-2-methoxybenzoate (Intermediate 2).

NMR (CDCl$_3$) δ 12.5-11.0 (br s, 1H), 7.6 (m, 2H), 7.55 (m, 3H), 7.25 (d, 1H), 6.9 (d, 1H), 4.4 (d, 1H), 4.1 (d, 1H), 3.9 (s, 3H), 2.7 (m, 2H), 1.25 (t, 3H).

LCMS (Method D) r/t 9.50 (M+H) 319.

Example 5

6-(Benzenesulphonylmethyl)-3-cyclopropyl-2-methoxybenzoic acid

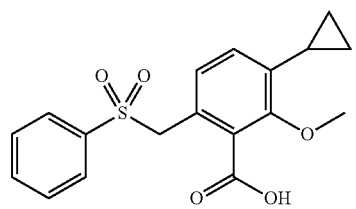

Prepared by proceeding in a similar manner to Example 3, starting from ethyl 6-(benzenesulphonylmethyl)-3-cyclopropyl-2-methoxybenzoate (Intermediate 25).

NMR (CDCl$_3$) δ 7.8 (dd, 2H), 7.65 (t, 1H), 7.5 (t, 2H), 7.1 (d, 1H), 6.9 (d, 1H), 4.8 (s, 2H), 3.95 (s, 3H), 2.2 (m, 1H), 1.05 (m, 2H), 0.8 (m, 2H).

LCMS (Method D) r/t 9.29 (M+Na) 369 (M−H) 345.

Example 6

6-(4-Chlorobenzenesulphonylmethyl)-3-ethyl-2-methoxybenzoic acid

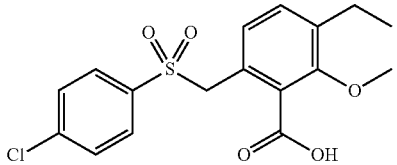

Prepared by proceeding in a similar manner to Example 3, starting from ethyl 6-(4-chlorobenzenesulphonylmethyl)-3-ethyl-2-methoxybenzoate (Intermediate 21).

NMR (CDCl$_3$) δ 7.7 (d, 2H), 7.5 (d, 2H), 7.35 (d, 1H), 7.1 (d, 1H), 4.8 (s, 2H), 3.85 (s, 3H), 2.7 (q, 2H), 1.25 (t, 3H).

LCMS (Method D) r/t 10.35 (M+Na) 391, (M−H) 367.

Example 7

6-(Benzenesulphonylmethyl)-3-bromo-2-methoxybenzoic acid

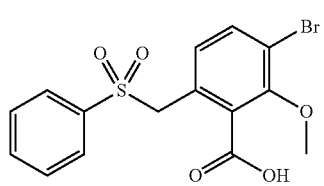 [SMILES: COc1c(Br)ccc(CS(=O)(=O)c2ccccc2)c1C(=O)O]

Prepared by proceeding in a similar manner to Example 3, starting from ethyl 6-(benzenesulphonylmethyl)-3-bromo-2-methoxy-benzoate (Intermediate 60).

NMR (CDCl$_3$) δ 7.7 (d, 2H), 7.65 (t, 1H), 7.55 (d, 1H), 7.5 (t, 2H), 6.9 (d, 1H), 4.6 (s, 2H), 3.9 (s, 3H).

LCMS (Method D) r/t 9.07 (M+Na) 407 & 409 (M−H) 383 & 385.

Example 8

6-(Benzenesulphonylmethyl)-2-methoxy-3-methylbenzoic acid

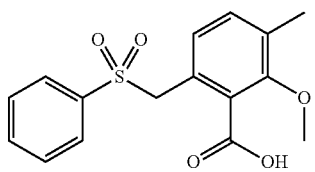 [SMILES: COc1c(C)ccc(CS(=O)(=O)c2ccccc2)c1C(=O)O]

Prepared by proceeding in a similar manner to Example 3, starting from ethyl 6-(benzenesulphonylmethyl)-2-methoxy-3-methylbenzoate (Intermediate 26).

NMR (CD$_3$OD) δ 7.7 (d, 2H), 7.65 (t, 1H), 7.5 (t, 2H), 7.2 (d, 1H), 6.9 (d, 1H), 4.6 (s, 2H), 3.75 (s, 3H), 2.3 (s, 3H).

LCMS (Method D) r/t 8.34 (M+Na) 343 (M−H) 319.

Example 9

3-Ethyl-2-methoxy-6-(2-methylbenzenesulphonylmethyl)benzoic acid

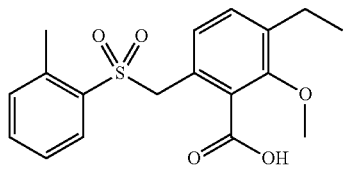 [SMILES: CCc1ccc(CS(=O)(=O)c2ccccc2C)c(C(=O)O)c1OC]

Prepared by proceeding in a similar manner to Example 3, starting from ethyl 3-ethyl-2-methoxy-6-(2-methylbenzenesulphonylmethyl)benzoate (Intermediate 22).

NMR (CDCl$_3$) δ 7.8 (d, 1H), 7.5 (t, (1H), 7.25 (m, 2H), 7.2 (d, 1H), 6.95 (d, 1H), 4.65 (s, 2H), 3.8 (s, 3H), 2.7 (q, 2H), 2.6 (s, 3H), 1.2 (t, 3H).

LCMS (Method D) r/t 9.90 (M+Na) 371 (M−H) 347.

Example 10

6-(Benzenesulphonylmethyl)-3-(furan-3-yl)-2-methoxybenzoic acid

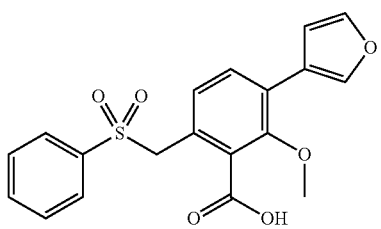 [SMILES: COc1c(-c2ccoc2)ccc(CS(=O)(=O)c2ccccc2)c1C(=O)O]

Prepared by proceeding in a similar manner to Example 3, starting from ethyl 6-(benzenesulphonylmethyl)-3-(furan-3-yl)-2-methoxybenzoate (Intermediate 27).

NMR (CDCl$_3$) δ 7.95 (s, 1H), 7.8 (d, 2H), 7.65 (t, 1H), 7.5 (m, 4H), 7.15 (d, 1H), 6.8 (s, 1H), 4.8 (s, 2H), 3.7 (s, 3H).

LCMS (Method D) r/t 9.35 (M+Na) 395 (M−H) 371.

Example 11

6-(1-Benzenesulphonylethyl)-3-ethyl-2-methoxybenzoic acid

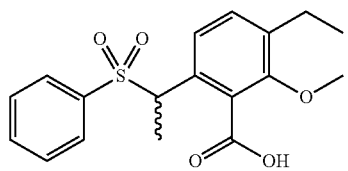

Prepared by proceeding in a similar manner to Example 3, starting from ethyl 6-(1-benzenesulphonylethyl)-3-ethyl-2-methoxybenzoate (Intermediate 3).

NMR (DMSO-$d_6$) δ 13.5-13.0 (br s, 1H), 7.7 (t, 1H), 7.6 (m, 4H), 7.35 (d, 1H), 7.3 (d, 1H), 4.55 (q, 1H), 3.65 (s, 3H), 2.6 (m, 2H), 1.55 (d, 3H), 1.15 (t, 3H).
LCMS (Method D) r/t 9.93 (M+Na) 371.

Example 12

6-(Benzenesulphonylmethyl)-2-methoxy-3-(oxazol-5-yl)-benzoic acid

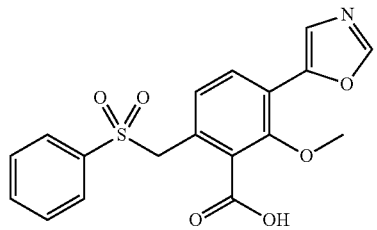 [SMILES: COc1c(-c2cnco2)ccc(CS(=O)(=O)c2ccccc2)c1C(=O)O]

Prepared by proceeding in a similar manner to Example 3, starting from ethyl 6-(benzenesulphonylmethyl)-2-methoxy-3-(oxazol-5-yl)benzoate (Intermediate 30).

NMR (CDCl$_3$) δ 8.0 (s, 1H), 7.7 (m, 3H), 7.65 (m, 1H), 7.6 (s, 1H), 7.5 (m, 2H), 7.1 (d, 1H), 4.65 (s, 2H), 3.8 (s, 3H).
LCMS (Method D) r/t 7.9 (M+H) 374.

Example 13

6-(Benzenesulphonylmethyl)-3-(isothiazol-5-yl)-2-methoxybenzoic acid

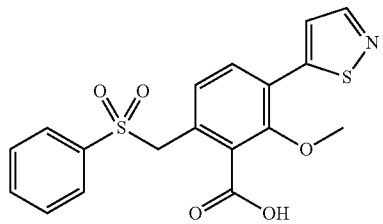

Prepared by proceeding in a similar manner to Examples 3, starting from ethyl 6-(benzenesulphonylmethyl)-3-(isothiazol-5-yl)-2-methoxybenzoate (Intermediate 31).

NMR (CDCl$_3$) δ 8.6 (s, 1H), 7.8 (m, 3H), 7.7 (t, 1H), 7.6 (s, 1H), 7.55 (t, 2H), 7.2 (d, 1H), 4.7 (s, 2H), 3.9 (s, 3H).
LCMS (Method D) r/t 8.45 (M+H) 390.

Example 14

6-(Benzenesulphonylmethyl)-2-methoxy-3-phenylbenzoic acid

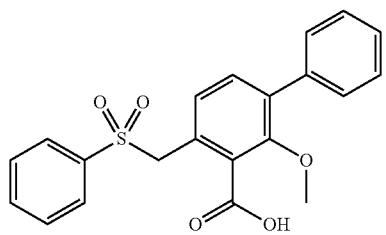

Prepared by proceeding in a similar manner to Example 3, starting from ethyl 6-(benzenesulphonylmethyl)-2-methoxy-3-phenylbenzoate (Intermediate 32).

NMR (CDCl$_3$) δ 7.85 (d, 2H), 7.65 (t, 1H), 7.6 (m, 4H), 7.45 (m, 4H), 7.25 (d, 1H), 4.85 (s, 2H), 3.45 (s, 3H).
LCMS (Method D) r/t 10.36 (M+Na) 405.

Example 15

6-(Benzenesulphonylmethyl)-2-methoxy-3-(pyrid-3-yl)benzoic acid

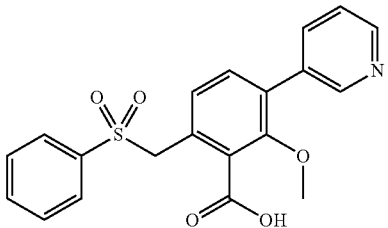

Prepared by proceeding in a similar manner to Example 3, starting from ethyl 6-(benzenesulphonylmethyl)-2-methoxy-3-(pyrid-3-yl)benzoate (Intermediate 33).

NMR (DMSO-$d_6$) δ 13.8-12.9 (br s, 1H), 8.95 (s, 1H), 8.8 (d, 1H), 8.4 (d, 1H), 7.9 (m, 1H), 7.8 (m, 3H), 7.65 (m, 2H), 7.6 (d, 1H), 7.2 (d, 1H), 4.85 (s, 2H), 3.4 (s, 3H).
LCMS (Method D) r/t 5.64 (M+H) 384.

Example 16

6-(Benzenesulphonylmethyl)-2-methoxy-3-(pyrazol-3-yl)benzoic acid

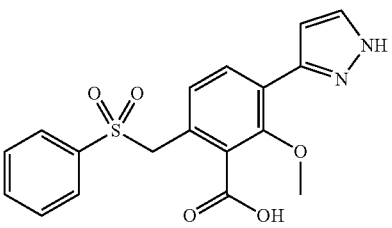 [SMILES: COc1c(-c2cc[nH]n2)ccc(CS(=O)(=O)c2ccccc2)c1C(=O)O]

Prepared by proceeding is a similar manner to Example 3, starting from ethyl 6-(benzenesulphonylmethyl)-2-methoxy-3-(pyrazol-3-yl)benzoate (Intermediate 45).

NMR (DMSO-d$_6$) δ 13.7-12.5 (br s, 1H), 7.8 (d, 1H), 7.75 (s, 1H), 7.7 (m, 3H), 7.6 (m, 2H), 7.0 (d, 1H), 6.7 (s, 1H), 4.75 (s, 2H), 3.6 (s, 3H).

LCMS (Method D) r/t 7.51 (M+H) 373.

Example 17

2-(Benzenesulphonylmethyl)-5-(furan-3-yl)benzoic acid

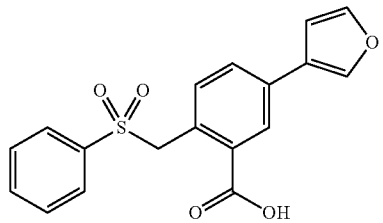 [SMILES: O=C(O)c1cc(-c2ccoc2)ccc1CS(=O)(=O)c1ccccc1]

Prepared by proceeding in a similar manner to Example 3, starting from methyl 2-(benzenesulphonylmethyl)-5-(furan-3-yl)benzoate (Intermediate 41).

NMR (DMSO-d$_6$) δ 13.3-12.9 9 (br s, 1H), 8.3 (s, 1H), 8.05 (s, 1H), 7.8 (s, 1H), 7.7 (m, 2H), 7.6 (m, 4H), 7.2 (d, 1H), 7.0 (s, 1H), 5.2 (s, 2H).

LCMS (Method D) r/t 9.52 (M+Na) 365, (M−H) 341.

Example 18

2-(Benzenesulphonylmethyl)-5-(oxazol-5-yl)benzoic acid

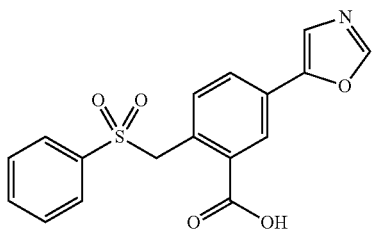 [SMILES: O=C(O)c1cc(-c2cnco2)ccc1CS(=O)(=O)c1ccccc1]

Prepared by proceeding in a similar manner to Example 3, starting from methyl 2-(benzenesulphonylmethyl)-5-(oxazol-5-yl)benzoate (Intermediate 42).

NMR (DMSO-d$_6$) δ 13.7-12.7 (br s, 1H), 8.5 (s, 1H), 8.15 (s, 1H), 7.85 (s, 1H), 7.8 (m, 1H), 7.7 (t, 1H), 7.65 (m, 2H), 7.6 (t, 2H), 7.3 (d, 1H), 5.3 (s, 2H),

LCMS (Method D) r/t 8.01 (M+H) 344.

Example 19

3-(Furan-3-yl)-2-methoxy-6-(2-methylbenzenesulphonylmethyl)benzoic acid

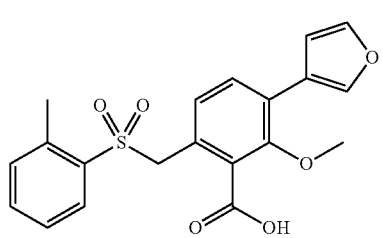

Prepared by proceeding in a similar manner to Example 3, starting from ethyl 3-(furan-3-yl)-2-methoxy-6-(2-methylbenzenesulphonylmethyl)benzoate (Intermediate 28).

NMR (DMSO-d$_6$) δ 13.6-13.2 (br s, 1H), 8.2 (s, 1H), 7.8 (s, 1H), 7.7 (d, 1H), 7.65 (d, 1H), 7.6 (d, 1H), 7.45 (d, 1H), 7.4 (t, 1H), 7.05 (d. 1H), 7.0 (s, 1H), 4.7 (s, 2H), 3.6 (s, 3H), 2.55 (s, 3H).

LCMS (Method C) r/t 4.32 (M+Na) 409, (M−H) 385.

Example 20

2-Methoxy-6-(2-methylbenzenesulphonylmethyl)benzoic acid

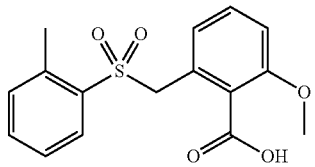 [SMILES: COc1cccc(CS(=O)(=O)c2ccccc2C)c1C(=O)O]

Prepared by proceeding in a similar manner to Example 3, starting from ethyl 2-methoxy-6-(2-methylbenzenesulphonylmethyl)benzoate (Intermediate 62).

NMR (CD$_3$OD) δ 7.75 (dd, 1H), 7.55 (dt, 1H), 7.3 (m, 3H), 7.0 (d, 1H), 6.85 (d, 1H), 4.7 (s, 2H), 3.85 (s, 3H), 2.6 (s, 3H).

LCMS (Method D) r/t 8.03 (M+Na) 343.

Example 21

6-(3-Chlorobenzenesulphonylmethyl)-3-(furan-3-yl)-2-methoxybenzoic acid

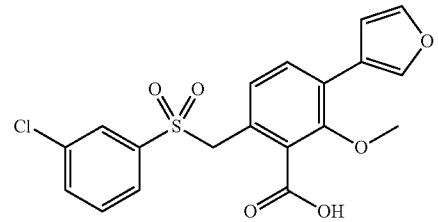 [SMILES: COc1c(-c2ccoc2)ccc(CS(=O)(=O)c2cccc(Cl)c2)c1C(=O)O]

Prepared by proceeding in a similar manner to Example 3, starting from ethyl 6-(3-chlorobenzenesulphonylmethyl)-3-(furan-3-yl)benzoate (Intermediate 29).

NMR (DMSO-d$_6$) δ 13.5-13.2 (br s, 1H), 8.2 (s, 1H), 7.8 (m, 1H), 7.75 (s, 1H), 7.7 (m, 4H), 7.05 (d, 1H), 73.0 (s, 1H), 4.8 (s, 2H), 3.6 (s, 3H).

LCMS (Method C) r/t 4.46 (M+Na) 429 and 431, (M−H) 405 and 407.

Example 22

6-(Benzenesulphonylmethyl)-3-(oxazol-4-yl)-2-methoxybenzoic acid

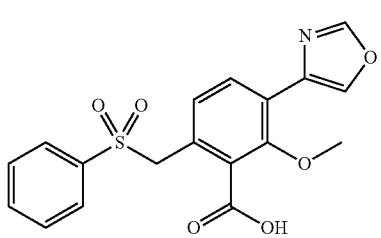

Prepared by proceeding in a similar manner to Example 3, starting from crude methyl 6-(benzenesulphonylmethyl)-3-(oxazol-4-yl)-2-methoxybenzoate (Intermediate 49) and using methanol in place of dioxane.

NMR (DMSO-d$_6$) δ 13.7-13.2 (br s, 1H), 8.5 (m, 2H), 7.95 (d, 1H), 7.7 (m, 3H), 7.6 (t, 2H), 7.05 (d, 1H), 4.8 (s, 2H), 3.7 (s, 3H).

LCMS (Method C) r/t 3.51 (M+H) 374.

Example 23

6-(Benzenesulphonylmethyl)-3-(isothiazol-4-yl)-2-methoxybenzoic acid

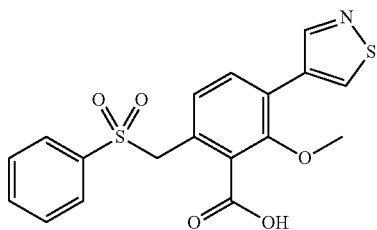 [SMILES: COc1c(-c2cnsc2)ccc(CS(=O)(=O)c2ccccc2)c1C(=O)O]

Prepared by proceeding in a similar manner to Example 3, starting from crude methyl 6-(benzenesulphonylmethyl)-3-(isothiazol-4-yl)-2-methoxybenzoate (Intermediate 57) using methanol in place of dioxane.

NMR (DMSO-d$_6$) δ 13.6-13.1 (br s, 1H), 9.35 (s, 1H), 8.95 (s, 1H), 7.7 (m, 3H), 7.65 (d, 1H), 7.6 (t, 2H), 7.1 (d, 1H), 4.8 (s, 2H), 3.5 (s, 3H).

LCMS (Method C) r/t 3.75 (M+H) 390.

Example 24

6-(Benzenesulphonylmethyl)-2-methoxy-3-(thiazol-2-yl)benzoic acid

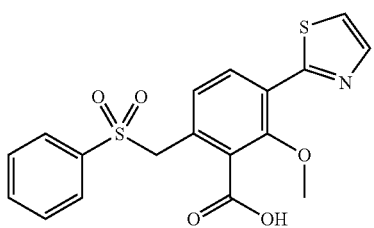 [SMILES: COc1c(-c2nccs2)ccc(CS(=O)(=O)c2ccccc2)c1C(=O)O]

A mixture of methyl 6-benzenesulphonylmethyl-2-methoxy-3-(thiazol-2-yl)benzoate (Intermediate 34, 0.1 g) and lithium hydroxide (1M aqueous solution, 1.25 ml) in methanol (2 ml) was stirred and heated at 80° C. for 2 hours. The solution was evaporated to dryness and the residue was purified by HPLC (C18) eluting with a mixture of methanol and water containing 0.1% formic acid, with a gradient of 4-98%. The resultant gum was triturated with ether and the solid was collected by filtration to give 6-(benzenesulphonylmethyl)-2-methoxy-3-(thiazol-2-yl)benzoic acid (0.025 g) as a pale pink solid.

NMR (DMSO-d$_6$) δ 8.2 (d, 1H), 8.0 (d, 1H), 7.9 (d, 1H), 7.75 (m, 3H), 7.6 (m, 2H), 7.1 (d, 1H), 4.85 (s, 2H), 3.8 (s, 3H)

LCMS (Method C) r/t 3.75 (M+H) 390

Example 25A and Example 25B (Z)-6-((2-(3-(Diethylamino)prop-1-enyl)benzenesulfonyl)methyl)-3-(furan-3-yl)-2-methoxybenzoic acid and (E)-6-((2-(3-(Diethylamino)prop-1-enyl)benzenesulfonyl)methyl)-3-(furan-3-yl)-2-methoxybenzoic acid

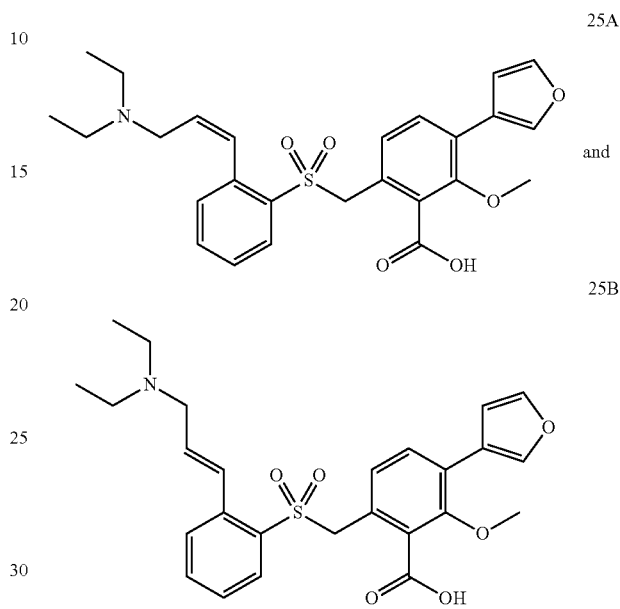

Prepared by proceeding in a similar manner to Examples 3, starting from a mixture of E and Z isomers of methyl 6-((2-(3-(diethylamino)prop-1-enyl)benzenesulfonyl)methyl)-3-(furan-3-yl)-2-methoxybenzoate (Intermediate 5). The isomers were separated by preparative HPLC (C6 phenyl), eluting with a mixture of acetonitrile and water containing 0.1% formic acid with a gradient of 20-40%.

25A: NMR (DMSO-d$_6$) δ 8.05 (s, 1H), 7.7 (s, 1H), 7.65 (t, 1H), 7.4 (m, 4H), 7.15 (br d, 1H), 6.95 (s, 1H), 6.7 (br s, 1H), 6.2 (m, 1H), 4.75 (s, 2H), 3.85 (br s, 2H), 3.5 (s, 3H), 3.0 (br s, 4H), 1.1 (t, 6H).

LCMS (Method C) r/t 3.27 (M+H) 384

25B: NMR (DMSO-d$_6$) δ 8.15 (s, 1H), 8.05 (d, 1H), 7.85 (d, 1H), 7.8 (d, 1H), 7.75 (s, 1H), 7.65 (t, 1H), 7.5 (d, 1H), 7.2 (br s, 1H), 7.0 (s, 1H), 6.7 (br s, 1H), 6.55 (m, 1H), 4.6 (s, 2H), 3.75 (br s, 2H), 3.7 (s, 3H), 3.1 (br s, 4H), 1.2 (t, 6H).

LCMS (Method C) r/t 3.34 (M+H) 484

Example 26

6-(Benzenesulphonylmethyl)-2-ethoxy-3-(furan-3-yl)benzoic acid

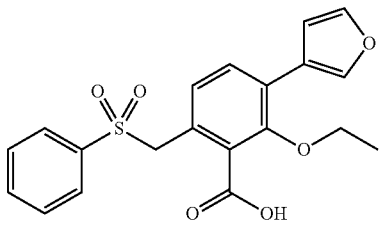 [SMILES: CCOc1c(-c2ccoc2)ccc(CS(=O)(=O)c2ccccc2)c1C(=O)O]

Prepared by proceeding in a similar manner to Example 3, starting from ethyl 6-(benzenesulphonylmethyl)-2-ethoxy-3-(furan-3-yl)benzoate (Intermediate 11).

NMR (DMSO-d$_6$) δ 13.5-13.1 (br s, 1H), 8.15 (s, 1H), 7.75 (s, 1H), 7.7 (m, 3H), 7.6 (m, 3H), 7.0 (d, 1H), 7.0 (s, 1H), 4.75 (s, 2H), 3.75 (q, 2H), 1.2 (t, 3H).
LCMS (Method C) r/t 4.30 (M+Na) 409.

Example 27

6-(Benzenesulphonylmethyl)-3-(furan-3-yl)-2-hydroxybenzoic acid

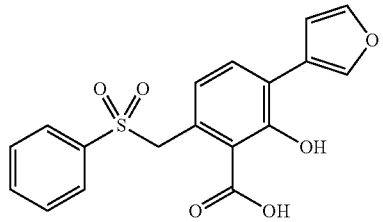 [SMILES: O=C(O)c1c(CS(=O)(=O)c2ccccc2)ccc(-c2ccoc2)c1O]

Prepared by proceeding in a similar manner to Example 3, starting from ethyl 6-(benzenesulphonylmethyl)-3-(furan-3-yl)-2-hydroxybenzoate (Intermediate 35).
NMR (DMSO-d$_6$) 8.3 (s, 1H), 7.65 (m, 4H), 7.55 (t, 2H), 7.4 (d, 1H), 7.0 (s, 1H), 6.45 (d, 1H), 5.65 (s, 2H).
LCMS (Method C) r/t 4.2 (M+Na) 381.

Example 28

6-(Benzenesulphonylmethyl)-3-(furan-3-yl)-2-(2-hydroxyethoxy)benzoic acid

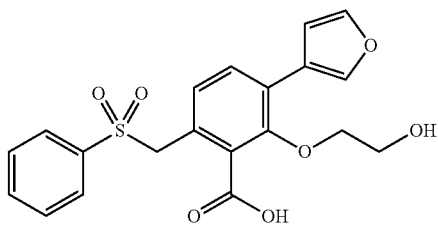 [SMILES: O=C(O)c1c(CS(=O)(=O)c2ccccc2)ccc(-c2ccoc2)c1OCCO]

Prepared by proceeding in a similar manner to Example 3, starting from ethyl 6-(benzenesulphonylmethyl)-3-(furan-3-yl)-2-(2-hydroxyethoxy)benzoate (Intermediate 15).
NMR (DMSO-d$_6$) δ 13.5-13.2 (br s, 1H), 8.4 (s, 1H), 7.7-7.5 (m, 7H), 7.05 (s, 1H), 7.0 (d, 1H), 4.95 (br s, 1H), 4.7 (s, 2H), 3.75 (t, 2H), 3.65 (t, 2H).
LCMS (Method C) r/t 3.67 (M+Na) 425.

Example 29

6-(Benzenesulphonylmethyl)-3-(furan-3-yl)-2-(2-methoxyethoxy)benzoic acid

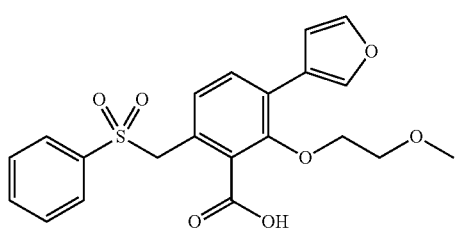 [SMILES: COCCOc1c(-c2ccoc2)ccc(CS(=O)(=O)c2ccccc2)c1C(=O)O]

Prepared by proceeding in a similar manner to Example 3, starting from methyl 6-(benzenesulphonylmethyl)-3-(furan-3-yl)-2-(2-methoxyethoxy)benzoate (Intermediate 16).
NMR (DMSO-d$_6$) δ 13.7-13.0 (8.3 (s, 1H), 7.75 (s, 1H), 7.7 (m, 3H), 7.6 (m, 3H), 7.0 (m, 2H), 4.75 (s, 2H), 3.85 (m, 2H), 3.55 (m, 2H), 3.25 (s, 3H)
LCMS (Method C) r/t 4.14 (M+Na) 439

Example 30

6-[2-(3-Diethylaminopropyl)benzenesulphonylmethyl]-3-(furan-3-yl)-2-methoxybenzoic acid

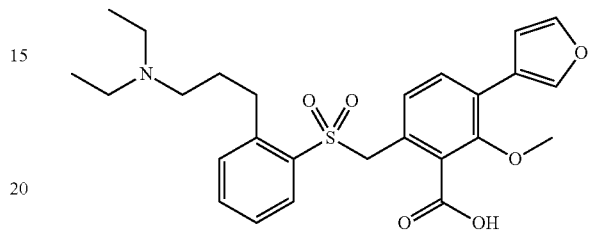

Prepared by proceeding in a similar manner to Example 3, starting from methyl 6-[2-(3-diethylaminopropyl)benzenesulphonylmethyl]-3-(furan-3-yl)-2-methoxybenzoate (Intermediate 4).
NMR (DMSO-d$_6$) δ 8.1 (s, 1H), 7.9 (d, 1H), 7.75 (s, 1H), 7.7 (t, 1H), 7.5 (m, 3H), 7.25 (d, 1H), 7.0 (s, 1H), 4.75 (s, 2H), 3.7 (s, 3H), 3.1 (m, 8H), 2.0 (br s, 2H), 1.2 (t, 6H).
LCMS (Method C) r/t 3.31 (M+H) 486.

Example 31

3-(3-Furan-3-yl)-2-methoxy-6-(pyrid-3-ylsulphonylmethyl)benzoic acid

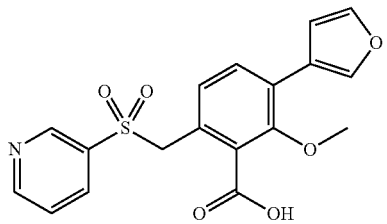 [SMILES: COc1c(-c2ccoc2)ccc(CS(=O)(=O)c2cccnc2)c1C(=O)O]

Prepared by proceeding in a similar manner to Example 3, starting from ethyl 3-(3-furan-3-yl)-2-methoxy-6-(pyrid-3-ylsulphonyl-methyl)benzoate (Intermediate 44).
NMR (DMSO-d$_6$) δ 13.6-13.1 (br s, 1H), 8.9 (d, 1H), 8.75 (s, 1H), 8.2 (s, 1H), 8.0 (dd, 1H), 7.8 (d, 1H), 7.7 (d, 1H), 7.65 (m, 1H), 7.1 (d, 1H), 7.0 (s, 1H), 4.85 (s, 2H), 3.6 (s, 3H).
LCMS (Method C) r/t 3.60 (M+H) 374.

Example 32

6-(Benzenesulphonylmethyl)-3-(isoxazol-3-yl)-2-methoxybenzoic acid

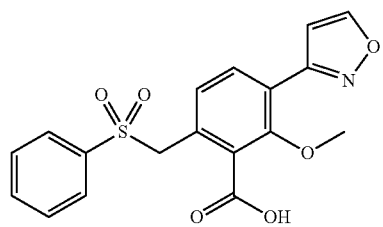

A mixture of ethyl 6-(benzenesulphonylmethyl)-3-(isoxazol-3-yl)-2-methoxybenzoate (Intermediate 47, 0.03 g), lithium hydroxide (1M aqueous solution, 0.4 ml) and dioxane (1 ml) was stirred at room temperature overnight then heated at 40° C. for 8 hours. It was left to stand at room temperature overnight then heated at 60° C. for 6 hours. The resultant mixture was acidified by addition of concentrated hydrochloric acid followed by addition of isopropanol (~0.5 ml). The mixture was purified by preparative HPLC (C18), eluting with a mixture of methanol and water containing 0.1% formic acid with a gradient of 40-98% to give 6-(benzenesulphonylmethyl)-3-(isoxazol-3-yl)-2-methoxybenzoic acid (0.02 g) as a clear glass.

NMR (DMSO-d6) δ 13.8-13.1 (br s, 1H), 9.1 (s, 1H), 7.75 (m, 4H), 7.65 (m, 2H), 7.1 (d. 1H), 7.0 (s, 1H), 4.8 (s, 2H), 3.6 (s, 3H).

LCMS (Method D) r/t 7.93 (M+Na) 396.

Example 33

3-(Furan-3-yl)-2-methoxy-6-(2-methoxybenzenesulphonylmethyl)benzoic acid

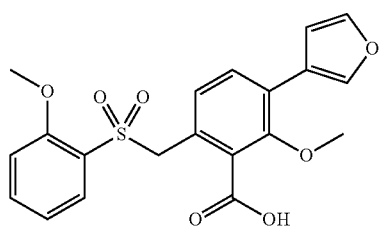 [SMILES: COc1ccccc1S(=O)(=O)Cc1ccc(-c2ccoc2)c(OC)c1C(=O)O]

Prepared by proceeding in a similar manner to Example 32, starting from methyl 3-(furan-3-yl)-2-methoxy-6-(2-methoxybenzenesulphonylmethyl)benzoate (Intermediate 39).

NMR (CDCl$_3$) δ 7.95 (s, 1H), 7.9 (d, 1H), 7.65 (t, 1H), 7.5 (m, 2H), 7.2 (d, 1H), 7.1 (m, 2H), 6.75 (s, 1H), 4.9 (s, 2H), 4.1 (s, 3H), 3.75 (s, 3H).

LCMS (Method C) r/t 4.07 (M+Na) 425

Example 34

3-(Furan-3-yl)-2-methoxy-6-(pyrid-2-ylsulphonylmethyl)benzoic acid

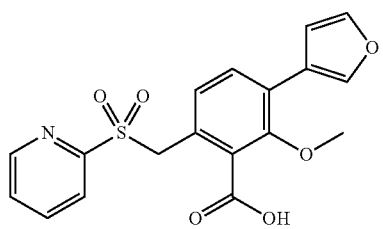 [SMILES: COc1c(-c2ccoc2)ccc(CS(=O)(=O)c2ccccn2)c1C(=O)O]

Prepared by proceeding in a similar manner to Example 27, starting from methyl 3-(furan-3-yl)-2-methoxy-6-(pyrid-2-ylsulphonylmethyl)benzoate (Intermediate 40).

NMR (DMSO-d$_6$) δ 13.6-13.2 (br s, 1H), 8.8 (d, 1H), 8.15 (s, 1H), 8.1 (t, 1H), 7.9 (d, 1H), 7.75 (m, 2H), 7.65 (d, 1H), 7.1 (d, 1H), 7.0 (s, 1H), 4.9 (s, 2H), 3.6 (s, 3H).

LCMS (Method C) r/t 3.69 (M+H) 374.

Example 35

3-Ethyl-6-(4-fluorobenzenesulphonylmethyl)-2-methoxybenzoic acid

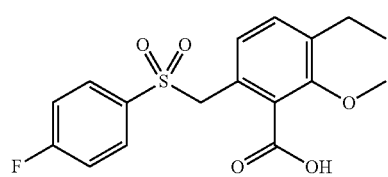 [SMILES: CCc1ccc(CS(=O)(=O)c2ccc(F)cc2)c(C(=O)O)c1OC]

Potassium trimethylsilanoate (0.257 g) was added to a solution of ethyl 3-ethyl-6-(4-fluorobenzenesulphonylmethyl)-2-methoxybenzoate (Intermediate 23, 0.076 g) in dry THF (10 ml). The resultant mixture was stirred at room temperature for 3 days. The mixture was diluted with water and washed with ethyl acetate. The aqueous layer was acidified by careful addition of concentrated hydrochloric acid and then extracted with ethyl acetate, washed with water, dried (MgSO$_4$) and filtered. The filtrate was evaporated to dryness and the residue was purified by preparative HPLC (C18), eluting with a mixture of methanol and water containing 0.1% formic acid with a gradient of 50-80% to give 3-ethyl-6-(4-fluorobenzenesulphonyl-methyl)-2-methoxybenzoic acid (0.014 g) as a white solid.

NMR (CDCl$_3$) δ 7.8 (m, 2H), 7.4 (d, 1H), 7.15 (m, 3H), 4.85 (s, 2H), 3.85 (s, 3H), 2.7 (q, 2H), 1.25 (t, 3H).

LCMS (Method D) r/t 9.6 (M+Na) 375.

Example 36

6-(Benzenesulphonylmethyl)-3-cyano-2-methoxybenzoic acid

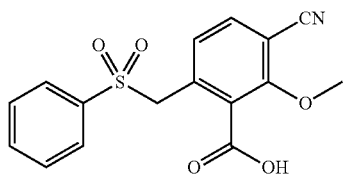 [SMILES: COc1c(C#N)ccc(CS(=O)(=O)c2ccccc2)c1C(=O)O]

A mixture of 6-(benzenesulphonylmethyl)-3-bromo-2-methoxybenzoic acid (Example 7, 0.1 g), zinc cyanide (0.036 g) and tetrakis-(triphenylphosphine) palladium (0.015 g) in DMF was stirred and heated in the microwave at 180° C. for 10 minutes. After cooling, the mixture was diluted with t-butyl methyl ether, dried (MgSO$_4$) and filtered. The filtrate was evaporated to dryness and the residue was purified by preparative HPLC (C18), eluting with a mixture of methanol and water containing 0.1% formic acid with a gradient of 35-98% to give 6-(benzenesulphonylmethyl)-3-cyano-2-methoxybenzoic acid (0.02 g) as a white solid.

NMR (DMSO-d$_6$) δ 7.9 (d, 1H), 7.75 (t, 1H), 7.7 (d, 2H), 7.65 (t, 2H), 7.1 (d, 1H), 4.9 (s, 2H), 3.95 (s, 3H).

LCMS (Method C) r/t 3.44 (M+Na) 354, (M−H) 330.

Example 37

6-(Benzenesulphonylmethyl)-3-(furan-2-yl)-2-methoxybenzoic acid

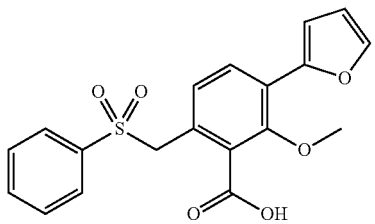 [SMILES: COc1c(-c2ccco2)ccc(CS(=O)(=O)c2ccccc2)c1C(=O)O]

A mixture of 6-(benzenesulphonylmethyl)-3-bromo-2-methoxybenzoic acid (Example 7, 0.1 g), 2-furylboronic acid (0.031 g), tri-tert-butylphosphinium tetrafluoroborate (0.0074 g), cesium carbonate (0.253 g) and tris-(dibenzylideneacetone)dipalladium (0.012 g) in dioxane (3 ml) and water (0.4 ml) was sealed in a vial under nitrogen and heated at 80° C. for 2 hours. After cooling, the mixture was diluted with t-butyl methyl ether, dried (MgSO$_4$) and filtered. The filtrate was evaporated to dryness and the residue was purified twice by preparative HPLC (C18), eluting with a mixture of methanol and water containing 0.1% formic acid with a gradient of 25-98% to give 6-(benzenesulphonylmethyl)-3-(furan-2-yl)-2-methoxybenzoic acid (0.032 g) as a white solid.

NMR (DMSO-d$_6$) δ 13.6-13.2 (br s, 1H), 7.85 (d, 1H), 7.7 (m, 4H), 7.6 (t, 2H), 7.05 (d, 1H), 7.0 (d, 1H), 6.65 (d. 1H), 4.75 (s, 2H), 3.7 (s, 3H).

LCMS (Method C) r/t 4.22 (M+Na) 395, (M−H) 371.

Example 38

2-(2-Aminoethoxy)-6-(benzenesulphonylmethyl)-3-(furan-3-yl)benzoic acid hydrochloride

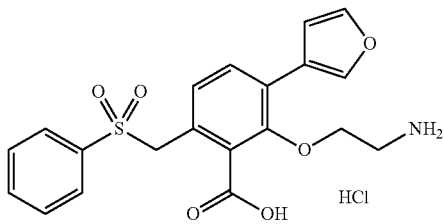 [SMILES: NCCOc1c(-c2ccoc2)ccc(CS(=O)(=O)c2ccccc2)c1C(=O)O ; Cl]

Hydrogen chloride (4M in dioxane, 2 ml) was added to a solution of 6-(benzenesulphonylmethyl)-2-[2-(t-butoxycarbonyl)aminoethoxy]-3-(furan-3-yl)benzoic acid (Intermediate 6, 0.018 g) in dioxane (0.5 ml) and the resultant mixture was stirred at room temperature for 2 hours. The mixture was evaporated to dryness and the residue was triturated with ether. The solid was collected by filtration then purified by chromatography on silica, eluting with a mixture of DCM, methanol, acetic acid and water in a ratio of 240:20:3:2 changing to 120:15:3:2. After evaporation of the solvent, the residue was treated with hydrochloric acid (1M) and evaporated to dryness to give 2-(2-aminoethoxy)-6-(benzenesulphonylmethyl)-3-(furan-3-yl)benzoic acid hydrochloride (0.008 g) as a white solid.

NMR (DMSO-d$_6$) δ 14.0-13.4 (br s, 1H), 8.2 (s, 1H), 8.0 (br s, 3H), 7.8 (s, 1H), 7.75 (m, 3H), 7.6 (m, 3H), 7.05 (d, 1H), 7.0 (d, 1H), 4.8 (s, 2H), 3.9 (t, 2H), 3.1 (br s, 2H).

LCMS (Method C) r/t 2.91 (M+H) 402.

Example 39

2-(2-Aminoethoxy)-6-(3-chlorobenzenesulphonylmethyl)-3-(furan-3-yl)benzoic acid hydrochloride

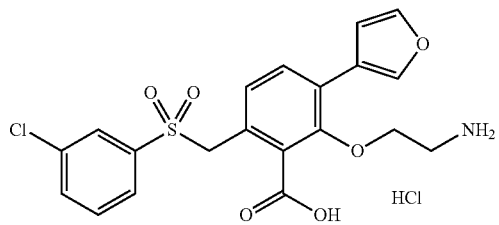 [SMILES: NCCOc1c(-c2ccoc2)ccc(CS(=O)(=O)c2cccc(Cl)c2)c1C(=O)O ; Cl]

Prepared by proceeding in a similar manner to Example 38, starting from 2-[2-(t-butoxycarbonyl)aminoethoxy]-6-(3-chlorobenzenesulphonylmethyl-3-(furan-3-yl)benzoic acid (Intermediate 7).

NMR (DMSO-d$_6$) δ 13.8-13.3 (br s, 1H), 8.2 (s, 1H), 8.1 (br s, 3H), 7.85 (m, 2H), 7.7 (s, 1H), 7.6 (m, 3H), 7.1 (d, 1H), 7.0 (s, 1H), 4.9 (s, 2H), 3.9 (t, 2H), 3.1 (br s, 2H).

LCMS (Method C) r/t 3.2 (M+H) 436 and 438.

Example 40

2-(2-Aminoethoxy)-6-(4-fluorobenzenesulphonylmethyl)-3-(furan-3-yl)benzoic acid hydrochloride

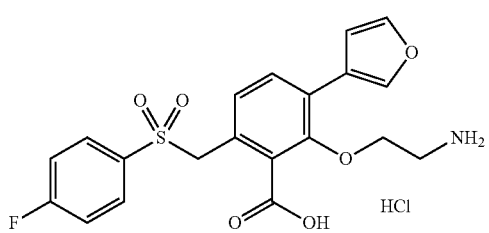 [SMILES: NCCOc1c(-c2ccoc2)ccc(CS(=O)(=O)c2ccc(F)cc2)c1C(=O)O ; Cl]

Prepared by proceeding in a similar manner to Example 38, starting from 2-[2-(t-butoxycarbonyl)aminoethoxy]-6-(4-fluorobenzenesulphonyl-methyl-3-(furan-3-yl)benzoic acid (Intermediate 8).

NMR (DMSO-d$_6$) δ 8.2 (s, 1H), 8.05 (br s, 3H), 7.85 (s, 1H), 7.75 (m, 2H), 7.65 (d, 1H), 7.45 (t, 2H), 7.1 (d, 1H), 7.0 (s, 1H), 4.8 (s, 2H), 3.9 (t, 2H), 3.1 (br s, 2H).

LCMS (Method C) r/t 3.02 (M+H) 420.

Example 41

2-(2-Aminoethoxy)-3-(furan-3-yl)-6-(2-methoxybenzenesulphonylmethyl)benzoic acid hydrochloride

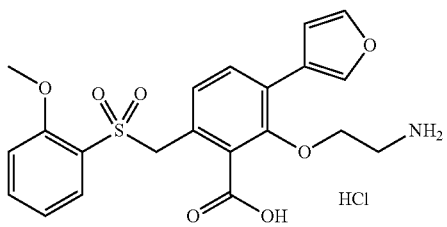 [SMILES: COc1ccccc1S(=O)(=O)Cc1ccc(-c2ccoc2)c(OCCN)c1C(=O)O ; Cl]

Prepared by proceeding in a similar manner to Example 38, starting from 2-[2-(t-butoxycarbonyl)aminoethoxy]-3-(furan-3-yl)-6-(2-methoxybenzenesulphonylmethyl)benzoic acid (Intermediate 9).

NMR (DMSO-$d_6$) δ 13.7-13.3 (br s, 1H), 8.2 (s, 1H), 8.05 (br s, 3H), 7.8 (s, 1H), 7.7 (t, 1H), 7.6 (m, 2H), 7.3 (d, 1H), 7.15 (d, 1H), 7.1 (t, 1H), 6.95 (s, 1H), 4.9 (s, 2H), 4.0 (s, 3H), 3.9 (t, 2H), 3.1 (br s, 2H).

LCMS (Method C) r/t 2.92 (M+H) 432.

Example 42

6-(Benzenesulphonylmethyl)-2-(2-dimethylaminoethoxy)-3-(furan-3-yl)benzoic acid hydrochloride

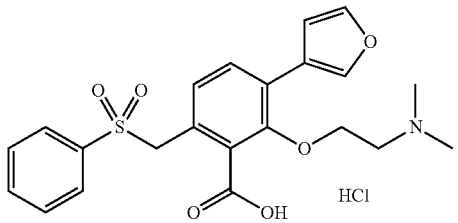 [SMILES: CN(C)CCOc1c(-c2ccoc2)ccc(CS(=O)(=O)c2ccccc2)c1C(=O)O ; Cl]

Prepared by proceeding in a similar manner to Example 3, starting from methyl 6-(benzenesulphonylmethyl)-2-(2-dimethylaminoethoxy)-3-(furan-3-yl)benzoate (Intermediate 17). The product after chromatography was treated with hydrochloric acid (1M) and then evaporated to dryness. The residue was triturated with ether and the solid was collected by filtration.

NMR (DMSO-$d_6$) δ 10.4-9.8 (br s, 1H), 8.25 (s, 1H), 7.85 (s, 1H), 7.75 (m, 3H), 7.6 (m, 3H), 7.1 (d, 1H), 7.0 (s, 1H), 4.8 (s, 2H), 3.95 (t, 2H), 3.4 (t, 2H), 2.8 (s, 6H).

LCMS (Method C) r/t 2.99 (M+H) 430.

Example 43

6-(2-Chlorobenzenesulphonylmethyl)-3-(furan-3-yl)-2-methoxybenzoic acid

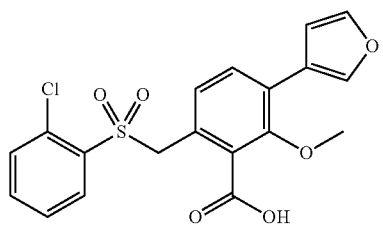 [SMILES: COc1c(-c2ccoc2)ccc(CS(=O)(=O)c2ccccc2Cl)c1C(=O)O]

Prepared by proceeding in a similar manner to Example 32, starting from methyl 6-(2-chlorobenzenesulphonylmethyl)-3-(furan-3-yl)-2-methoxybenzoate (Intermediate 94).

NMR (CDCl$_3$) δ 7.95 (d, 2H), 7.6 (m, 2H), 7.5 (m, 2H), 7.4 (m, 1H), 7.2 (d, 1H), 6.85 (s, 1H), 5.05 (s, 2H), 3.7 (s, 3H).

LCMS (Method C) r/t 4.29 (M+Na) 429, (M–H) 405.

Example 44

6-(3-Fluorobenzenesulphonylmethyl)-3-(furan-3-yl)-2-methoxybenzoic acid

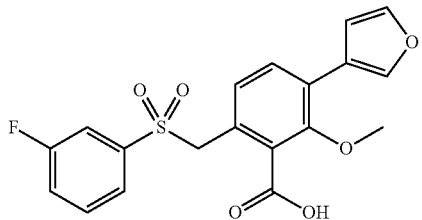 [SMILES: COc1c(-c2ccoc2)ccc(CS(=O)(=O)c2cccc(F)c2)c1C(=O)O]

Prepared by proceeding in a similar manner to Example 27, starting from methyl 6-(3-fluorobenzenesulphonylmethyl)-3-(3-furan-3-yl)-2-methoxybenzoate (Intermediate 95).

NMR (CDCl$_3$) δ 7.95 (s, 1H), 7.6 (m, 3H), 7.45 (m, 2H), 7.35 (t, 1H), 7.2 (d, 1H), 6.8 (s, 1H), 4.8 (s, 2H), 3.75 (s, 3H).

LCMS (Method C) r/t 4.24 (M+Na) 413, (M–H) 389.

Example 45

6-(2-Fluorobenzenesulphonylmethyl)-3-(furan-3-yl)-2-methoxybenzoic acid

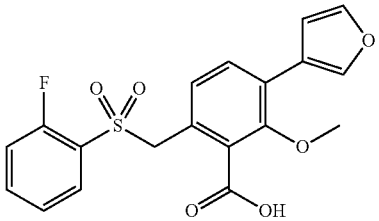

Prepared by proceeding in a similar manner to Example 27, starting from methyl 6-(2-fluorobenzenesulphonylmethyl)-3-(furan-3-yl)-2-methoxybenzoate (Intermediate 96).

NMR (CDCl$_3$) δ 8.0 (s, 1H), 7.8 (t, 1H), 7.65 (m, 1H), 7.5 (m, 2H), 7.25 (m, 3H), 6.8 (s, 1H), 5.0 (s, 2H), 3.7 (s, 3H).

LCMS (Method C) r/t 4.14 (M+Na) 413 (M–H) 389.

Example 46

3-(Furan-3-yl)-2-methoxy-6-(3-methoxybenzenesulphonylmethyl)benzoic acid

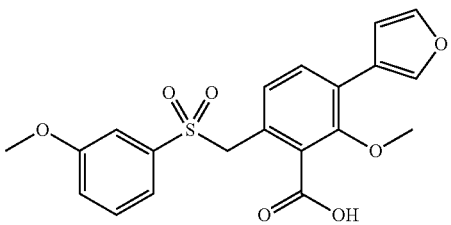 [SMILES: COc1cccc(S(=O)(=O)Cc2ccc(-c3ccoc3)c(OC)c2C(=O)O)c1]

Prepared by proceeding in a similar manner to Example 27, starting from methyl 3-(furan-3-yl)-2-methoxy-6-(3-methoxybenzenesulphonylmethyl)-benzoate (Intermediate 97).

NMR (CDCl$_3$) δ 7.95 (s, 1H), 7.55 (m, 2H), 7.4 (m, 2H), 7.25 (m, 1H), 7.2 (d, 1H), 7.15 (m, 1H), 6.8 (s, 1H), 4.8 (s, 2H), 3.8 (s, 3H), 3.7 (s, 3H).

LCMS (Method C) r/t 4.21 (M+Na) 425 (M−H) 401.

Example 47

2-(2-Aminoethoxy)-6-(benzenesulphonylmethyl)-3-ethylbenzoic acid hydrochloride

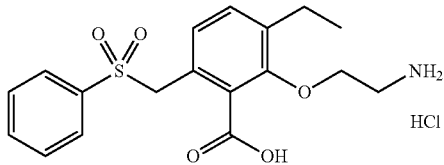 [SMILES: CCc1ccc(CS(=O)(=O)c2ccccc2)c(C(=O)O)c1OCCN ; Cl]

Prepared by proceeding in similar manner to Example 33, starting from 6-(benzenesulphonylmethyl)-2-(2-t-butoxycarbonylaminoethoxy)-3-ethylbezoic acid (Intermediate 107).

NMR (DMSO-d$_6$) δ 13.12.5 (br s, 1H), 8.2 (br s, 3H), 7.75 (t, 1H), 7.5 (d, 2H), 7.4 (t, 2H), 7.3 (d, 1H), 7.0 (d, 1H), 4.8 (s, 2H), 4.05 (t, 2H), 3.1 (br s, 2H), 2.7 (q, 2H), 1.2 (t, 3H).

LCMS (Method C) r/t 2.76 (M+H) 364.

Example 48

2-(3-Aminopropoxy)-6-(benzenesulphonylmethyl)-3-(furan-3-yl)benzoic acid hydrochloride

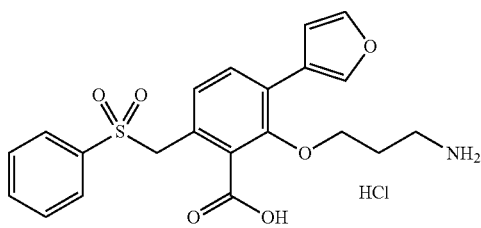 [SMILES: NCCCOc1c(-c2ccoc2)ccc(CS(=O)(=O)c2ccccc2)c1C(=O)O ; Cl]

Prepared by proceeding in similar manner to Example 33, starting from 6-(benzenesulphonylmethyl)-2-(3-t-butoxycarbonylaminopropoxy)-3-(furan-3-yl)benzoic acid (Intermediate 106).

NMR (DMSO-d$_6$) δ 13.8-13.2 (br s, 1H), 8.15 (s, 1H), 7.95 (br s, 3H), 7.8 (s, 1H), 7.75 (m, 3H), 7.6 (m, 3H), 7.0 (m, 2H), 4.8 (s, 2H), 3.8 (t, 2H), 2.9 (br s, 2H), 1.95 (m, 2H).

LCMS (Method C) r/t 3.02 (M+H) 416.

Example 49

6-(Benzenesulphonylmethyl)-2-methoxy-3-(thien-2-yl)benzoic acid

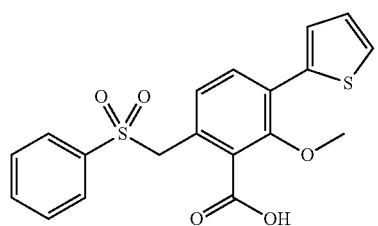

Prepared by proceeding in a similar manner to Example 3, starting from methyl 6-(benzenesulphonylmethyl)-2-methoxy-3-(thien-2-yl)benzoate (Intermediate 112).

NMR (DMSO-d$_6$) δ 7.8 (m, 4H), 7.6 (m, 4H), 7.15 (dd, 1H), 7.0 (d, 1H), 4.8 (s, 2H), 3.65 (s, 3H);

LCMS (Method C) r/t 4.36 (M+Na) 411, (M−H) 387

Example 50

6-(Benzenesulphonylmethyl)-2-methyoxy-3-(thien-3-yl)benzoic acid

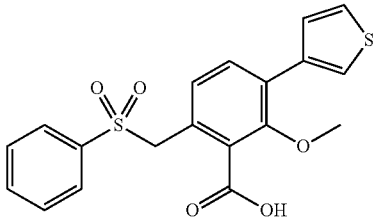

Prepared by proceeding in a similar manner to Example 3, starting from methyl 6-(benzenesulphonylmethyl)-2-methoxy-3-(thien-3-yl)benzoate (Intermediate 113).

NMR (DMSO-d$_6$) δ 13.4-13.2 (br s, 1H), 7.9 (s, 1H), 7.75 (m, 3H), 7.65 (m, 3H), 7.6 (m, 1H), 7.55 (d, 1H), 7.05 (d, 1H), 4.75 (s, 2H), 3.45 (s, 3H).

LCMS (Method C) r/t 4.36 (M+Na) 411.

Example 51

6-(4-Fluorobenzenesulphonylmethyl)-3-(furan-3-yl)-2-methoxybenzoic acid

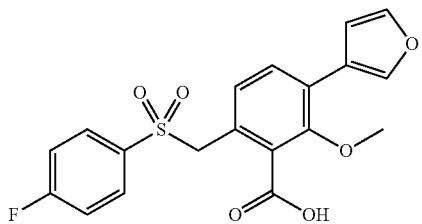 [SMILES: COc1c(-c2ccoc2)ccc(CS(=O)(=O)c2ccc(F)cc2)c1C(=O)O]

Prepared by proceeding in a similar manner to Example 27, starting from methyl 6-(4-fluorobenzenesulphonylmethyl)-3-(furan-3-yl)-2-methoxybenzoate (Intermediate 116).

NMR (DMSO-d$_6$) δ 8.15 (s, 1H), 7.8 (s, 1H), 7.75 (m, 2H), 7.65 (d, 1H), 7.45 (t, 2H), 7.05 (d, 1H), 7.0 (s, 1H), 4.75 (s, 2H), 3.6 (s, 3H).

LCMS (Method C) r/t 4.2 (M+Na) 413 (M−H) 389.

Example 52

6-(Benzenesulphonylmethyl)-2-(cyanomethoxy)-3-(furan-3-yl)benzoic acid

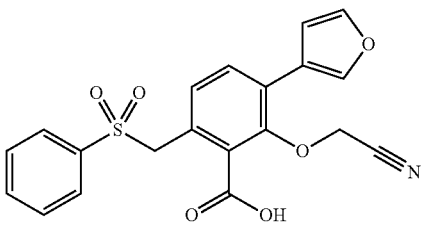 [SMILES: N#CCOc1c(-c2ccoc2)ccc(CS(=O)(=O)c2ccccc2)c1C(=O)O]

t-Butyl 6-(benzenesulphonylmethyl)-2-(cyanomethoxy)-3-(furan-3-yl)benzoate (Intermediate 119, 0.043 g) was dissolved in DCM (2 ml) and water (1 drop) was added followed by trifluoroacetic acid (1 ml). The mixture was stirred at room temperature for 15 minutes then it was evaporated to dryness. The residue was redissolved in DCM and re-evaporated twice. The residue was purified by preparative HPLC (C18) eluting with a mixture of acetonitrile and water containing 0.1% formic acid with a gradient of 40-55%. After evaporation, the residue was triturated with ether and the solid was collected by filtration to give 6-(benzenesulphonylmethyl)-2-(cyanomethoxy)-3-(furan-3-yl)benzoic acid (0.024 g) as a white solid.

NMR (DMSO-$d_6$) δ 13.9-13.5 (br s, 1H), 8.2 (s, 1H), 7.85 (s, 1H), 7.75 (t, 1H), 7.7 (m, 2H), 7.6 (m, 3H), 7.1 (d, 1H), 7.0 (s, 1H), 4.85 (s, 2H), 4.7 (s, 2H).

LCMS (Method C) r/t 3.98 (M+Na) 420.

Example 53

2-(2-Aminoethylamino)-6-(benzenesulphonylmethyl)-3-(furan-3-yl)-benzoic acid hydrochloride

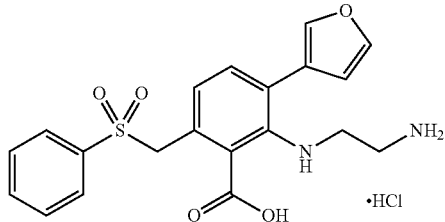 [SMILES: NCCNc1c(-c2ccoc2)ccc(CS(=O)(=O)c2ccccc2)c1C(=O)O ; Cl]

6-(Benzenesulphonylmethyl)-2-[2-(t-butoxycarbonylamino)ethylamino]-3-(furan-3-yl)benzoic acid (Intermediate 121, 0.1 g) was added to a solution of trifluoroacetic acid (3 ml) in DCM (3 ml) and the resultant mixture was stirred for 45 minutes. The mixture was evaporated to dryness and the residue was purified by chromatography on silica, eluting with a mixture of DCM:MeOH:AcOH:water (120:15:3:2). The volume of the product containing fractions was reduced to 5 mL, concentrated HCl (1 ml) was added and the mixture was evaporated to dryness. The solid was triturated with diethyl ether, collected by filteration and dried at 60° C. under vacuum to give 2-(2-aminoethylamino)-6-(benzenesulphonylmethyl)-3-(furan-3-yl)benzoic acid hydrochloride (0.056 g), as a white solid.

NMR (DMSO-$d_6$) δ 8.1 (dd, 1H), 7.85 (br, 1H), 7.8-7.75 (m, 1H), 7.75 (m, 3H), 7.65 (m, 2H), 7.35 (d, 1H), 6.9 (dd, 1H), 6.8 (d, 1H), 4.9 (s, 2H), 3.0 (t, 2H), 2.75 (m, 2H).

LCMS (Method C) r/t 2.94 (M+H) 401.

Example 54

6-(Benzenesulphonylmethyl)-3-(furan-3-yl)-2-[2-(methylamino)-ethoxy]benzoic acid hydrochloride

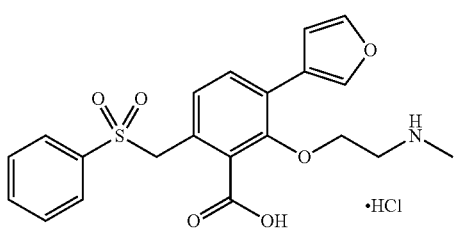 [SMILES: CNCCOc1c(-c2ccoc2)ccc(CS(=O)(=O)c2ccccc2)c1C(=O)O ; Cl]

Prepared by proceeding in a similar manner to Example 38, starting from 6-(benzenesulphonylmethyl)-2-[2-(N-t-butoxycarbonyl-N-methylamino)ethoxy]-3-(furan-3-yl)benzoic acid (Intermediate 124).

NMR (DMSO-$d_6$) δ 8.9 (br, s, 1H), 8.2 (dd, 1H), 7.8 (t, 1H), 7.75-7.7 (m, 3H), 7.65 (m, 2H), 7.6 (d, 1H), 7.05 (d, 1H), 7.0 (d, d1H), 4.8 (s, 2H), 3.95 (t, 2H), 3.2 (t, 2H), 2.6 (s, 3H).

LCMS (Method C) r/t 2.95 (M+H) 416.

Example 55

6-(Benzenesulphonylmethyl)-3-ethyl-2-(2-methyl-2H-pyrazol-3-yl)-benzoic acid

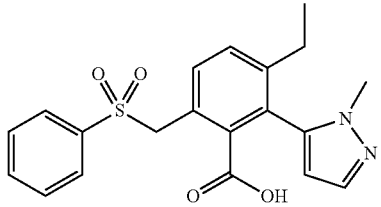 [SMILES: CCc1ccc(CS(=O)(=O)c2ccccc2)c(C(=O)O)c1-c1ccnn1C]

Prepared by proceeding in a similar manner to Example 3, starting from methyl 6-(benzenesulphonylmethyl)-3-ethyl-2-(2-methyl-2H-pyrazol-3-yl)benzoate (Intermediate 126) as a yellow solid.

NMR (DMSO-$d_6$) δ 7.7 (m, 1H), 7.65 (m, 2H), 7.6 (m, 2H), 7.45 (d, 1H), 7.4 (m, 2H), 6.1 (d, 1H), 4.85-4.75 (m, 2H), 3.4 (s, 3H), 2.35 (m, 1H), 2.15 (m, 1H), 1.0 (t, 3H).

LCMS (Method C) r/t 3.88 (M+H) 385.

Example 56

2-(2-Aminopropoxy)-6-(benzenesulphonylmethyl)-3-(furan-3-yl)-benzoic acid hydrochloride

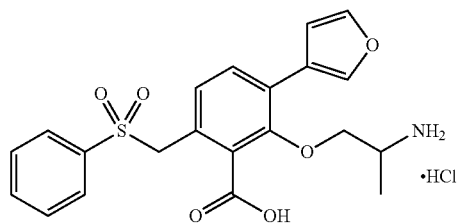 [SMILES: CC(N)COc1c(-c2ccoc2)ccc(CS(=O)(=O)c2ccccc2)c1C(=O)O ; Cl]

Prepared by proceeding in a similar manner to Example 38, starting from 6-(benzenesulphonylmethyl)-2-[2-(N-t-butoxycarbonylamino)propoxy]-3-(furan-3-yl)benzoic acid (Intermediate 128).

NMR (DMSO-$d_6$) δ 8.2 (s, 1H), 8.1 (br, s, 2H), 7.8 (t, 1H), 7.75-7.65 (m, 3H), 7.65 (d, 2H), 7.6 (d, 1H), 7.05 (d, 1H), 7.0 (d, 1H), 4.8 (s, 2H), 3.8 (dd, 1H), 3.7 (dd, 1H), 3.45-3.35 (m, 1H), 1.2 (d, 3H).

LCMS (Method C) r/t 2.98 (M+H) 416.

Example 57

6-(Benzenesulphonylmethyl)-3-ethyl-2-(1-methyl-1H-pyrazol-3-yl)-benzoic acid

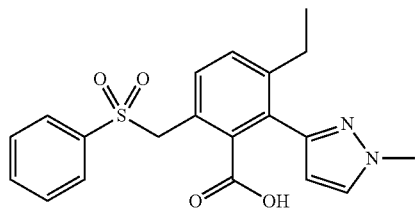 [SMILES: CCc1ccc(CS(=O)(=O)c2ccccc2)c(C(=O)O)c1-c1ccn(C)n1]

Prepared by proceeding in a similar manner to Example 3, starting from methyl 6-(benzenesulphonylmethyl)-3-ethyl-2-(1-methyl-1H-pyrazol-3-yl)benzoate (Intermediate 130).

NMR (DMSO-$d_6$) δ 7.75 (m, 3H), 7.7 (d, 1H), 7.65-7.6 (m, 2H), 7.3 (d, 1H), 7.15 (d, 1H), 6.15 (d, 1H), 4.75 (s, 2H), 3.85 (s, 3H), 2.5 (q, 2H), 1.0 (t, 3H).

LCMS (Method C) r/t 3.86 (M+H) 385.

Example 58

2-(3-Aminopropyl)-6-(benzenesulphonylmethyl)-3-(furan-3-yl)-benzoic acid hydrochloride

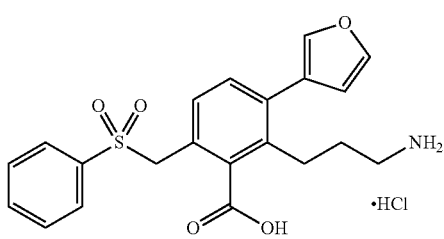 [SMILES: NCCCc1c(-c2ccoc2)ccc(CS(=O)(=O)c2ccccc2)c1C(=O)O ; Cl]

Concentrated hydrochloric acid was added to a solution of methyl 6-(benzenesulphonylmethyl)-2-(3-t-butoxycarbonylaminopropyl)-3-(furan-3-yl)benzoate (Intermediate 131) in 1,4-dioxane (8 ml) and water (2 ml) and the mixture was stirred for 30 minutes. This was evaporated to dryness and the residue was purified by chromatography on silica eluting with a mixture of DCM:MeOH:AcOH:water (120:15:3:2) to give methyl 2-(3-aminopropyl)-6-(benzenesulphonylmethyl)-3-(furan-3-yl)benzoate as a colourless gum. This material was dissolved in a mixture of dioxane and water (3:1) and lithium hydroxide monohydrate (0.188 g) was added. The reaction was heated in the microwave at 150° C. for one hour. After cooling, concentrated hydrochloric acid was added and the mixture was evaporated to dryness. The residue was purified by chromatography on silica eluting with a mixture of DCM:MeOH:AcOH:water (240:20:3:2), then again with DCM:MeOH:AcOH:water (120:15:3:2). The volume of the product containing fractions was reduced to 5 ml by evaporation and concentrated hydrochloric acid (1 ml) was added to the mixture. The mixture was evaporated to dryness and the residue was triturated with diethyl ether and the solid was collected by filtration and dried under vacuum at 60° C. to give 2-(3-aminopropyl)-6-(benzenesulphonylmethyl)-3-(furan-3-yl)benzoic acid hydrochloride (0.045 g), as a white solid.

NMR (DMSO-$d_6$) δ 7.9 (s, 1H), 7.8 (t, 3H,), 7.75 (m, 3H), 7.65 (d, 1H), 7.3 (d, 1H), 7.15 (d, 1H), 6.75 (dd, 1H), 4.75 (s, 2H), 2.75 (m, 2H), 2.6 (m, 2H), 1.65 (m, 2H).

LCMS (Method C) r/t 2.96 (M+H) 400.

Example 59

6-(Benzenesulphonylmethyl)-2-methoxy-3-(pyrazol-1-yl)benzoic acid

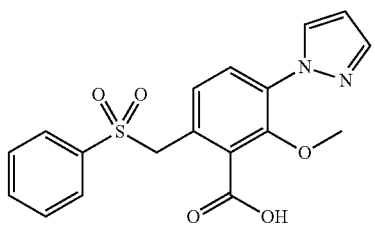 [SMILES: COc1c(-n2cccn2)ccc(CS(=O)(=O)c2ccccc2)c1C(=O)O]

A mixture of 6-(benzenesulphonylmethyl)-3-bromo-2-methoxybenzoic acid (Intermediate 133, 0.1 g), copper (II) oxide (0.004 g), cesium carbonate (0.254 g) and pyrazole (0.018 g) in DMF (2 ml) was sealed in a microwave vial in an atmosphere of nitrogen and heated at 100° C. for 18 hours. After cooling, ethyl acetate was added, and the mixture was filtered through celite. The filtrate was evaporated to dryness and the residue was purified by HPLC, eluting with a mixture of acetonitrile and water containing 0.1% formic acid with a gradient of 40-60% to give 6-(benzenesulphonylmethyl)-2-methoxy-3-(pyrazol-1-yl)benzoic acid (0.026 g) as a white solid.

NMR (DMSO-$d_6$) δ 8.2 (dd, 1H), 7.8 (m, 1H), 7.75 (m, 3H), 7.7-7.6 (m, 3H), 7.1 (d, 1H), 6.6 (dd, 1H), 4.8 (s, 2H), 3.4 (s, 3H).

LCMS (Method C) r/t 3.52 (M+H) 373.

Example 60

2-(Benzenesulphonylmethyl)-5-(2-methyl-2H-pyrazol-3-yl)benzoic acid

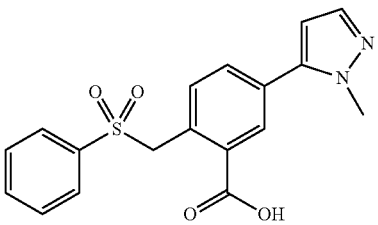

Prepared as a white solid by proceeding in a similar manner to Example 3, starting from methyl 2-(benzenesulphonylmethyl)-5-(2-methyl-2H-pyrazol-3-yl)benzoate (Intermediate 134).

NMR (DMSO-$d_6$) δ 7.95 (d, 1H), 7.75 (m, 1H), 7.7 (m, 3H), 7.6 (m, 2H), 7.5 (d, 1H), 7.35 (d, 1H), 6.5 (d, 1H), 5.3 (s, 2H), 3.85 (s, 3H).

LCMS (Method C) r/t 3.45 (M+H) 357.

Example 61

2-(Benzenesulphonylmethyl)naphthalene-1-carboxylic acid

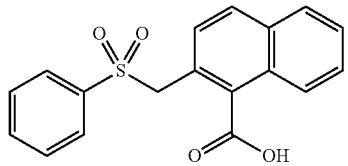 [SMILES: O=C(O)c1c(CS(=O)(=O)c2ccccc2)ccc2ccccc12]

Prepared by proceeding in a similar manner to Example 3, starting from methyl 2-(benzenesulphonylmethyl)naphthalene-1-carboxylate (Intermediate 135).

NMR (DMSO-$d_6$) δ 8.05-8.00 (m, 1H), 7.95 (m, 2H), 7.7 (m, 3H), 7.65-7.55 (m, 4H), 7.3 (d, 1H), 5.0 (s, 2H).
LCMS (Method C) r/t 3.99 (M+Na) 349.

Example 62

3-(Furan-3-yl)-6-(2-hydroxybenzenesulphonylmethyl)-2-methoxybenzoic acid

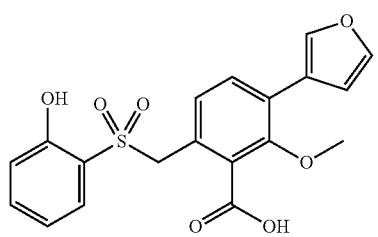 [SMILES: COc1c(-c2ccoc2)ccc(CS(=O)(=O)c2ccccc2O)c1C(=O)O]

Prepared by proceeding in a similar manner to Example 24, starting from methyl 3-(furan-3-yl)-6-(2-hydroxybenzenesulphonylmethyl)-2-methoxybenzoate (Intermediate 137).

NMR (DMSO-$d_6$) δ 8.15 (dd, 1H), 7.75 (t, 1H), 7.55 (d, 1H), 7.5 (m, 2H), 7.1 (d, 1H), 7.0 (d, 1H), 6.95 (dd, 1H), 6.9 (t, 1H), 4.85 (s, 2H), 3.6 (s, 3H).
LCMS (Method C) r/t 3.78 (M+Na) 411.

Example 63

3-(Furan-3-yl)-6-(3-hydroxybenzenesulphonylmethyl)-2-methoxy-benzoic acid

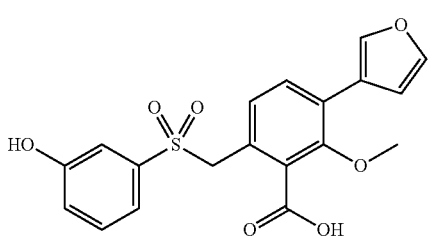 [SMILES: COc1c(-c2ccoc2)ccc(CS(=O)(=O)c2cccc(O)c2)c1C(=O)O]

Prepared by proceeding in a similar manner to Example 24, starting from methyl 3-(furan-3-yl)-6-(3-hydroxybenzenesulphonylmethyl)-2-methoxybenzoate (Intermediate 140)
NMR (DMSO-$d_6$) δ 10.2 (br, 1H), 8.2 (s, 1H), 7.8 (t, 1H), 7.65 (d, 1H), 7.45 (t, 1H), 7.15 (d, 1H), 7.1 (m, 2H), 7.0 (m, 2H), 4.7 (s, 2H), 3.65 (s, 3H).
LCMS (Method C) r/t 3.75 (M+Na) 411.

Example 64

2-(Benzenesulphonylmethyl)-5-(2-methylfuran-3-yl)benzoic acid

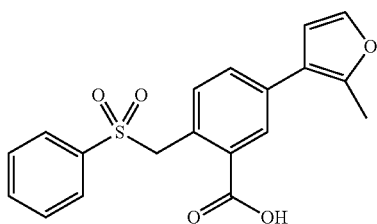

Prepared by proceeding in a similar manner to Example 3, starting from methyl 2-(benzenesulphonylmethyl)-5-(2-methylfuran-3-yl)benzoate (Intermediate 143) as a white solid.

NMR (DMSO-$d_6$) δ 7.9 (d, 1H), 7.7 (d, 1H), 7.65 (m, 2H), 7.6 (m, 4H), 7.25 (d, 1H), 6.75 (d, 1H), 5.2 (s, 2H), 2.45 (s, 3H).
LCMS (Method C) r/t 4.34 (M+Na) 379.

Example 65

6-(Benzenesulphonylmethyl)-3-ethyl-2-(1H-pyrazol-3-yl)benzoic acid

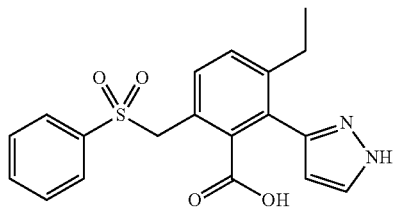 [SMILES: CCc1ccc(CS(=O)(=O)c2ccccc2)c(C(=O)O)c1-c1cc[nH]n1]

Prepared by proceeding in a similar manner to Example 3, starting from methyl 6-(benzenesulphonylmethyl)-3-ethyl-2-(1H-pyrazol-3-yl)benzoate (Intermediate 144).

NMR (DMSO-$d_6$) δ 7.75 (m, 3H), 7.65 (t, 3H), 7.35 (d, 1H), 7.15 (d, 1H), 6.2 (d, 1H), 4.75 (s, 2H), 2.5 (q, 2H), 1.0 (t, 3H).
LCMS (Method C) r/t 3.67 (M+H) 371.

Example 66

3-(Furan-3-yl)-2-methoxy-6-(piperidine-1-ylsulphonylmethyl)benzoic acid

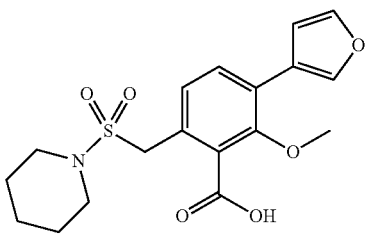 [SMILES: COc1c(-c2ccoc2)ccc(CS(=O)(=O)N2CCCCC2)c1C(=O)O]

Prepared by proceeding in a similar manner to Example 3, starting from methyl 3-(furan-3-yl)-2-methoxy-6-(piperidine-1-ylsulphonylmethyl)benzoate (Intermediate 146) as a white solid.

NMR (CDCl₃) δ 7.9 (dd, 1H), 7.55 (d, 1H), 7.5 (t, 1H), 7.3 (d, 1H), 6.75 (dd, 1H), 4.5 (s, 2H), 3.75 (s, 3H), 3.2 (t, 4H), 1.6 (m, 4H), 1.55 (m, 2H).

LCMS (Method C) r/t 4.21 (M+Na) 402.

Example 67

3-(Furan-3-yl)-2-methoxy-6-(pyrrolidin-1-ylsulphonylmethyl)-benzoic acid

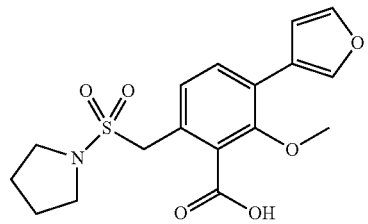 [SMILES: COc1c(-c2ccoc2)ccc(CS(=O)(=O)N2CCCC2)c1C(=O)O]

Prepared by proceeding in a similar manner to Example 3, starting from methyl 3-(furan-3-yl)-2-methoxy-6-(pyrrolidin-1-ylsulphonylmethyl)benzoate (Intermediate 149) as a white solid.

NMR (CDCl₃) δ 7.95 (s, 1H), 7.55 (d, 1H), 7.5 (s, 1H), 7.35 (d, 1H), 6.8 (s, 1H), 4.6 (s, 2H), 3.75 (s, 3H), 3.3 (t, 4H), 1.9 (m, 4H).

LCMS (Method C) r/t 3.97 (M+Na) 388.

Example 68

6-[2-(2-Diethylaminoethylamino)benzenesulphonylmethyl]-3-(furan-3-yl)-2-methoxybenzoic acid

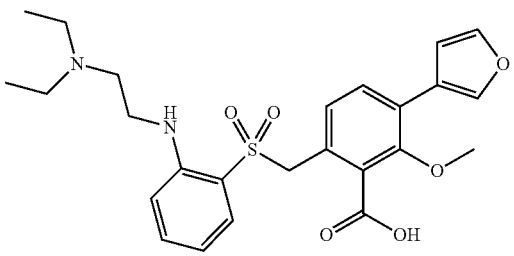 [SMILES: CCN(CC)CCNc1ccccc1S(=O)(=O)Cc1ccc(-c2ccoc2)c(OC)c1C(=O)O]

Prepared by proceeding in a similar manner to Example 3, starting from methyl 6-[2-(2-diethylaminoethylamino)benzenesulphonylmethyl]-3-(furan-3-yl)-2-methoxybenzoate (Intermediate 151) as a white solid.

NMR (CDCl₃) δ 8.0 (s, 1H), 7.85 (d, 1H), 7.45 (m, 1H), 7.4 (d, 1H), 7.3 (d, 1H), 6.85 (t, 1H), 6.8 (d, 1H), 6.75 (d, 1H), 6.5 (s, 1H), 3.8 (s, 3H), 3.55 (s, 2H), 3.35 (s, 2H), 3.2 (s, 4H), 1.45 (m, 2H), 1.35 (t, 6H).

LCMS (Method C) r/t 3.42 (M+H) 487.

Example 69

6-(Benzenesulphonylmethyl)-2-ethyl-3-(furan-3-yl)benzoic acid

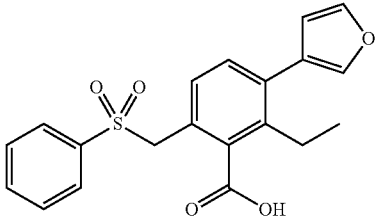

Lithium hydroxide monohydrate (0.075 g) was added to a solution of methyl 6-(benzenesulphonylmethyl)-2-ethyl-3-(furan-3-yl)benzoate (Intermediate 152, 0.092 g) in dioxane (1 ml) and water (1 ml) and the resultant solution was stirred and heated in the microwave at 150° C. for 4.5 hours. Ethyl acetate and water were added and the organic layer was separated, then acidified with concentrated hydrochloric acid. The mixture was extracted with ethyl aceate, dried (Na₂SO₄) and filtered. The filtrate was evaporated to dryness then azeotroped with toluene. The residue was triturated with ether and the solid was collected by filtration and dried to give 6-(benzenesulphonylmethyl)-2-ethyl-3-(furan-3-yl)benzoic acid (0.027 g) as a white solid.

NMR (DMSO-d₆) δ 7.85 (dd, 1H,), 7.8 (t, 1H), 7.75 (m, 3H), 7.6 (dd, 2H), 7.3 (d, 1H), 7.1 (d, 1H), 6.7 (dd, 1H), 4.7 (s, 2H), 2.7 (q, 2H), 0.95 (t, 3H).

LCMS (Method C) r/t 4.44 (M+Na) 393.

Example 70

6-[2-(2-Diethylaminoethoxy)benzenesulphonylmethyl]-3-(furan-3-yl)-2-methoxybenzoic acid

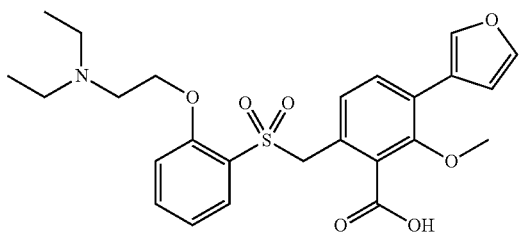 [SMILES: CCN(CC)CCOc1ccccc1S(=O)(=O)Cc1ccc(-c2ccoc2)c(OC)c1C(=O)O]

Prepared by proceeding in a similar manner to Example 69, starting from methyl 6-[2-(2-diethylaminoethoxy)benzenesulphonylmethyl]-3-(furan-3-yl)-2-methoxybenzoate (Intermediate 153) as a white solid.

NMR (DMSO-d₆) δ 8.15 (s, 1H), 7.75 (t, 2H), 7.65 (d, 2H), 7.35 (d, 1H), 7.15 (d, 1H), 7.1 (d, 1H), 7.0 (s, 1H), 4.9 (s, 2H), 4.6 (t, 2H), 3.7 (t, 2H), 3.6 (s, 3H), 3.4 (dd, 4H), 1.3 (t, 6H).

LCMS (Method C) r/t 3.30 (M+H) 488.

Example 71

6-(Benzenesulphonylmethyl)-3-(furan-3-yl)-2-(prop-1-yn-1-yl)benzoic acid

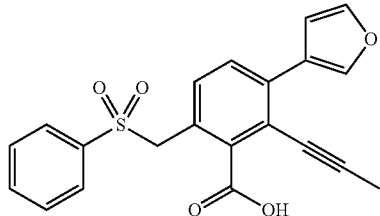 [SMILES: CC#Cc1c(-c2ccoc2)ccc(CS(=O)(=O)c2ccccc2)c1C(=O)O]

Prepared by proceeding in a similar manner to Example 3, starting from methyl 6-(benzenesulphonylmethyl)-3-(furan-3-yl)-2-(prop-1-yn-1-yl)benzoate (Intermediate 154) as a white solid.

NMR (DMSO-$d_6$) δ 8.25 (s, 1H), 7.75 (t, 1H), 7.75 (m, 3H), 7.6 (t, 2H), 7.55 (d, 1H), 7.2 (d, 1H), 7.0 (d, 1H), 4.7 (s, 2H), 2.05 (s, 3H).

LCMS (Method C) r/t 4.26 (M+Na) 403.

Example 72

2-(Benzenesulphonylmethyl)-6-methoxybenzoic acid

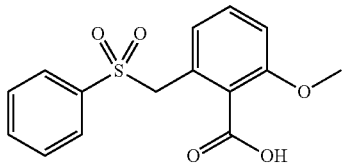 [SMILES: COc1cccc(CS(=O)(=O)c2ccccc2)c1C(=O)O]

Prepared by proceeding in a similar manner to Example 3, starting from methyl 2-(benzenesulphonylmethyl)-6-methoxybenzoate (Intermediate 155) as a white solid.

NMR (DMSO-$d_6$) δ 7.7 (m, 3H), 7.6 (dd, 2H), 7.3 (t, 1H), 7.1 (d, 1H), 6.75, (m, 1H), 4.7 (s, 2H), 3.75 (s, 3H).

LCMS (Method C) r/t 3.37 (M+Na) 329.

Example 73

6-(Cyclohexanesulphonylmethyl)-3-(furan-3-yl)-2-methoxybenzoic acid

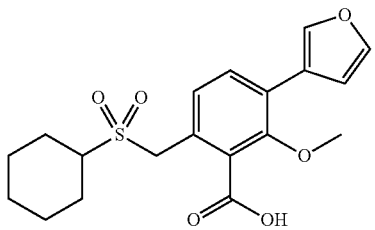 [SMILES: COc1c(-c2ccoc2)ccc(CS(=O)(=O)C2CCCCC2)c1C(=O)O]

Prepared by proceeding in a similar manner to Example 24, starting from methyl 6-(cyclohexanesulphonylmethyl)-3-(furan-3-yl)-2-methoxybenzoate (Intermediate 156)

NMR (DMSO-$d_6$) δ 8.2 (dd, 1H), 7.8 (t, 1H), 7.7 (d, 1H), 7.3 (d, 1H), 7.0 (dd, 1H), 4.5 (s, 2H), 3.65 (s, 3H), 3.15-2.95 (m, 1H), 2.05 (d, 2H), 1.85 (d, 2H), 1.65 (d, 1H), 1.4 (m, 2H), 1.3 (d, 2H), 1.2 (dd, 1H).

LCMS (Method C) r/t 4.25 (M+Na) 401.

Example 74

6-(Benzenesulphonylmethyl)-2-(carbamoylmethoxy)-3-(furan-3-yl)-benzoic acid

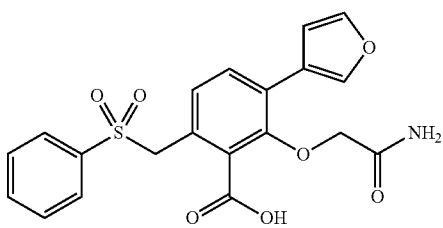 [SMILES: NC(=O)COc1c(-c2ccoc2)ccc(CS(=O)(=O)c2ccccc2)c1C(=O)O]

Prepared by proceeding in a similar manner to Example 53, starting from t-butyl 6-(benzenesulphonylmethyl)-2-(carbamoylmethoxy)-3-(furan-3-yl)benzoate (Intermediate 159).

NMR (DMSO-$d_6$) δ 8.3 (br, s, 1H), 7.8 (t, 1H), 7.7 (dd, 3H), 7.6 (d, 3H), 7.55 (br, s, 1H), 7.45 (s, 1H), 7.05 (d, 1H), 7.0 (s, 1H), 4.8 (s, 2H), 4.05 (s, 2H).

LCMS (Method C) r/t 3.48 (M+H) 416.

Example 75

(Z)-6-((2-(3-(diethylamino)prop-1-enyl)-4-fluorobenzenesulfonyl)methyl)-3-(furan-3-yl)-2-methoxybenzoic acid

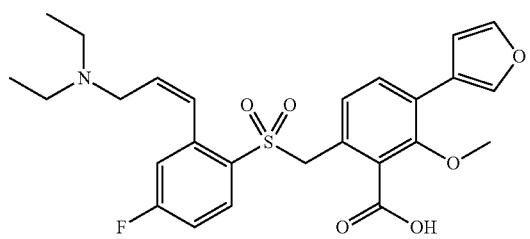 [SMILES: CCN(CC)C/C=C\c1cc(F)ccc1S(=O)(=O)Cc1ccc(-c2ccoc2)c(OC)c1C(=O)O]

Prepared by proceeding in a similar manner to Example 3, starting from (Z)-methyl 6-((2-(3-(diethylamino)prop-1-enyl)-4-fluorobenzenesulfonyl)methyl)-3-(furan-3-yl)-2-methoxybenzoate (Intermediate 160).

NMR (CDCl$_3$) δ 8.0 (m, 1H), 7.8 (d, 1H), 7.55 (m, 1H), 7.45 (m, 1H), 7.4 (d, 2H), 6.95 (s, 1H), 6.85 (dd, 1H), 6.8 (d, 1H), 6.1 (m, 1H), 4.7 (br, s, 2H), 3.9 (br, s, 2H), 3.6 (s, 3H), 3.25 (m, 4H), 1.35 (t, 6H).

LCMS (Method C) r/t 3.34 (M+H) 502.

Example 76

3-(Furan-3-yl)-6-(3-hydroxypyrrolidine-1-ylsulphonylmethyl)-2-methoxybenzoic acid

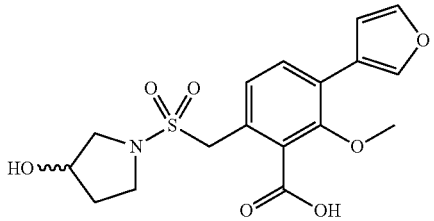 [SMILES: COc1c(-c2ccoc2)ccc(CS(=O)(=O)N2CCC(O)C2)c1C(=O)O]

Prepared by proceeding in a similar manner to Example 3, starting from methyl 3-(furan-3-yl)-6-(3-hydroxypyrrolidin-1-ylsulphonylmethyl)-2-methoxybenzoate (Intermediate 165) as a white solid.

NMR (DMSO$_6$) δ 8.15 (s, 1H), 7.8 (t, 1H), 7.65 (d, 1H), 7.3 (d, 1H), 7.0 (d, 1H), 4.45 (d, 2H), 4.25 (br, s, 1H), 3.65 (s, 3H), 3.25 (m, 4H), 3.1 (d, 1H), 1.9 (m, 1H), 1.8 (m, 1H).

LCMS (Method C) r/t 3.37 (M+Na) 404.

Example 77

2-(Azetidin-3-yloxy)-6-(benzenesulphonylmethyl)-3-(furan-3-yl)-benzoic acid hydrochloride salt

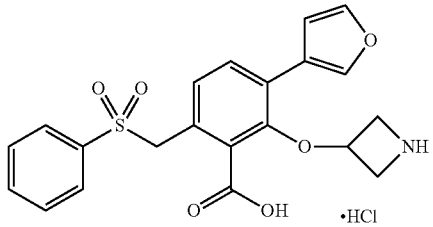 [SMILES: O=C(O)c1c(CS(=O)(=O)c2ccccc2)ccc(-c2ccoc2)c1OC1CNC1 ; Cl]

Prepared by proceeding in a similar manner to Example 38, starting from t-butyl 3-[3-(benzenesulphonylmethyl)-2-carboxy-6-(furan-3-yl)phenoxy]-azetidine-1-carboxylate (Intermediate 167). The crude product was dissolved in HCl (4M in dioxane, 0.5 ml) and then evaporated to dryness. The residue was triturated with diethyl ether and the solid was collected by filtration to give 2-(azetidin-3-yloxy)-6-(benzenesulphonylmethyl)-3-(furan-3-yl)benzoic acid hydrochloride salt.

NMR (DMSO-d$_6$) δ 8.15 (s, 1H), 7.8 (t, 1H), 7.75 (m, 3H), 7.65 (t, 2H), 7.55 (d, 1H), 7.05 (d, 1H), 6.9 (dd, 1H), 4.8 (s, 2H), 4.55 (t, 1H), 4.05 (m, 2H), 3.9 (m, 2H).

LCMS (Method C) r/t 2.86 (M+H) 414.

Example 78

6-(Bicyclo[2.2.2]octane-2-ylsulphonylmethyl)-3-(furan-3-yl)-2-methoxybenzoic acid

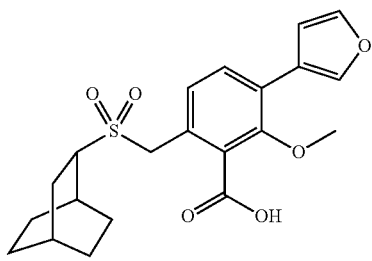 [SMILES: COc1c(-c2ccoc2)ccc(CS(=O)(=O)C2(C)CC3CCC2CC3)c1C(=O)O]

Prepared by proceeding in a similar manner to Example 3, starting from methyl 6-(bicyclo[2.2.2]octane-2-ylsulphonylmethyl)-3-(furan-3-yl)-2-methoxybenzoate (Intermediate 169).

NMR (DMSO-d$_6$) δ 8.15 (m, 1H), 7.75 (m, 1H), 7.65 (d, 1H), 7.25 (d, 1H), 6.95 (dd, 1H), 4.4 (s, 2H), 3.6 (s, 3H), 2.1 (m, 1H), 1.9 (m, 1H), 1.75 (m, 2H), 1.65 (m, 1H), 1.45 (m, 7H), 1.35 (m, 1H).

LCMS (Method C) r/t 4.57 (M+Na) 427.

Example 79

6-(Bicyclo[2.2.2]octane-2-ylsulphonylmethyl)-2-methoxy-3-(tetrahydrofuran-3-yl)benzoic acid

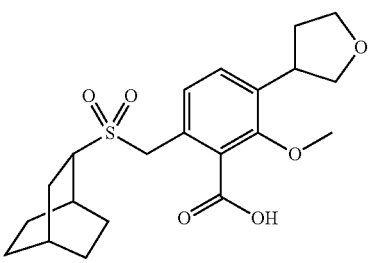 [SMILES: COc1c(C2CCOC2)ccc(CS(=O)(=O)C2(C)CC3CCC2CC3)c1C(=O)O]

Prepared by proceeding in a similar manner to Example 3, starting from methyl 6-(bicyclo[2.2.2]octane-2-ylsulphonylmethyl)-2-methoxy-3-(tetrahydrofuran-3-yl)benzoate (Intermediate 175).

NMR (DMSO-d$_6$) δ 7.45 (d, 1H), 7.2 (d, 1H), 4.4 (s, 2H), 4.05 (t, 1H), 3.95 (dt, 1H), 3.8 (q, 1H), 3.75 (s, 3H), 3.7-3.6 (m, 1H), 3.55 (t, 1H), 3.4 (q, 1H), 2.3 (m, 1H), 2.1 (m, 1H), 2.0 (m, 2H), 1.8 (m, 2H), 1.7 (m, 1H), 1.55 (m, 3H,) 1.5 (m, 3H), 1.35 (m, 1H).

LCMS (Method C) r/t 4.01 (M+H) 409.

Example 80

6-(7-Azabicyclo[2.2.1]heptane-7-ylsulphonylmethyl)-3-(furan-3-yl)-2-methoxybenzoic acid

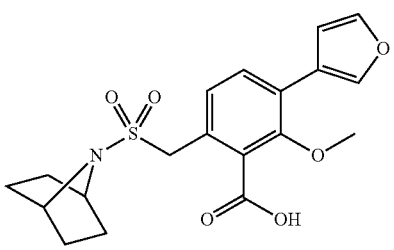 [SMILES: COc1c(-c2ccoc2)ccc(CS(=O)(=O)N2C3CCC2CC3)c1C(=O)O]

Prepared by proceeding in a similar manner to Example 3, starting from methyl 6-(7-azabicyclo[2.2.1]heptane-7-ylsulphonylmethyl)-3-(furan-3-yl)-2-methoxybenzoate (Intermediate 176) as a white solid.

NMR (CDCl$_3$) δ 7.95 (s, 1H), 7.55 (d, 1H), 7.5 (t, 1H), 7.35 (d, 1H), 6.8 (m, 1H), 4.65 (s, 2H), 4.05 (m, 2H), 3.75 (s, 3H), 1.9 (m, 4H), 1.45 (m, 4H).

LCMS (Method C) r/t 4.32 (M+Na) 414.

Example 81

6-(4,4-Difluoropiperidine-1-ylsulphonylmethyl)-3-(furan-3-yl)-2-methoxybenzoic acid

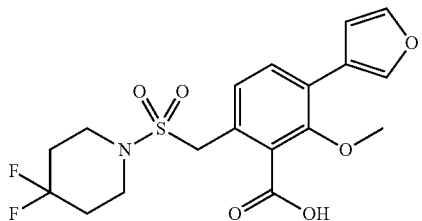 [SMILES: COc1c(-c2ccoc2)ccc(CS(=O)(=O)N2CCC(F)(F)CC2)c1C(=O)O]

Prepared by proceeding in a similar manner to Example 3, starting from methyl 6-(4,4-difluoropiperidine-1-ylsulphonylmethyl)-3-(furan-3-yl)-2-methoxybenzoate (Intermediate 178) as a white solid.

NMR (DMSO-$d_6$) δ 8.2 (dd, 1H), 7.8 (t, 1H), 7.75 (d, 1H), 7.35 (d, 1H), 7.05 (dd, 1H), 4.55 (s, 2H), 3.65 (s, 3H), 3.3 (m, 4H), 2.0 (m, 4H).

LCMS (Method C) r/t 4.30 (M+Na) 438.

Example 82

6-(Bicyclo[2.2.1]heptane-7-ylsulphonylmethyl)-3-(furan-3-yl)-2-methoxybenzoic acid

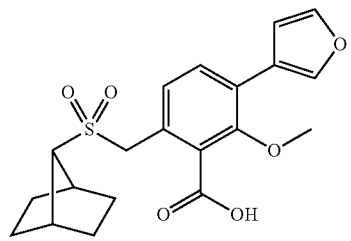 [SMILES: COc1c(-c2ccoc2)ccc(CS(=O)(=O)C2C3CCC2CC3)c1C(=O)O]

Prepared by proceeding in a similar manner to Example 3, starting from methyl 6-(bicyclo[2.2.2]heptane-7-ylsulphonylmethyl)-3-bromo-2-methoxybenzoate (Intermediate 180).

NMR (DMSO-$d_6$) δ 8.2 (dd, 1H), 7.8 (t, 1H), 7.7 (d, 1H), 7.3 (d, 1H), 7.0 (dd, 1H), 4.5 (s, 2H), 3.65 (s, 3H), 3.2 (s, 1H), 2.45 (s, 2H), 1.95 (d, 2H), 1.6 (d, 2H), 1.2 (d, 4H).

LCMS (Method C) r/t 4.41 (M+H) 413.

Example 83

6-(Benzenesulphonylmethyl)-3-(furan-3-yl)-2-methylamino benzoic acid

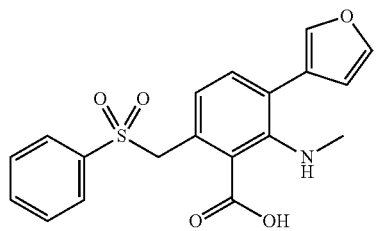 [SMILES: CNc1c(-c2ccoc2)ccc(CS(=O)(=O)c2ccccc2)c1C(=O)O]

Prepared by proceeding in a similar manner to Example 3, starting from methyl 6-(benzenesulphonylmethyl)-3-(furan-3-yl)-2-methylaminobenzoate (Intermediate 184).

NMR (DMSO-$d_6$) δ 8.0 (m, 1H), 7.75 (t, 1H), 7.7 (m, 3H), 7.6 (t, 2H), 7.25 (d, 1H), 6.8 (dd, 1H), 6.65 (d, 1H), 4.9 (s, 2H), 2.55 (s, 3H).

LCMS (Method C) r/t 3.39 (M+H) 372.

Example 84

6-(8-Azabicyclo[3.2.1]octane-8-ylsulphonylmethyl)-3-(furan-3-yl)-2-methoxybenzoic acid

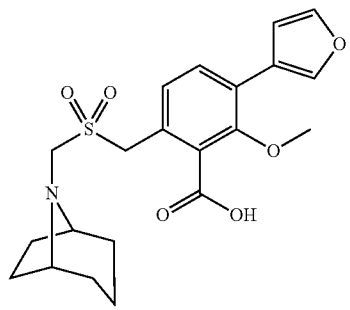 [SMILES: COc1c(-c2ccoc2)ccc(CS(=O)(=O)CN2C3CCCC2CC3)c1C(=O)O]

Prepared by proceeding in a similar manner to Example 3, starting from methyl 6-(8-azabicyclo[3.2.1]octane-8-ylsulphonylmethyl)-3-(furan-3-yl)-2-methoxybenzoate (Intermediate 185) as a white solid.

NMR (DMSO-$d_6$) δ 8.2 (dd, 1H), 7.8 (m, 1H), 7.7 (d, 1H), 7.35 (d, 1H), 7.0 (dd, 1H), 4.5 (s, 2H), 4.0 (s, 3H), 3.65 (m, 2H), 1.95-1.8 (m, 2H), 1.7 (m, 4H), 1.6 (m, 2H), 1.45 (m, 2H).

LCMS (Method C) r/t 4.49 (M+Na) 428.

Example 85

2-(Benzenesulphonylmethyl)-8-methoxynaphthalene-1-carboxylic acid

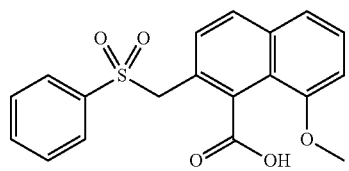 [SMILES: COc1cccc2ccc(CS(=O)(=O)c3ccccc3)c(C(=O)O)c12]

Prepared by proceeding in a similar manner to Example 3, starting from methyl 2-(benzenesulphonylmethyl)-8-methoxynaphthalene-1-carboxylate (Intermediate 187) as a white solid.

NMR (DMSO-$d_6$) δ 7.9 (d, 1H), 7.7 (d, 3H), 7.6 (t, 2H), 7.5 (m, 2H), 7.45 (d, 1H), 7.05 (dd, 1H), 4.75 (s, 2H), 3.85 (s, 3H).

LCMS (Method C) r/t 3.90 (M+Na) 379.

Example 86

6-[2-(3-Diethylaminopropylamino)benzenesulphonylmethyl]-3-(furan-3-yl)-2-methoxybenzoic acid

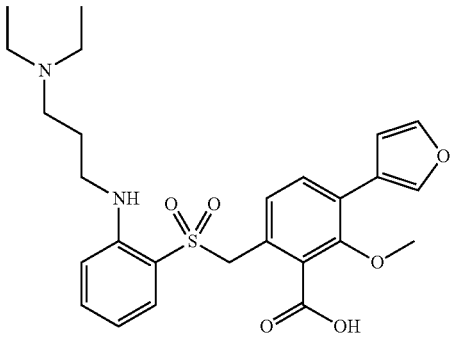 [SMILES: CCN(CC)CCCNc1ccccc1S(=O)(=O)Cc1ccc(-c2ccoc2)c(OC)c1C(=O)O]

Prepared by proceeding in a similar manner to Example 3, starting from methyl 6-[2-(3-diethylaminopropylamino)benzenesulphonylmethyl]-3-(furan-3-yl)-2-methoxybenzoate (Intermediate 192) as a white solid.

NMR (DMSO-$d_6$) δ 8.15 (d, 1H), 7.75 (m, 1H), 7.6 (dd, 1H), 7.5 (m, 2H), 7.25 (d, 1H), 7.0 (dd, 1H), 6.9 (d, 1H), 6.75 (t, 1H), 6.0 (br, s, 1H), 4.6 (s, 2H), 3.7 (s, 3H), 3.4 (q, 2H), 3.25 (m, 2H), 3.1 (m, 4H), 2.15 (m, 2H), 1.2 (t, 6H).

LCMS (Method C) r/t 3.34 (M+H) 501.

Example 87

(Z)-2-(Cyanomethoxy)-6-((2-(3-(diethylamino)prop-1-enyl)-4-fluorobenzenesulfonyl)methyl)-3-(furan-3-yl)benzoic acid

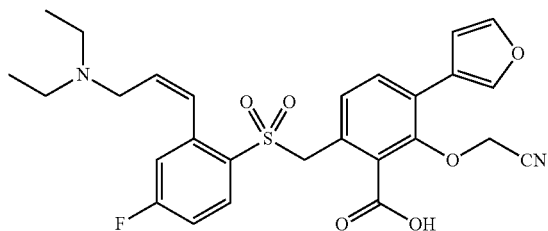 [SMILES: CCN(CC)C/C=C\c1cc(F)ccc1S(=O)(=O)Cc1ccc(-c2ccoc2)c(OCC#N)c1C(=O)O]

Prepared by proceeding in a similar manner to Example 53, starting from (Z)-t-butyl 2-(cyanomethoxy)-6-((2-(3-(diethylamino)prop-1-enyl)-4-fluorobenzenesulfonyl)methyl)-3-(furan-3-yl)benzoate (Intermediate 193).

NMR (CD$_3$OD) δ 7.95 (dd, 1H), 7.6 (m, 2H), 7.55 (t, 1H), 7.45 (m, 2H), 7.15 (m, 2H), 6.8 (dd, 1H), 6.2 (m, 1H), 4.7 (s, 2H), 4.55 (s, 2H), 4.1 (d, 2H), 3.25 (m, 4H), 1.3 (t, 6H).

LCMS (Method C) r/t 3.38 (M+H) 527.

Example 88

(Z)-3-(Furan-3-yl)-2-methoxy-6-((2-(3-(piperidin-1-yl)prop-1-enyl)benzenesulfonyl)methyl)benzoic acid

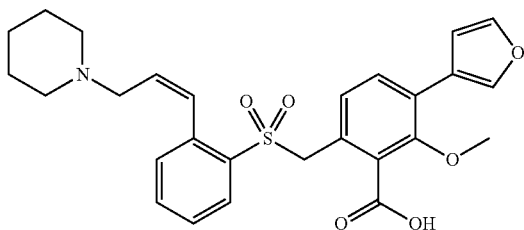 [SMILES: COc1c(-c2ccoc2)ccc(CS(=O)(=O)c2ccccc2/C=C\CN2CCCCC2)c1C(=O)O]

(Z)-Methyl 3-(furan-3-yl)-2-methoxy-6-((2-(3-(piperidin-1-yl)prop-1-enyl)benzenesulfonyl)methyl)benzoate (Intermediate 198, 0.069 g) was added to a solution of lithium hydroxide monohydrate (0.051 g) in water (0.7 ml) and dioxane (3 ml) and the resultant mixture was stirred and heated at 65° C. for 4 days. After cooling, the mixture was diluted with water and washed with diethyl ether. The aqueous layer was acidified with 1M HCl and extracted with ethyl acetate, washed with brine, dried (Na$_2$SO$_4$) and filtered. The filtrate was evaporated to dryness and the residue was purified by HPLC (C6 phenyl column) eluting with 1:1 methanol:water containing 0.1% formic acid to give (Z)-3-(Furan-3-yl)-2-methoxy-6-((2-(3-(piperidin-1-yl)prop-1-enyl)benzenesulfonyl)methyl)benzoic acid as a white solid.

NMR (CDCl$_3$) δ 7.95 (dd, 1H), 7.85 (d, 1H), 7.55 (t, 2H), 7.45 (t, 1H), 7.4 (m, 2H), 7.3 (t, 1H), 7.15 (d, 1H), 6.75 (dd, 1H), 6.15 (m, 1H), 4.75 (s, 2H), 3.9 (s, 2H), 3.8 (s, 2H), 3.55 (s, 3H), 2.55 (s, 2H), 1.85 (s, 5H), 1.4 (m, 1H).

LCMS (Method C) r/t 3.30 (M+H) 496.

Example 89

6-(Benzenesulphonylmethyl)-3-(furan-3-yl)-2,4-dimethoxybenzoic acid

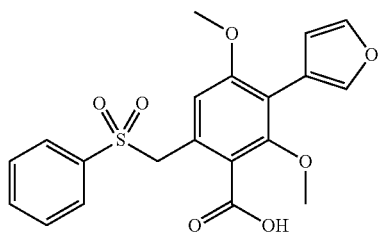 [SMILES: COc1cc(CS(=O)(=O)c2ccccc2)c(C(=O)O)c(OC)c1-c1ccoc1]

Prepared by proceeding in a similar manner to Example 3, starting from ethyl 6-(benzenesulphonylmethyl)-3-(furan-3-yl)-2,4-dimethoxybenzoate (Intermediate 200).

NMR (DMSO-$d_6$) δ 7.95 (dd, 1H), 7.75 (m, 4H), 7.65 (dd, 2H), 6.85 (dd, 1H), 6.55 (s, 1H), 4.8 (s, 2H), 3.6 (s, 3H), 3.45 (s, 3H).

LCMS (Method C) r/t 4.16 (M+Na) 425.

Example 90

6-[2-(2-Diethylaminomethylazetidin-1-yl)-benzenesulphonylmethyl]-3-(furan-3-yl)-2-methoxybenzoic acid

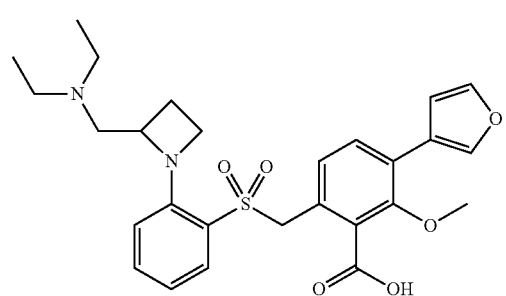 [SMILES: CCN(CC)CC1CCN1c1ccccc1S(=O)(=O)Cc1ccc(-c2ccoc2)c(OC)c1C(=O)O]

Prepared by proceeding in a similar manner to Intermediate 124, starting from methyl 6-[2-(2-diethylaminomethylazetidin-1-yl)benzenesulphonylmethyl]-3-(furan-3-yl)-2-methoxybenzoate (Intermediate 205) as a white solid NMR (DMSO-$d_6$) δ 8.15 (s, 1H), 8.0 (d, 1H), 7.75 (m, 2H), 7.65 (d, 1H), 7.45 (d, 1H), 7.4 (d, 1H), 7.25 (d, 1H), 7.0 (d, 1H), 5.0 (s, 2H), 3.9 (m, 2H), 3.7 (s, 3H), 3.35 (s, 2H), 3.15 (m, 2H), 2.95 (m, 1H), 2.5 (m, 4H), 1.25 (t, 6H).

LCMS (Method C) r/t 3.40 (M+H) 513.

Example 91

6-(Benzenesulphonylmethyl)-2-(cyanomethylamino)-3-(furan-3-yl)benzoic acid

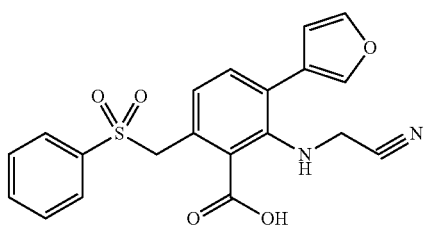 [SMILES: N#CCNc1c(-c2ccoc2)ccc(CS(=O)(=O)c2ccccc2)c1C(=O)O]

A solution of 5-(benzenesulphonylmethyl)-8-(furan-3-yl)-1,2-dihydro-benzo[d][1,3]oxazin-4-one (Intermediate 210, 0.115 g) and sodium cyanide (0.03 g) in DMSO (4 ml) was stirred and heated at 60° C. for 2 hours. After cooling, the mixture was diluted with water, acidified with acetic acid and extracted with ethyl acetate. The organic layer was dried ($Na_2SO_4$) and filtered. The filtrate was evaporated to dryness and the residue was purified by chromatography on silica, eluting with a mixture of DCM:methanol:water:acetic acid (350:20:3:2). The product was crystallized from DCM and cyclohexane to give 6-(benzenesulphonylmethyl)-2-(cyanomethylamino)-3-(furan-3-yl)benzoic acid (0.106 g).

NMR (DMSO-$d_6$) δ 8.05 (t, 1H), 7.8 (t, 1H), 7.75 (m, 1H), 7.7 (m, 2H), 7.6 (t, 2H), 7.35 (d, 1H), 6.85 (dd, 1H), 6.8 (d, 1H), 5.0 (s, 2H), 3.8 (s, 2H).

LCMS (Method C) r/t 4.04 (M+Na) 419.

Example 92

6-(Benzenesulphonylmethyl)-3-(imidazol-1-yl)-2-methoxybenzoic acid

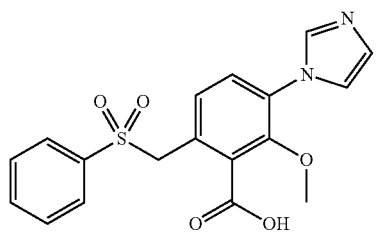 [SMILES: COc1c(-n2ccnc2)ccc(CS(=O)(=O)c2ccccc2)c1C(=O)O]

A mixture of 6-(benzenesulphonylmethyl)-3-bromo-2-methoxybenzoic acid (Intermediate 133, 0.20 g), copper (I) oxide (0.008 g), salicylaldoxime (0.032 g), imidazole (0.08 g), cesium carbonate (0.5 g) in acetonitrile (4 ml) was sealed under nitrogen in a microwave vial and heated at 160° C. for 1 hour. After cooling, ethyl acetate was added and the solid was filtered off. The filtrate was evaporated to dryness and the residue was purified by HPLC, eluting with a mixture of methanol and water containing 0.1% formic acid with a gradient of 20-98% to give 6-benzenesulphonylmethyl-3-(imidazol-1-yl)-2-methoxybenzoic acid as a white solid.

NMR (CD$_3$OD) δ 8.65 (s, 2H), 8.1 (s, 1H), 7.8 (m, 2H), 7.7 (t, 1H), 7.6 (t, 2H), 7.5 (d, 1H), 7.25 (d, 1H), 4.8 (s, 2H), 3.55 (s, 3H).

LCMS (Method C) r/t 2.10 (M+H) 373.

Example 93

6-(Benzenesulphonylmethyl)-2-methoxy-3-(thiazol-5-yl)benzoic acid

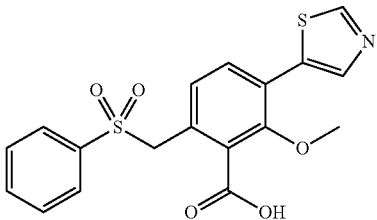 [SMILES: COc1c(-c2cncs2)ccc(CS(=O)(=O)c2ccccc2)c1C(=O)O]

A mixture of 6-(benzenesulphonylmethyl)-3-bromo-2-methoxybenzoic acid (Intermediate 133, 0.1 g), tetrakis-(triphenylphosphine) palladium (0.03 g), lithium chloride (0.1 g) and 5-tetrabutylstannyl thiazole (0.1 g) in dioxane (3 ml) was sealed in a microwave vial, under nitrogen and heated to 160° C. for 45 minutes. After cooling, ethyl acetate was added and the solid was filtered off. The filtrate was evaporated to dryness and the residue was purified by HPLC, eluting with a mixture of methanol and water containing 0.1% formic acid with a gradient of 70-98% to give 6-(benzenesulphonylmethyl)-2-methoxy-3-(thiazol-5-yl)benzoic acid as a white solid.

NMR (CD$_3$OD) δ 9.0 (s, 1H), 8.3 (s, 1H), 7.8 (m, 2H), 7.7 (m, 1H), 7.65 (d, 1H), 7.55 (t, 2H), 7.1 (d, 1H), 4.7 (s, 2H), 3.75 (s, 3H).

LCMS (Method C) r/t 3.42 (M+H) 390.

Example 94

3-(Furan-3-yl)-2-methoxy-6-[(S-phenylsulphonimidoyl)methyl]benzoic acid

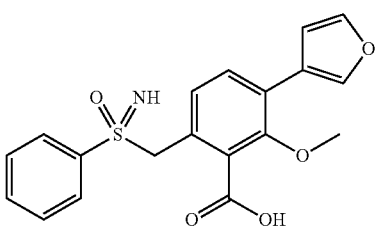

Prepared by proceeding in a similar manner to Example 3, starting from 6-(furan-3-yl)-5-methoxy-2-oxo-2-phenyl-1H-2-λ*6*-benzo[d][1,2]thiazin-4-one (Intermediate 214) as a beige solid.

NMR (DMSO-$d_6$) δ 8.15 (s, 1H), 7.75 (s, 1H), 7.7 (d, 2H), 7.65 (t, 1H), 7.55 (m, 3H), 7.0 (s, 1H), 6.9 (d, 1H), 4.6-4.5 (m, 2H), 3.6 (s, 3H).

LCMS (Method C) r/t 3.63 (M−H) 370.

Example 95

3-(Furan-3-yl)-2-methoxy-6-[(N-methyl-S-phenyl-sulphonimidoyl)methyl]benzoic acid

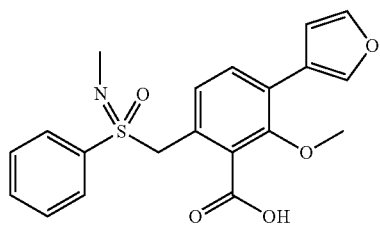 [SMILES: CN=S(=O)(Cc1ccc(-c2ccoc2)c(OC)c1C(=O)O)c1ccccc1]

Prepared by proceeding in a similar manner to Example 53, starting from t-butyl 3-(furan-3-yl)-2-methoxy-6-[(N-methyl-S-phenylsulphonimidoyl)methyl]benzoate (Intermediate 218).

NMR (DMSO-$d_6$) δ 8.15 (s, 1H), 7.75 (t, 1H), 7.7 (m, 2H), 7.6 (d, 1H), 7.55 (t, 3H), 7.0 (d, 1H), 6.9 (d, 1H), 4.75-4.6 (m, 2H), 3.6 (s, 3H), 2.55 (s, 3H).

LCMS (Method C) r/t 3.75 (M+H) 386.

Example 96

6-[(N-cyano-S-phenylsulphonimidoyl)methyl]-3-(furan-3-yl)-2-methoxybenzoic acid

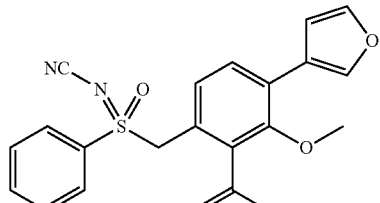

Prepared by proceeding in a similar manner to Example 24, starting from benzyl 6-[(N-cyano-S-phenylsulphonimidoyl) methyl]-3-(furan-3-yl)-2-methoxybenzoate (Intermediate 224).

NMR (DMSO-$d_6$) δ 8.15 (s, 1H), 7.8 (m, 3H), 7.75 (t, 1H), 7.7 (t, 2H), 7.55 (d, 1H), 7.0 (d, 1H), 6.95 (d, 1H), 5.3-5.2 (m, 2H), 3.6 (s, 3H).

LCMS (Method C) r/t 3.99 (M+H) 397.

Intermediate 1

2-(Phenylthiomethyl)-5-ethylbenzoic acid

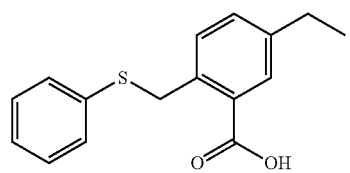 [SMILES: CCc1ccc(CSc2ccccc2)c(C(=O)O)c1]

Thiophenol (0.128 ml) was added to a mixture of 6-ethyl-3H-isobenzofuran-1-one (Intermediate 18, 0.202 g) and potassium carbonate (0.344 g) in dry DMF (1.3 ml). The resultant mixture was stirred and heated at 110° C. for 2 hours. After cooling, the mixture was diluted with water and acidified by addition of hydrochloric acid (1M). The resultant solid was collected by filtration, washed with water and dried under vacuum to give 2-(phenylthiomethyl)-5-ethylbenzoic acid (0.288 g) as a white solid.

LCMS (Method E) r/t 4.84 (M−H) 271.

Intermediate 2

Ethyl 6-(benzenesulphinylmethyl)-3-ethyl-2-methoxybenzoate

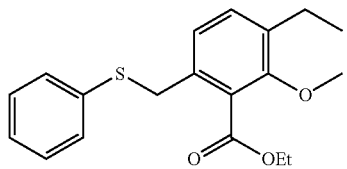 [SMILES: CCOC(=O)c1c(CSc2ccccc2)ccc(CC)c1OC]

3-Chloroperbenzoic acid (0.07 g) was added to a stirred solution of ethyl 6-(phenylthiomethyl)-3-ethyl-2-methoxybenzoate (Intermediate 19, 0.315 g) in DCM (5 ml) and the resultant mixture was stirred at room temperature overnight. The solution was evaporated to dryness and the residue was purified by chromatography on silica, eluting with a mixture of ethyl acetate and cyclohexane with a gradient of 0-100% to give ethyl 6-(benzenesulphinylmethyl)-3-ethyl-2-methoxybenzoate (0.095 g) as a clear gum.

NMR (CDCl$_3$) δ 7.5 (m, 2H), 7.45 (m, 3H), 7.15 (d, 1H), 6.80 (d, 1H), 4.4 (q, 2H), 4.15 (d, 1H), 4.05 (d, 1H), 3.8 (s, 3H), 2.65 (q, 2H), 1.4 (t, 3H), 1.2 (t, 3H).

Intermediate 3

Ethyl 6-(1-benzenesulphonylethyl)-3-ethyl-2-methoxybenzoate

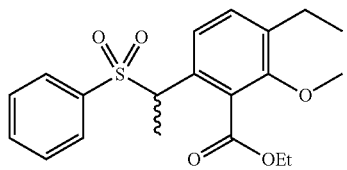 [SMILES: CCOC(=O)c1c(C(C)S(=O)(=O)c2ccccc2)ccc(CC)c1OC]

Sodium hydride (60% oil dispersion, 0.009 g) was added to a stirred and cooled solution of ethyl 6-(benzenesulphonylmethyl)-3-ethyl-2-methoxybenzoate (Intermediate 20, 0.075 g) in DMF (1 ml) at 0° C. under an atmosphere of nitrogen. After stirring for 15 minutes iodomethane (0.014 ml) was added and the resultant mixture was stirred at room temperature for 1 hour. Ammonium chloride (saturated aqueous solution) was added followed by water and the mixture was extracted with ethyl acetate, washed with water, brine, dried (MgSO$_4$) and filtered. The filtrate was evaporated to dryness and the residue was purified by chromatography on silica, eluting with a mixture of ethyl acetate and cyclohexane with a gradient of 0-20% to give ethyl 6-(1-benzenesulphonylethyl)-3-ethyl-2-methoxybenzoate (0.063 g) as a colourless oil.

NMR (CDCl₃) δ 7.55 (m, 3H), 7.4 (m, 3H), 7.3 (d, 1H), 4.5 (q, 1H), 4.35 (m, 1H), 4.2 (m, 1H), 3.65 (s, 3H), 2.65 (m, 2H), 1.75 (d, 3H), 1.3 (t, 3H), 1.25 (t, 3H).

Intermediate 4

Methyl 6-[2-(3-diethylaminopropyl)benzenesulphonylmethyl]-3-(furan-3-yl)-2-methoxybenzoate

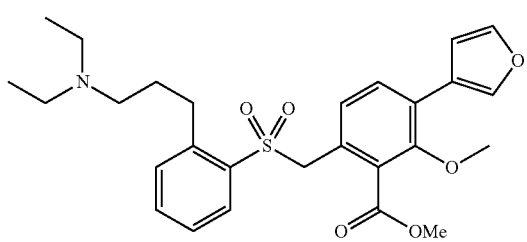 [SMILES: CCN(CC)CCCc1ccccc1S(=O)(=O)Cc1ccc(-c2ccoc2)c(OC)c1C(=O)OC]

A mixture of methyl 6-[2-(3-diethylaminoprop-1-en-1-yl)benzenesulphonyl-methyl]-3-(furan-3-yl)-2-methoxybenzoate (mixture of E and Z isomers, Intermediate 5, 0.03 g) and palladium on carbon (10%, 0.006 g) in methanol (1.2 ml) was stirred in an atmosphere of hydrogen (balloon) for 1 hour. The mixture was filtered through Celite and the filtrate was evaporated to dryness to give methyl 6-[2-(3-diethylaminopropyl)benzenesulphonylmethyl]-3-(furan-3-yl)-2-methoxybenzoate (0.028 g) as a colourless oil.

LCMS (Method E) r/t 3.07 (M+H) 500.

Intermediate 5

Methyl 6-((2-(3-(diethylamino)prop-1-enyl)benzenesulfonyl)methyl)-3-(furan-3-yl)-2-methoxybenzoate (mixture of E and Z isomers)

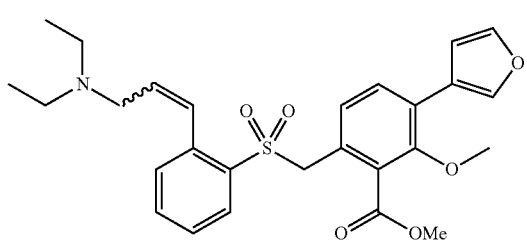 [SMILES: CCN(CC)CC=Cc1ccccc1S(=O)(=O)Cc1ccc(-c2ccoc2)c(OC)c1C(=O)OC]

Carbon tetrabromide (0.05 g) was added to a solution of methyl 3-(furan-3-yl)-6#2-(3-hydroxyprop-1-enyl)phenylsulfonyl)methyl)-2-methoxybenzoate (mixture of E and Z isomers, Intermediate 44, 0.044 g) and triphenyl phosphine (0.039 g) in DCM (1 ml) and the resultant solution was stirred at room temperature for 30 minutes. The resultant solution was evaporated to dryness and the residue was purified by chromatography on silica, eluting with ether to give the intermediate bromide. This material was dissolved in THF (1 ml) and diethylamine (0.1 ml) was added. The mixture was stirred for 2 hours then diluted with DCM, dried (MgSO₄) and filtered through Celite. The filtrate was evaporated to dryness to give methyl 6-((2-(3-(diethylamino)prop-1-enyl)benzenesulfonyl)methyl)-3-(furan-3-yl)-2-methoxybenzoate as a mixture of E and Z isomers.

LCMS (Method F) r/t 3.05 (M+H) 498.

Intermediate 6

6-(Benzenesulphonylmethyl)-2-[2-(t-butoxycarbonyl)aminoethoxy]-3-(furan-3-yl)benzoic acid

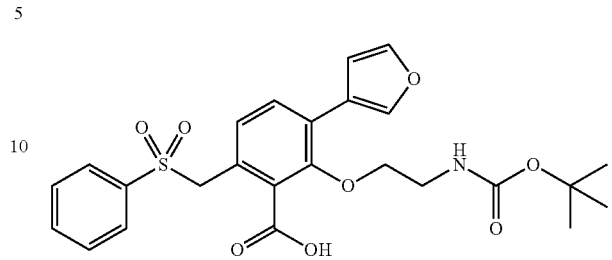

A mixture of ethyl 6-(benzenesulphonylmethyl)-2-[2-(t-butoxycarbonyl)aminoethoxy]-3-(furan-3-yl)benzoate (Intermediate 10, 0.03 g) and lithium hydroxide monohydrate (0.012 g) in dioxane (1 ml) and water (0.2 ml) was stirred and heated at 90° C. for 3 hours. The mixture was allowed to stand at room temperature overnight then treated with further lithium hydroxide monohydrate (0.012 g). The resultant mixture was stirred and heated at 100° C. for 4 hours. After cooling, the mixture was diluted with water and washed with ethyl acetate. The aqueous layer was carefully acidified by addition of formic acid and then extracted with ethyl acetate. The organic layer was dried (Na₂SO₄) and filtered. The filtrate was evaporated to dryness to give 6-(benzenesulphonylmethy)1-2-[2-(t-butoxycarbonyl)-aminoethoxy]-3-(furan-3-yl)benzoic acid (0.019 g) as an oil.

LCMS (Method E) r/t 4.27 (M+H) 502.

Intermediate 7

2-[2-(t-Butoxycarbonyl)aminoethoxy]-6-(3-chlorobenzenesulphonyl-methyl-3-(furan-3-yl)benzoic acid

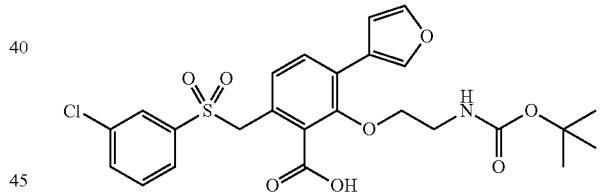

Prepared by proceeding in a similar manner to Intermediate 6, starting from methyl 2-[2-(t-butoxycarbonyl)aminoethoxy]-6-(3-chlorobenzene-sulphonylmethyl-3-(furan-3-yl)benzoate (Intermediate 11) and used without further characterization.

Intermediate 8

2-[2-(t-Butoxycarbonyl)aminoethoxy]-6-(4-fluorobenzenesulphonylmethyl)-3-(furan-3-yl)benzoic acid

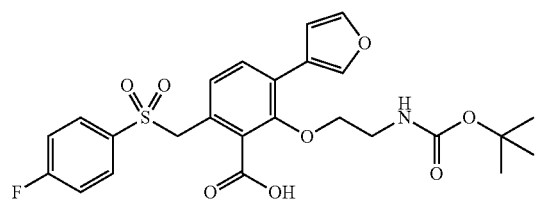 [SMILES: CC(C)(C)OC(=O)NCCOc1c(-c2ccoc2)ccc(CS(=O)(=O)c2ccc(F)cc2)c1C(=O)O]

Prepared by proceeding in a similar manner to Intermediate 6, starting from methyl 2-[2-(t-butoxycarbonyl)aminoethoxy]-6-(4-fluorobenzenesulphonylmethyl-3-(furan-3-yl)benzoate (Intermediate 13).

NMR (CDCl$_3$) δ 8.2 (s, 1H), 7.75 (t, 1H), 7.7 (m, 2H), 7.6 (d, 1H), 7.45 (t, 2H), 7.05 (d, 1H), 7.0 (s, 1H), 6.95 (br s, 1H), 4.75 (s, 2H), 3.7 (t, 2H), 3.2 (m, 2H), 1.4 (s, 9H).

Intermediate 9

2-[2-(t-butoxycarbonyl)aminoethoxy]-3-(furan-3-yl)-6-(2-methoxybenzenesulphonylmethyl)benzoic acid

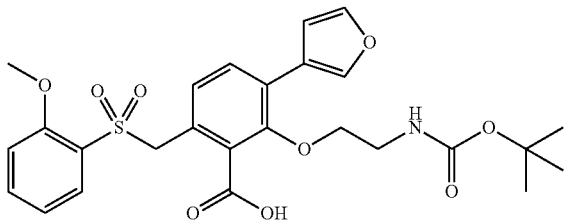 [SMILES: COc1ccccc1S(=O)(=O)Cc1ccc(-c2ccoc2)c(OCCNC(=O)OC(C)(C)C)c1C(=O)O]

Prepared by proceeding in a similar manner to Intermediate 6, starting from methyl 2-[2-(t-butoxycarbonyl)aminoethoxy]-3-(furan-3-yl)-6-(2-methoxybenzenesulphonylmethyl)benzoate (Intermediate 14).

NMR (DMSO-d$_6$) δ 8.15 (s, 1H), 7.75 (t, 1H), 7.7 (dt, 1H), 7.6 (m, 2H), 7.3 (d, 1H), 7.1 (d, 1H), 7.05 (t, 1H), 7.0 (s, 1H), 6.95 (br s, 1H), 4.85 (s, 2H), 4.0 (s, 3H), 3.7 (t, 2H), 3.2 (br s, 2H), 1.4 (s, 9H).

Intermediate 10

Ethyl 6-(benzenesulphonylmethyl)-2-[2-(t-butoxycarbonyl)aminoethoxy]-3-(furan-3-yl)-benzoate

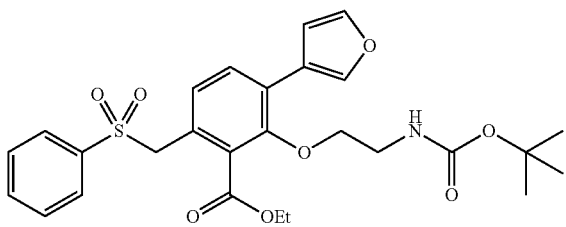

A solution of 2-[N-(t-butoxycarbonyl)amino]ethyl bromide (0.032 g) in DMF (0.5 ml) was added to a stirred cooled solution of ethyl 6-(benzenesulphonylmethyl)-3-(furan-3-yl)-2-hydroxybenzoate (Intermediate 36, 0.05 g) and cesium carbonate (0.065 g) in DMF (0.5 ml) at 0° C. The resultant mixture was allowed to warm to room temperature, stirred for 3 hours then partitioned between ethyl acetate and water. The organic layer was washed with water, dried (MgSO$_4$) and filtered. The filtrate was evaporated to dryness and the residue was purified by chromatography on silica, eluting with a mixture of ethyl acetate and cyclohexane with a gradient of 20-25% to give ethyl 6-(benzenesulphonylmethyl)-2-[2-(t-butoxycarbonyl)amino-ethoxy]-3-(furan-3-yl)-benzoate (0.031 g) as a colourless gum.

NMR (CDCL$_3$) 7.85 (m, 1H), 7.7 (m, 2H), 7.65 (t, 1H), 7.5 (m, 3H), 7.4 (d, 1H), 7.05 (d, 1H), 6.75 (m, 1H), 4.95 (br s, 1H), 4.55 (s, 2H), 4.4 (q, 2H), 3.8 (t, 2H), 3.35 (m, 2H), 1.45 (s, 9H), 1.4 (t, 3H).

Intermediate 11

Ethyl 6-(benzenesulphonylmethyl)-2-ethoxy-3-(furan-3-yl)benzoate

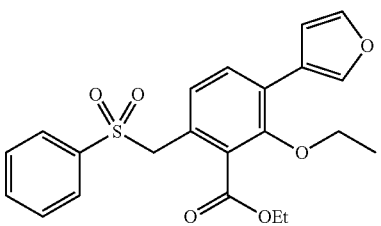

Prepared by proceeding in a similar manner to Intermediate 10, starting from ethyl 6-(benzenesulphonylmethyl)-3-(furan-3-yl)-2-hydroxybenzoate (Intermediate 36) and iodoethane.

NMR (CDCl$_3$) δ 7.95 (s, 1H), 7.7 (d, 2H), 7.6 (t, 1H), 7.5 (m, 3H), 7.4 (d, 1H), 7.05 (d, 1H), 6.75 (s, 1H), 4.55 (s, 2H), 4.3 (q, 2H), 3.75 (q, 2H), 1.4 (t, 3H), 1.25 (t, 2H).

Intermediate 12

Methyl 2-[2-(t-butoxycarbonyl)aminoethoxy]-6-(3-chlorobenzenesulphonyl-methyl)-3-(furan-3-yl)benzoate

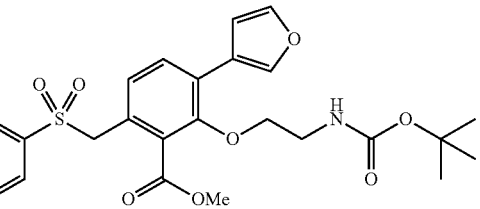

Prepared by proceeding in a similar manner to Intermediate 10, starting from methyl 6-(3-chlorobenzenesulphonylmethyl)-3-(furan-3-yl)-2-hydroxybenzoate (Intermediate 37) and 2-[N-(t-butoxycarbonyl)amino]ethyl bromide.

NMR (CDCl$_3$) δ 7.85 (s, 1H), 7.65 (t, 1H), 7.6 (d, 1H), 7.55 (d, 1H), 7.5 (t, 1H), 7.4 (m, 2H), 7.1 (d, 1H), 6.75 (s, 1H), 4.9 (br s, 1H), 4.55 (s, 2H), 3.85 (s, 3H), 3.75 (t, 2H), 3.3 (br s, 2H), 1.45 (s, 9H).

Intermediate 13

Methyl 2-[2-(t-butoxycarbonyl)aminoethoxy]-6-(4-fluorobenzenesulphonyl-methyl)-3-(furan-3-yl)benzoate

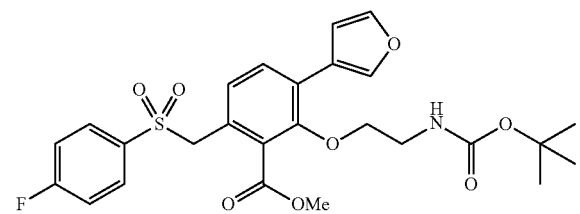 [SMILES: COC(=O)c1c(CS(=O)(=O)c2ccc(F)cc2)ccc(-c2ccoc2)c1OCCNC(=O)OC(C)(C)C]

Prepared by proceeding in a similar manner to Intermediate 10, starting from methyl 6-(4-fluorobenzenesulphonylmethyl)-3-(furan-3-yl)-2-hydroxybenzoate (Intermediate 38) and 2-[N-(t-butoxycarbonyl)amino]ethyl bromide.

NMR (CDCl$_3$) δ 7.85 (s, 1H), 7.65 (m, 2H), 7.5 (t, 1H), 7.45 (d, 1H), 7.15 (t, 2H), 7.05 (d, 1H), 6.7 (s, 1H), 4.9 (br s, 1H), 4.55 (s, 2H), 3.9 (s, 3H), 3.75 (t, 2H), 3.35 (br s, 2H), 1.45 (s, 9H).

Intermediate 14

Methyl 2-[2-(t-butoxycarbonyl)aminoethoxy]-3-(furan-3-yl)-6-(2-methoxybenzenesulphonylmethyl)benzoate

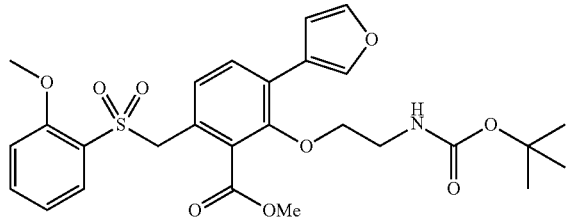

Prepared by proceeding in a similar manner to Intermediate 10, starting from methyl 3-(furan-3-yl)-2-hydroxy-6-(2-methoxybenzenesulphonylmethyl)benzoate (Intermediate 39) and 2-[N-(t-butoxycarbonyl)amino]ethyl bromide.

NMR (CDCl$_3$) δ 7.8 (s, 1H), 7.75 (dd, 1H), 7.55 (dt, 1H), 7.45 (t, 1H), 7.35 (d, 1H), 7.05 (m, 3H), 6.7 (s, 1H), 5.0 (br s, 1H), 4.8 (s, 2H), 4.05 (s, 3H), 3.95 (s, 3H), 3.75 (t, 2H), 3.35 (m, 2H), 1.45 (s, 9H).

Intermediate 15

Methyl 6-(benzenesulphonylmethyl)-3-(furan-3-yl)-2-(2-methoxy-ethoxy)benzoate

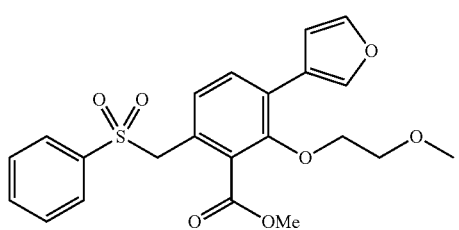 [SMILES: COCCOc1c(-c2ccoc2)ccc(CS(=O)(=O)c2ccccc2)c1C(=O)OC]

Prepared by proceeding in a similar manner to Intermediate 10, starting from methyl 6-(benzenesulphonylmethyl)-3-(furan-3-yl)-2-hydroxybenzoate (Intermediate 114) and 2-bromoethyl methyl ether.

NMR (CDCl$_3$) δ 8.05 (s, 1H), 7.65 (d, 2H), 7.6 (t, 1H), 7.45 (m, 4H), 7.1 (d, 1H), 6.75 (s, 1H), 4.55 (s, 2H), 3.85 (m, 2H), 3.8 (s, 3H), 3.55 (m, 2H), 3.35 (s, 3H).

Intermediate 16

Methyl 6-(benzenesulphonylmethyl)-2-(2-dimethylaminoethoxy)-3-(furan-3-yl)benzoate

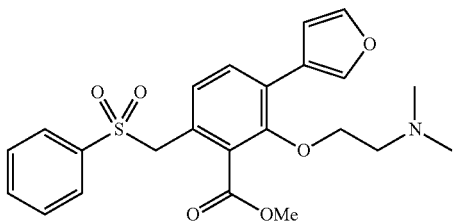

A mixture of methyl 6-(benzenesulphonylmethyl)-3-(furan-3-yl)-2-hydroxybenzoate (Intermediate 114, 0.08 g), N,N-dimethylethanolamine (0.024 g) and triphenylphosphine (0.085 g) in dry THF (1 ml) was stirred and cooled to 0° C. A solution of di-isopropyl azodicarboxylate (0.065 g) in dry THF (1 ml) was added dropwise. The resultant mixture was stirred at 0° C. for 10 minutes then at room temperature overnight. Further triphenylphosphine (0.028 g) and di-isopropyl azodicarboxylate (0.022 g) was added and the mixture was stirred at room temperature for 1.5 hours then left to stand at room temperature overnight. The mixture was added to a SCX-2 column and eluted with acetonitrile followed by 2M ammonia in methanol. After evaporation of the basic eluent, the residue was repurified using an SCX-2 column, eluting with methanol followed by 2M ammonia in methanol to give methyl 6-(benzenesulphonylmethyl)-2-(2-dimethylaminoethoxy)-3-(furan-3-yl)benzoate (0.07 g) as a gum.

NMR (CDCl$_3$) δ 8.0 (s, 1H), 7.65 (d, 2H), 7.6 (t, 1H), 7.45 (m, 3H), 7.4 (d, 1H), 7.05 (d, 1H), 6.75 (s, 1H), 4.55 (s, 2H), 3.85 (s, 3H), 3.8 (t, 2H), 2.55 (t, 2H), 2.25 (s, 6H).

Intermediate 17

Ethyl 6-(benzenesulphonylmethyl)-3-(furan-3-yl)-2-(2-hydroxy-ethoxy)benzoate

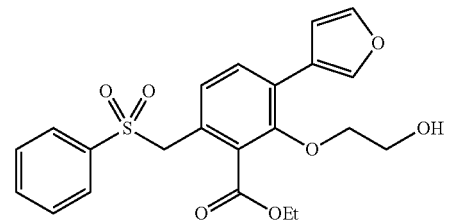

A solution of 2-bromoethanol (0.034 g) in DMF (1 ml) was added to a stirred mixture of ethyl 6-(benzenesulphonylmethyl)-3-(furan-3-yl)-2-hydroxybenzoate (Intermediate 36, 0.1 g) and cesium carbonate (0.127 g) in DMF (1 ml). The resultant mixture was stirred at room temperature for 3 hours. Further 2-bromoethanol (0.017 g) was added and the mixture was stirred at room temperature for a further 3 days. Cesium carbonate (0.085 g) and 2-bromoethanol (0.024 g) were added and the mixture was stirred for 1 hour. 2-Bromoethanol (0.015 g) was added and the mixture was stirred for a further 1 hour. The resultant mixture was partitioned between ethyl acetate and water and the aqueous layer was further extracted with ethyl acetate. The combined organic layers were washed with water, dried (Na$_2$SO$_4$) and filtered. The filtrate was evaporated to dryness and the residue was purified by chromatography on silica, eluting with a mixture of ethyl acetate and cyclohexane with a gradient of 30-50%. The product was again purified by chromatography on silica, eluting with a mixture of ethyl acetate and pentane with a gradient of 25-30% to give ethyl 6-(benzenesulphonylmethyl)-3-(furan-3-yl)-2-(2-hydroxyethoxy)benzoate (0.037 g) as a white solid.

LCMS (Method E) r/t 3.85 (M+Na) 453.

Intermediate 18

6-Ethyl-3H-isobenzofuran-1-one

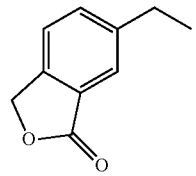

A mixture of 6-bromo-3H-isobenzofuran-1-one (Intermediate 72, 0.7 g) and potassium phosphate (1.9 g) in THF (7.3 ml) and water (3.7 ml) was degassed and palladium chloride dppf adduct with DCM (0.134 g) and triethyl borane (1M solution in THF, 4.3 ml) were added. The resultant mixture was stirred and heated at 100° C. for 1.5 hours. After cooling to room temperature, the mixture was diluted with ethyl acetate and washed with water and brine then dried (Na$_2$SO$_4$) and filtered. The filtrate was evaporated to dryness and the residue was purified by chromatography on silica, eluting with a mixture of ethyl acetate and cyclohexane with a gradient of 0-30% to give 6-ethyl-3H-isobenzofuran-1-one (0.435 g) as a colourless oil.

LCMS (method F) r/t 3.58 (M+H) 163.

Intermediate 19

Ethyl 6-(phenylthiomethyl)-3-ethyl-2-methoxybenzoate

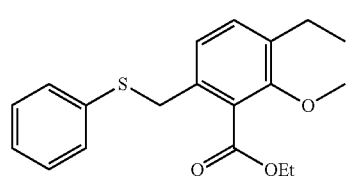 [SMILES: CCOC(=O)c1c(CSc2ccccc2)ccc(CC)c1OC]

Prepared by proceeding in a similar manner to Intermediate 18, starting from ethyl 3-bromo-6-(phenylthiomethyl)-2-methoxybenzoate (Intermediate 73) and triethyl borane.

LCMS (method E) r/t 4.80 M+H) 331.

Intermediate 20

Ethyl 6-(benzenesulphonylmethyl)-3-ethyl-2-methoxybenzoate

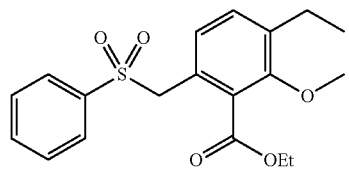 [SMILES: CCOC(=O)c1c(CS(=O)(=O)c2ccccc2)ccc(CC)c1OC]

Prepared by proceeding in a similar manner to Intermediate 18, starting from ethyl 6-(benzenesulphonylmethyl)-3-bromo-2-methoxybenzoate (Intermediate 61) and triethylborane.

LCMS (Method E) r/t 4.19 (M+Na) 385.

Intermediate 21

Ethyl 6-(4-chlorobenzenesulphonylmethyl)-3-ethyl-2-methoxybenzoate

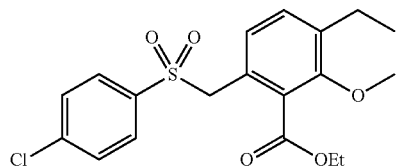 [SMILES: CCOC(=O)c1c(CS(=O)(=O)c2ccc(Cl)cc2)ccc(CC)c1OC]

Prepared by proceeding in a similar manner to Intermediate 18, starting from ethyl 6-(4-chlorobenzenesulphonylmethyl)-3-bromo-2-methoxybenzoate (Intermediate 84) and triethyl borane.

NMR (CDCl$_3$) δ 7.55 (d, 2H), 7.4 (d, 2H), 7.25 (d, 1H), 7.0 (d, 1H), 4.55 (s, 2H), 4.3 (q, 2H), 3.75 (s, 3H), 2.7 (q, 2H), 1.35 (t, 3H), 1.25 (t, 3H).

Intermediate 22

Ethyl 3-ethyl-2-methoxy-6-(2-methylbenzenesulphonylmethyl)benzoate

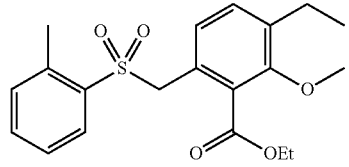 [SMILES: CCOC(=O)c1c(CS(=O)(=O)c2ccccc2C)ccc(CC)c1OC]

Prepared by proceeding in a similar manner to Intermediate 18, starting from ethyl 3-bromo-2-methoxy-6-(2-methylbenzenesulphonylmethyl)benzoate (Intermediate 62) and triethyl borane.

NMR (CDCl₃) δ 7.8 (d, 1H), 7.45 (t, 1H), 7.3 (m, 2H), 7.2 (d, 1H), 6.95 (d, 1H), 4.55 (s, 2H), 4.3 (q, 2H), 3.75 (s, 3H), 2.65 (q, 2H), 2.55 (s, 3H), 1.4 (t, 3H), 1.2 (t, 3H).

Intermediate 23

Ethyl 2-methoxy-6-(2-methylbenzenesulphonylmethyl)benzoate

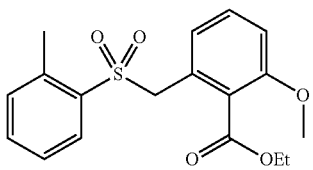 [SMILES: CCOC(=O)c1c(CS(=O)(=O)c2ccccc2C)cccc1OC]

Isolated from the reaction of ethyl 3-bromo-2-methoxy-6-(2-methylbenzene-sulphonylmethyl)benzoate (Intermediate 62) and triethyl borane.

NMR (CDCl₃) δ 7.8 (dd, 1H), 7.45 (dt, 1H), 7.25 (m, 3H), 6.9 (d, 1H), 6.85 (d, 1H), 4.55 (s, 2H), 4.3 (q, 2H), 3.8 (s, 3H), 2.6 (s, 3H), 1.35 (t, 3H).

Intermediate 24

Ethyl 3-ethyl-6-(4-fluorobenzenesulphonylmethyl)-2-methoxybenzoate

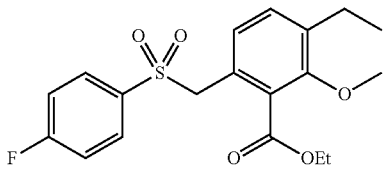

Prepared by proceeding in a similar manner to Intermediate 18, starting from ethyl 3-bromo-6-(4-fluorobenzene-sulphonylmethyl)-2-methoxy-benzoate (Intermediate 85) and triethyl borane.

NMR (CDCl₃) δ 7.65 (m, 2H), 7.2 (d, 1H), 7.1 (t, 2H), 7.0 (d, 1H), 4.5 (s, 2H), 4.3 (q, 2H), 3.75 (s, 3H), 2.7 (q, 2H), 1.35 (t, 3H), 1.2 (t, 3H).

Intermediate 25

Ethyl 6-(benzenesulphonylmethyl)-2-methoxy-3-propylbenzoate

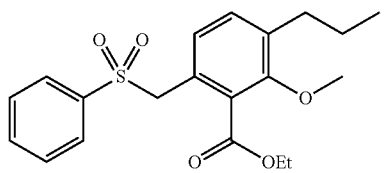 [SMILES: CCCc1ccc(CS(=O)(=O)c2ccccc2)c(C(=O)OCC)c1OC]

A mixture of ethyl 6-(benzenesulphonylmethyl)-3-bromo-2-methoxybenzoate (Intermediate 61, 0.1 g), palladium chloride dppf adduct with DCM (0.01 g), copper (I) iodide (0.003 g) and n-propyl zinc bromide (0.5M solution in THF, 0.96 ml) in THF (0.5 ml) was stirred and heated in the microwave at 160° C. for 10 minutes. After cooling, the mixture was filtered and the filtrate was evaporated to dryness. The residue was purified by chromatography on silica, eluting with a mixture of ethyl acetate and cyclohexane with a gradient of 0-60% to give ethyl 6-(benzenesulphonylmethyl)-2-methoxy-3-propylbenzoate (0.034 g) as a clear gum.

LCMS (Method F) r/t 4.47 (M+Na) 399.

Intermediate 26

Ethyl 6-(benzenesulphonylmethyl)-3-cyclopropyl-2-methoxybenzoate

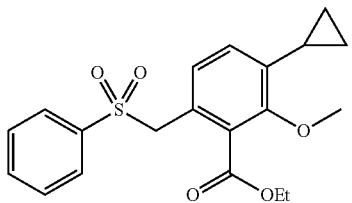 [SMILES: CCOC(=O)c1c(CS(=O)(=O)c2ccccc2)ccc(C2CC2)c1OC]

A mixture of ethyl 6-(benzenesulphonylmethyl)-3-bromo-2-methoxybenzoate (Intermediate 61, 0.347 g), cyclopropyl boronic acid monohydrate (0.087 g), palladium chloride dppf adduct with DCM (0.07 g) and cesium carbonate (0.8 g) in THF (9 ml) and water (1 ml) was sealed in a microwave vial and degassed. The mixture was then heated in the microwave at 140° C. for 15 minutes. After cooling, the mixture was dried (MgSO₄) and filtered through Celite. The filtrate was evaporated to dryness and the residue was purified by chromatography on silica, eluting with a mixture of t-butyl methyl ether and cyclohexane with a gradient from 0-60% to give ethyl 6-(benzenesulphonylmethyl)-cyclopropyl-2-methoxybenzoate (0.187 g) as a gum.

NMR (CDCl₃) δ 7.65 (dd, 2H), 7.6 (t, 1H), 7.45 (t, 2H), 6.95 (d, 1H), 6.8 (d, 1H), 4.5 (s, 2H), 4.3 (q, 2H), 3.85 (s, 3H), 2.15 (m, 1H), 1.35 (t, 3H), 1.05 (m, 2H), 0.7 (m, 2H).

Intermediate 27

Ethyl 6-(benzenesulphonylmethyl)-2-methoxy-3-methylbenzoate

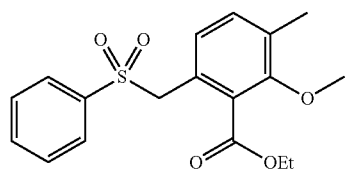 [SMILES: CCOC(=O)c1c(CS(=O)(=O)c2ccccc2)ccc(C)c1OC]

A mixture of ethyl 6-(benzenesulphonylmethyl)-3-bromo-2-methoxybenzoate (Intermediate 61, 0.332 g), potassium methyltrifluoro borate (0.0675 g), palladium chloride dppf adduct with DCM (0.066 g) and cesium carbonate (0.786 g) in THF (9 ml) and water (1 ml) was sealed in a microwave vial and degassed. The mixture was then heated in the microwave at 160° C. for 30 minutes. After cooling, the mixture was dried (MgSO₄) and filtered through Celite, and the pad was washed with ethyl acetate. The filtrate was evaporated to dryness and the residue was purified by chromatography on silica, eluting with a mixture of ethyl acetate and cyclohexane with a gradient of 0-50% to give ethyl 6-(benzenesulphonylmethyl)-2-methoxy-3-methylbenzoate (0.05 g) as a colourless gum.

NMR (CDCl₃) δ 7.65 (d, 2H), 7.6 (t, 1H), 7.45 (t, 2H), 7.15 (d, 1H), 6.95 (d, 1H), 4.55 (s, 2H), 4.3 (q, 2H), 3.75 (s, 3H), 2.3 (s, 3H), 1.35 (t, 3H).

Intermediate 28

Ethyl 6-(benzenesulphonylmethyl)-3-(furan-3-yl)-2-methoxybenzoate

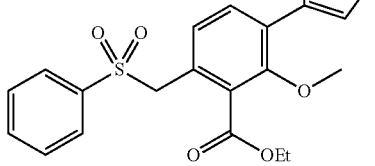

A mixture of ethyl 6-(benzenesulphonylmethyl)-3-bromo-2-methoxybenzoate (Intermediate 61, 0.13 g), furan-3-yl boronic acid (0.036 g), palladium chloride dppf adduct with DCM (0.026 g) and cesium carbonate (0.3 g) in THF (3.5 ml) and water (0.5 ml) was sealed in a microwave vial and degassed. The mixture was then heated in the microwave at 140° C. for 10 minutes. After cooling, the mixture was poured into water and extracted with ethyl acetate. The organic phase was dried (MgSO₄) and filtered. The filtrate was evaporated to dryness and the residue was purified by chromatography on silica, eluting with a mixture of ethyl acetate and cyclohexane with a gradient of 0-60% to give ethyl 6-(benzenesulphonyl-methyl)-3-(furan-3-yl)-2-methoxy-benzoate (0.08 g) as a colourless gum.

LCMS (Method F) r/t 4.14 (M+Na) 423.

Intermediate 29

Ethyl 3-(furan-3-yl)-2-methoxy-6-(2-methylbenzenesulphonylmethyl)benzoate

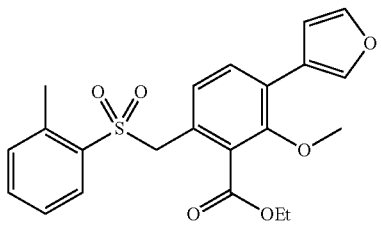 [SMILES: CCOC(=O)c1c(CS(=O)(=O)c2ccccc2C)ccc(-c2ccoc2)c1OC]

Prepared by proceeding in a similar manner to Intermediate 28, starting from ethyl 3-bromo-2-methoxy-6-(2-methylbenzenesulphonylmethyl)benzoate (Intermediate 62) and furan-3-yl boronic acid.

NMR (CDCl₃) δ 7.9 (s, 1H), 7.8 (d, 1H), 7.5 (m, 1H), 7.45 (s, 1H), 7.4 (d, 1H), 7.3 (m, 2H), 7.05 (d, 1H), 6.75 (s, 1H), 4.6 (s, 2H), 4.35 (q, 2H), 3.65 (s, 3H), 2.6 (s, 3H), 1.4 (t, 3H).

Intermediate 30

Ethyl 6-(3-chlorobenzenesulphonylmethyl)-3-(furan-3-yl)-2-methoxybenzoate

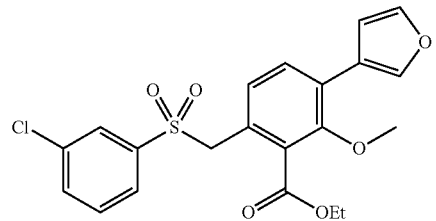

Prepared by proceeding in a similar manner to Intermediate 28, starting from ethyl 3-bromo-6-(3-chlorobenzenesulphonylmethyl)-2-methoxybenzoate (Intermediate 64) and furan-3-yl boronic acid.

NMR (CDCl₃) δ 7.95 (s, 1H), 7.65 (s, 1H), 7.6 (m, 2H), 7.5 (m, 2H), 7.4 (t, 1H), 7.1 (d, 1H), 6.75 (s, 1H), 4.55 (s, 2H), 4.3 (q, 2H), 3.6 (s, 3H), 1.6 (t, 3H).

Intermediate 31

Ethyl 6-(benzenesulphonylmethyl)-2-methoxy-3-(oxazol-5-yl)benzoate

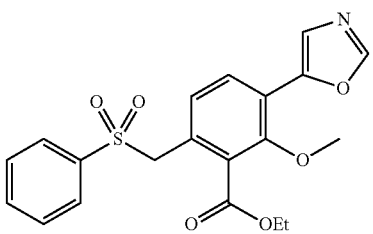 [SMILES: CCOC(=O)c1c(CS(=O)(=O)c2ccccc2)ccc(-c2cnco2)c1OC]

A mixture of ethyl 6-(benzenesulphonylmethyl)-3-bromo-2-methoxybenzoate (Intermediate 61, 0.1 g), 5-(4,4,5,5-tetramethyl-1,3,2-dioxaborolan-2-yl)oxazole (0.071 g), tetrakis-(triphenylphosphine) palladium (0.028 g), potassium fluoride monohydrate (0.102 g) and sodium bromide (0.045 g) in toluene (2 ml) was heated in a sealed tube under nitrogen at 125° C. for 18 hours. The mixture was diluted with ethyl acetate, washed with water, dried (MgSO₄) and filtered. The filtrate was evaporated to dryness and the residue was purified by chromatography on silica, eluting with a mixture of ethyl acetate and cyclohexane with a gradient of 0-100% to give ethyl 6-(benzenesulphonylmethyl)-2-methoxy-3-(oxazol-5-yl)benzoate (0.075 g) as a yellow gum.

LCMS (method E) r/t 3.81 (M+H) 402.

Intermediate 32

Ethyl 6-(benzenesulphonylmethyl)-3-(isothiazol-5-yl)-2-methoxybenzoate

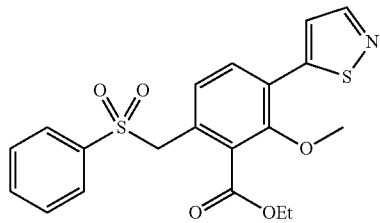 [SMILES: CCOC(=O)c1c(CS(=O)(=O)c2ccccc2)ccc(-c2ccns2)c1OC]

Prepared by proceeding in a similar manner to Intermediate 31, starting from ethyl 6-(benzenesulphonylmethyl)-3-bromo-2-methoxybenzoate (Intermediate 61) and 5-(4,4,5,5-tetramethyl-1,3,2-dioxaborolan-2-yl)isothiazole.

NMR (CDCl$_3$) δ 8.5 (d, 1H), 7.7 (m, 3H), 7.65 (t, 1H), 7.6 (d, 1H), 7.5 (t, 2H), 7.1 (d, 1H), 4.6 (s, 2H), 4.35 (q, 2H), 3.75 (s, 3H), 1.4 (t, 3H).

Intermediate 33

Ethyl 6-(benzenesulphonylmethyl)-2-methoxy-3-phenylbenzoate

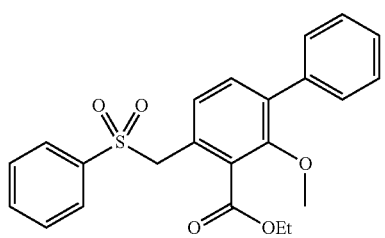 [SMILES: CCOC(=O)c1c(CS(=O)(=O)c2ccccc2)ccc(-c2ccccc2)c1OC]

Prepared by proceeding in a similar manner to Intermediate 28, starting from ethyl 6-(benzenesulphonylmethyl)-3-bromo-2-methoxybenzoate (Intermediate 61) and phenylboronic acid.

NMR (CDCl$_3$) δ 7.75 (d, 2H), 7.65 (t, 1H), 7.55 (m, 4H), 7.45 (t, 2H), 7.35 (m, 2H), 7.1 (d, 1H), 4.55 (s, 2H), 4.35 (q, 2H), 3.35 (s, 3H), 1.35 (t, 3H).

Intermediate 34

Ethyl 6-(benzenesulphonylmethyl)-2-methoxy-3-(pyrid-3-yl)benzoate

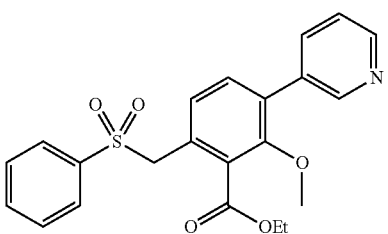 [SMILES: CCOC(=O)c1c(CS(=O)(=O)c2ccccc2)ccc(-c2cccnc2)c1OC]

Prepared by proceeding in a similar manner to Intermediate 28, starting from ethyl 6-benzenesulphonylmethyl-3-bromo-2-methoxybenzoate (Intermediate 61) and 3-pyridylboronic acid.

NMR (CDCl$_3$) δ 8.8 (s, 1H), 8.65 (d, 1H), 7.9 (dt, 1H), 7.75 (m, 2H), 7.65 (tt, 1H), 7.5 (t, 2H), 7.35 (m, 2H), 7.15 (d, 1H), 4.6 (s, 2H), 4.35 (q, 2H), 3.4 (s, 3H), 1.4 (t, 3H).

Intermediate 35

Methyl 6-(benzenesulphonylmethyl)-2-methoxy-3-(thiazol-2-yl)benzoate

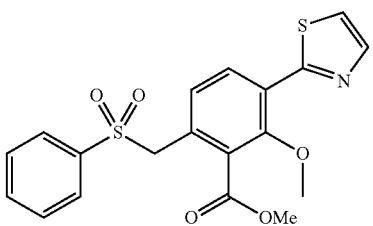 [SMILES: COC(=O)c1c(CS(=O)(=O)c2ccccc2)ccc(-c2nccs2)c1OC]

A mixture of methyl 6-(benzenesulphonylmethyl)-2-methoxy-3-(4,4,5,5-tetramethyl-1,3,2-dioxaborolan-2-yl)benzoate (Intermediate 59, 0.284 g), tetrakis-(triphenylphosphine) palladium (0.05 g), 2-bromothiazole (0.267 g), potassium fluoride monohydrate (0.25 g) and sodium bromide (0.117 g) in α,α,α-trifluorotoluene (5 ml) was degassed and then heated in the microwave at 175° C. for 2 hours. Ethyl acetate was added and the mixture was filtered. The filtrate was evaporated to dryness and the residue was purified by chromatography on silica, eluting with a mixture of ethyl acetate and cyclohexane with a gradient of 0-100% to give methyl 6-benzenesulphonylmethyl-2-methoxy-3-(thiazol-2-yl)-benzoate (0.05 g) as a brown oil.

LCMS (Method F) r/t 3.84 (M+H) 404.

Intermediate 36

Ethyl 6-(benzenesulphonylmethyl)-3-(furan-3-yl)-2-hydroxy-benzoate

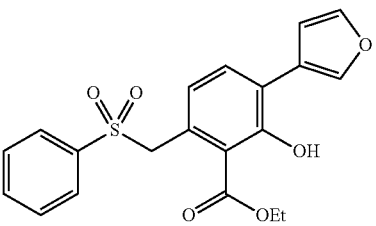 [SMILES: CCOC(=O)c1c(CS(=O)(=O)c2ccccc2)ccc(-c2ccoc2)c1O]

A mixture of ethyl 6-(benzenesulphonylmethyl)-3-bromo-2-hydroxybenzoate (Intermediate 52, 0.39 g), furan-3-yl boronic acid (0.16 g), potassium fluoride monohydrate (0.45 g), tetrakis-(triphenylphosphine) palladium (0.11 g), and sodium bromide (0.15 g) in α,α,α-trifluorotoluene (10 ml) and dioxane (2 ml) was degassed and heated in the microwave at 175° C. for 30 minutes. After cooling, the mixture was partitioned between ethyl acetate and water. The aqueous layer was further extracted with ethyl acetate and the combined organic layers were dried (Na$_2$SO$_4$) and filtered. The filtrate was evaporated to dryness and the residue was purified by chromatography on silica, eluting with a mixture of ethyl acetate and cyclohexane with a gradient of 15-30% to give ethyl 6-benzenesulphonylmethyl-3-(furan-3-yl)-2-hydroxybenzoate (0.25 g) as a white solid.

LCMS (Method E) r/t 4.46 (M+Na) 409.

Intermediate 37

Methyl 6-(3-chlorobenzenesulphonylmethyl)-3-(furan-3-yl)-2-hydroxybenzoate

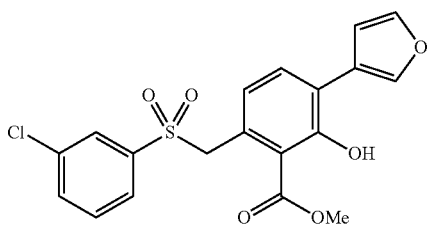 [SMILES: COC(=O)c1c(CS(=O)(=O)c2cccc(Cl)c2)ccc(-c2ccoc2)c1O]

Prepared by proceeding in a similar manner to Intermediate 36, starting from methyl 3-bromo-6-(3-chlorobenzenesulphonylmethyl)-2-hydroxy-benzoate (Intermediate 54) and furan-3-yl boronic acid.

NMR (CDCl$_3$) δ 11.8 (s, 1H), 8.15 (s, 1H), 7.65 (t, 1H), 7.55 (dt, 1H), 7.5 (d, 1H), 7.45 (t, 1H), 7.4 (m, 2H), 7.75 (dd, 1H), 6.55 (d, 1H), 4.9 (s, 2H), 3.95 (s, 3H).

Intermediate 38

Methyl 6-(4-fluorobenzenesulphonylmethyl)-3-(furan-3-yl)-2-hydroxybenzoate

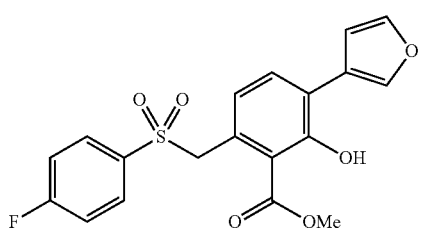 [SMILES: COC(=O)c1c(CS(=O)(=O)c2ccc(F)cc2)ccc(-c2ccoc2)c1O]

Prepared by proceeding in a similar manner to Intermediate 36, starting from methyl 3-bromo-6-(4-fluorobenzenesulphonylmethyl)-2-hydroxybenzoate (Intermediate 55) and furan-3-yl boronic acid.

NMR (CDCl$_3$) δ 11.8 (s, 1H), 8.2 (s, 1H), 7.6 (m, 2H), 7.5 (m, 2H), 7.1 (t, 2H), 6.75 (s, 1H), 6.5 (d, 1H), 4.9 (s, 2H), 3.95 (s, 3H).

Intermediate 39

Methyl 3-(furan-3-yl)-2-hydroxy-6-(2-methoxybenzenesulphonylmethyl)-benzoate

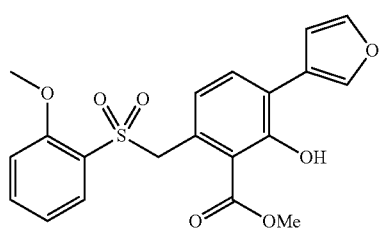 [SMILES: COC(=O)c1c(CS(=O)(=O)c2ccccc2OC)ccc(-c2ccoc2)c1O]

Prepared by proceeding in a similar manner to Intermediate 36, starting from methyl 3-bromo-2-hydroxy-6-(2-methoxybenzenesulphonylmethyl)benzoate (Intermediate 67) and furan-3-yl boronic acid.

NMR (DMSO-d$_6$) δ 10.5 (s, 1H), 8.2 (s, 1H), 7.75 (t, 1H), 7.7 (dt, 1H), 7.65 (d, 1H), 7.55 (dd, 1H), 7.3 (d, 1H), 7.05 (t, 1H), 7.0 (s, 1H), 6.75 (d, 1H), 5.0 (s, 2H), 4.0 (s, 3H), 3.85 (s, 3H).

Intermediate 40

Methyl 3-(3-furan-3-yl)-2-methoxy-6-(2-methoxybenzenesulphonylmethyl)-benzoate

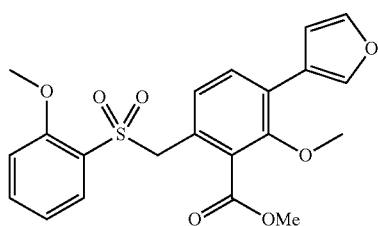

Prepared by proceeding in a similar manner to Intermediate 36, starting from methyl 3-bromo-2-methoxy-6-(2-methoxybenzenesulphonylmethyl)benzoate (Intermediate 70) and furan-3-yl boronic acid.

NMR (CDCl$_3$) δ 7.9 (s, 1H), 7.8 (dd, 1H), 7.55 (dt, 1H), 7.45 (t, 1H), 7.4 (d, 1H), 7.1 (d, 1H), 7.05 (m, 2H), 6.75 (s, 1H), 4.75 (s, 2H), 4.05 (s, 3H), 3.95 (s, 3H), 3.65 (s, 3H).

Intermediate 41

Methyl 3-(3-furan-3-yl)-2-methoxy-6-(pyrid-2-ylsulphonylmethyl)benzoate

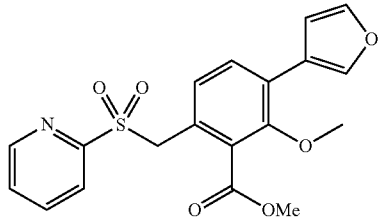 [SMILES: COC(=O)c1c(CS(=O)(=O)c2ccccn2)ccc(-c2ccoc2)c1OC]

Prepared by proceeding in a similar manner to Intermediate 36, starting from methyl 3-bromo-2-methoxy-6-(pyrid-2-ylsulphonylmethyl)benzoate (Intermediate 71) and furan-3-yl boronic acid.

NMR (CDCl$_3$) δ 8.8 (d, 1H), 7.9 (m, 3H), 7.55 (m, 1H), 7.5 (s, 1H), 7.4 (d, 1H), 7.1 (d, 1H), 6.75 (s, 1H), 4.85 (s, 2H), 3.95 (s, 3H), 3.65 (s, 3H).

Intermediate 42

Methyl 2-(benzenesulphonylmethyl)-5-(furan-3-yl)benzoate

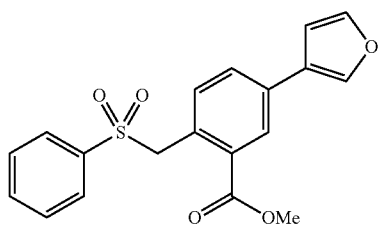 [SMILES: COC(=O)c1cc(-c2ccoc2)ccc1CS(=O)(=O)c1ccccc1]

A mixture of methyl 2-benzenesulphonylmethyl-5-bromobenzoate (Intermediate 63, 0.2 g), furan-3-yl boronic acid (0.091 g), tetrakis-(triphenylphosphine) palladium (0.063 g), potassium fluoride monohydrate (0.0.23 g) and sodium bromide (0.1 g) in α,α,α-trifluorotoluene (2.5 ml) was sealed in a microwave vial and the mixture was degassed then heated in the microwave at 175° C. for 30 minutes. After cooling, the mixture was diluted with DCM and filtered. The filtrate was evaporated to dryness and the residue was purified by chromatography on silica, eluting with a mixture of ethyl acetate and cyclohexane with a gradient of 0-40% to give methyl 2-(benzenesulphonylmethyl)-5-(furan-3-yl)benzoate (0.149 g) as a white solid.

NMR (CDCl₃) δ 8.0 (d, 1H), 7.8 (m, 1H), 7.7 (m, 1H), 7.65 (m, 1H), 7.6 (m, 2H), 7.5 (m, 1H), 7.45 (t, 2H), 7.35 (d, 1H), 6.7 (m, 1H), 5.05 (s, 2H), 3.75 (s, 3H).

Intermediate 43

Methyl 2-(benzenesulphonylmethyl)-5-(oxazol-5-yl)benzoate

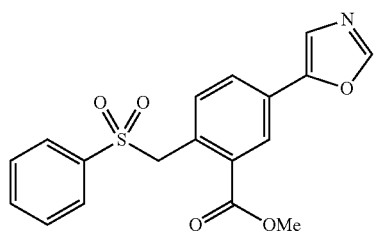 [SMILES: COC(=O)c1cc(-c2cnco2)ccc1CS(=O)(=O)c1ccccc1]

Prepared by proceeding in a similar manner to Intermediate 42, starting from methyl 2-(benzenesulphonylmethyl)-5-bromobenzoate (Intermediate 63) and 5-(4,4,5,5-tetramethyl-1,3,2-dioxaborolan-2-yl)oxazole.

LCMS (Method E) r/t 3.65 (M+H) 358.

Intermediate 44

Methyl 3-(furan-3-yl)-6-((2-(3-hydroxyprop-1-enyl)benzenesulfonyl)methyl)-2-methoxybenzoate (mixture of E and Z isomers)

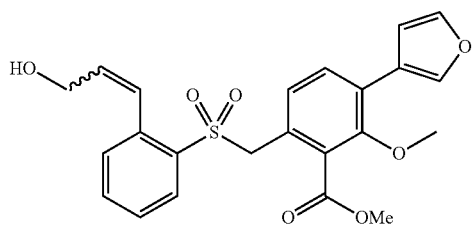 [SMILES: COC(=O)c1c(CS(=O)(=O)c2ccccc2C=CCO)ccc(-c2ccoc2)c1OC]

Prepared by proceeding in a similar manner to Intermediate 42, starting from methyl 3-bromo-6-((2-(3-hydroxyprop-1-enyl)benzenesulfonyl)methyl)-2-methoxybenzoate (mixture of E and Z isomers, Intermediate 60) and furan-3-yl boronic acid.

LCMS (Method E) r/t 3.92 (M+Na) 465.

Intermediate 45

Ethyl 3-(3-furan-3-yl)-2-methoxy-6-(pyrid-3-ylsulphonylmethyl)benzoate

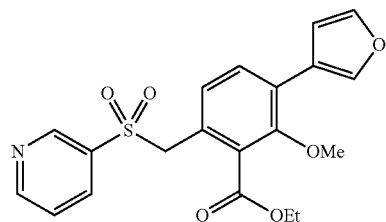 [SMILES: CCOC(=O)c1c(CS(=O)(=O)c2cccnc2)ccc(-c2ccoc2)c1OC]

A mixture of ethyl 3-bromo-2-methoxy-6-(pyrid-3-ylsulphonylmethyl)benzoate (Intermediate 86, 0.13 g), furan-3-yl boronic acid (0.038 g), tri-t-butylphosphine tetrafluoroborate (0.009 g), cesium carbonate (0.303 g) and tris(dibenzylideneacetone) dipalladium (0.015 g) in dioxane (3 ml) and water (0.5 ml) was sealed in a vial and heated at 80° C. under nitrogen for 2 hours. After cooling, the mixture was diluted with t-butyl methyl ether, dried (MgSO₄) and filtered. The filtrate was evaporated to dryness and the residue was purified by preparative HPLC (C18), eluting with a mixture of methanol and water containing 0.1% formic acid with a gradient of 35-98%. The residue was treated again with further furan-3-yl boronic acid (0.038 g), tri-t-butylphosphine tetrafluoroborate (0.009 g), cesium carbonate (0.303 g) and tris(dibenzylideneacetone) dipalladium (0.015 g) in dioxane (3 ml) and water (0.5 ml), sealed and heated at 80° C. for an additional 2 hours. After cooling, the mixture was diluted with t-butyl methyl ether, dried (MgSO₄) and filtered. The filtrate was evaporated to dryness and purified by chromatography on silica, eluting with a mixture of ethyl acetate and cyclohexane with a gradient of 0-50% to give ethyl 3-(3-furan-3-yl)-2-methoxy-6-(3-pyridylsulphonylmethyl)-benzoate (0.098 g) as a gum.

LCMS (Method E) r/t 3.96 (M+H) 402.

Intermediate 46

Ethyl 6-(benzenesulphonylmethyl)-2-methoxy-3-(pyrazol-3-yl)benzoate

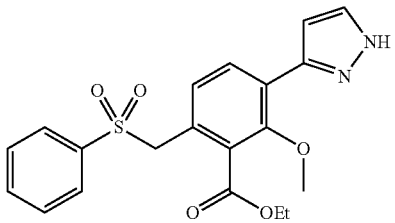

Acetyl chloride (0.1 ml) was added to methanol (10 ml) cooled in ice and the resultant solution was added to ethyl 6-(benzenesulphonylmethyl)-2-methoxy-3-[1-(tetrahydropyran-2-yl)pyrazol-5-yl]benzoate (Intermediate 47, 0.05 g). The resultant mixture was stirred at room temperature for 1 hour then evaporated to dryness. The residue was treated with sodium bicarbonate (saturated aqueous solution) and extracted with DCM, dried (MgSO₄) and filtered. The filtrate was evaporated to dryness to give ethyl 6-(benzenesulphonylmethyl)-2-methoxy-3-(3-pyrazolyl)benzoate (0.041 g) as a gum.

LCMS (Method E) r/t 3.79 (M+H) 401.

Intermediate 47

Ethyl 6-(benzenesulphonylmethyl)-2-methoxy-3-[1-(2-tetrahydro-pyranyl)pyrazol-5-yl]benzoate

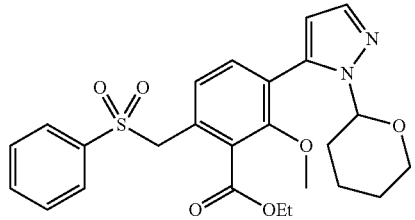 [SMILES: CCOC(=O)c1c(CS(=O)(=O)c2ccccc2)ccc(-c2ccnn2C2CCCCO2)c1OC]

Prepared by proceeding in a similar manner to Intermediate 31, starting from ethyl 6-(benzenesulphonylmethyl)-3-bromo-2-methoxybenzoate (Intermediate 61) and 1-(tetrahydropyran-2-yl)-5-(4,4,5,5-tetramethyl-1,3,2-dioxaborolany-2-yl)pyrazole.

NMR (CDCl$_3$) δ 7.8 (d, 2H), 7.65 (tt, 2H), 7.55 (t, 2H), 7.4 (d, 1H), 7.1 (d, 1H), 6.4 (d, 1H), 5.1 (dd, 1H), 4.65 (d, 1H), 4.55 (d, 1H), 4.35 (m, 2H), 4.0 (m, 1H), 3.45 (t, 1H), 3.4 (s, 3H), 2.55 (m, 1H), 1.9 (m, 1H), 1.8-1.5 (m, 4H), 1.4 (t, 3H).

Intermediate 48

Ethyl 6-(benzenesulphonylmethyl)-3-(isoxazol-3-yl)-2-methoxybenzoate

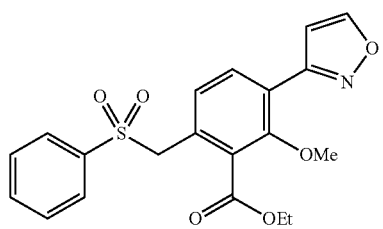 [SMILES: CCOC(=O)c1c(CS(=O)(=O)c2ccccc2)ccc(-c2ccon2)c1OC]

A solution of ethyl 6-(benzenesulphonylmethyl)-3-(5-hydroxy-4,5-dihydroisoxazol-3-yl)-2-methoxybenzoate (Intermediate 49, 0.041 g) in ethanol (3 ml) was stirred and heated in the microwave at 140° C. for 15 minutes then at 160° C. for 75 minutes. After cooling, the solution was evaporated to dryness and the residue was purified by chromatography on silica, eluting with a mixture of ethyl acetate and cyclohexane with a gradient of 0-50% to give ethyl 6-(benzenesulphonylmethyl)-3-(isoxazol-3-yl)-2-methoxybenzoate (0.03 g) as a gum.

NMR (CDCl$_3$) δ 8.5 (d, 1H), 7.85 (d, 1H), 7.7 (d, 2H), 7.65 (t, 1H), 7.5 (t, 2H), 7.05 (d, 1H), 6.85 (d, 1H), 4.6 (s, 2H), 4.35 (q, 2H), 3.65 (s, 3H), 1.4 (t, 3H).

Intermediate 49

Ethyl 6-(benzenesulphonylmethyl)-3-(5-hydroxy-4,5-dihydroisoxazol-3-yl)-2-methoxybenzoate

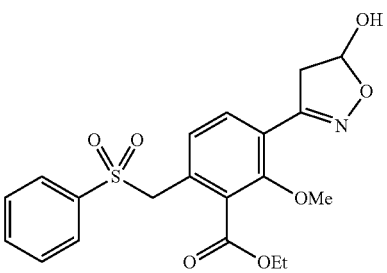 [SMILES: CCOC(=O)c1c(CS(=O)(=O)c2ccccc2)ccc(C2=NOC(O)C2)c1OC]

A mixture of crude ethyl 3-acetyl-6-(benzenesulphonylmethyl)-2-methoxybenzoate (Intermediate 56, 0.33 g) and Brederick's reagent (0.2 ml) in dioxane (3 ml) was stirred and heated in the microwave at 150° C. for 10 minutes. After cooling, the solution was evaporated to dryness and the residue was dissolved in ethanol (15 ml) and treated with hydroxylamine hydrochloride (0.13 g) and pyridine (0.15 ml). The resultant mixture was stirred and heated at reflux overnight. After cooling, the mixture was evaporated to dryness and the residue was partitioned between DCM and water. The organic layer was dried (MgSO$_4$) and filtered. The filtrate was evaporated to dryness and the residue was purified by chromatography on silica, eluting with a mixture of ethyl acetate and cyclohexane with a gradient of 0-100% to give ethyl 6-(benzenesulphonylmethyl)-3-(5-hydroxy-4,5-dihydroisoxazol-3-yl)-2-methoxybenzoate (0.041 g) as a gum.

NMR (CDCl$_3$) 7.7 (d, 2H), 7.65 (m, 2H), 7.5 (t, 2H), 7.0 (d, 1H), 5.65 (m, 1H), 4.6 (s, 2H), 4.35 (q, 2H), 3.75 (s, 3H), 3.45 (m, 2H) 1.4 (t, 3H).

Intermediate 50

Methyl 6-(benzenesulphonylmethyl)-3-(oxazol-4-yl)-2-methoxybenzoate

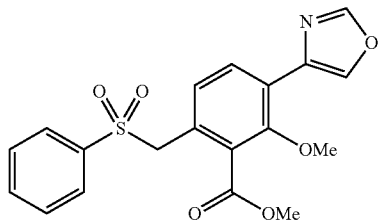 [SMILES: COC(=O)c1c(CS(=O)(=O)c2ccccc2)ccc(-c2cocn2)c1OC]

A mixture of methyl 6-(benzenesulphonylmethyl)-3-(2-bromoacetyl)-2-methoxy-benzoate (Intermediate 51, 0.9 g) and ammonium formate (0.45 g) in formic acid (5 ml) was sealed in a vial and heated at 80° C. for 3 hours then at 100° C. for 6 hours. After standing at room temperature overnight, the mixture was heated at 120° C. for 4 hours. The mixture was diluted with water and extracted with ethyl acetate, dried (MgSO$_4$) and filtered. The filtrate was evaporated to dryness to give methyl 6-(benzenesulphonylmethyl)-3-(oxazol-4-yl)-2-methoxy-benzoate (0.22 g) as a yellow gum which was used directly without further purification or characterisation.

Intermediate 51

Methyl 6-(benzenesulphonylmethyl)-3-(2-bromoacetyl)-2-methoxybenzoate

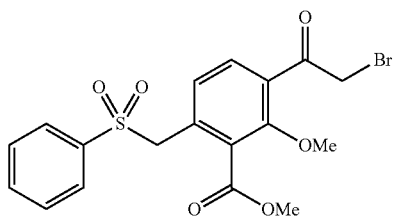 [SMILES: COC(=O)c1c(CS(=O)(=O)c2ccccc2)ccc(C(=O)CBr)c1OC]

A solution of bromine (0.29 g) in acetic acid (2.3 ml) was added dropwise to a solution of methyl 3-acetyl-6-(benzenesulphonylmethyl)-2-methoxybenzoate (Intermediate 57, 0.965 g) in acetic acid (20 ml) over 2 hours. The mixture was poured into water containing methanol (~1 ml) and the resultant mixture was extracted with ethyl acetate, washed with sodium metabisulphite (saturated aqueous solution), dried (MgSO$_4$) and filtered. The filtrate was evaporated to dryness to give methyl 6-(benzenesulphonylmethyl)-3-(2-bromoacetyl)-2-methoxybenzoate (1.2 g) as a colourless oil.

NMR (CDCl$_3$) δ 7.65 (m, 3H), 7.6 (d, 1H), 7.5 (t, 2H), 7.05 (d, 1H), 4.6 (s, 2H), 4.5 (s, 2H), 3.9 (s, 3H), 3.8 (s, 3H).

Intermediate 52

Ethyl 6-(benzenesulphonylmethyl)-3-bromo-2-hydroxybenzoate

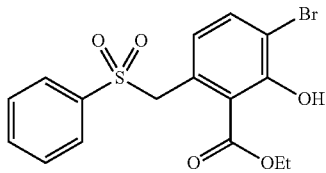 [SMILES: CCOC(=O)c1c(CS(=O)(=O)c2ccccc2)ccc(Br)c1O]

Boron tribromide (1M solution in DCM, 5.85 ml) was added dropwise to a stirred, cooled solution of ethyl 6-(benzenesulphonylmethyl)-3-bromo-2-methoxybenzoate (Intermediate 61, 2.3 g) in dry DCM (45 ml) at −70° C. The resultant mixture was stirred at −70° C. for 40 minutes, then allowed to warm to room temperature. It was stirred at room temperature for 2 hours then poured into sodium bicarbonate (saturated aqueous solution). The layers were separated and the aqueous layer was extracted with further DCM. The combined organic layers were washed with brine, dried (Na$_2$SO$_4$) and filtered. The filtrate was evaporated to dryness to give ethyl 6-(benzenesulphonylmethyl)-3-bromo-2-hydroxybenzoate (1.64 g) as a white solid.

LCMS (Method F) r/t 3.68 (M+Na) 421 and 423.

Intermediate 53

Methyl 3-bromo-6-bromomethyl-2-hydroxybenzoate

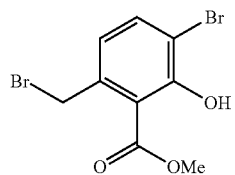

Prepared by proceeding in a similar manner to Intermediate 52, starting from methyl 3-bromo-6-bromomethyl-2-methoxybenzoate (Intermediate 89).

NMR (CDCl$_3$) δ 11.9 (s, 1H), 7.65 (d, 1H), 6.8 (d, 1H), 7.75 (s, 2H), 4.05 (s, 3H).

Intermediate 54

Methyl 3-bromo-6-(3-chlorobenzenesulphonylmethyl)-2-hydroxybenzoate

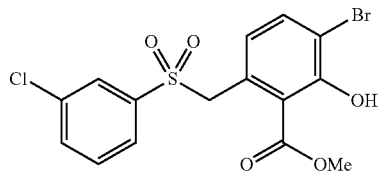 [SMILES: COC(=O)c1c(CS(=O)(=O)c2cccc(Cl)c2)ccc(Br)c1O]

Aluminium chloride (0.7 g) was added to a stirred solution of methyl 3-bromo-6-(3-chlorobenzenesulphonylmethyl)-2-methoxybenzoate (Intermediate 68, 0.76 g) and N,N-dimethylaniline (1.27 g) in DCM (8 ml) and the resultant mixture was stirred for 30 minutes. The mixture was partitioned between ethyl acetate and hydrochloric acid (1M) and the organic layer was washed with sodium bicarbonate (saturated aqueous solution), dried (Na$_2$SO$_4$) and filtered. The filtrate was evaporated to dryness and the residue was triturated with ether. The solid was collected by filtration to give methyl 3-bromo-6-(3-chlorobenzenesulphonylmethyl)-2-hydroxybenzoate (0.61 g) as a white solid.

NMR (DMSO-d$_6$) δ 7.8 (m, 1H), 7.65 (m, 3H), 7.55 (dt, 1H), 6.65 (d, 1H), 4.9 (s, 2H), 3.8 (s, 3H).

Intermediate 55

Methyl 3-bromo-6-(4-fluorobenzenesulphonylmethyl)-2-hydroxybenzoate

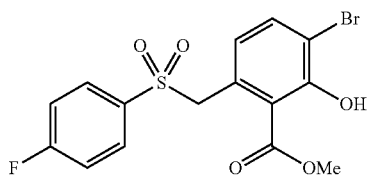 [SMILES: COC(=O)c1c(CS(=O)(=O)c2ccc(F)cc2)ccc(Br)c1O]

Prepared by proceeding in a similar manner to Intermediate 54, starting from methyl 3-bromo-6-(4-fluorobenzenesulphonylmethyl)-2-methoxybenzoate (Intermediate 69).

NMR (DMSO-d$_6$) δ 7.7 (m, 2H), 7.65 (d, 1H), 7.45 (t, 2H), 6.65 (d, 1H), 4.85 (s, 2H), 3.75 (s, 3H).

Intermediate 56

Ethyl 3-acetyl-6-(benzenesulphonylmethyl)-2-methoxybenzoate

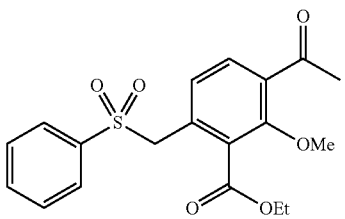 [SMILES: CCOC(=O)c1c(CS(=O)(=O)c2ccccc2)ccc(C(C)=O)c1OC]

A mixture of ethyl 6-(benzenesulphonylmethyl)-3-bromo-2-methoxybenzoate (Intermediate 61, 0.82 g), triethylamine (0.7 ml), 1,3-bis(diphenylphosphino)propane (0.04 g) and palladium chloride (0.01 g) in ethylene glycol (4 ml) was sealed in a vial under nitrogen and the mixture was stirred and heated to 140° C. Butyl vinyl ether (0.8 ml) was then added and the resultant mixture was stirred and heated at 140° C. for 2 hours. After cooling, the mixture was diluted with DCM and 1M hydrochloric acid was added. The mixture was stirred at room temperature for 30 minutes then the two layers were separated and the aqueous layer was extracted with further DCM. The combined organic layers were dried (MgSO$_4$) and filtered. The filtrate was evaporated to dryness. The residue was purified by chromatography on silica, eluting with a mixture of ethyl acetate and cyclohexane with a gradient of 0-80%) to give crude ethyl 3-acetyl-6-(benzenesulphonylmethyl)-2-methoxybenzoate (0.33 g) as an oil.

LCMS (method F) r/t 3.7 (M+Na) 399.

NMR analysis indicated that the compound contained ~30% of an isomer. The material was used without further purification.

Intermediate 57

Methyl 3-acetyl-6-(benzenesulphonylmethyl)-2-methoxybenzoate

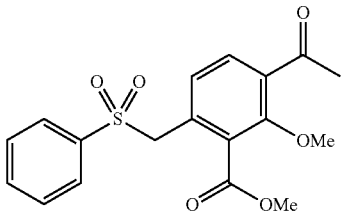 [SMILES: COC(=O)c1c(CS(=O)(=O)c2ccccc2)ccc(C(C)=O)c1OC]

A mixture of methyl 6-(benzenesulphonylmethyl)-3-bromo-2-methoxybenzoate (Intermediate 65, 1.0 g), 1-ethoxyvinyl tributyl stannane (0.9 ml), tetrakis-(triphenylphosphine) palladium (0.29 g) and lithium chloride (1.0 g) in dioxane (15 ml) was stirred and heated in the microwave at 150° C. for 15 minutes. The solution was filtered and the filtrate was diluted with 1M hydrochloric acid and then stirred at room temperature for 5 hours. The resultant mixture was extracted with DCM, dried (MgSO$_4$) and filtered. The filtrate was evaporated to dryness and the residue was purified by chromatography on silica, eluting with a mixture of ethyl acetate and cyclohexane with a gradient of 0-75%) to give methyl 3-acetyl-6-(benzenesulphonylmethyl)-2-methoxybenzoate (0.965 g) as an oil.

NMR (CDCl$_3$) δ 7.7 (d, 2H), 7.65 (t, 1H), 7.6 (d, 1H), 7.5 (t, 2H), 7.05 (d, 1H), 4.6 (s, 2H), 3.9 (s, 3H), 3.8 (s, 3H), 2.6 (s, 3H).

Intermediate 58

Methyl 6-(benzenesulphonylmethyl)-3-(isothiazol-4-yl)-2-methoxybenzoate

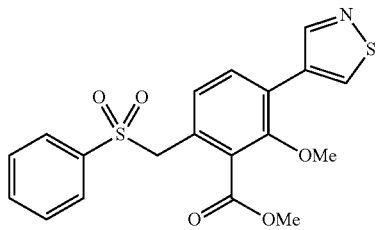 [SMILES: COC(=O)c1c(CS(=O)(=O)c2ccccc2)ccc(-c2cnsc2)c1OC]

A mixture of methyl 6-(benzenesulphonylmethyl)-2-methoxy-3-(4,4,5,5-tetramethyl-1,3,2-dioxaborolan-2-yl) benzoate (Intermediate 59, 0.15 g), tri-tert-butyl-phosphinium tetrafluoroborate (0.01 g), cesium carbonate (0.34 g), tris-(dibenzylideneacetone)-dipalladium (0.016 g), and 4-bromoisothiazole (0.06 g) in dioxane (3.2 ml) and water (0.4 ml) was degassed and then heated in the microwave at 120° C. for 20 minutes. After cooling, the mixture was diluted with ether, dried (MgSO$_4$) and filtered. The filtrate was evaporated to dryness and the residue was purified by chromatography on silica, eluting with a mixture of ethyl acetate and cyclohexane with a gradient of 0-60% to give crude methyl 6-(benzenesulphonylmethyl)-3-(isothiazol-4-yl)-2-methoxy-benzoate (0.044 g) as an oil. The material was used without further purification or characterisation.

Intermediate 59

Methyl 6-(benzenesulphonylmethyl)-2-methoxy-3-(4,4,5,5-tetramethyl-1,3,2-dioxaborolan-2-yl)benzoate

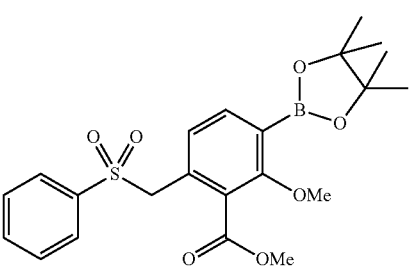 [SMILES: COC(=O)c1c(CS(=O)(=O)c2ccccc2)ccc(B2OC(C)(C)C(C)(C)O2)c1OC]

A mixture of methyl 6-(benzenesulphonylmethyl)-3-bromo-2-methoxybenzoate (Intermediate 65, 1.0 g), palladium chloride dppf adduct with DCM (0.12 g), bis-pinacolatodiboron (0.675 g) and potassium acetate (0.71 g) in dioxane (12.5 ml) and water (1.5 ml) was heated in a sealed vial at 120° C. for 2 hours. After cooling, the mixture was partitioned between ethyl acetate and sodium bicarbonate (saturated aqueous solution). The organic layer was dried (MgSO$_4$) and filtered through Celite. The filtrate was evaporated to dryness and the residue was purified by chromatography on silica, eluting with a mixture of ethyl acetate and cyclohexane with a gradient of 0-100% to give methyl 6-(benzenesulphonylmethyl)-2-methoxy-3-(4,4,5,5-tetramethyl-1,3,2-dioxaborolan-2-yl)benzoate (0.58 g) as a colourless oil.

NMR (CDCl₃) δ 7.7 (d, 1H), 7.65 (m, 2H), 7.6 (m, 1H), 7.45 (t, 2H), 7.05 (d, 1H), 4.55 (s, 2H), 3.80 (s, 3H), 3.75 (s, 3H), 1.35 (s, 12H).

Intermediate 60

Methyl 3-bromo-6-((2-(3-hydroxyprop-1-enyl)benzenesulfonyl)methyl)-2-methoxybenzoate (mixture of E and Z isomers)

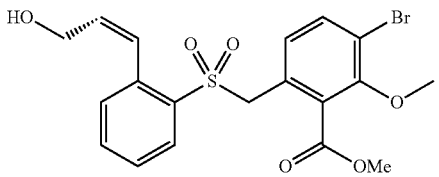

Bis-(tri-tert-butylphosphine)palladium (0.031 g) was added to a degassed solution of methyl 3-bromo-6-(2-bromobenzenesulphonylmethyl)-2-methoxybenzoate (Intermediate 66, 0.286 g) and 3-tributylstannyl-(Z)-prop-2-en-1-ol (prepared according to Webb et al, *Tetrahedron*, 2008, 64, 4778, 0.27 ml) in toluene (3 ml) and the resultant mixture was stirred at room temperature for 3 hours then heated at 30° C. for 2 hours. After cooling, the mixture was filtered through Celite and the filtrate was evaporated to dryness. The residue was purified by chromatography on silica, eluting with a mixture of ethyl acetate and cyclohexane with a gradient of 0-60% to give methyl 3-bromo-6-((2-(3-hydroxyprop-1-enyl)benzenesulfonyl)methyl)-2-methoxybenzoate as a mixture of E and Z isomers.

NMR (CDCl₃) δ 8.0 (dd, 0.4H), 7.9 (dd, 0.6H), 7.65-7.4 (m, 4H), 7.3 (d, 0.4H), 7.1 (d, 0.6H), 6.95 (d 0.6H), 6.9 (d, 0.4H), 6.3 (dt, 0.4H), 6.1 (dt, 0.6H), 4.55 (2s, 2H), 4.4 (br s, 0.8H), 4.25 (d, 1.2H), 4.0 (s, 1.2H), 3.91 (s, 1.2H), 3.9 (s, 1.8H), 3.88 (s, 1.8H).

Intermediate 61

Ethyl 6-(benzenesulphonylmethyl)-3-bromo-2-methoxybenzoate

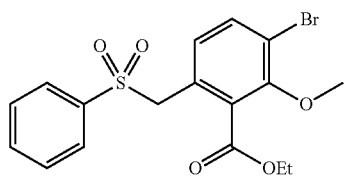 [SMILES: CCOC(=O)c1c(CS(=O)(=O)c2ccccc2)ccc(Br)c1OC]

Hydrogen peroxide (30% aqueous solution, 0.4 ml) was added to a solution of ethyl 3-bromo-6-(phenylthiomethyl)-2-methoxybenzoate (Intermediate 87, 0.314 g) in acetic acid (10 ml). The resultant mixture was stirred and heated at 60° C. for 2 hours. After cooling the mixture was evaporated to dryness and the residue was dissolved in DCM and washed with NaHCO₃ (saturated aqueous solution), dried (MgSO₄) and filtered. The filtrate was evaporated to dryness to give ethyl 6-(benzenesulphonylmethyl)-3-bromo-2-methoxybenzoate (0.331 g) as a colourless gum.

NMR (CDCl₃) δ 7.7 (d, 2H), 7.65 (t, 1H), 7.55 (d, 1H), 7.5 (t, 2H), 6.9 (d, 1H), 4.5 (s, 2H), 4.3 (q, 2H), 3.85 (s, 3H), 1.35 (t, 3H).

Intermediate 62

Ethyl 3-bromo-2-methoxy-6-(2-methylbenzenesulphonylmethyl)benzoate

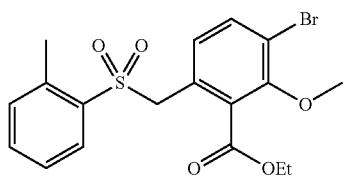 [SMILES: CCOC(=O)c1c(CS(=O)(=O)c2ccccc2C)ccc(Br)c1OC]

Prepared by proceeding in a similar manner to Intermediate 61, starting from ethyl 3-bromo-2-methoxy-(2-methylphenylthiomethyl)benzoate (Intermediate 77).

NMR (CDCl₃) δ 7.75 (d, 1H), 7.55 (d, 1H), 7.5 (t, 1H), 7.3 (m, 2H), 6.9 (d, 1H), 4.55 (s, 2H), 4.35 (q, 2H), 3.9 (s, 3H), 2.6 (s, 3H), 1.4 (t, 3H).

Intermediate 63

Methyl 2-(benzenesulphonylmethyl)-5-bromobenzoate

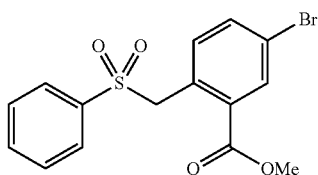 [SMILES: COC(=O)c1cc(Br)ccc1CS(=O)(=O)c1ccccc1]

Prepared by proceeding in a similar manner to Intermediate 61, starting from methyl 5-bromo-2-(phenylthiomethyl)benzoate (Intermediate 78).

NMR (CDCl₃) δ 8.05 (d, 1H), 7.65 (m, 2H), 7.6 (m, 2H), 7.45 (t, 2H), 7.2 (d, 1H), 5.0 (s, 2H), 3.75 (s, 3H).

Intermediate 64

Ethyl 3-bromo-6-(3-chlorobenzenesulphonylmethyl)-2-methoxybenzoate

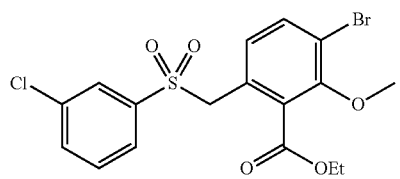 [SMILES: CCOC(=O)c1c(CS(=O)(=O)c2cccc(Cl)c2)ccc(Br)c1OC]

Prepared by proceeding in a similar manner to Intermediate 61, starting from ethyl 3-bromo-6-(3-chlorophenylthiomethyl)-2-methoxybenzoate (Intermediate 79).

NMR (CDCl₃) δ 7.65 (s, 1H), 7.6 (d, 2H), 7.55 (d, 1H), 7.45 (t, 1H), 7.0 (d, 1H), 4.55 (s, 2H), 4.3 (q, 2H), 3.85 (s, 3H), 1.4 (t, 3H).

Intermediate 65

Methyl 6-(benzenesulphonylmethyl)-3-bromo-2-methoxybenzoate

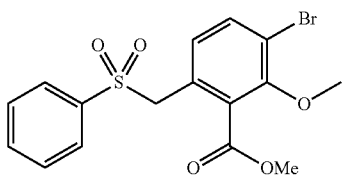 [SMILES: COC(=O)c1c(CS(=O)(=O)c2ccccc2)ccc(Br)c1OC]

Prepared by proceeding in a similar manner to Intermediate 61, starting from methyl 3-bromo-6-(phenylthiomethyl)-2-methoxybenzoate (Intermediate 80).

NMR (CDCl₃) δ 7.7 (d, 2H), 7.65 (t, 1H), 7.6 (d, 1H), 7.5 (t, 2H), 6.95 (d, 1H), 4.5 (s, 2H), 3.9 (s, 3H), 3.85 (s, 3H).

Intermediate 66

Methyl 3-bromo-6-(2-bromobenzenesulphonylmethyl)-2-methoxybenzoate

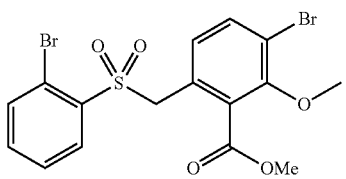

Prepared by proceeding in a similar manner to Intermediate 61, starting from methyl 3-bromo-6-(2-bromophenylthiomethyl)-2-methoxybenzoate (Intermediate 81).

NMR (CDCl₃) δ 7.9 (dd, 1H), 7.8 (dd, 1H), 7.55 (d, 1H), 7.45 (m, 2H), 6.95 (d, 1H), 4.8 (s, 2H), 3.95 (s, 3H), 3.85 (s, 3H).

Intermediate 67

Methyl 3-bromo-2-hydroxy-6-(2-methoxybenzenesulphonylmethyl)benzoate

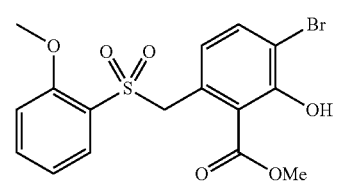 [SMILES: COC(=O)c1c(CS(=O)(=O)c2ccccc2OC)ccc(Br)c1O]

Prepared by proceeding in a similar manner to Intermediate 61, starting from methyl 3-bromo-2-hydroxy-6-(2-methoxyphenylthiomethyl)benzoate (Intermediate 82).

NMR (DMSO-d₆) δ 7.7 (dt, 1H), 7.6 (d, 1H), 7.55 (dd, 1H), 7.3 (d, 1H), 7.05 (t, 1H), 6.7 (d, 1H), 4.85 (s, 2H), 4.0 (s, 3H), 3.8 (s, 3H).

Intermediate 68

Methyl 3-bromo-6-(3-chlorobenzenesulphonylmethyl)-2-methoxybenzoate

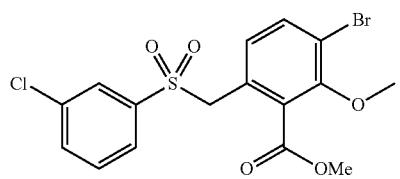 [SMILES: COC(=O)c1c(CS(=O)(=O)c2cccc(Cl)c2)ccc(Br)c1OC]

Hydrogen peroxide (30% aqueous solution, 0.42 ml) was added to a solution of methyl 3-bromo-6-(3-chlorophenylthiomethyl)-2-methoxybenzoate (Intermediate 74, 0.82 g) in acetic acid (5 ml) and the resultant mixture was stirred at room temperature for 20 hours. The mixture was evaporated to dryness and the residue was partitioned between ethyl acetate and water. The organic layer was dried (Na₂SO₄) and filtered. The filtrate was evaporated to dryness to give methyl 3-bromo-6-(3-chlorobenzenesulphonylmethyl)-2-methoxybenzoate (0.765 g) as a colourless gum which was used without further characterisation.

Intermediate 69

Methyl 3-bromo-6-(4-fluorobenzenesulphonylmethyl)-2-methoxybenzoate

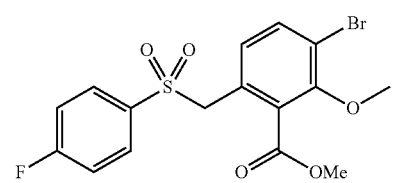 [SMILES: COC(=O)c1c(CS(=O)(=O)c2ccc(F)cc2)ccc(Br)c1OC]

Prepared by proceeding in a similar manner to Intermediate 68, starting from methyl 3-bromo-6-(4-fluorophenylthiomethyl)-2-methoxybenzoate (Intermediate 75) and used without further characterisation.

Intermediate 70

Methyl 3-bromo-2-methoxy-6-(2-methoxybenzenesulphonylmethyl)benzoate

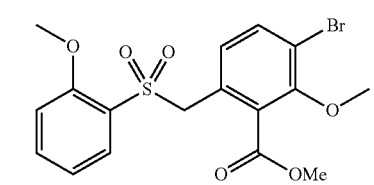 [SMILES: COC(=O)c1c(CS(=O)(=O)c2ccccc2OC)ccc(Br)c1OC]

Prepared by proceeding in a similar manner to Intermediate 68, starting from methyl 3-bromo-2-methoxy-6-(2-methoxyphenylthiomethyl)benzoate (Intermediate 76).

NMR (CDCl$_3$) δ 7.75 (dd, 1H), 7.6 (dt, 1H), 7.5 (d, 1H), 7.05 (m, 2H), 6.95 (d, 1H), 4.75 (s, 2H), 4.0 (s, 3H), 3.95 (s, 3H), 3.85 (s, 3H).

Intermediate 71

Methyl 3-bromo-2-methoxy-6-(2pyrid-2-ylsulphonylmethyl)benzoate

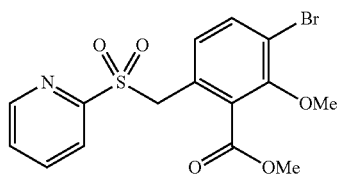 [SMILES: COC(=O)c1c(CS(=O)(=O)c2ccccn2)ccc(Br)c1OC]

Prepared by proceeding in a similar manner to Intermediate 68, starting from methyl 3-bromo-2-methoxy-6-(pyrid-2-ylthiomethyl)benzoate (Intermediate 83).
NMR (CDCl$_3$) δ 8.75 (d, 1H), 7.85 (d, 2H), 7.55 (m, 2H), 6.95 (d, 1H), 4.85 (s, 2H), 3.95 (s, 3H), 3.85 (s, 3H).

Intermediate 72

6-Bromo-3H-isobenzofuran-1-one

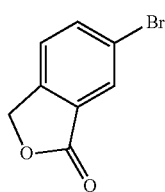 [SMILES: O=C1OCc2ccc(Br)cc21]

Iodosobenzene-1,1-diacetate (5.39 g) was added in portions to a stirred, degassed suspension of 5-bromo-2-methylbenzoic acid (3.0 g) and potassium bromide (1.66 g) in dry DCM (70 ml) under an atmosphere of nitrogen. The resultant mixture was stirred and heated at 40° C. overnight. After cooling to room temperature, the mixture was washed with NaHCO$_3$ (saturated aqueous solution), sodium sulphite (saturated aqueous solution), dried (Na$_2$SO$_4$) and filtered. The filtrate was evaporated to dryness and the residue was purified by chromatography on silica, eluting with a mixture of ethyl acetate and cyclohexane with a gradient of 0-30% to give 6-bromo-3H-isobenzofuran-1-one (1.3 g) as a white solid.
NMR (CDCl$_3$) δ 8.1 (d, 1H), 7.8 (dd, 1H), 7.35 (d, 1H), 5.3 (s, 2H).

Intermediate 73

Ethyl 3-bromo-6-(phenylthiomethyl)-2-methoxybenzoate

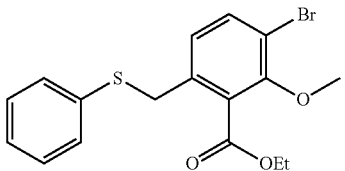 [SMILES: CCOC(=O)c1c(CSc2ccccc2)ccc(Br)c1OC]

A mixture of ethyl 3-bromo-6-bromomethyl-2-methoxybenzoate (Intermediate 87, 0.434 g), thiophenol (0.139 ml) and potassium carbonate (0.34 g) in dry DMF (4 ml) was stirred and heated at 50° C. for 1 hour. After cooling to room temperature, the mixture was diluted with water and extracted with ether. The organic layer was washed with water, dried (Na$_2$SO$_4$) and filtered. The filtrate was evaporated to dryness and the residue was purified by chromatography on silica, eluting with a mixture of ethyl acetate and cyclohexane with a gradient of 0-10% to give ethyl 3-bromo-6-(phenylthiomethyl)-2-methoxybenzoate (0.367 g) as a colourless oil.
NMR (CDCl$_3$) δ 7.45 (d, 1H), 7.25 (m, 5H), 6.9 (d, 1H), 4.4 (q, 2H), 4.1 (s, 2H), 3.9 (s, 3H), 1.35 (t, 3H).

Intermediate 74

Methyl 3-bromo-6-(3-chlorophenylthiomethyl)-2-methoxybenzoate

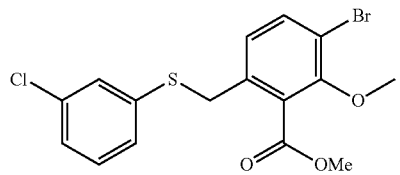

Prepared by proceeding in a similar manner to Intermediate 73, starting from methyl 3-bromo-6-bromomethyl-2-methoxybenzoate (Intermediate 89) and 3-chlorothiophenol.
NMR (CDCl$_3$) δ 7.5 (d, 1H), 7.25 (m, 1H), 7.15 (m, 3H), 6.9 (d, 1H), 4.1 (s, 2H), 3.95 (s, 3H), 3.9 (s, 3H).

Intermediate 75

Methyl 3-bromo-6-(4-fluorophenylthiomethyl)-2-methoxybenzoate

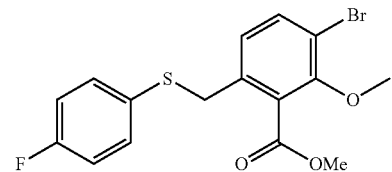 [SMILES: COC(=O)c1c(CSc2ccc(F)cc2)ccc(Br)c1OC]

Prepared by proceeding in a similar manner to Intermediate 73, starting from methyl 3-bromo-6-bromomethyl-2-methoxybenzoate (Intermediate 89) and 4-fluorothiophenol and used without further characterisation.

Intermediate 76

Methyl 3-bromo-2-methoxy-6-(2-methoxyphenylthiomethyl)benzoate

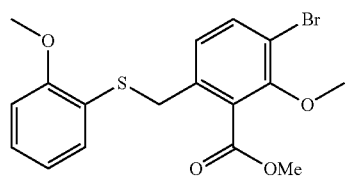 [SMILES: COC(=O)c1c(CSc2ccccc2OC)ccc(Br)c1OC]

Prepared by proceeding in a similar manner to Intermediate 73, starting from methyl 3-bromo-6-bromomethyl-2-methoxybenzoate (Intermediate 89) and 2-methoxythiophenol.
NMR (CDCl$_3$) δ 7.45 (d, 1H), 7.2 (m, 2H), 6.9 (d, 1H), 6.85 (t, 2H), 4.05 (s, 2H), 3.95 (s, 3H), 3.85 (2s, 6H).

Intermediate 77

Ethyl 3-bromo-2-methoxy-(2-methylphenylthiomethyl)benzoate

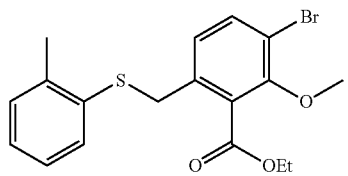 [SMILES: CCOC(=O)c1c(CSc2ccccc2C)ccc(Br)c1OC]

A mixture of ethyl 3-bromo-6-bromomethyl-2-methoxybenzoate (Intermediate 87, 0.262 g), 2-methylthiophenol (0.096 ml) and potassium carbonate (0.28 g) in THF (5 ml) was stirred at room temperature for 3 days. The resultant mixture was partitioned between ethyl acetate and NaHCO$_3$ (saturated aqueous solution). The separated organic phase was dried (MgSO$_4$) and filtered. The filtrate was evaporated to dryness and the residue was purified by chromatography on silica, eluting with a mixture of ethyl acetate and cyclohexane with a gradient of 0-30% to give ethyl 3-bromo-2-methoxy-(2-methylphenylthiomethyl)benzoate (0.24 g) as a gum.

NMR (CDCl$_3$) δ 7.45 (d, 1H), 7.25 (m, 1H), 7.1 (m, 3H), 6.85 (d, 1H), 4.4 (q, 2H), 4.05 (s, 2H), 3.9 (s, 3H), 2.3 (s, 3H), 1.4 (t, 3H).

Intermediate 78

Methyl 5-bromo-2-(phenylthiomethyl)benzoate

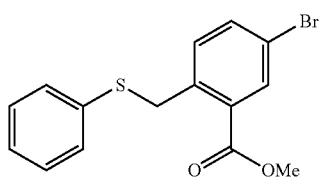 [SMILES: COC(=O)c1cc(Br)ccc1CSc1ccccc1]

Prepared by proceeding in a similar manner to Intermediate 77, starting from methyl 5-bromo-2-bromomethylbenzoate (prepared according to Lartia et al, *J Org Chem,* 2008, 73, 1732) and thiophenol.

LCMS (method E) r/t 4.82 (M+Na) 361.

Intermediate 79

Ethyl 3-bromo-6-(3-chlorophenylthiomethyl)-2-methoxybenzoate

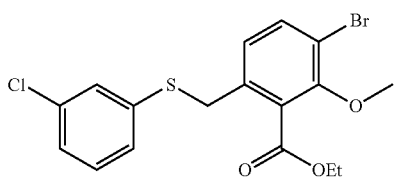 [SMILES: CCOC(=O)c1c(CSc2cccc(Cl)c2)ccc(Br)c1OC]

Prepared by proceeding in a similar manner to Intermediate 77, starting from ethyl 3-bromo-6-bromomethyl-2-methoxybenzoate (Intermediate 87) and 3-chlorothiophenol.

NMR (CDCl$_3$) δ 7.5 (d, 1H), 7.25 (m, 1H), 7.15 (m, 3H), 6.9 (d, 1H), 4.4 (q, 2H), 4.1 (s, 2H), 3.9 (s, 3H), 1.4 (t, 3H).

Intermediate 80

Methyl 3-bromo-6-(phenylthiomethyl)-2-methoxybenzoate

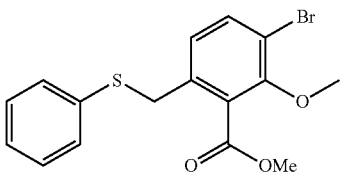 [SMILES: COC(=O)c1c(CSc2ccccc2)ccc(Br)c1OC]

Prepared by proceeding in a similar manner to Intermediate 77, starting from methyl 3-bromo-6-bromomethyl-2-methoxybenzoate (Intermediate 89) and thiophenol and used without further characterization.

Intermediate 81

Methyl 3-bromo-6-(2-bromophenylthiomethyl)-2-methoxybenzoate

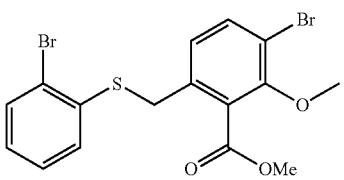

Prepared by proceeding in a similar manner to Intermediate 77, starting from methyl 3-bromo-6-bromomethyl-2-methoxybenzoate (Intermediate 89) and 2-bromothiophenol.

NMR (CDCl$_3$) δ 7.55 (d, 1H), 7.5 (d, 1H), 7.2 (d, 1H), 7.15 (m, 1H), 7.05 (m, 1H), 6.95 (d, 1H), 4.1 (s, 2H), 3.95 (s, 3H), 3.9 (s, 3H).

Intermediate 82

Methyl 3-bromo-2-hydroxy-6-(2-methoxyphenylthiomethyl)benzoate

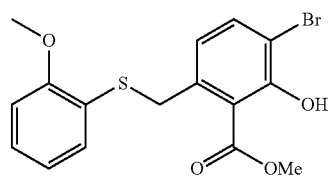 [SMILES: COC(=O)c1c(CSc2ccccc2OC)ccc(Br)c1O]

A mixture of methyl 3-bromo-6-bromomethyl-2-hydroxybenzoate (Intermediate 53, 0.6 g), 2-methoxythiophenol (0.518 g) and potassium carbonate (0.766 g) in THF (10 ml) was stirred and heated at 60° C. for 3 hours. After cooling, the mixture was partitioned between ethyl acetate and water and the separated organic layer was washed with potassium hydroxide solution, dried (Na$_2$SO$_4$) and filtered. The filtrate was evaporated to dryness and the residue was purified by chromatography on silica, eluting with a mixture of ethyl acetate and cyclohexane with a gradient of 0-15% to give methyl 3-bromo-2-hydroxy-6-(2-methoxyphenylthiomethyl)-benzoate (0.46 g) as a white solid which was used without further characterisation.

Intermediate 83

Methyl 3-bromo-2-methoxy-6-(pyrid-2-ylthiomethyl)benzoate

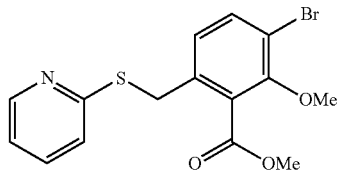 [SMILES: COC(=O)c1c(CSc2ccccn2)ccc(Br)c1OC]

Prepared by proceeding in a similar manner to Intermediate 82, starting from methyl 3-bromo-6-bromomethylbenzoate (Intermediate 89) and 2-pyridinethiol.

NMR (CDCl₃) δ 8.45 (d, 1H), 7.45 (m, 2H), 7.2 (d, 1H), 7.15 (d, 1H), 7.0 (m, 1H), 4.45 (s, 2H), 3.95 (s, 3H), 3.9 (s, 3H).

Intermediate 84

Ethyl 6-(4-chlorobenzenesulphonylmethyl)-3-bromo-2-methoxybenzoate

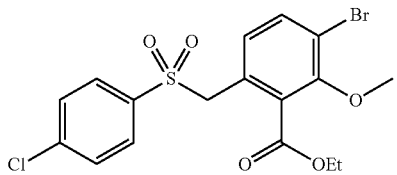 [SMILES: CCOC(=O)c1c(CS(=O)(=O)c2ccc(Cl)cc2)ccc(Br)c1OC]

A mixture of ethyl 3-bromo-6-(dibromomethyl)-2-methoxybenzoate (Intermediate 88, 0.25 g), sodium bicarbonate (0.122 g) and sodium 4-chlorobenzenesulphinate (0.29 g) in dimethylacetamide (4 ml) and water (1 ml) was stirred and heated at 90° C. for 5 hours. After cooling, the mixture was diluted with water and loaded onto a water washed C-18 column which was then flushed with water and eluted with DCM and ethyl acetate. The organic eluent was dried (MgSO₄) and filtered. The filtrate was evaporated to dryness and the residue was purified by chromatography on silica, eluting with a mixture of ethyl acetate and cyclohexane with a gradient of 0-100% to give ethyl 6-(4-chlorobenzenesulphonylmethyl)-3-bromo-2-methoxy-benzoate (0.15 g) as a gum.

NMR (CDCl₃) 7.6 (2d, 3H), 7.45 (d, 2H), 6.95 (d, 1H), 4.5 (s, 2H), 4.3 (q, 2H), 3.85 (s, 3H), 1.35 (t, 3H).

Intermediate 85

Ethyl 3-bromo-6-(4-fluorobenzenesulphonylmethyl)-2-methoxybenzoate

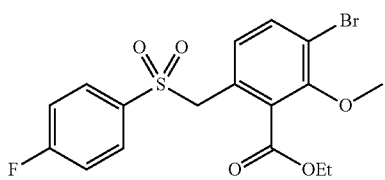 [SMILES: CCOC(=O)c1c(CS(=O)(=O)c2ccc(F)cc2)ccc(Br)c1OC]

Sodium 4-fluorobenzenesulphinate (0.517 g) was added to a suspension of ethyl 3-bromo-6-bromomethyl-2-methoxybenzoate (Intermediate 87, 0.4 g) and sodium bicarbonate (0.24 g) in dimethylacetamide (8 ml) and water (2 ml) and the mixture was stirred at room temperature for 3 hours. The resultant mixture was diluted with water and loaded onto a C-18 SPE column. The column was flushed with water then eluted with DCM and ethyl acetate. The organic eluent was dried (MgSO₄) and filtered. The filtrate was evaporated to dryness and the residue was purified by chromatography on silica, eluting with a mixture of t-butyl methyl ether and cyclohexane with a gradient of 0-60% to give ethyl 3-bromo-6-(4-fluorobenzenesulphonyl-methyl)-2-methoxybenzoate (0.37 g) as a colourless gum.

NMR (CDCl₃) δ 7.7 (m, 2H), 7.6 (d, 1H), 7.15 (t, 2H), 6.95 (d, 1H), 4.5 (s, 2H), 4.3 (q, 2H), 3.85 (s, 3H), 1.35 (t, 3H).

Intermediate 86

Ethyl 3-bromo-2-methoxy-6-(pyrid-3-ylsulphonylmethyl)benzoate

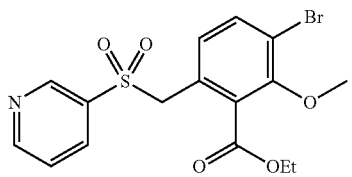 [SMILES: CCOC(=O)c1c(CS(=O)(=O)c2cccnc2)ccc(Br)c1OC]

Prepared by proceeding in a similar manner to Intermediate 85, starting from ethyl 3-bromo-6-bromomethyl-2-methoxybenzoate (Intermediate 87) and sodium 3-pyridinesulphonate (prepared according to Crowell et al, *J. med. Chem.*, 1989, 32, 2436).

NMR (CDCl₃) δ 8.85 (br s, 2H), 7.9 (d, 1H), 7.6 (d, 1H), 7.4 (m, 1H), 7.05 (s, 1H), 4.55 (s, 2H), 4.3 (q, 2H), 3.85 (s, 3H), 1.35 (t, 3H).

Intermediate 87 and intermediate 88

Ethyl 3-bromo-6-bromomethyl-2-methoxybenzoate and ethyl 3-bromo-6-(dibromomethyl)-2-methoxybenzoate

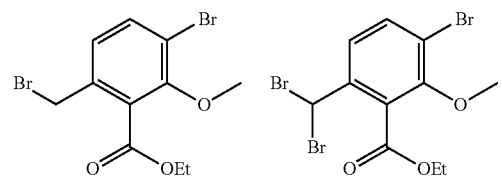

A mixture of ethyl 3-bromo-2-methoxy-6-methylbenzoate (Intermediate 90, 12.2 g), N-bromosuccinimide (8.0 g) and AIBN (0.1 g) in DCE (250 ml) was stirred and irradiated with a 500 W tungsten filament lamp for 40 minutes. Further N-bromosuccinimide (1 g) was added and illumination was continued for 30 minutes. Further N-bromosuccinimde (2.6 g) was added in portions with illumination until no starting material remained. After cooling, the mixture was filtered and the filtrate was evaporated to dryness. The residue was purified by chromatography on silica, eluting with a mixture of dichloromethane and cyclohexane with a gradient of 0-100% to give two main fractions. Fraction 1 gave ethyl 3-bromo-6-(dibromomethyl)-2-methoxybenzoate (2.25 g) as a colourless oil.

NMR (CDCl₃) δ 7.7 (d, 1H), 7.65 (d, 1H), 6.75 (s, 1H), 4.45 (q, 2H), 3.9 (s, 3H), 1.45 (t, 3H).

Fraction 2 gave ethyl 3-bromo-6-bromomethyl-2-methoxybenzoate (2.84 g) as a colourless oil.

NMR (CDCl₃) δ 7.55 (d, 1H), 7.05 (d, 1H), 4.5 (s, 2H), 4.45 (q, 2H), 3.9 (s, 3H), 1.45 (t, 3H).

Intermediate 89

Methyl 3-bromo-6-bromomethyl-2-methoxybenzoate

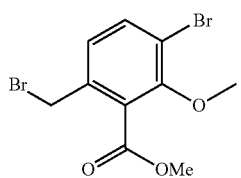

A solution of methyl 3-bromo-2-methoxy-6-methylbenzoate (Intermediate 91, 20 g) in 1,2-dichloroethane (400 ml) was stirred and illuminated with a 500 W tungsten filament lamp and treated with a catalytic amount of AIBN. Solid 1,3-dibromo-5,5-dimethylhydantoin (20 g) was gradually added over 3 hours until NMR analysis indicated complete conversion to the desired benzyl bromide. After cooling, the mixture was evaporated to dryness and the residue was triturated with cyclohexane and filtered. The filtrate was evaporated to dryness and the residue was purified by chromatography on silica, eluting with a mixture of DCM and cyclohexane with a gradient of 1-25% to give methyl 3-bromo-6-bromomethyl-2-methoxybenzoate (16.3 g) as an orange solid.

NMR (CDCl₃) δ 7.6 (d, 1H), 7.05 (d, 1H), 4.45 (s, 2H), 4.0 (s, 3H), 3.9 (s, 3H).

Intermediate 90

Ethyl 3-bromo-2-methoxy-6-methylbenzoate

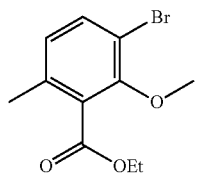

Dimethyl sulphate (2.3 ml) was added to a suspension of ethyl 3-bromo-2-hydroxy-6-methylbenzoate (Intermediate 92, 5.19 g) and potassium carbonate (5.64 g) in dry acetone (70 ml) and the resultant mixture was stirred and heated at reflux for 2 hours. After cooling to room temperature, the mixture was filtered and the filtrate was evaporated to dryness. The residue was dissolved in ether and washed with NaHCO₃ (saturated aqueous solution), dried (Na₂SO₄) and filtered. The filtrate was evaporated to dryness to give crude ethyl 3-bromo-2-methoxy-6-methylbenzoate (5.4 g) as a colourless oil.

NMR (CDCl₃) δ 7.45 (d, 1H), 6.85 (d, 1H), 4.4 (q, 2H), 3.85 (s, 3H), 2.25 (s. 3H), 1.4 (t, 3H).

Intermediate 91

Methyl 3-bromo-2-methoxy-6-methylbenzoate

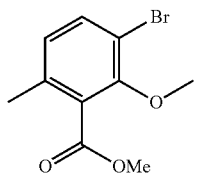

Prepared by proceeding in a similar manner to Intermediate 90, starting from methyl 3-bromo-2-hydroxy-6-methylbenzoate (Intermediate 93).

NMR (CDCl₃) δ 7.45 (d, 1H), 6.85 (d, 1H), 3.95 (s, 3H), 3.9 (s, 3H), 2.25 (s, 3H).

Intermediate 92

Ethyl 3-bromo-2-hydroxy-6-methylbenzoate

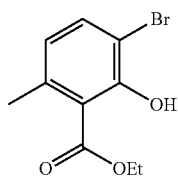

A solution of N-bromosuccinimide (3.97 g) in DCM (170 ml) was added dropwise to a stirred, cooled solution of ethyl 2-hydroxy-6-methylbenzoic acid (prepared according to Hauser et al, *Synthesis*, 1980 814, 4.02 g) and di-isopropylamine (0.31 ml) in DCM (50 ml) while maintaining the temperature at 0° C. (±5° C.). On completion of the addition, the cooling bath was removed and the mixture was stirred at room temperature overnight. The mixture was concentrated and ether was added. The resultant solid was removed by filtration and the filtrate was evaporated to dryness. The residue was purified by chromatography on silica, eluting with a mixture of ether and pentane with a gradient of 0-50% to give ethyl 3-bromo-2-hydroxy-6-methylbenzoate (5.19 g) as a colourless oil.

NMR (CDCl₃) δ 12.0 (s, 1H), 7.5 (d, 1H), 6.6 (d, 1H), 4.45 (q, 2H), 2.5 (s, 3H), 1.45 (t, 3H).

Intermediate 93

Methyl 3-bromo-2-hydroxy-6-methylbenzoate

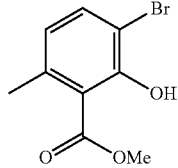

A solution of bromine (16.8 ml) in acetic acid (150 ml) was added dropwise to a stirred and cooled solution of methyl 6-methyl-2-oxocyclohex-3-enecarboxylate (prepared according to Hauser et al, Synthesis 1980 814, 28.2 g) in acetic acid at 0° C. The resultant mixture was stirred and heated at reflux for 24 hours. After cooling, the mixture was partitioned between ethyl acetate and water. The organic layer was separated and washed with sodium bicarbonate (saturated aqueous solution) and brine, then dried (MgSO$_4$ and activated charcoal) and filtered through Celite. The filtrate was evaporated to dryness to give methyl 3-bromo-2-hydroxy-6-methylbenzoate (30.8 g) as an oil.

NMR (CDCl$_3$) δ 11.95 (s, 1H), 7.55 (d, 1H), 6.65 (d, 1H), 4.9 (s, 3H), 2.5 (s, 3H).

Intermediate 94

Methyl 6-(2-chlorobenzenesulphonylmethyl)-3-(furan-3-yl)-2-methoxybenzoate

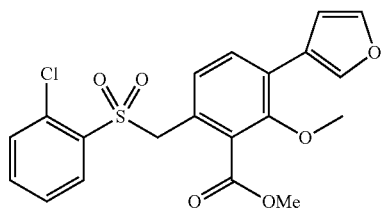 [SMILES: COC(=O)c1c(CS(=O)(=O)c2ccccc2Cl)ccc(-c2ccoc2)c1OC]

Prepared by proceeding in a similar manner to Intermediate 36, starting from methyl 3-bromo-6-(2-chlorobenzenesulphonylmethyl)-3-methoxybenzoate, (Intermediate 98) and furan-3-yl boronic acid.

NMR (CDCl$_3$) δ 7.9 (s, 1H), 7.8 (dd, 1H), 7.55 (m, 2H), 7.5 (t, 1H), 7.4 (d, 1H), 7.35 (dt, 1H), 7.1 (d, 1H), 6.75 (s, 1H), 4.85 (s, 2H), 3.95 (s, 3H), 3.65 (s, 3H).

Intermediate 95

Methyl 6-(3-fluorobenzenesulphonylmethyl)-3-(furan-3-yl)-2-methoxybenzoate

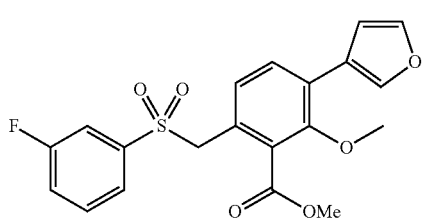 [SMILES: COC(=O)c1c(CS(=O)(=O)c2cccc(F)c2)ccc(-c2ccoc2)c1OC]

Prepared by proceeding in a similar manner to Intermediate 36, starting from methyl 3-bromo-6-(3-fluorobenzenesulphonylmethyl)-2-methoxybenzoate (Intermediate 99) and furan-3-yl boronic acid.

NMR (CDCl$_3$) δ 7.95 (s, 1H), 7.5 (t, 1H), 7.45 (m, 3H), 7.4 (m, 1H), 7.35 (m, 1H), 7.1 (d, 1H), 6.75 (s, 1H), 4.55 (s, 2H), 3.85 (s, 3H), 3.6 (s, 3H).

Intermediate 96

Methyl 6-(2-fluorobenzenesulphonylmethyl)-3-(furan-3-yl)-2-methoxybenzoate

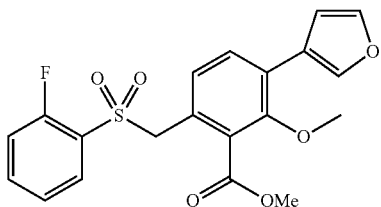 [SMILES: COC(=O)c1c(CS(=O)(=O)c2ccccc2F)ccc(-c2ccoc2)c1OC]

Prepared by proceeding in a similar manner to Intermediate 36, starting from methyl 3-bromo-6-(2-fluorobenzenesulphonylmethyl)-2-methoxybenzoate (Intermediate 100) and furan-3-yl boronic acid.

NMR (CDCl$_3$) δ 7.9 (s, 1H), 7.75 (dt, 1H), 7.6 (m, 1H), 7.5 (t, 1H), 7.45 (d, 1H), 7.25 (t, 2H), 7.15 (d, 1H), 6.75 (s, 1H), 4.7 (s, 2H), 3.95 (s, 3H), 3.65 (s, 3H).

Intermediate 97

Methyl 3-(furan-3-yl)-2-methoxy-6-(3-methoxybenzene-sulphonylmethyl)benzoate

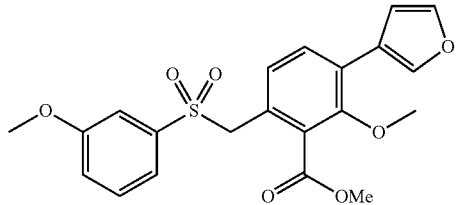 [SMILES: COC(=O)c1c(CS(=O)(=O)c2cccc(OC)c2)ccc(-c2ccoc2)c1OC]

Prepared by proceeding in a similar manner to Intermediate 36, starting from methyl 3-bromo-2-methoxy-6-(3-methoxybenzenesulphonylmethyl)benzoate (Intermediate 101) and furan-3-yl boronic acid.

NMR (CDCl$_3$) δ 7.95 (s, 1H), 7.5 (t, 1H), 7.45 (d, 1H), 7.35 (t, 1H), 7.3 (dt, 1H), 7.15 (m, 2H), 7.1 (d, 1H), 6.75 (s, 1H), 4.55 (s, 2H), 3.85 (s, 3H), 3.75 (s, 3H), 3.6 (s, 3H)

Intermediate 98

Methyl 3-bromo-6-(2-chlorobenzenesulphonylmethyl)-3-methoxybenzoate

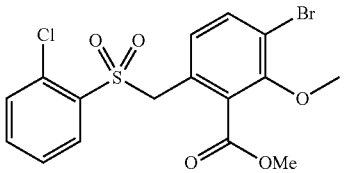

Prepared by proceeding in a similar manner to Intermediate 68, starting from methyl 3-bromo-6-(2-chlorophenylthiomethyl)-2-methoxybenzoate (Intermediate 102).

NMR (CDCl$_3$) δ 7.85 (dd, 1H), 7.55 (m, 2H), 7.5 (d, 1H), 7.35 (m, 1H), 6.95 (d, 1H), 4.8 (s, 2H), 3.95 (s, 3H), 3.85 (s, 3H).

Intermediate 99

Methyl 3-bromo-6-(3-fluorobenzenesulphonylmethyl)-2-methoxybenzoate

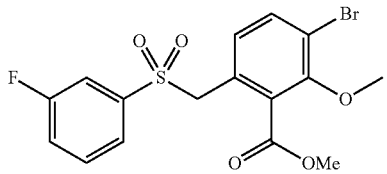 [SMILES: COC(=O)c1c(CS(=O)(=O)c2cccc(F)c2)ccc(Br)c1OC]

Prepared by proceeding in a similar manner to Intermediate 68, starting from methyl 3-bromo-6-(3-fluorophenylthiomethyl)-2-methoxybenzoate (Intermediate 103).

NMR (CDCl$_3$) δ 7.6 (d, 1H), 7.45 (m, 2H), 7.35 (m, 2H) 6.95 (d, 1H), 4.5 (s, 2H), 3.85 (2s, 6H).

Intermediate 100

Methyl 3-bromo-6-(2-fluoroenzenesulphonylmethyl)-2-methoxybenzoate

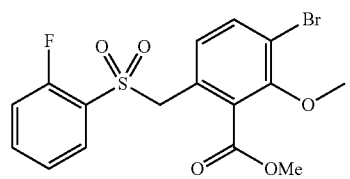 [SMILES: COC(=O)c1c(CS(=O)(=O)c2ccccc2F)ccc(Br)c1OC]

Prepared by proceeding in a similar manner to Intermediate 68, starting from methyl 3-bromo-6-(2-fluorophenylthiomethyl)-2-methoxybenzoate (Intermediate 104).

NMR (CDCl$_3$) δ 7.75 (dt, 1H), 7.65 (m, 1H), 7.55 (d, 1H), 7.25 (m, 2H), 7.0 (d, 1H), 4.7 (s, 2H), 3.95 (s, 3H), 3.85 (s, 3H).

Intermediate 101

Methyl 3-bromo-2-methoxy-6-(3-methoxybenzenesulphonylmethyl)benzoate

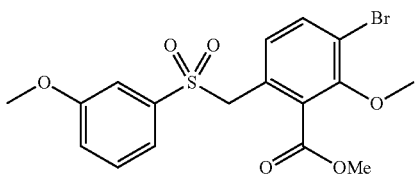

Prepared by proceeding in a similar manner to Intermediate 68, starting from methyl 3-bromo-2-methoxy-6-(3-methoxyphenylthiomethyl)benzoate (Intermediate 105).

NMR (CDCl$_3$) δ 7.6 (d, 1H), 7.4 (t, 1H), 7.25 (m, 1H), 7.15 (m, 2H), 6.95 (d, 1H), 4.5 (s, 2H), 3.85 (s, 3H), 3.8 (s, 3H), 3.75 (s, 3H).

Intermediate 102

Methyl 3-bromo-6-(2-chlorophenylthiomethyl)-2-methoxybenzoate

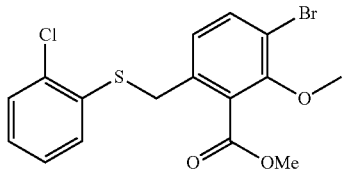 [SMILES: COC(=O)c1c(CSc2ccccc2Cl)ccc(Br)c1OC]

Prepared by proceeding in a similar manner to Intermediate 73, starting from methyl 3-bromo-6-bromomethyl-2-methoxybenzoate (Intermediate 89) and 2-chlorothiophenol.

NMR (CDCl$_3$) δ 7.45 (d, 1H), 7.35 (m, 1H), 7.2 (m, 1H), 7.15 (m, 2H), 6.95 (d, 1H), 4.1 (s, 2H), 3.95 (s, 3H), 3.9 (s, 3H).

Intermediate 103

Methyl 3-bromo-6-(3-fluorophenylthiomethyl)-2-methoxybenzoate

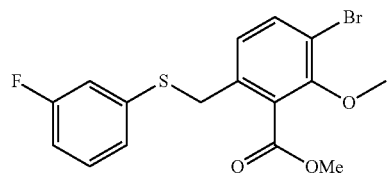 [SMILES: COC(=O)c1c(CSc2cccc(F)c2)ccc(Br)c1OC]

Prepared by proceeding in a similar manner to Intermediate 73, starting from methyl 3-bromo-6-bromomethyl-2-methoxybenzoate (Intermediate 89) and 3-fluorothiophenol.

NMR (CDCl$_3$) δ 7.5 (d, 1H), 7.2 (m, 1H), 7.0 (m, 2H), 6.95 (d, 1H), 6.9 (dt, 1H), 4.1 (s, 2H), 3.95 (s, 3H), 3.9 (s, 3H).

Intermediate 104

Methyl 3-bromo-6-(2-fluorophenylthiomethyl)-2-methoxybenzoate

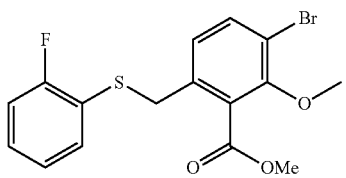 [SMILES: COC(=O)c1c(CSc2ccccc2F)ccc(Br)c1OC]

Prepared by proceeding in a similar manner to Intermediate 73, starting from methyl 3-bromo-6-bromommethyl-2-methoxybenzoate (Intermediate 89) and 2-fluorothiophenol.

NMR (CDCl₃) δ 7.45 (d, 1H), 7.25 (m, 2H), 7.0 (m, 2H), 6.85 (d, 1H), 4.05 (s, 2H), 3.95 (s, 3H), 3.85 (s, 3H).

Intermediate 105

Methyl 3-bromo-2-methoxy-6-(3-methoxyphenylthiomethyl)benzoate

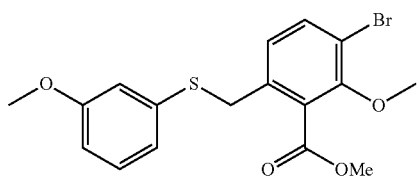

Prepared by proceeding in a similar manner to Intermediate 73, starting from methyl 3-bromo-6-bromomethyl-2-methoxybenzoate (Intermediate 89) and 3-methoxythiophenol.

NMR (CDCl₃) δ 7.45 (s, 1H), 7.15 (t, 1H), 6.9 (d, 1H), 6.85 (d, 1H), 6.8 (t, 1H), 6.75 (dd, 1H), 4.1 (s, 2H), 3.95 (s, 3H), 3.9 (s, 3H), 3.75 (s, 3H)

Intermediate 106

6-(Benzenesulphonylmethyl)-2-(3-t-butoxycarbonylaminopropoxy)-3-(furan-3-yl)benzoic acid

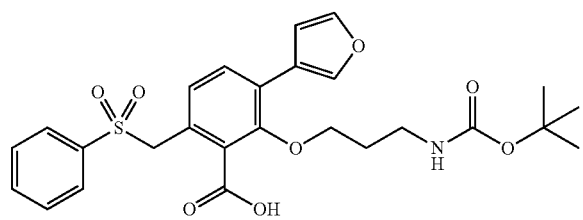 [SMILES: CC(C)(C)OC(=O)NCCCOc1c(-c2ccoc2)ccc(CS(=O)(=O)c2ccccc2)c1C(=O)O]

Prepared by proceeding in a similar manner to Intermediate 6, starting from methyl 6-(benzenesulphonylmethyl)-2-(3-t-butoxycarbonylaminopropoxy)-3-(furan-3-yl)benzoate (Intermediate 109).

NMR (CDCl₃) δ 7.9 (s, 1H), 7.75 (d, 2H), 7.65 (t, 1H), 7.5 (m, 3H), 7.45 (d, 1H), 7.15 (d, 1H), 6.75 (s, 1H), 4.6 (s, 2H), 3.8 (t, 2H), 3.3 (br s, 2H), 1.8 (m, 2H), 1.5 (s, 9H).

Intermediate 107

6-(Benzenesulphonylmethyl)-2-(2-t-butoxycarbonylaminoethoxy)-3-ethylbenzoic acid

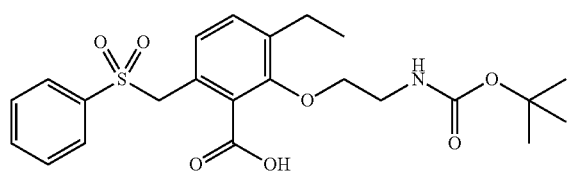 [SMILES: CCc1ccc(CS(=O)(=O)c2ccccc2)c(C(=O)O)c1OCCNC(=O)OC(C)(C)C]

A mixture of methyl 6-(benzenesulphonylmethyl)-2-(2-t-butoxycarbonylaminoethoxy)-3-ethylbenzoate (Intermediate 108, 0.125 g), and lithium hydroxide (0.066 g) in dioxane (1.4 ml) and water (0.4 ml) was stirred and heated in the microwave at 130° C. for 45 minutes. The mixture was evaporated to dryness and the residue was partitioned between ethyl acetate and water. The aqueous layer was acidified with hydrochloric acid (1M) and extracted with ethyl acetate, washed with water, dried (Na₂SO₄) and filtered. The filtrate was evaporated to dryness to give 6-(benzenesulphonylmethyl)-2-(2-t-butoxyaminoethoxy)-3-ethylbenzoic acid (0.075 g) as a colourless gum.

NMR (CDCl₃) δ 7.75 (d, 2H), 7.6 (t, 1H), 7.5 (t, 2H), 7.3 (d, 1H), 7.05 (d, 1H), 4.65 (s, 2H), 3.9 (br s, 2H), 3.5 (br s, 2H), 2.7 (q, 2H), 1.5 (s, 9H), 1.2 (t, 3H).

Intermediate 108

Methyl 6-(benzenesulphonylmethyl)-2-(2-t-butoxycarbonylaminoethoxy)-3-ethylbenzoate

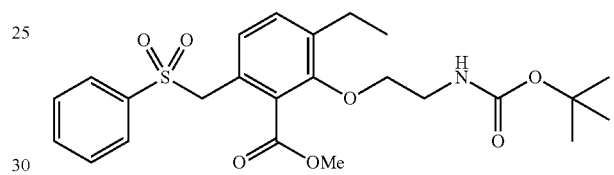

Prepared by proceeding in a similar manner to Intermediate 10, starting from methyl 6-(benzenesulphonylmethyl)-3-ethyl-2-hydroxybenzoate (Intermediate 110) and 2-(t-butoxycarbonylamino)ethyl bromide NMR (CDCl₃) δ 7.65 (d, 2H), 7.6 (t, 1H), 7.45 (t, 2H), 7.2 (d, 1H), 6.95 (d, 1H), 4.5 (s, 2H) 3.85 (t, 2H), 3.8 (s, 3H), 3.4 (m, 2H), 2.65 (q, 2H), 1.45 (s, 9H), 1.2 (t, 3H).

Intermediate 109

Methyl 6-(benzenesulphonylmethyl)-2-(3-t-butoxycarbonylaminopropoxy)-3-(furan-3-yl)benzoate

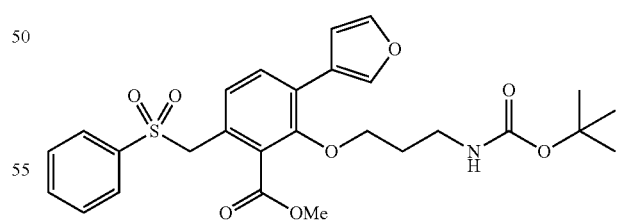

Prepared by proceeding in a similar manner to Intermediate 10, starting from methyl 6-(benzenesulphonylmethyl)-3-(furan-3-yl)-2-hydroxybenzoate (Intermediate 114) and 3-(t-butoxycarbonylamino)propyl bromide.

NMR (CDCl₃) δ 7.85 (s, 1H), 7.7 (d, 2H), 7.65 (t, 1H), 7.5 (m, 3H), 7.4 (d, 1H), 7.05 (d, 1H), 6.75 (s, 1H), 4.5 (s, 2H), 3.85 (s, 3H), 3.7 (t, 2H), 3.2 (br s, 2H), 1.8 (m, 2H), 1.45 (s, 9H).

Intermediate 110

Methyl 6-(benzenesulphonylmethyl)-3-ethyl-2-hydroxybenzoate

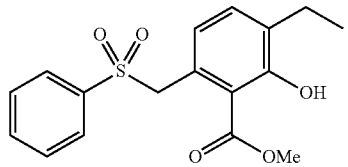 [SMILES: CCc1ccc(CS(=O)(=O)c2ccccc2)c(C(=O)OC)c1O]

Prepared by proceeding in a similar manner to Intermediate 54, starting from methyl 6-(benzenesulphonylmethyl)-3-ethyl-2-methoxybenzoate (Intermediate 111).

NMR (CDCl$_3$) δ 11.2 (s, 1H), 7.6 (m, 3H), 7.45 (t, 2H), 7.15 (d, 1H), 6.45 (d, 1H), 4.85 (s, 2H), 3.9 (s, 3H), 2.65 (q, 2H), 1.2 (t, 3H).

Intermediate 111

Methyl 6-(benzenesulphonylmethyl)-3-ethyl-2-methoxybenzoate

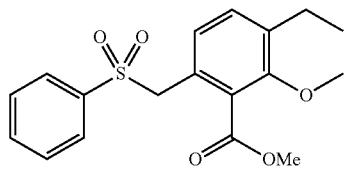 [SMILES: CCc1ccc(CS(=O)(=O)c2ccccc2)c(C(=O)OC)c1OC]

A mixture of methyl 6-(benzenesulphonylmethyl)-3-bromo-2-methoxybenzoate (Intermediate 65, 1.31 g) and potassium phosphate (2.02 g) in THF (9 ml) and water (4.5 ml) was degassed and palladium chloride dppf adduct with DCM (0.134 g) and triethyl borane (1M solution in THF, 4.6 ml) were added. The mixture was stirred and heated in the microwave at 140° C. for 18 minutes. The mixture was partitioned between ethyl acetate and water and the organic layer was separated, dried (Na$_2$SO$_4$) and filtered. The filtrate was evaporated to dryness and the residue was purified by chromatography on silica, eluting with a mixture of ethyl acetate and cyclohexane with a gradient of 5-40% to give methyl 6-(benzenesulphonylmethyl)-3-ethyl-2-methoxybenzoate (0.754 g) as a colourless oil.

NMR (CDCl$_3$) δ 7.65 (d, 2H), 7.6 (t, 1H), 7.45 (t, 2H), 7.2 (d, 1H), 6.95 (d, 1H), 4.5 (s, 2H), 3.8 (s, 3H), 3.7 (s, 3H), 2.65 (q, 2H), 1.2 (t, 3H).

Intermediate 112

Methyl 6-(benzenesulphonylmethyl)-2-methoxy-3-(thien-2-yl)-benzoate

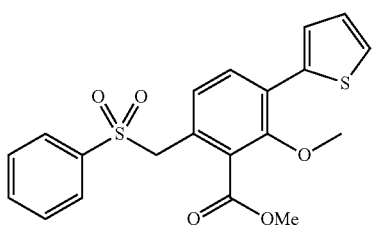 [SMILES: COC(=O)c1c(CS(=O)(=O)c2ccccc2)ccc(-c2cccs2)c1OC]

Prepared by proceeding in a manner similar to Intermediate 28, starting from methyl 6-(benzenesulphonylmethyl)-3-bromo-2-methoxybenzoate (Intermediate 65) and 2-(4,4,5,5-tetramethyl-1,3,2-dioxaborolan-2-yl)thiophene.

NMR (CDCl$_3$) δ 7.7 (m, 2H), 7.6 (m, 2H), 7.5 (m, 3H), 7.4 (dd, 1H), 7.1 (dd, 1H), 7.05 (d, 1H), 4.55 (s, 2H), 3.85 (s, 3H), 3.6 (s, 3H).

Intermediate 113

Methyl 6-(benzenesulphonylmethyl)-2-methoxy-3-(thien-3-yl)benzoate

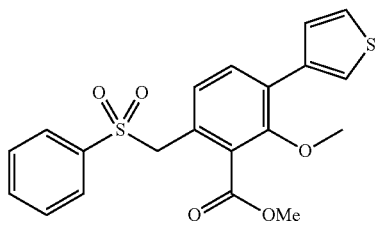 [SMILES: COC(=O)c1c(CS(=O)(=O)c2ccccc2)ccc(-c2ccsc2)c1OC]

Prepared by proceeding in a similar manner to Intermediate 28, starting from methyl 6-(benzenesulphonylmethyl)-3-bromo-2-methoxybenzoate (Intermediate 65) and thiophene-3-boronic acid.

NMR (CDCl$_3$) δ 7.7 (m, 2H), 7.65 (m, 2H), 7.5 (m, 3H), 7.4 (m, 2H), 7.1 (d, 1H), 4.55 (s, 2H), 3.85 (s, 3H), 3.5 (s, 3H).

Intermediate 114

Methyl 6-(benzenesulphonylmethyl)-3-(furan-3-yl)-2-hydroxybenzoate

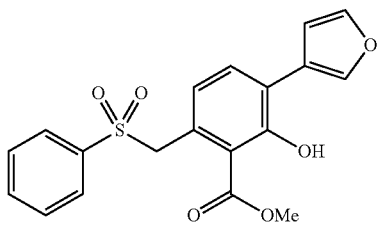

Prepared by proceeding in a similar manner to Intermediate 45, starting from methyl 6-(benzenesulphonylmethyl)-3-bromo-2-hydroxybenzoate (Intermediate 115) and furan-3-yl boronic acid.

NMR (CDCl$_3$) δ 11.8 (s, 1H), 8.2 (s, 1H), 7.6 (m, 3H), 7.45 (m, 4H), 6.75 (s, 1H), 6.55 (d, 1H), 4.9 (s, 2H), 3.95 (s, 3H).

Intermediate 115

Methyl 6-(benzenesulphonylmethyl)-3-bromo-2-hydroxybenzoate

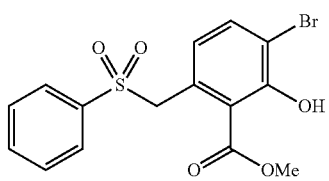 [SMILES: COC(=O)c1c(CS(=O)(=O)c2ccccc2)ccc(Br)c1O]

Prepared by proceeding in a similar manner to Intermediate 54, starting from methyl 6-(benzenesulphonylmethyl)-3-bromo-2-methoxybenzoate (Intermediate 65).

NMR (CDCl₃) δ 11.6 (s, 1H), 7.6 (m, 3H), 7.55 (d, 1H), 7.5 (t, 2H), 6.4 (d, 1H), 4.85 (s, 2H), 3.95 (s, 3H).

Intermediate 116

Methyl 6-(4-fluorobenzenesulphonylmethyl)-3-(furan-3-yl)-2-methoxybenzoate

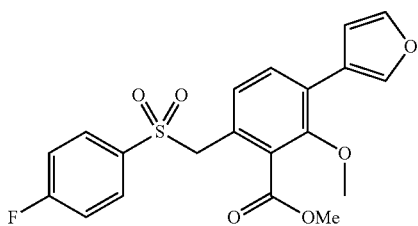 [SMILES: COC(=O)c1c(CS(=O)(=O)c2ccc(F)cc2)ccc(-c2ccoc2)c1OC]

Prepared by proceeding in a manner similar to Intermediate 36, starting from methyl 3-bromo-6-(4-fluorobenzenesulphonylmethyl)-2-methoxybenzoate (Intermediate 117) and furan-3-yl boronic acid.

NMR (CDCl₃) δ 7.95 (s, 1H), 7.7 (m, 2H), 7.5 (s, 1H), 7.45 (d, 1H), 7.15 (t, 2H), 7.05 (d, 1H), 6.75 (s, 1H), 4.55 (s, 2H), 3.85 (s, 3H), 3.6 (s, 3H).

Intermediate 117

Methyl 3-bromo-6-(4-fluorobenzenesulphonylmethyl)-2-methoxybenzoate

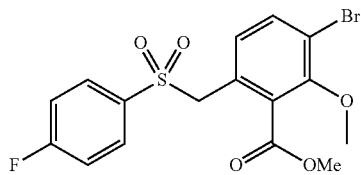 [SMILES: COC(=O)c1c(CS(=O)(=O)c2ccc(F)cc2)ccc(Br)c1OC]

Prepared by proceeding in a manner similar to Intermediate 68, starting from methyl 3-bromo-6-(4-fluorophenylthiomethyl)-3-methoxybenzoate (Intermediate 118).

NMR (CDCl₃) δ 7.65 (m, 2H), 7.6 (d, 1H), 7.15 (t, 2H), 6.95 (d, 1H), 4.5 (s, 2H), 3.85 (2 s, 6H).

Intermediate 118

Methyl 3-bromo-6-(4-fluorophenylthiomethyl)-3-methoxybenzoate

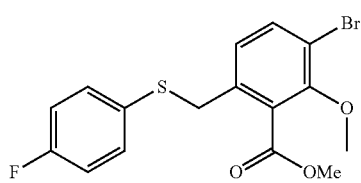 [SMILES: COC(=O)c1c(CSc2ccc(F)cc2)ccc(Br)c1OC]

Prepared by proceeding in a manner similar to Intermediate 73, starting from methyl 3-bromo-6-bromomethyl-2-methoxybenzoate (Intermediate 89) and 4-fluorothiophenol.

NMR (CDCl₃) δ 7.45 (d, 1H), 7.25 (m, 2H), 6.95 (t, 2H), 6.75 (d, 1H), 4.0 (s, 2H), 3.9 (s, 3H), 3.85 (s, 3H).

Intermediate 119 t-Butyl 6-(benzenesulphonylmethyl)-2-(cyanomethoxy)-3-(furan-3-yl)benzoate

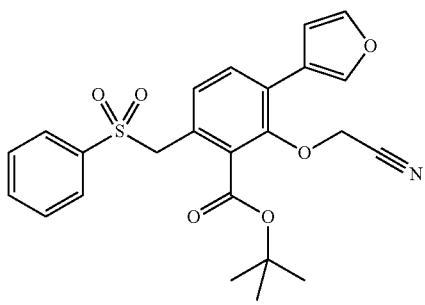 [SMILES: CC(C)(C)OC(=O)c1c(CS(=O)(=O)c2ccccc2)ccc(-c2ccoc2)c1OCC#N]

Prepared by proceeding in a similar manner to Intermediate 10, starting from t-butyl 6-(benzenesulphonylmethyl)-3-(furan-3-yl)-2-hydroxybenzoate (Intermediate 120) and bromoacetonitrile.

NMR (CDCl₃) δ 7.9 (s, 1H), 7.75 (d, 2H), 7.65 (t, 1H), 7.55 (t, 1H), 7.5 (t, 2H), 7.4 (d, 1H), 7.2 (d, 1H), 6.75 (s, 1H), 4.5 (2s, 4H), 1.65 (s, 9H).

Intermediate 120 t-butyl 6-(benzenesulphonylmethyl)-3-(furan-3-yl)-2-hydroxybenzoate

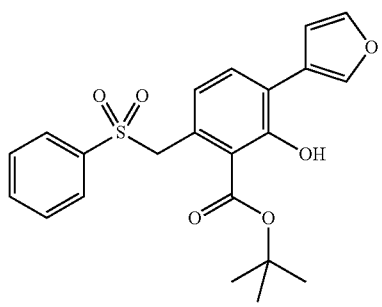 [SMILES: CC(C)(C)OC(=O)c1c(CS(=O)(=O)c2ccccc2)ccc(-c2ccoc2)c1O]

A solution of dicyclohexylcarbodiimide (0.124 g) in THF (1 ml) was added dropwise to a mixture of 6-(benzenesulphonylmethyl)-3-(furan-3-yl)-2-hydroxybenzoic acid (Intermediate 114, 0.358 g) and 4-dimethylaminopyridine (0.0032 g) and t-butanol (3 ml) in THF (1 ml). The resultant mixture was stirred at room temperature for 4 hours. The solid was removed by filtration and the filtrate was washed with citric acid (5% aqueous solution), sodium bicarbonate (saturated aqueous solution) and brine, dried (Na₂SO₄) and filtered. The filtrate was evaporated to dryness and the residue was purified by chromatography on silica eluting with a mixture of ethyl acetate and cyclohexane (20%) to give t-butyl 6-(benzenesulphonylmethyl)-3-(furan-3-yl)-2-hydroxybenzoate (0.19 g) as a waxy white solid.

NMR (CDCl₃) δ 12.2 (s, 1H), 8.1 (s, 1H), 7.6 (m, 3H), 7.45 (m, 3H), 7.35 (d, 1H), 6.75 (s, 1H), 6.2 (d, 1H), 4.9 (s, 2H), 1.7 (s, 9H).

Intermediate 121

6-(Benzenesulphonylmethyl)-2-[2-(t-butoxycarbonylamino)-ethylamino]-3-(furan-3-yl)benzoic acid

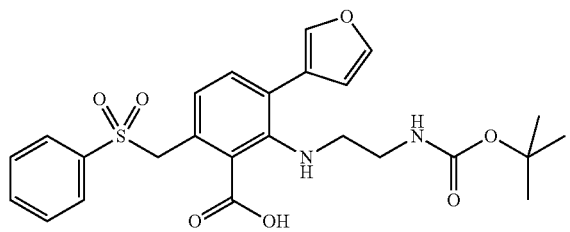 [SMILES: CC(C)(C)OC(=O)NCCNc1c(-c2ccoc2)ccc(CS(=O)(=O)c2ccccc2)c1C(=O)O]

Methyl 6-(benzenesulphonylmethyl)-2-[2-(t-butoxycarbonylamino)-ethylamino]-3-(furan-3-yl)benzoate (Intermediate 122, 0.115 g) was added to a solution of lithium hydroxide monohydrate (0.168 g) in water (1 ml) and dioxane (3 ml) and the mixture was heated at 100° C. for 1 hour. The reaction was cooled to room temperature, diluted with water and washed with diethyl ether. The aqueous layer was acidified with acetic acid and extracted with ethyl acetate, dried (Na₂SO₄) and filtered. The filtrate was evaporated to dryness and the residue was purified by chromatography on silica, eluting with a mixture of DCM:MeOH:AcOH:water (350:20:3:2) to give 6-(benzenesulphonylmethyl)-2-[2-(tert-butoxycarbonylamino)-ethylamino]-3-(furan-3-yl)benzoic acid (0.1 g) as a pale yellow gum.

NMR (DMSO-d₆) δ 8.05 (s, 1H), 7.75 (m, 3H), 7.6 (t, 2H), 7.25 (t, 2H), 7.2 (m, 1H), 6.85 (s, 1H), 6.75 (s, 1H), 6.7 (d, 1H), 4.9 (s, 2H), 2.9 (m, 2H), 2.8 (m, 2H), 1.35 (s, 9H).

Intermediate 122

Methyl 6-(benzenesulphonylmethyl)-2-[2-(tert-butoxycarbonylamino)ethylamino]-3-(furan-3-yl)benzoate

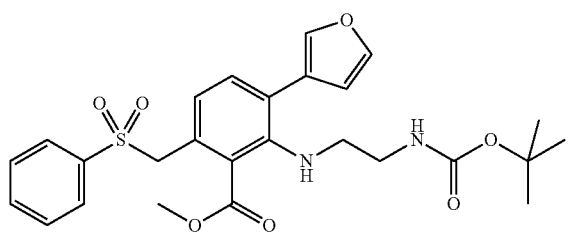 [SMILES: COC(=O)c1c(CS(=O)(=O)c2ccccc2)ccc(-c2ccoc2)c1NCCNC(=O)OC(C)(C)C]

A solution of methyl 6-(benzenesulphonylmethyl)-3-(furan-3-yl)-2-(trifluoromethanesulphonyloxy)benzoate (Intermediate 123, 0.05 g), N-(t-butoxycarbonyl)ethylenediamine (0.048 g), palladium acetate (0.006 g), cesium carbonate (0.065 g) and (+/−)BINAP (0.034 g) in toluene (1.5 ml) was stirred and heated at 100° C., under nitrogen for 20 hours. After cooling, the reaction mixture was partitioned between water and ethyl acetate. The organic layer was dried (Na₂SO₄) and filtered. The filtrate was evaporated to dryness and the residue was purified by chromatography on silica, eluting with a mixture of ethyl acetate and cyclohexane with a gradient of 10-35%, to give methyl 6-(benzenesulphonylmethyl)-2-[2-(t-butoxycarbonylamino)ethylamino]-3-(furan-3-yl)benzoate (0.023 g) as a yellow gum.

NMR (CDCl₃) δ 7.68 (m, 3H), 7.60 (m, 1H), 7.50-7.45 (m, 3H), 7.15 (d, 1H), 6.7 (d, 1H), 6.6 (d, 1H), 4.65 (s, 2H), 3.9 (s, 3H), 3.05 (m, 2H), 2.9 (m, 2H), 1.4 (s, 9H).

Intermediate 123

Methyl 6-(benzenesulphonylmethyl)-3-(furan-3-yl)-2-(trifluoromethanesulphonyloxy)benzoate

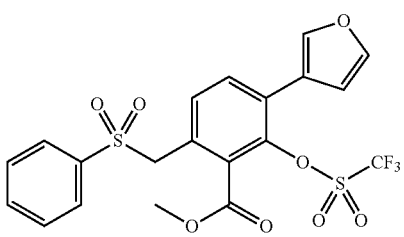 [SMILES: COC(=O)c1c(CS(=O)(=O)c2ccccc2)ccc(-c2ccoc2)c1OS(=O)(=O)C(F)(F)F]

Trifluoromethanesulphonic anhydride (0.28 g) was added to an ice cold solution of methyl 6-(benzenesulphonylmethyl)-3-(furan-3-yl)-2-hydroxybenzoate (Intermediate 114, 0.09 g) and pyridine (0.16 g) in DCM (3 ml) and the resultant mixture was stirred for 5 hours. Ethyl acetate was added and the organic layer was washed with 1M HCl and saturated aqueous sodium bicarbonate then filtered through a phase separator. The filtrate was evaporated to dryness and the residue was purified by chromatography on silica, eluting with a mixture of ethyl acetate and cyclohexane with a gradient of 5-25% to give methyl 6-(benzenesulphonylmethyl)-3-(furan-3-yl)-2-trifluoromethane-sulphonyloxy)benzoate (0.58 g) as a colourless oil which crystallized on standing to give a white solid.

NMR (CDCl₃) δ 7.75 (dd, 3H), 7.65 (m, 1H), 7.55-7.50 (m, 4H), 7.3 (d, 1H), 6.65 (dd, 1H,), 4.85 (s, 2H), 3.9 (s, 3H).

Intermediate 124

6-(Benzenesulphonylmethyl)-2-[2-(N-t-butoxycarbonyl-N-methylamino)ethoxy]-3-(furan-3-yl)benzoic acid

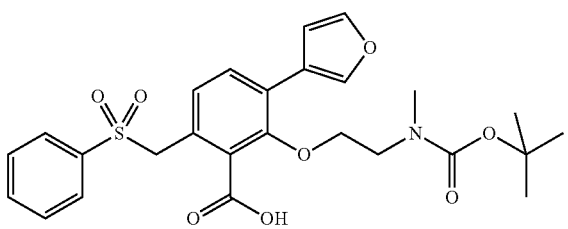 [SMILES: CN(CCOc1c(-c2ccoc2)ccc(CS(=O)(=O)c2ccccc2)c1C(=O)O)C(=O)OC(C)(C)C]

Methyl 6-(benzenesulphonylmethyl)-2-[2-(N-t-butoxycarbonyl-N-methylamino)ethoxy]-3-(furan-3-yl)benzoate (Intermediate 125, 0.054 g) was added to a solution of lithium hydroxide monohydrate (0.034 g) in water (0.3 ml) and dioxane (1 ml) and the mixture was stirred and heated at 130° C. for 30 minutes. The reaction mixture was cooled to room temperature, and partitioned between water and ethyl acetate.

The aqueous layer was acidified with formic acid and extracted with ethyl acetate, dried (Na$_2$SO$_4$) and filtered. The filtrate was evaporated to dryness to give 6-(benzenesulphonylmethyl)-2-[2-(N-t-butoxycarbonyl-N-methylamino)ethoxy]-3-(furan-3-yl)benzoic acid (0.043 g).

NMR (CDCl$_3$) δ 7.9 (t, 1H), 7.8 (m, 2H), 7.6 (d, 1H), 7.50 (m, 3H), 7.5 (m, 1H), 7.2 (m, 1H), 6.8 (d, 1H), 4.7 (s, 2H), 3.85 (s, 2H), 3.7 (s, 3H), 2.95 (m, 2H), 1.45 (s, 9H).

Intermediate 125

Methyl 6-(benzenesulphonylmethyl)-2-[2-(N-t-butoxycarbonyl-N-methylamino)ethoxy]-3-(furan-3-yl)benzoate

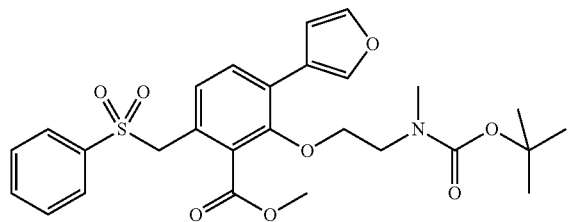 [SMILES: COC(=O)c1c(CS(=O)(=O)c2ccccc2)ccc(-c2ccoc2)c1OCCN(C)C(=O)OC(C)(C)C]

Tri-n-butylphosphine (0.054 g) was added dropwise to a cooled solution of di-isopropyl azodicarboxylate (0.065 g) in dry THF (1 ml) at 0° C. The resultant solution was warmed to room temperature for 10 minutes then re-cooled to 0° C. A mixture of methyl 6-(benzenesulphonylmethyl)-3-(furan-3-yl)-2-hydroxybenzoate (Intermediate 114, 0.05 g) and t-butyl N-(2-hydroxyethyl)-N-methylcarbamate (0.025 g) in THF (1 ml) was added dropwise and the reaction mixture was warmed to room temperature and stirred for 3 hours. Ethyl acetate and water were added and the organic layer was dried (Na$_2$SO$_4$) and filtered. The filtrate was evaporated to dryness and the residue was purified by chromatography on silica, eluting with a mixture of ethyl acetate and cyclohexane (1:3) to give methyl 6-(benzenesulphonylmethyl)-2-[2-(N-t-butoxycarbonyl-N-methylamino)ethoxy]-3-(furan-3-yl)benzoate (0.054 g) as a gum.

LCMS (Method E) r/t 4.44 (M+Na) 552.

Intermediate 126

Methyl 6-(benzenesulphonylmethyl)-3-ethyl-2-(2-methyl-2H-pyrazol-3-yl)benzoate

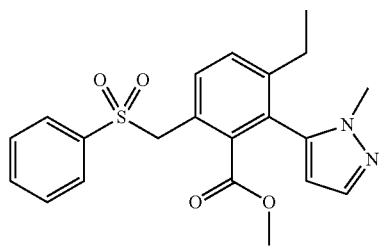 [SMILES: CCc1ccc(CS(=O)(=O)c2ccccc2)c(C(=O)OC)c1-c1ccnn1C]

Prepared by proceeding in a similar manner to Intermediate 36, starting from methyl 6-(benzenesulphonylmethyl)-3-ethyl-2-(trifluoromethanesulphonyloxy)benzoate (Intermediate 127) and 1-methyl-1H-pyrazole-5-boronic acid pinacol ester.

LCMS (Method G) r/t 4.19 (M+H) 399.

Intermediate 127

Methyl 6-(benzenesulphonylmethyl)-3-ethyl-2-(trifluoromethanesulphonyloxy)benzoate

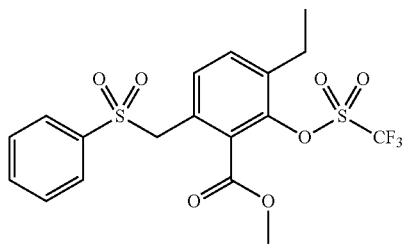 [SMILES: CCc1ccc(CS(=O)(=O)c2ccccc2)c(C(=O)OC)c1OS(=O)(=O)C(F)(F)F]

Prepared by proceeding in a similar manner to Intermediate 123, starting from methyl 6-(benzenesulphonylmethyl)-3-ethyl-2-hydroxybenzoate (Intermediate 110) as a white solid.

NMR (CDCl$_3$) δ 7.7 (m, 2H), 7.65 (m, 1H), 7.5 (t, 2H), 7.4 (d, 1H), 7.3 (s, 1H), 4.75 (s, 2H), 3.85 (s, 3H), 2.8 (q, 2H), 1.3 (t, 3H).

Intermediate 128

6-(Benzenesulphonylmethyl)-2-[2-(N-t-butoxycarbonylamino)-propoxy]-3-(furan-3-yl)benzoic acid

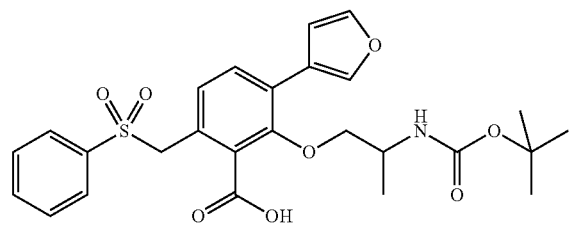 [SMILES: CC(COc1c(-c2ccoc2)ccc(CS(=O)(=O)c2ccccc2)c1C(=O)O)NC(=O)OC(C)(C)C]

Prepared by proceeding in a similar manner to Example 3, starting from methyl 6-(benzenesulphonylmethyl)-2-[2-(N-t-butoxycarbonylamino)propoxy]-3-(furan-3-yl)benzoate (Intermediate 129).

LCMS (Method E) r/t 4.30 (M+H) 516.

Intermediate 129

Methyl 6-(benzenesulphonylmethyl)-2-[2-(N-t-butoxycarbonylamino)propoxy]-3-(furan-3-yl)benzoate

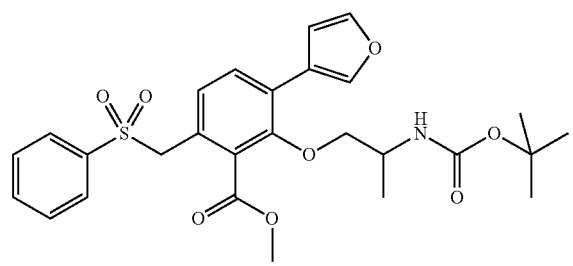 [SMILES: COC(=O)c1c(CS(=O)(=O)c2ccccc2)ccc(-c2ccoc2)c1OCC(C)NC(=O)OC(C)(C)C]

Prepared by proceeding in a similar manner to Intermediate 125, starting from methyl 6-(benzenesulphonylmethyl)-3-(furan-3-yl)-2-hydroxybenzoate (Intermediate 114) and 2-(N-t-butoxycarbonylamino)-1-propanol as a white solid.

NMR (CDCl₃) δ 7.8 (s, 1H), 7.7 (m, 2H), 7.65 (m, 1H), 7.5 (m, 3H), 7.35 (d, 1H), 7.0 (d, 1H), 6.7 (d, 1H), 4.8 (br, 1H), 4.55 (d, 1H), 4.5 (d, 1H), 3.85 (s, 3H), 3.6 (m, 2H), 1.45 (s, 9H), 1.15 (d, 3H).

Intermediate 130

Methyl 6-benzenesulphonylmethyl-3-ethyl-2-(1-methyl-1H-pyrazol-3-yl)benzoate

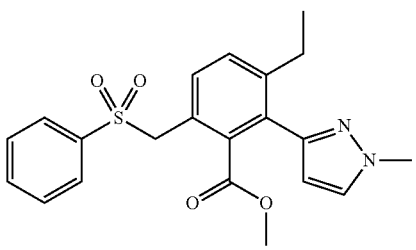 [SMILES: CCc1ccc(CS(=O)(=O)c2ccccc2)c(C(=O)OC)c1-c1ccn(C)n1]

Prepared by proceeding in a similar manner to Intermediate 36, starting from methyl 6-(benzenesulphonylmethyl)-3-ethyl-2-(trifluoromethanesulphonyloxy)benzoate (Intermediate 127) and 1-methyl-1H-pyrazole-3-boronic acid pinacol ester.

NMR (CDCl₃) δ 7.7 (dd, 2H), 7.6 (m, 1H), 7.45 (t, 2H), 7.35 (d, 1H), 7.3 (d, 1H), 7.15 (d, 1H), 6.2 (d, 1H), 4.6 (s, 2H), 3.9 (s, 3H), 3.4 (s, 3H), 2.65 (q, 2H), 1.1 (t, 3H).

Intermediate 131

Methyl 6-(benzenesulphonylmethyl)-2-(3-t-butoxycarbonylamino-propyl)-3-(furan-3-yl)benzoate

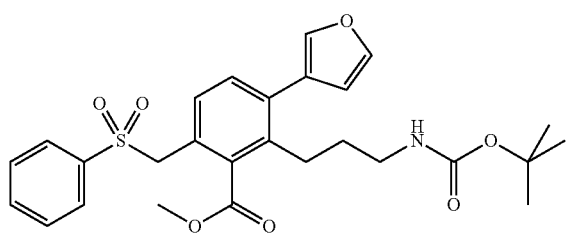 [SMILES: COC(=O)c1c(CS(=O)(=O)c2ccccc2)ccc(-c2ccoc2)c1CCCNC(=O)OC(C)(C)C]

10% Palladium on carbon (0.05 g) was added to a solution of methyl 6-(benzenesulphonylmethyl)-2-(3-t-butyoxycarbonylamino-prop-1-yn-1-yl)-3-(furan-3-yl)benzoate (Intermediate 132, 0.22 g) in ethanol (10 ml) and THF (10 ml) and the mixture was stirred at room temperature in an atmosphere of hydrogen (balloon) for 60 hours. The mixture was filtered through Celite and the filtrate was evaporated to dryness. The residue was purified by chromatography on silica eluting with a mixture of ethyl acetate and cyclohexane with a gradient of 25-60% to give methyl 6-(benzenesulphonylmethyl)-2-(3-t-butoxycarbonylaminopropyl)-3-(furan-3-yl)benzoate (0.115 g) as a colourless gum.

NMR (CDCl₃) δ 7.7 (d, 2H), 7.6 (t, 1H), 7.45 (m, 4H), 7.25 (d, 1H), 7.15 (d, 1H), 6.45 (dd, 1H), 4.5 (s, 2H), 3.8 (s, 3H), 2.95 (m, 2H), 2.65 (m, 2H), 1.5 (m, 2H), 1.4 (s, 9H).

Intermediate 132

Methyl 6-(benzenesulphonylmethyl)-2-(3-t-butyoxycarbonylamino-prop-1-yn-1-yl)-3-(furan-3-yl)benzoate

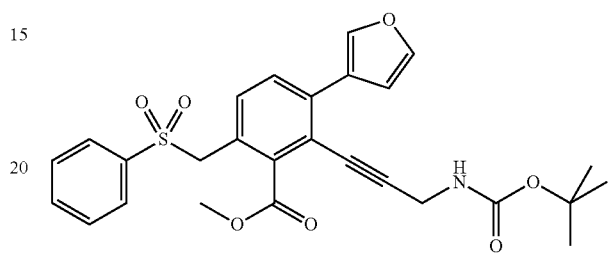

Methyl 6-(benzenesulphonylmethyl)-3-(furan-3-yl)-2-(trifluoromethanesulphonyloxy)-benzoate (Intermediate 123, 0.756 g), N-Boc-propargylamine (0.698 g), copper (I) iodide (0.014 g) and bis(triphenylphosphine)palladium(II) chloride (0.026 g) were added to a solution of triethylamine (0.152 g) in acetonitrile (10 ml) and the mixture was heated at 70° C., under nitrogen, for 17 hours. After cooling, the reaction mixture was partitioned between water and ethyl acetate. The organic layer was dried (Na₂SO₄) and filtered. The filtrate was evaporated to dryness and the residue was purified by chromatography on silica eluting with a mixture of ethyl acetate and DCM with a gradient of 0-10%. After evaporation of the appropriate fractions, the resulting residue was triturated with diethyl ether and the solid was collected by filtration to give methyl 6-(benzenesulphonylmethyl)-2-(3-t-butyoxycarbonylaminoprop-1-yn-1-yl)-3-(furan-3-yl)benzoate (0.225 g) as a white solid.

LCMS (Method G) r/t 4.69 (M+H-Boc) 410

Intermediate 133

6-(Benzenesulphonylmethyl)-3-bromo-2-methoxybenzoic acid

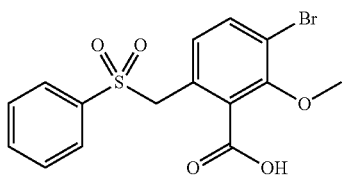 [SMILES: COc1c(Br)ccc(CS(=O)(=O)c2ccccc2)c1C(=O)O]

Prepared by proceeding in a similar manner to Intermediate 121, starting from methyl 6-(benzenesulphonylmethyl)-3-bromo-2-methoxybenzoate (Intermediate 65).

NMR (DMSO-d₆) δ 7.75 (m, 1H), 7.7 (m, 3H), 7.65 (m, 2H), 6.95 (s, 1H), 4.75 (s, 2H), 3.8 (s, 3H).

Intermediate 134

Methyl 2-(benzenesulphonylmethyl)-5-(2-methyl-2H-pyrazol-3-yl)benzoate

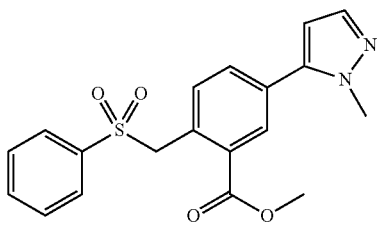 [SMILES: COC(=O)c1cc(-c2ccnn2C)ccc1CS(=O)(=O)c1ccccc1]

Prepared by proceeding in a similar manner to Example 37, starting from methyl 2-(benzenesulphonylmethyl)-5-bromobenzoate (Intermediate 63) and 1-methyl-1H-pyrazole-5-boronic acid pinacol ester.

NMR (CDCl$_3$) δ 7.95 (d, 1H), 7.7 (dd, 2H), 7.6 (d, 1H), 7.55 (dd, 2H), 7.45 (m, 3H), 6.35 (d, 1H), 5.1 (s, 2H), 3.9 (s, 3H), 3.8 (s, 3H).

Intermediate 135

Methyl 2-(benzenesulphonylmethyl)naphthalene-1-carboxylate

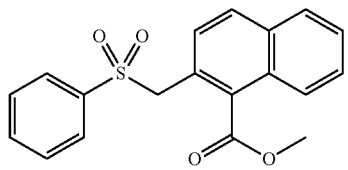 [SMILES: COC(=O)c1c(CS(=O)(=O)c2ccccc2)ccc2ccccc12]

A mixture of methyl 2-bromomethylnaphthalene-1-carboxylate (Intermediate 136, 0.377 g), benzenesulphinic acid sodium salt (0.416 g), sodium hydrogen carbonate (0.213 g) in DMA (20 ml) was stirred at room temperature for 18 hours. The mixture was partitioned between water and ethyl acetate and the organic layer was separated, washed with brine, dried (MgSO$_4$) and filtered. The filtrate was evaporated to dryness and the residue was purified by chromatography on silica, eluting with a mixture of DCM and pentane with a gradient of 30-70% to give 2-(benzenesulphonylmethyl)-naphthalene-1-methyl carboxylate (0.158 g) as an opaque gum.

NMR (CDCl$_3$) δ 7.9 (dd, 1H), 7.85 (m, 2H), 7.65 (m, 2H), 7.6 (m, 1H), 7.55 (dd, 2H), 7.45 (m, 2H), 7.3 (d, 1H), 4.75 (s, 2H), 3.9 (s, 3H).

Intermediate 136

Methyl 2-bromomethylnaphthalene-1-carboxylate

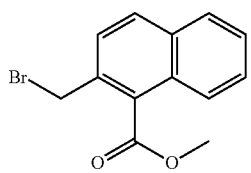 [SMILES: COC(=O)c1c(CBr)ccc2ccccc12]

N-Bromosuccinimide (0.748 g) was added to a solution of methyl 2-methylnapthalene-1-carboxylate (0.7 g) in acetonitrile (30 ml) and the mixture was heated to reflux. Benzoyl peroxide (0.093 g) was added and the reaction mixture was heated at reflux for 4 hours. After cooling, ethyl acetate was added and the solution was washed with water, dried (MgSO$_4$) and filtered. The filtrate was evaporated to dryness and the residue was purified by chromatography on silica, eluting with a mixture of DCM and pentane with a gradient of 7.5-25% to give methyl 2-bromomethylnaphthalene-1-carboxylate (0.529 g) as a yellow solid.

NMR (CDCl$_3$) δ 7.9 (dd, 2H), 7.55 (m, 2H), 7.5 (d, 2H), 4.7 (s, 2H), 4.1 (s, 3H).

Intermediate 137

Methyl 3-(furan-3-yl)-6-(2-hydroxybenzenesulphonylmethyl)-2-methoxybenzoate

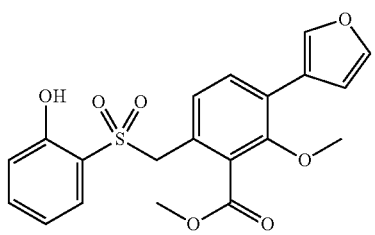 [SMILES: COC(=O)c1c(CS(=O)(=O)c2ccccc2O)ccc(-c2ccoc2)c1OC]

Prepared by proceeding in a similar manner to Intermediate 36, starting from methyl 3-bromo-6-(2-hydroxybenzenesulphonylmethyl)-2-methoxybenzoate (Intermediate 138).

NMR (CDCl$_3$) δ 8.65 (s, 1H), 7.95 (dd, 1H), 7.5 (m, 2H), 7.45 (d, 1H), 7.4 (dd, 1H), 7.0 (d, 1H), 6.95 (m, 2H), 6.75 (dd, 1H), 4.6 (s, 2H), 3.9 (s, 3H), 3.65 (s, 3H).

Intermediate 138

Methyl 3-bromo-6-(2-hydroxybenzenesulphonylmethyl)-2-methoxybenzoate

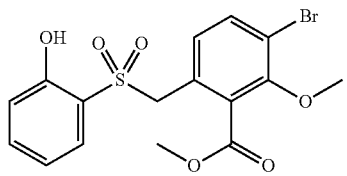 [SMILES: COC(=O)c1c(CS(=O)(=O)c2ccccc2O)ccc(Br)c1OC]

A mixture of methyl 3-bromo-6-(2-hydroxyphenylthiomethyl)-2-methoxybenzoate (Intermediate 139, 0.288 g), and 50% hydrogen peroxide (0.3 ml) in acetic acid (5 ml) was stirred at room temperature for 16 hours then heated at 90° C. for 2 hours. After cooling, the mixture was evaporated to dryness. Ethyl acetate was added and the organic layer was washed with saturated aqueous sodium hydrogen carbonate solution, dried (Na$_2$SO$_4$) and filtered the filtrate was evaporated to dryness and the residue was purified by chromatography on silica, eluting with a mixture of ethyl acetate and cyclohexane with a gradient of 20-45% to give methyl 3-bromo-6-(2-hydroxybenzenesulphonylmethyl)-2-methoxybenzoate (0.258 g) as a colourless gum.

NMR (CDCl$_3$) δ 8.6 (br, s, 1H), 7.55 (d, 1H), 7.5 (m, 1H), 7.4 (dd, 1H), 6.95 (m, 2H), 6.85 (d, 1H), 4.55 (s, 2H), 3.9 (s, 3H), 3.85 (s, 3H).

Intermediate 139

Methyl 3-bromo-6-(2-hydroxyphenylthiomethyl)-2-methoxybenzoate

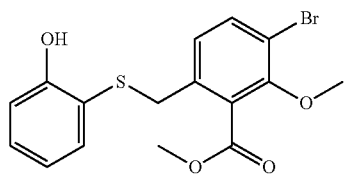 [SMILES: COC(=O)c1c(CSc2ccccc2O)ccc(Br)c1OC]

Prepared by proceeding in a similar manner to Intermediate 82, starting from methyl 3-bromo-6-bromomethyl-2-methoxybenzoate (Intermediate 89) and 2-mercaptophenol and used without further characterization.

Intermediate 140

Methyl 3-(furan-3-yl)-6-(3-hydroxybenzenesulphonylmethyl)-2-methoxybenzoate

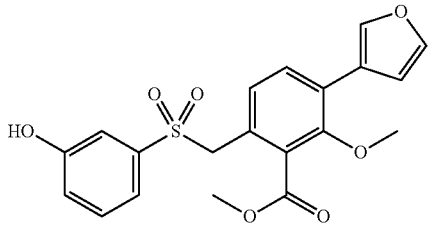 [SMILES: COC(=O)c1c(CS(=O)(=O)c2cccc(O)c2)ccc(-c2ccoc2)c1OC]

Prepared by proceeding in a similar manner to Intermediate 36, starting from methyl 3-bromo-6-(3-hydroxybenzenesulphonylmethyl)-2-methoxybenzoate (Intermediate 141)

NMR (CDCl$_3$) δ 7.9 (dd, 1H) 7.5 (t, 1H), 7.45 (s, 1H), 7.35 (t, 1H), 7.25 (m, 1H), 7.15 (t, 1H), 7.1 (ddd, 1H), 7.05 (d, 1H), 6.75 (dd, 1H), 5.75 (br. s, 1H), 4.55 (s, 2H), 3.85 (s, 3 H), 3.6 (s, 3H).

Intermediate 141

Methyl 3-bromo-6-(3-hydroxybenzenesulphonylmethyl)-2-methoxybenzoate

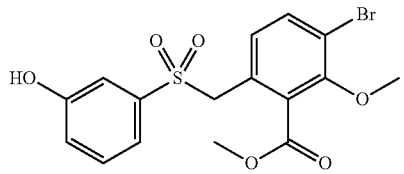 [SMILES: COC(=O)c1c(CS(=O)(=O)c2cccc(O)c2)ccc(Br)c1OC]

Prepared by proceeding in a similar manner to Intermediate 138, starting from methyl 3-bromo-6-(3-hydroxyphenylthiomethyl)-2-methoxybenzoate (Intermediate 142).

NMR (CDCl$_3$): 7.6 (d, 1H), 7.4 (t, 1H), 7.25 (m, 1H), 7.2 (t, 1H), 7.1 (ddd, 1H), 6.95 (d, 1H), 5.65 (br, s, 1H), 4.55 (s, 2H), 3.9 (s, 3H), 3.9 (s, 3H).

Intermediate 142

Methyl 3-bromo-6-(3-hydroxyphenylthiomethyl)-2-methoxybenzoate

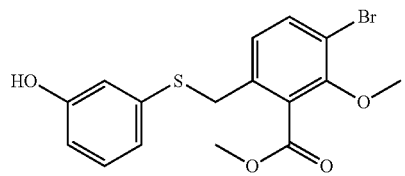 [SMILES: COC(=O)c1c(CSc2cccc(O)c2)ccc(Br)c1OC]

Prepared by proceeding in a similar manner to Intermediate 82, starting from methyl 3-bromo-6-bromomethyl-2-methoxybenzoate (Intermediate 89) and 3-mercaptophenol and used without further characterization.

Intermediate 143

Methyl 2-(benzenesulphonylmethyl)-5-(2-methylfuran-3-yl)benzoate

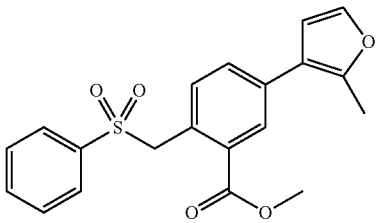 [SMILES: COC(=O)c1cc(-c2ccoc2C)ccc1CS(=O)(=O)c1ccccc1]

Prepared by proceeding in a similar manner to Example 36, starting from methyl 2-(benzenesulphonylmethyl)-5-bromobenzoate (Intermediate 63) and 2-methylfuran-5-boronic acid pinacol ester.

NMR (CDCl$_3$) δ 7.9 (d, 1H), 7.7 (m, 2H), 7.6 (d, 1H), 7.5 (m, 3H), 7.35 (s, 2H), 6.55 (d, 1H), 5.05 (s, 2H), 3.75 (s, 3H), 2.45 (s, 3H).

Intermediate 144

Methyl 6-(benzenesulphonylmethyl)-3-ethyl-2-(1H-pyrazol-3-yl)benzoate

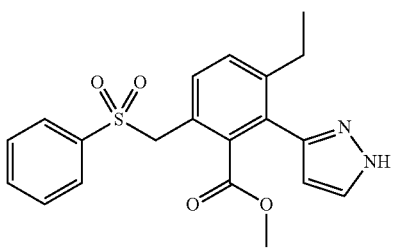 [SMILES: CCc1ccc(CS(=O)(=O)c2ccccc2)c(C(=O)OC)c1-c1cc[nH]n1]

Prepared by proceeding in a similar manner to Example 53, starting from methyl 6-(benzenesulphonylmethyl)-3-ethyl-2-[2-(tetrahydropyran-2-yl)-2H-pyrazol-3-yl]benzoate (Intermediate 145) as an opaque solid.

NMR (CDCl$_3$) δ 7.75 (m, 2H), 7.65 (m, 2H), 7.5 (t, 3H), 7.35 (d, 1H), 7.3 (d, 1H), 6.3 (br, s, 1H), 4.6 (s, 2H), 3.4 (s, 3H), 2.6 (q, 2H), 1.1 (t, 3H).

Intermediate 145

Methyl 6-(benzenesulphonylmethyl)-3-ethyl-2-[2-(tetrahydropyran-2-yl)-2H-pyrazol-3-yl]benzoate

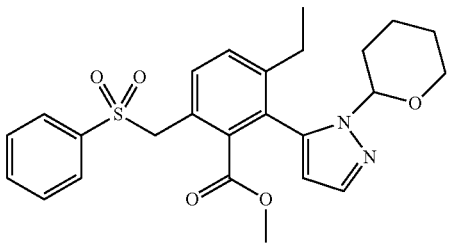 [SMILES: CCc1ccc(CS(=O)(=O)c2ccccc2)c(C(=O)OC)c1-c1ccnn1C1CCCCO1]

Prepared by proceeding in a similar manner to Intermediate 36, starting from methyl 6-(benzenesulphonylmethyl)-3-ethyl-2-(trifluoromethanesulphonyloxy)benzoate (Intermediate 127) and 1-(2-tetrahydropyranyl)-1H-pyrazole-5-boronic acid pinacol ester as an opaque foam which was used without further characterization.

Intermediate 146

Methyl 3-(furan-3-yl)-2-methoxy-6-(piperidin-1-ylsulphonylmethyl)benzoate

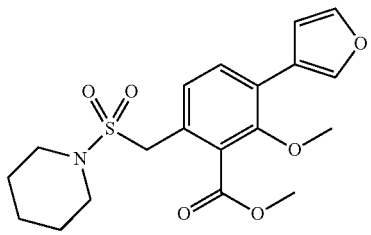

Prepared by proceeding in a similar manner to Intermediate 36, starting from methyl 3-bromo-2-methoxy-6-(piperidin-1-ylsulphonylmethyl)benzoate (Intermediate 147) and furan-3-boronic acid as a white solid.

NMR (CDCl$_3$) δ 7.95 (s, 1H), 7.5 (m, 2H), 7.3 (d, 1H), 6.8 (dd, 1H), 4.35 (s, 2H), 4.0 (s, 3H), 3.7 (s, 3H), 3.15 (t, 4H), 1.55 (d, 6H).

Intermediate 147

Methyl 3-bromo-2-methoxy-6-(piperidin-1-ylsulphonylmethyl)benzoate

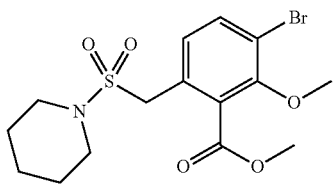 [SMILES: COC(=O)c1c(CS(=O)(=O)N2CCCCC2)ccc(Br)c1OC]

A mixture of thionyl chloride (0.176 g) and DMF (0.02 g) was added to a solution of (4-bromo-3-methoxy-2-methoxycarbonylphenyl)-methanesulphonic acid sodium salt (Intermediate 148, 0.134 g) in DCM (5 ml) and the mixture was heated to 50° C. for 2 hours. After cooling, the mixture was filtered and the solid was washed with toluene. The filtrate was evaporated to dryness. DCM and piperidine (0.157 g) were added to the resultant residue and the mixture was stirred at room temperature for 4 hours. The mixture was evaporated to dryness and the residue was purified by chromatography on silica, eluting with a mixture of ethyl acetate and cyclohexane with a gradient of 5-20% to give methyl 3-bromo-2-methoxy-6-(piperidin-1-ylsulphonylmethyl)benzoate (0.150 g) as a colourless oil.

NMR (CDCl$_3$) δ 7.65 (d, 1H), 7.15 (d, 1H), 4.3 (s, 2H), 3.95 (s, 3H), 3.9 (s, 3H), 3.15 (t, 4H), 1.6 (m, 6H).

Intermediate 148

(4-Bromo-3-methoxy-2-methoxycarbonylphenyl)-methanesulphonic acid sodium salt

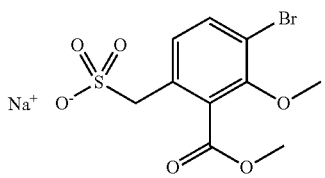 [SMILES: [Na+] ; COC(=O)c1c(CS(=O)(=O)[O-])ccc(Br)c1OC]

A mixture of methyl 3-bromo-6-bromomethyl-2-methoxybenzoate (Intermediate 89, 1.0 g) and sodium sulphite (0.445 g) in ethanol (1 ml) and water (10 ml) was stirred and heated at reflux for 2 hours. After cooling, the mixture was evaporated to dryness to give (4-bromo-3-methoxy-2-methoxycarbonylphenyl)-methanesulphonic acid sodium salt (1.07 g) as a white solid which was used without further characterization.

Intermediate 149

Methyl 3-(furan-3-yl)-2-methoxy-6-(pyrrolidin-1-ylsulphonylmethyl)benzoate

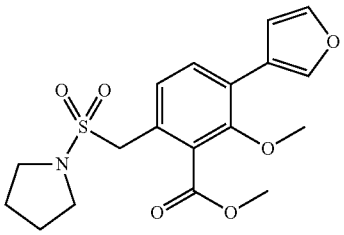 [SMILES: COC(=O)c1c(CS(=O)(=O)N2CCCC2)ccc(-c2ccoc2)c1OC]

Prepared by proceeding in a similar manner to Intermediate 36, starting from methyl 3-bromo-2-methoxy-6-(pyrrolidin-1-ylsulphonylmethyl)benzoate (Intermediate 150) as a colourless oil.

NMR (CDCl$_3$) δ 7.95 (dd, 1H), 7.5 (dd, 2H), 7.4 (s, 1H), 6.8 (d, 1H), 4.4 (s, 2H), 4.0 (s, 3H), 3.7 (s, 3H), 3.25 (m, 4H), 1.9 (m, 4H).

Intermediate 150

Methyl 3-bromo-2-methoxy-6-(pyrrolidine-1-ylsulphonylmethyl)benzoate

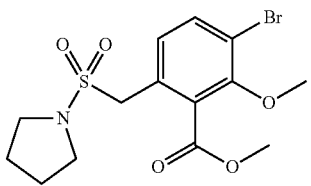 [SMILES: COC(=O)c1c(CS(=O)(=O)N2CCCC2)ccc(Br)c1OC]

Prepared by proceeding in a similar manner to Intermediate 147, starting from methyl (4-bromo-3-methoxy-2-methoxycarbonylphenyl)-methanesulphonic acid sodium salt (Intermediate 148) and pyrrolidine as a white solid.
NMR (CDCl$_3$) δ 7.65 (d, 1H), 7.2 (d, 1H), 4.35 (s, 2H), 3.95 (s, 3H), 3.9 (s, 3H), 3.25 (m, 4H), 1.9 (m, 4H).

Intermediate 151

Methyl 6-[2-(2-diethylaminoethylamino)benzenesulphonylmethyl]-3-(furan-3-yl)-2-methoxybenzoate

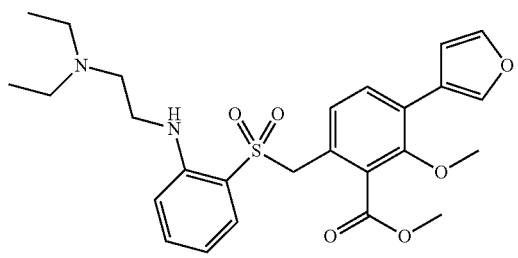 [SMILES: CCN(CC)CCNc1ccccc1S(=O)(=O)Cc1ccc(-c2ccoc2)c(OC)c1C(=O)OC]

Prepared by proceeding in a similar manner to Intermediate 192, starting from methyl 6-(2-fluorobenzenesulphonylmethyl)-3-(furan-3-yl)-2-methoxybenzoate (Intermediate 96) and N,N,-diethylethylenediamine, as brown solid.
LCMS (Method G) r/t 3.31 (M+H) 501.

Intermediate 152

Methyl 6-(benzenesulphonylmethyl)-2-ethyl-3-(furan-3-yl)benzoate

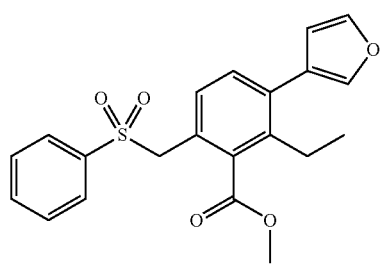 [SMILES: CCc1c(-c2ccoc2)ccc(CS(=O)(=O)c2ccccc2)c1C(=O)OC]

A mixture of potassium phosphate tribasic (0.244 g), methyl 6-(benzenesulphonylmethyl)-3-(furan-3-yl)-2-(trifluoromethanesulphonyloxy)benzoate (Intermediate 123, 0.2 g) in THF (2 ml) and water (1 ml) was sealed in a microwave vial and degassed with argon. Palladium (II) chloride dppf complexed with DCM (0.02 g) and triethylborane (0.29 ml) were added and the mixture was heated in the microwave at 140° C. for 15 minutes. After cooling, ethyl acetate and water were added and the organic layer was separated, washed with brine, dried (MgSO$_4$) and filtered. The filtrate was evaporated to dryness and the residue was purified by chromatography on silica eluting with a mixture of ethyl acetate and cyclohexane with a gradient of 10-18% to give methyl 6-(benzenesulphonylmethyl)-2-ethyl-3-(furan-3-yl)benzoate (0.092 g) as a white solid.
NMR (CDCl$_3$) δ 7.7 (dd, 2H), 7.65 (t, 1H), 7.55-7.45 (m, 4H), 7.25 (d, 1H), 7.15 (d, 1H), 6.50 (dd, 1H), 4.5 (s, 2H), 3.8 (s, 3H), 6.7 (q, 2H), 1.0 (t, 3H).

Intermediate 153

Methyl 6-[2-(2-diethylaminoethoxy)benzenesulphonylmethyl]-3-(furan-3-yl)-2-methoxybenzoate

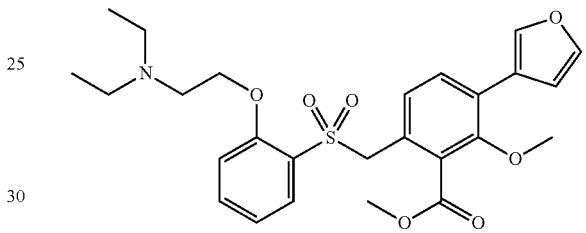

A solution of methyl 3-(furan-3-yl)-6-(2-hydroxybenzenesulphonylmethyl)-2-methoxybenzoate (Intermediate 137, 0.081 g), cesium carbonate (0.144 g) and N-(2-bromoethyl)-N,N,-diethylamine hydrochloride (0.058 g) in DMF (5 ml) was stirred at room temperature. On completion of the reaction, water and DCM were added and the organic layer was separated, dried (MgSO$_4$) and filtered. The filtrate was evaporated to dryness and the residue was purified by chromatography on silica eluting with a mixture of methanol and DCM (1:19) to give methyl 6-[2-(2-diethylaminoethoxy)benzenesulphonylmethyl]-3-(furan-3-yl)-2-methoxybenzoate (0.101 g) as a colourless oil.
NMR (CDCl$_3$) δ 7.9 (dd, 1H), 7.75 (dd, 1H), 7.55 (m, 1H), 7.45 (t, 1H), 7.35 (d, 1H), 7.1 (d, 1H), 7.0 (t, 2H), 6.7 (dd, 1H), 4.85 (s, 2H), 4.35 (s, 2H), 3.95 (s, 3H), 3.65 (s, 3H), 3.1 (s, 2H), 2.8 (d, 4H), 1.15 (t, 6H).

Intermediate 154

Methyl 6-(benzenesulphonylmethyl)-3-(furan-3-yl)-2-(prop-1-yn-1-yl)benzoate

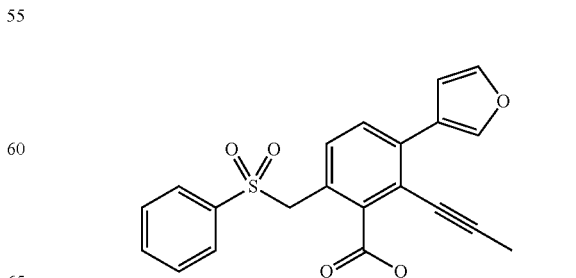

Methyl 6-(benzenesulphonylmethyl)-3-(furan-3-yl)-2-(trifluoromethanesulphonyl-oxy)benzoate (Intermediate 123, 0.2 g), propyne (0.174 g), copper (I) iodide (0.008 g) and bis-(triphenylphosphine)palladium(II) chloride (0.029 g) were added to a solution of diisopropylamine (0.168 g) in DMF (2 ml) in a microwave vial. The mixture was degassed with argon and then heated in the microwave at 100° C. for 1 hour. After cooling, saturated aqueous ammonium chloride solution and ethyl acetate were added. The organic layer was separated, washed with water, dried (Na$_2$SO$_4$) and filtered. The filtrate was evaporated to dryness and the residue was purified by chromatography on silica, eluting with a mixture of ethyl acetate and cyclohexane with a gradient of 7-25%. The resultant yellow gum was triturated with diethyl ether and the solid was collected by filtration to give methyl 6-(benzenesulphonylmethyl)-3-(furan-3-yl)-2-(prop-1-yn-1-yl) benzoate (0.057 g) as a white solid.

NMR (CDCl$_3$) δ 8.0 (s, 1H), 7.7 (dd, 2H), 7.6 (d, 1H), 7.5 (m, 3H), 7.4 (d, 1H), 7.2 (d, 1H), 6.8 (d, 1H), 4.5 (s, 2H), 3.8 (s, 3H), 2.05 (s, 3H).

Intermediate 155

Methyl 2-(benzenesulphonylmethyl)-6-methoxybenzoate

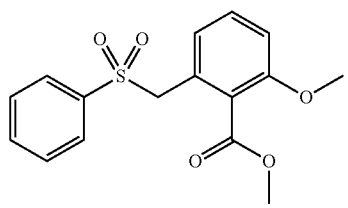 [SMILES: COC(=O)c1c(CS(=O)(=O)c2ccccc2)cccc1OC]

Isolated from the reaction between methyl 6-(benzenesulphonylmethyl)-3-bromo-2-methoxybenzoate (Intermediate 65) and triethylborane, following the procedure of Intermediate 152.

NMR (CDCl$_3$) δ 7.7 (m, 2H), 7.6 (m, 1H), 7.45 (t, 2H), 7.3 (m, 1H), 6.95 (d, 1H), 6.85 (d, 1H), 4.55 (s, 2H), 3.85 (s, 3H), 3.8 (d, 3H).

Intermediate 156

Methyl 6-(cyclohexanesulphonylmethyl)-3-(furan-3-yl)-2-methoxybenzoate

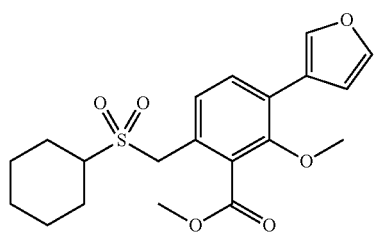 [SMILES: COC(=O)c1c(CS(=O)(=O)C2CCCCC2)ccc(-c2ccoc2)c1OC]

Prepared by proceeding in a similar manner to Intermediate 36, starting from methyl 3-bromo-6-(cyclohexanesulphonylmethyl)-2-methoxybenzoate (Intermediate 157).

NMR (CDCl$_3$) δ 7.9 (s, 1H), 7.55 (d, 1H), 7.5 (t, 1H), 7.3 (d, 1H), 6.75 (m, 1H), 4.35 (s, 2H), 3.95 (s, 3H), 3.7 (s, 3H), 2.85 (m, 1H), 2.1 (d, 2H), 1.9 (m, 2H), 1.7 (m, 1H), 1.6-1.5 (m, 2H), 1.25 (m, 3H).

Intermediate 157

Methyl 3-bromo-6-cyclohexanesulphonylmethyl)-2-methoxybenzoate

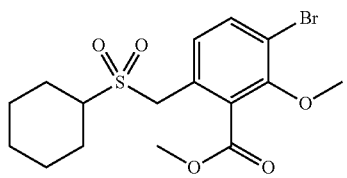 [SMILES: COC(=O)c1c(CS(=O)(=O)C2CCCCC2)ccc(Br)c1OC]

Prepared by proceeding in a similar manner to Intermediate 138, starting from methyl 3-bromo-6-(cyclohexylthiomethyl)-2-methoxybenzoate (Intermediate 158).

NMR (CDCl$_3$) δ 7.65 (d, 1H), 7.15 (d, 1H), 4.35 (s, 2H), 3.95 (s, 3H), 3.95 (s, 3H), 2.85 (m, 1H), 2.15 (d, 2H), 1.95 (d, 2H), 1.75 (d, 1H), 1.6-1.5 (m, 2H), 1.25 (m, 3H).

Intermediate 158

Methyl 3-bromo-6-(cyclohexylthiomethyl)-2-methoxybenzoate

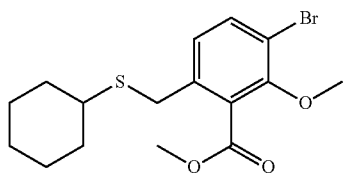 [SMILES: COC(=O)c1c(CSC2CCCCC2)ccc(Br)c1OC]

Prepared by proceeding in a similar manner to Intermediate 82, starting from methyl 3-bromo-6-bromomethyl-2-methoxybenzoate (Intermediate 89) and cyclohexanethiol and used without further purification.

Intermediate 159 t-Butyl 6-(benzenesulphonylmethyl)-2-(carbamoylmethoxy)-3-(furan-3-yl)benzoate

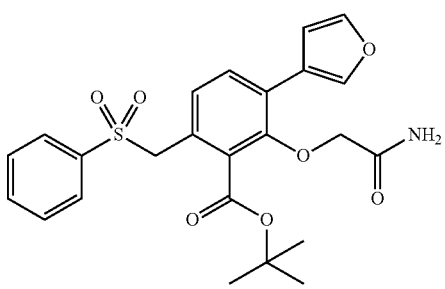 [SMILES: CC(C)(C)OC(=O)c1c(CS(=O)(=O)c2ccccc2)ccc(-c2ccoc2)c1OCC(N)=O]

Prepared by proceeding in a similar manner to Intermediate 10, starting from t-butyl 6-(benzenesulphonylmethyl)-3-(furan-3-yl)-2-hydroxybenzoate (Intermediate 120) and 2-bromoacetamide.

NMR (CDCl₃) δ 7.8 (s, 1H), 7.75 (m, 2H), 7.65 (d, 1H), 7.55 (m, 3H), 7.4 (d, 1H), 7.1 (d, 1H), 6.7 (dd, 1H), 4.55 (s, 2H), 4.3 (s, 2H), 1.6 (s, 9H).

Intermediate 160

(Z)-Methyl 6-((2-(3-(diethylamino)prop-1-enyl)-4-fluorobenzenesulfonyl)methyl)-3-(furan-3-yl)-2-methoxybenzoate

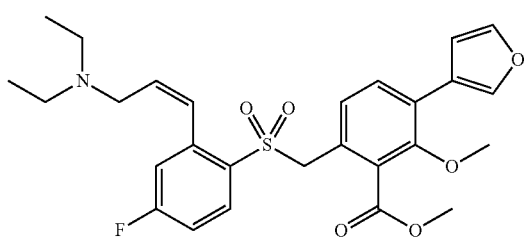 [SMILES: CCN(CC)C/C=C\c1cc(F)ccc1S(=O)(=O)Cc1ccc(-c2ccoc2)c(OC)c1C(=O)OC]

A mixture of (Z)-methyl 3-bromo-6-((2-(3-(diethylamino)prop-1-enyl)-4-fluorobenzenesulfonyl)methyl)-2-methoxybenzoate (Intermediate 161, 0.163 g), furan-3-yl boronic acid (0.041 g), palladium (II) chloride dppf complexed with DCM (0.025 g), cesium carbonate (0.282 g) in water (0.5 ml) and dioxane (3 ml) was degassed and then heated in the microwave at 140° C. for 10 minutes. After cooling, the mixture was partitioned between ethyl acetate and water. The aqueous layer was further extracted with ethyl acetate and the combined organic layers were washed with brine, dried (Na₂SO₄) and filtered. The filtrate was evaporated to dryness and the residue was purified by chromatography on silica, eluting with a mixture of methanol and DCM with a gradient of 0-5% to give (Z)-methyl 6-((2-(3-(diethylamino)prop-1-enyl)-4-fluorobenzenesulfonyl)methyl)-3-(furan-3-yl)-2-methoxybenzoate as an orange oil.

NMR (CDCl₃) δ 7.9 (dd, 1H), 7.9 (dd, 1H), 7.5 (t, 1H), 7.4 (d, 1H), 7.2 (dd, 1H), 7.05 (m, 2H), 6.95 (d, 1H), 6.75 (dd, 1H), 6.15 (dt, 1H), 4.55 (s, 2H), 3.95 (s, 3H), 3.65 (s, 3H), 3.25 (d, 2H), 2.6 (q, 4H), 1.0 (t, 6H).

Intermediate 161

(Z)-Methyl 3-bromo-6-((2-(3-(diethylamino)prop-1-enyl)-4-fluorobenzenesulfonyl)methyl)-2-methoxybenzoate

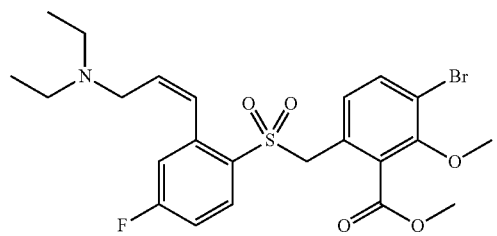 [SMILES: CCN(CC)C/C=C\c1cc(F)ccc1S(=O)(=O)Cc1ccc(Br)c(OC)c1C(=O)OC]

Prepared by proceeding in a similar manner to Intermediate 5, starting from (Z)-methyl 3-bromo-6-((4-fluoro-2-(3-hydroxyprop-1-enyl)benzenesulfonyl)methyl)-2-methoxybenzoate (Intermediate 162).

NMR (CDCl₃) δ 7.9 (dd, 1H), 7.6 (d, 1H), 7.1 (m, 2H), 7.05 (d, 1H), 6.85 (d, 1H), 6.2 (m, 1H), 4.55 (s, 2H), 3.95 (s, 3H), 3.9 (s, 3H), 3.25 (d, 2H), 2.7 (d, 4H), 1.1 (t, 6H).

Intermediate 162

(Z)-Methyl 3-bromo-6-((4-fluoro-2-(3-hydroxyprop-1-enyl)benzenesulfonyl)methyl)-2-methoxybenzoate

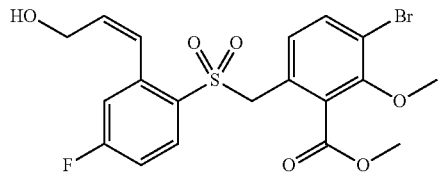 [SMILES: COC(=O)c1c(CS(=O)(=O)c2ccc(F)cc2/C=C\CO)ccc(Br)c1OC]

A mixture of methyl 3-bromo-6-(2-bromo-4-fluorobenzenesulphonylmethyl)-2-methoxybenzoate (Intermediate 163, 0.916 g), 3-tributylstannyl-(Z)-prop-2-en-1-ol (prepared according to Webb et al, *Tetrahedron*, 2008, 64, 4778, 0.833 g) and tris(dibenzylideneacetone)dipalladium (0) (0.085 g) in toluene (12 ml) was degassed with argon. Tri-tert-butylphosphine (1M in toluene, 0.20 ml) was added and the mixture was again degassed then heated to 30° C. for 3 hours. After cooling, the mixture was diluted with ethyl acetate and filtered through a PTFE cone. The filtrate was evaporated to dryness and the residue was purified by chromatography on silica, eluting with a mixture of ethyl acetate and pentane containing 1% triethylamine with a gradient of 0-100%, to give (Z)-methyl 3-bromo-6-((4-fluoro-2-(3-hydroxyprop-1-enyl)benzenesulfonyl)methyl)-2-methoxybenzoate (0.198 g) as a yellow oil.

NMR (CDCl₃) δ 7.95 (dd, 1H), 7.6 (d, 1H), 7.1 (dt, 1H), 7.05 (s, 1H), 7.0 (m, 1H), 6.95 (d, 1H), 6.1 (dt, 1H), 4.5 (s, 2H), 4.25 (dd, 2H), 3.9 (s, 3H), 3.9 (s, 3H).

Intermediate 163

Methyl 3-bromo-6-(2-bromo-4-fluorobenzenesulphonylmethyl)-2-methoxybenzoate

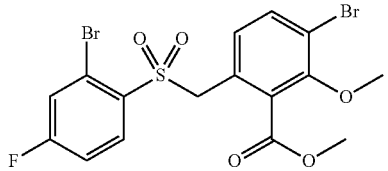 [SMILES: COC(=O)c1c(CS(=O)(=O)c2ccc(F)cc2Br)ccc(Br)c1OC]

Prepared by proceeding in a similar manner to Intermediate 61, starting from methyl 3-bromo-6-(2-bromo-4-fluorophenylthiomethyl)-2-methoxybenzoate (Intermediate 164), as a colourless oil.

NMR (CDCl₃) δ 7.9 (dd, 1H), 7.55 (t, 1H), 7.5 (d, 1H), 7.1 (ddd, 1H), 6.95 (d, 1H), 4.8 (s, 2H), 3.95 (s, 3H), 3.85 (s, 3H).

Intermediate 164

Methyl 3-bromo-6-(2-bromo-4-fluorophenylthiomethyl)-2-methoxybenzoate

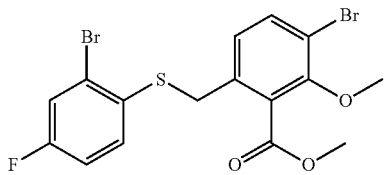 [SMILES: COC(=O)c1c(CSc2ccc(F)cc2Br)ccc(Br)c1OC]

Prepared by proceeding in a similar manner to Intermediate 77, starting from methyl 3-bromo-6-bromomethyl-2-methoxybenzoate (Intermediate 89) and 2-bromo-4-fluorothiophenol and used without further characterization.

Intermediate 165

Methyl 3-(furan-3-yl)-6-(3-hydroxypyrrolidin-1-ylsulphonylmethyl)-2-methoxybenzoate

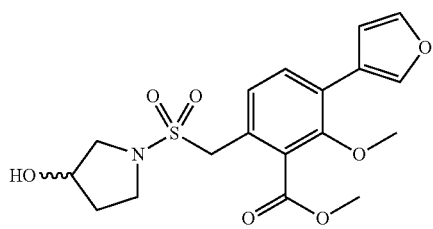 [SMILES: COC(=O)c1c(CS(=O)(=O)N2CCC(O)C2)ccc(-c2ccoc2)c1OC]

Prepared by proceeding in a similar manner to Intermediate 36, starting from methyl 3-bromo-6-(3-hydroxypyrrolidin-1-ylsulphonylmethyl)-2-methoxybenzoate (Intermediate 166).

NMR (CDCl$_3$) δ 7.95 (s, 1H), 7.55 (d, 1H), 7.5 (t, 1H), 7.4 (d, 1H), 6.8 (d, 1H), 4.4 (br, s, 1H), 4.35 (s, 2H), 4.0 (s, 3H), 3.7 (s, 3H), 3.45 (m, 2H), 3.3 (dd, 1H), 3.1 (d, 1H), 2.05 (s, 1H), 2.0 (s, 1H), 1.95 (m, 1H).

Intermediate 166

Methyl 3-bromo-6-(3-hydroxypyrrolidin-1-ylsulphonylmethyl)-2-methoxybenzoate

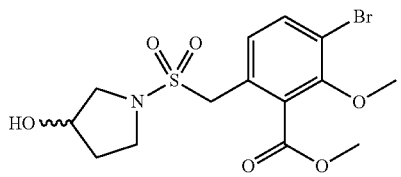 [SMILES: COC(=O)c1c(CS(=O)(=O)N2CCC(O)C2)ccc(Br)c1OC]

Prepared as a colourless oil by proceeding in a similar manner to Intermediate 147, starting from methyl (4-bromo-3-methoxy-2-methoxycarbonylphenyl)methanesulphonic acid sodium salt (Intermediate 148, 0.134 g) and 3-pyrrolidinol (0.12 g).

NMR (CDCl$_3$) δ 7.65 (d, 1H), 7.3 (d, 1H), 4.4 (br, s, 1H), 4.35 (s, 2H), 4.0 (s, 3H), 3.9 (s, 3H), 3.45 (m, 1H), 3.4 (m, 1H), 3.3 (dt, 1H), 3.15 (dt, 1H), 2.4 (s, 1H), 2.0 (m, 1H), 1.95 (m, 1H).

Intermediate 167 t-Butyl 3-[3-(benzenesulphonylmethyl)-2-carboxy-6-(furan-3-yl)-phenoxy)-azetidine-1-carboxylate

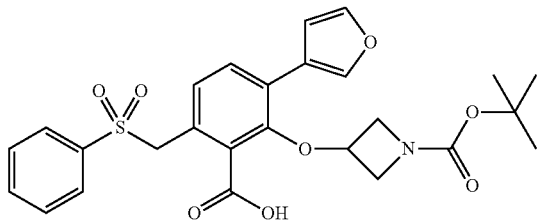 [SMILES: CC(C)(C)OC(=O)N1CC(Oc2c(-c3ccoc3)ccc(CS(=O)(=O)c3ccccc3)c2C(=O)O)C1]

Prepared by proceeding in a similar manner to Example 3, starting from t-butyl 3-[3-(benzenesulphonylmethyl)-6-(furan-3-yl)-2-(methoxycarbonyl)phenoxy]azetidine-1-carboxylate (Intermediate 168).

NMR (CDCl$_3$) δ 7.8 (m, 3H), 7.65 (m, 1H), 7.55 (m, 3H), 7.45 (d, 1H), 7.15 (d, 1H), 6.7 (dd, 1H), 4.65 (s, 2H), 4.55 (m, 1H), 4.0 (m, 4H), 1.45 (s, 9H).

Intermediate 168 t-Butyl 3-[3-(benzenesulphonylmethyl)-6-(furan-3-yl)-2-(methoxycarbonyl)phenoxy]azetidine-1-carboxylate

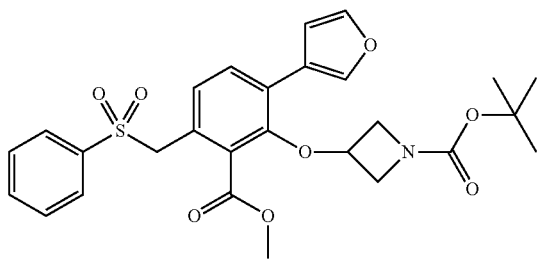 [SMILES: COC(=O)c1c(CS(=O)(=O)c2ccccc2)ccc(-c2ccoc2)c1OC1CN(C(=O)OC(C)(C)C)C1]

Tri-n-butylphosphine (0.087 g) was added dropwise to a solution of di-isopropyl azodicarboxylate (0.099 g) in dry THF (2 ml) at 0° C. The mixture was warmed to room temperature for 10 minutes then re-cooled to 0° C. A mixture of methyl 6-(benzenesulphonylmethyl)-3-(furan-3-yl)-2-hydroxybenzoate (Intermediate 114, 0.05 g) and N-Boc-azetidin-3-ol (0.045 g) in THF (1 ml) was added dropwise and then the reaction mixture was warmed to room temperature for 10 minutes then heated to 55° C. for 6 hours. After cooling, ethyl acetate and water were added and the organic layer was separated, dried (Na$_2$SO$_4$) and filtered. The filtrate was evaporated to dryness and the residue was purified by chromatography on silica, eluting with a mixture of ethyl acetate and cyclohexane (1:3) to give t-butyl 3-[3-(benzenesulphonylmethyl)-6-(furan-3-yl)-2-(methoxycarbonyl)phenoxy]azetidine-1-carboxylate (0.316 g) as a gum.

NMR (CDCl$_3$) δ 7.75 (s, 1H), 7.7 (m, 2H), 7.65 (d, 1H), 7.5 (m, 3H), 7.4 (d, 1H), 7.1 (d, 1H), 6.65 (dd, 1H), 4.55 (s, 2H), 4.45 (t, 1H), 3.9 (d, 4H), 3.85 (s, 3H), 1.4 (s, 9H).

Intermediate 169

Methyl 6-(bicyclo[2.2.2]octane-2-ylsulphonylmethyl)-3-(furan-3-yl)-2-methoxybenzoate

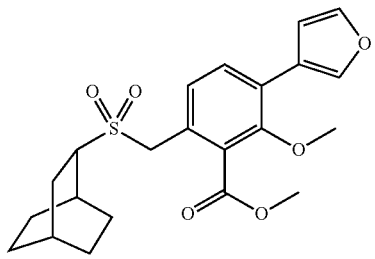 [SMILES: COC(=O)c1c(CS(=O)(=O)C2CC3CCC2CC3)ccc(-c2ccoc2)c1OC]

A mixture of methyl 6-(bicyclo[2.2.2]oct-5-ene-2-ylsulphonylmethyl)-3-(furan-3-yl)-2-methoxybenzoate (Intermediate 170, 0.26 g) and palladium on carbon (10%, 0.01 g) in THF (15 ml) and ethanol (10 ml) was stirred in an atmosphere of hydrogen (balloon) for 1 hour. The mixture was filtered through Celite and the filtrate was evaporated to dryness. The residue was purified by chromatography on silica, eluting with a mixture of ethyl acetate in cyclohexane with a gradient of 10-50% to give methyl 6-(bicyclo[2.2.2]octane-2-ylsulphonylmethyl)-3-(furan-3-yl)-2-methoxybenzoate (0.029 g).

LCMS (Method G) r/t 4.68 (M+H) 419.

Intermediate 170

Methyl 6-(bicyclo[2.2.2]oct-5-ene-2-ylsulphonylmethyl)-3-(furan-3-yl)-2-methoxybenzoate

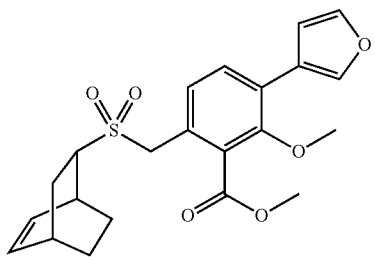 [SMILES: COC(=O)c1c(CS(=O)(=O)C2CC3C=CC2CC3)ccc(-c2ccoc2)c1OC]

Prepared by proceeding in a similar manner to Intermediate 36, starting from methyl 6-(bicyclo[2.2.2]oct-5-ene-2-ylsulphonylmethyl)-3-bromo-2-methoxybenzoate.

NMR (CDCl$_3$) δ 7.95 (dd, 1H), 7.55 (s, 1H), 7.5 (dd, 1H), 7.3 (d, 1H), 6.8 (dd, 1H), 6.35 (t, 1H), 6.25 (t, 1H), 4.25 (s, 2H), 4.0 (s, 3H), 3.7 (s, 3H), 3.25 (m, 1H), 3.1 (m, 1H), 2.7 (m, 1H), 1.9 (ddd, 1H), 1.7 (m, 1H), 1.6 (m, 1H), 1.5 (m, 1H), 1.35 (m, 1H), 1.3 (m, 1H).

Intermediate 171

Methyl 6-(bicyclo[2.2.2]oct-5-ene-2-ylsulphonylmethyl)-3-bromo-2-methoxybenzoate

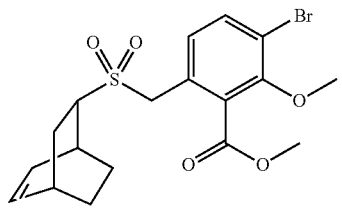

A solution of methyl 3-bromo-2-methoxy-6-(vinylsulphonylmethyl)benzoate (Intermediate 172, 0.5 g), and cyclohexadiene (0.343 g) in toluene (0.5 ml) was sealed in a vial and heated at 125° C. for 3 days. After cooling, the mixture was evaporated to dryness and the residue was purified by chromatography on silica eluting with a mixture of ethyl acetate and cyclohexane with a gradient of 10-40% to give methyl 6-(bicyclo[2.2.2]oct-5-ene-2-ylsulphonylmethyl)-3-bromo-2-methoxybenzoate (0.455 g) as a white solid.

NMR (CDCl$_3$) δ 7.65 (d, 1H), 7.15 (d, 1H), 6.4 (t, 1H), 6.25 (t, 1H), 4.2 (d, 2H), 3.95 (s, 3H), 3.95 (s, 3H), 3.25 (m, 1H), 3.15 (m, 1H), 2.75 (m, 1H), 1.9 (ddd, 1H), 1.65 (m, 1H), 1.6 (m, 1H), 1.5 (m, 1H), 1.4-1.3 (m, 1H), 1.3 (m, 1H).

Intermediate 172

Methyl 3-bromo-2-methoxy-6-(vinylsulphonylmethyl)benzoate

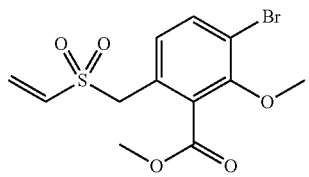 [SMILES: C=CS(=O)(=O)Cc1ccc(Br)c(OC)c1C(=O)OC]

Methyl 3-bromo-6-(2-hydroxyethanesulphonylmethyl)-2-methoxybenzoate (Intermediate 173, 0.68 g) and methanesulphonyl chloride (0.424 g) were added to a solution of triethylamine (0.561 g) in DCM (10 ml) and the resultant mixture was stirred in an ice bath for 1 hour. DCM was added and the solution was washed with water, dried (Na$_2$SO$_4$) and filtered. The filtrate was evaporated to dryness and the residue was purified by chromatography on silica, eluting with a mixture of ethyl acetate and cyclohexane with a gradient of 10-40% to give methyl 3-bromo-2-methoxy-6-(vinylsulphonylmethyl)benzoate (0.521 g) as a colourless gum which crystallized on standing to a white solid.

NMR (CDCl$_3$) δ 7.65 (d, 1H), 7.15 (d, 1H), 6.55 (dd, 1H), 6.3 (d, 1H), 6.1 (d, 1H), 4.35 (s, 2H), 3.95 (s, 3H), 3.9 (s, 3H).

Intermediate 173

Methyl 3-bromo-6-(2-hydroxyethanesulphonylmethyl)-2-methoxybenzoate

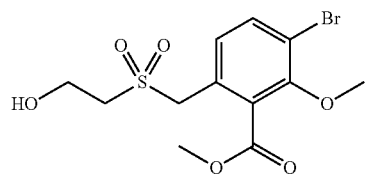 [SMILES: COC(=O)c1c(CS(=O)(=O)CCO)ccc(Br)c1OC]

Prepared by proceeding in a similar manner to Intermediate 138, starting from methyl 3-bromo-6-(2-hydroxyethylthiomethyl)-2-methoxybenzoate (Intermediate 174).

NMR (CDCl$_3$) δ 7.65 (d, 1H), 7.2 (d, 1H), 4.45 (s, 2H), 4.1 (s, 3H), 3.95 (s, 3H), 3.9 (m, 2H), 3.2 (t, 2H).

Intermediate 174

Methyl 3-bromo-6-(2-hydroxyethylthiomethyl)-2-methoxybenzoate

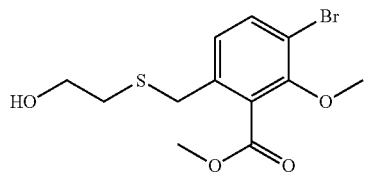 [SMILES: COC(=O)c1c(CSCCO)ccc(Br)c1OC]

Prepared by proceeding in a similar manner to Intermediate 82, starting from methyl 3-bromo-6-bromomethyl-2-methoxybenzoate (Intermediate 89) and 2-mercaptolethanol.

NMR (CDCl$_3$) δ 7.55 (d, 1H), 7.05 (d, 1H), 4.0 (s, 3H), 3.9 (s, 3H), 3.75 (s, 2H), 3.65 (t, 2H), 2.65 (t, 2H).

Intermediate 175

Methyl 6-(bicyclo[2.2.2]octane-2-ylsulphonylmethyl)-2-methoxy-3-(tetrahydrofuran-3-yl)benzoate

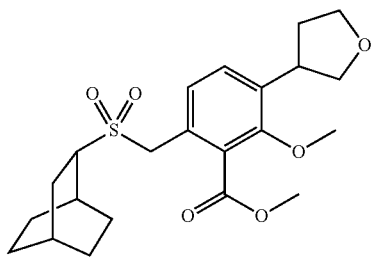 [SMILES: COC(=O)c1c(CS(=O)(=O)C2CC3CCC2CC3)ccc(C2CCOC2)c1OC]

Isolated as a by-product from the preparation of methyl 6-(bicyclo[2.2.2]octane-2-ylsulphonylmethyl)-3-(furan-3-yl)-2-methoxybenzoate (Intermediate 169).

NMR (CDCl$_3$) δ 7.4 (d, 1H), 7.25 (d, 1H), 4.3 (t, 2H), 4.1 (m, 2H), 3.95 (s, 3H), 3.9 (q, 1H), 3.8 (s, 3H), 3.75 (m, 1H), 3.7 (dd, 1H), 3.1 (t, 1H), 2.4 (m, 1H), 2.25 (m, 1H), 2.15 (s, 1H), 1.95 (m, 2H), 1.8 (m, 2H), 1.65 (m, 2H), 1.5 (s, 2H), 1.55-1.4 (m, 3H).

Intermediate 176

Methyl 6-(7-azabicyclo[2.2.1]heptane-7-ylsulphonylmethyl)-3-(furan-3-yl)-2-methoxybenzoate

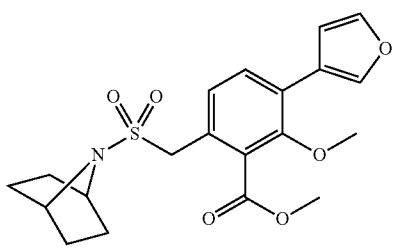 [SMILES: COC(=O)c1c(CS(=O)(=O)N2C3CCC2CC3)ccc(-c2ccoc2)c1OC]

Prepared by proceeding in a similar manner to Intermediate 36, starting from methyl 6-(7-azabicyclo[2.2.1]heptane-7-ylsulphonylmethyl)-3-bromo-2-methoxybenzoate (Intermediate 177) as a white solid.

NMR (CDCl$_3$) δ 7.95 (s, 1H), 7.55 (d, 2H), 7.35 (d, 1H), 6.8 (s, 1H), 4.45 (s, 2H), 4.0 (s, 3H), 3.95 (m, 2H), 3.7 (s, 3H), 1.9 (d, 4H), 1.4 (t, 4H).

Intermediate 177

Methyl 6-(7-azabicyclo[2.2.1]heptane-7-ylsulphonylmethyl)-3-bromo-2-methoxybenzoate

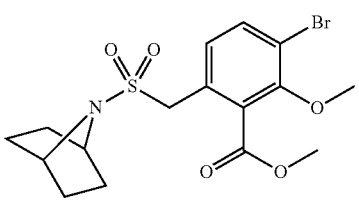 [SMILES: COC(=O)c1c(CS(=O)(=O)N2C3CCC2CC3)ccc(Br)c1OC]

Thionyl chloride (0.476 g) and DMF (1M solution in toluene, 0.3 ml) were added to a solution of (4-bromo-3-methoxy-2-methoxycarbonylphenyl)methanesulphonic acid sodium salt (Intermediate 148, 0.316 g) in toluene (3 ml) and the mixture was heated to 75° C. for 2 hours. The mixture was cooled and filtered and the solid was washed with toluene. The filtrate was evaporated to dryness. A solution of 7-azabicyclo[2.2.1]heptane (isolated from 0.111 g of the hydrochloride salt) in DCM (30 ml) was added to the resultant residue and the mixture was stirred at room temperature for 18 hours. DCM and water were added and the organic layer was separated, washed with water, dried (MgSO$_4$) and filtered. The filtrate was evaporated to dryness and the residue was purified by chromatography on silica, eluting with a mixture of ethyl acetate and cyclohexane with a gradient of 5-10% to give methyl 6-(7-azabicyclo[2.2.1]heptane-7-ylsulphonylmethyl)-3-bromo-2-methoxybenzoate (0.279 g) as a colourless oil.

NMR (CDCl$_3$) δ 7.65 (d, 1H), 7.2 (d, 1H), 4.4 (s, 2H), 4.0 (s, 3H), 4.0 (m, 2H), 3.95 (s, 3H), 1.85 (d, 4H), 1.4 (d, 4H).

Intermediate 178

Methyl 6-(4,4-difluoropiperidine-1-ylsulphonylmethyl)-3-(furan-3-yl)-2-methoxybenzoate

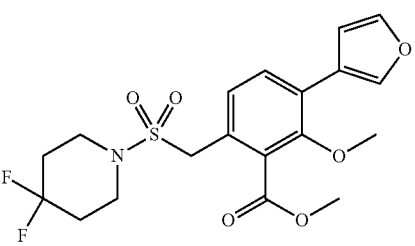 [SMILES: COC(=O)c1c(CS(=O)(=O)N2CCC(F)(F)CC2)ccc(-c2ccoc2)c1OC]

Prepared by proceeding in a similar manner to Intermediate 36, starting from methyl 3-bromo-6-(4,4-difluoropiperidine-1-ylsulphonylmethyl)-2-methoxybenzoate (Intermediate 179), as a white solid.

NMR (CDCl₃) δ 7.95 (t, 1H), 7.55 (d, 1H), 7.5 (t, 1H), 7.3 (d, 1H), 6.8 (dd, 1H), 4.4 (s, 2H), 4.0 (s, 3H), 3.7 (s, 3H), 3.3 (t, 4H), 2.0-1.9 (m, 4H).

Intermediate 179

Methyl 3-bromo-6-(4,4-difluoropiperidine-1-ylsulphonylmethyl)-2-methoxybenzoate

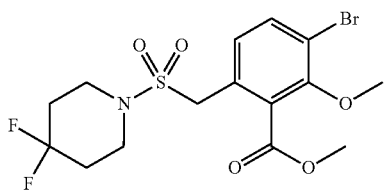 [SMILES: COC(=O)c1c(CS(=O)(=O)N2CCC(F)(F)CC2)ccc(Br)c1OC]

Prepared by proceeding in a similar manner to Intermediate 177, starting from methyl (4-bromo-3-methoxy-2-methoxycarbonylphenyl)-methanesulphonic acid sodium salt (Intermediate 148) and 4,4-difluoropiperidine (isolated from the hydrochloride salt) as a white solid.

NMR (CDCl₃) δ 7.7 (d, 1H), 7.2 (d, 1H), 4.35 (s, 2H), 4.0 (s, 3H), 3.95 (s, 3H), 3.3 (m, 4H), 2.0 (m, 4H).

Intermediate 180

Methyl 6-(bicyclo[2.2.1]heptane-7-ylsulphonylmethyl)-3-(furan-3-yl)-2-methoxybenzoate

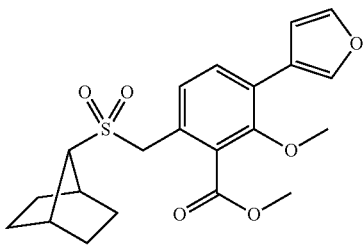 [SMILES: COC(=O)c1c(CS(=O)(=O)C2C3CCC2CC3)ccc(-c2ccoc2)c1OC]

Prepared by proceeding in a similar manner to Intermediate 36, starting from methyl 6-(bicyclo[2.2.2]heptan-7-ylsulphonylmethyl)-3-bromo-2-methoxybenzoate (Intermediate 181) and furan-3-yl boronic acid.

NMR (CDCl₃) δ 7.95 (m, 1H), 7.55 (d, 1H), 7.59 (t, 1H), 7.35 (d, 1H), 6.8 (dd, 1H), 4.35 (s, 2H), 3.95 (s, 3H), 3.65 (s, 3H), 3.0 (s, 1H), 2.5 (m, 2H), 2.15 (m, 2H), 1.6 (m, 2H), 1.5 (s, 1H), 1.25 (m, 3H).

Intermediate 181

Methyl 6-(bicyclo[2.2.1]heptane-7-ylsulphonylmethyl)-3-bromo-2-methoxybenzoate

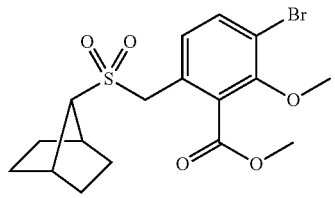 [SMILES: COC(=O)c1c(CS(=O)(=O)C2C3CCC2CC3)ccc(Br)c1OC]

Prepared by proceeding in a similar manner to Intermediate 138, starting from methyl 6-(bicyclo[2.2.1]heptan-7-ylthiomethyl)-3-bromo-2-methoxybenzoate (Intermediate 182).

LCMS (Method G) r/t 4.52 (M+H) 418.

Intermediate 182

Methyl 6-(bicyclo[2.2.1]hept-7-ylthiomethyl)-3-bromo-2-methoxybenzoate

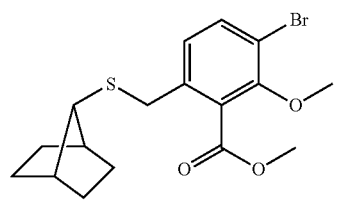 [SMILES: COC(=O)c1c(CSC2C3CCC2CC3)ccc(Br)c1OC]

A mixture of methyl 3-bromo-6-bromomethyl-2-methoxybenzoate (Intermediate 89, 0.338 g), bicyclo[2.2.1]heptane-7-thiol (Intermediate 183, 0.148 g) and potassium carbonate (0.345 g) in THF (5 ml) was stirred and heated at 60° C. for 3 days. After cooling, the mixture was partitioned between ethyl acetate and water and the organic layer was separated, dried (Na₂SO₄) and filtered. The filtrate was evaporated to dryness and the residue was purified by chromatography on silica, eluting with a mixture of ethyl acetate and cyclohexane with a gradient of 0-10% to give methyl 6-(bicyclo[2.2.1]hept-7-ylthiomethyl)-3-bromo-2-methoxybenzoate (0.244 g).

NMR (CDCl₃) δ 7.55 (d, 1H), 7.05 (d, 1H), 3.95 (s, 3H), 3.9 (s, 3H), 3.7 (s, 2H), 2.7 (s, 1H), 2.05 (m, 2H), 1.8 (d, 2H), 1.55 (m, 2H), 1.45 (m, 1H), 1.25 (m, 1H), 1.15 (d, 2H).

Intermediate 183

Bicyclo[2.2.1]heptane-7-thiol

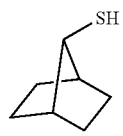

7-Benzylthiobicyclo[2.2.1]heptane (0.301 g) was dissolved in THF (1 ml) and cooled to −78° C. Ammonia gas was passed into the solution, then the reaction was warmed to −30° C., sodium was added in portions over 30 minutes and the mixture was stirred for 2 hours. After warming to room temperature, pentane and water were added. The mixture was acidified with 2M HCl and the organic layer was separated, dried (Na₂SO₄) and filtered. The filtrate was evaporated to dryness to give bicyclo[2.2.1]heptane-7-thiol (0.151 g) as a pale yellow oil.

NMR (CDCl₃) δ 2.95 (d, 1H), 2.05 (m, 2H), 1.9 (m, 2H), 1.6 (m, 2H), 1.4 (d, 1H), 1.3 (m, 2H), 1.25 (m, 1H).

Intermediate 184

Methyl 6-(benzenesulphonylmethyl)-3-(furan-3-yl)-2-methylaminobenzoate

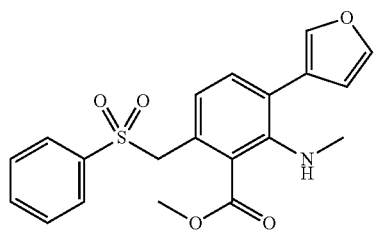 [SMILES: CNc1c(-c2ccoc2)ccc(CS(=O)(=O)c2ccccc2)c1C(=O)OC]

Prepared by proceeding in a similar manner to Intermediate 122, starting from methyl 6-(benzenesulphonylmethyl)-3-(furan-3-yl)-2-(trifluoromethanesulphonyloxy)-benzoate (Intermediate 123) and 2M methylamine in THF.

NMR (CDCl$_3$) δ 7.7 (m, 1H), 7.7 (m, 2H), 7.6 (m, 1H), 7.5 (t, 1H), 7.45 (t, 2H), 7.15 (d, 1H), 6.65 (m, 1H), 6.6 (d, 1H), 4.65 (s, 2H), 3.9 (s, 3H), 2.65 (s, 3H).

Intermediate 185

Methyl 6-(8-azabicyclo[3.2.1]octane-8-ylsulphonylmethyl)-3-(furan-3-yl)-2-methoxybenzoate

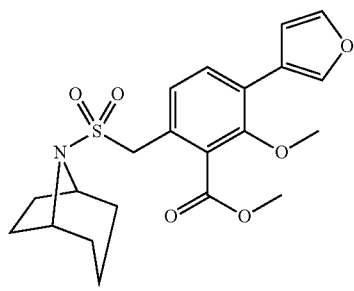 [SMILES: COC(=O)c1c(CS(=O)(=O)N2C3CCCC2CC3)ccc(-c2ccoc2)c1OC]

Prepared by proceeding in a similar manner to Intermediate 36, starting from methyl 6-(8-azabicyclo[3.2.1]octane-8-ylsulphonylmethyl)-3-bromo-2-methoxybenzoate (Intermediate 186) as a white solid.

NMR (CDCl$_3$) δ 7.95 (s, 1H), 7.5 (m, 2H), 7.3 (d, 1H), 6.8 (d, 1H), 4.4 (s, 2H), 4.05 (m, 2H), 4.0 (s, 3H), 3.7 (s, 3H), 1.95 (m, 2H), 1.65 (d, 4H), 1.55 (m, 2H), 1.45 (m, 2H).

Intermediate 186

Methyl 6-(8-azabicyclo[3.2.1]octane-8-ylsulphonylmethyl)-3-bromo-2-methoxybenzoate

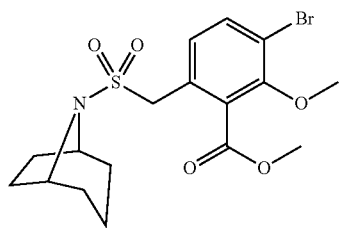 [SMILES: COC(=O)c1c(CS(=O)(=O)N2C3CCCC2CC3)ccc(Br)c1OC]

Prepared by proceeding in a similar manner to Intermediate 177, starting from methyl (4-bromo-3-methoxy-2-methoxycarbonylphenyl)-methanesulphonic acid sodium salt (Intermediate 148) and 8-azabicyclo[3.2.1]octane, as a white solid.

NMR (CDCl$_3$) δ 7.65 (d, 1H), 7.15 (d, 1H), 4.35 (s, 2H), 4.05 (m, 2H), 3.95 (s, 3H), 3.9 (s, 3H), 1.95 (m, 2H), 1.7 (m, 4H), 1.55 (m, 2H), 1.45 (m, 2H).

Intermediate 187

Methyl 2-(benzenesulphonylmethyl)-8-methoxynaphthalene-1-carboxylate

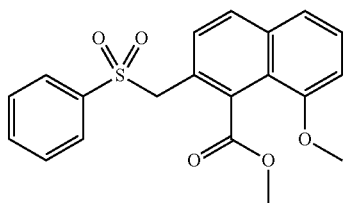 [SMILES: COC(=O)c1c(CS(=O)(=O)c2ccccc2)ccc2cccc(OC)c12]

Prepared by proceeding in a similar manner to Intermediate 4, starting from methyl 2-(benzenesulphonylmethyl)-5-bromo-8-methoxynaphthalene-1-carboxylate (Intermediate 188), as a white solid.

NMR (CDCl$_3$) δ 7.8 (d, 1H), 7.65 (m, 2H), 7.6 (m, 2H), 7.45 (m, 3H), 7.4 (d, 1H,), 6.85 (t, 1H), 4.65 (d, 1H), 4.45 (s, 1H), 3.85 (s, 3H), 3.75 (s, 3H).

Intermediate 188

Methyl 2-(benzenesulphonylmethyl)-5-bromo-8-methoxynaphthalene-1-carboxylate

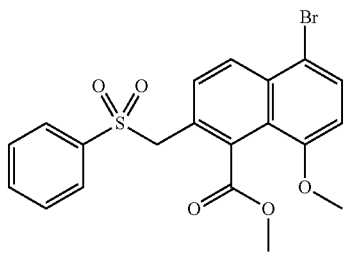 [SMILES: COC(=O)c1c(CS(=O)(=O)c2ccccc2)ccc2c(Br)ccc(OC)c12]

A mixture of methyl 5-bromo-2-bromomethyl-8-methoxynapthalene-1-carboxylate (Intermediate 189, 0.716 g), benzenesulphinic acid sodium salt (0.68 g) and sodium hydrogen carbonate (0.35 g) in DMA (15 ml) and water (3 ml) was heated at 50° C. for 2 hours. After cooling, water was added and the mixture was extracted with diethyl ether. The organic layer was washed with water, dried (MgSO$_4$) and filtered. The filtrate was evaporated to dryness and the residue was purified by chromatography on silica eluting with a mixture of ethyl acetate and cyclohexane with a gradient of 0-100% to give methyl 2-(benzenesulphonylmethyl)-5-bromo-8-methoxynaphthalene-1-carboxylate (0.236 g) as an oil which crystallised on standing.

LCMS (Method H) r/t 3.83 (M+Na) 471/473

Intermediate 189

Methyl 5-bromo-2-bromomethyl-8-methoxynaphthalene-1-carboxylate

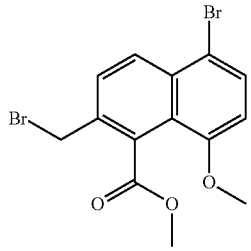 [SMILES: COC(=O)c1c(CBr)ccc2c(Br)ccc(OC)c12]

Prepared by proceeding in a similar manner to Intermediate 89, starting from methyl 8-methoxy-2-methylnaphthalene-1-carboxylate (Intermediate 190).

NMR (CDCl$_3$) δ 8.25 (d, 1H), 7.7 (d, 1H), 6.8 (s, 1H), 6.75 (d, 1H), 4.65 (d, 1H), 4.5 (d, 1H), 4.0 (s, 3H), 3.95 (s, 3H).

Intermediate 190

Methyl 8-methoxy-2-methylnaphthalene-1-carboxylate

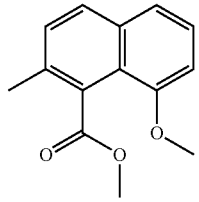

A mixture of methyl 8-bromo-2-methylnaphthalene-1-carboxylate (Intermediate 191, 1.0 g), sodium methoxide (25% wt/solution in methanol, 5 g), copper iodide (0.37 g), and pyridine (13 ml) in methanol (13 ml) was stirred and heated at reflux for 3 days. After cooling, the mixture was diluted with water, acidified with concentrated hydrochloric acid and extracted with ethyl acetate. The organic layer was separated, washed with 1M HCl and brine, dried (MgSO$_4$) and filtered. The filtrate was evaporated to dryness and the residue was purified by chromatography on silica eluting with a mixture of ethyl acetate and cyclohexane with a gradient of 0-25% to give methyl 8-methoxy-2-methylnaphthalene-1-carboxylate (0.33 g) as a lilac oil.

NMR (CDCl$_3$) δ 7.75 (d, 1H), 7.4 (m, 1H), 7.35 (d, 1H), 7.3 (m, 1H), 6.85 (d, 1H), 4.0 (s, 3H), 3.95 (s, 3H), 2.45 (s, 3H).

Intermediate 191

Methyl 8-bromo-2-methylnaphthalene-1-carboxylate

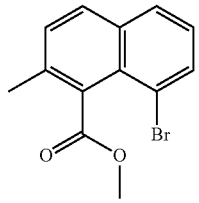 [SMILES: COC(=O)c1c(C)ccc2cccc(Br)c12]

Methyl 2-methylnaphthalene-1-carboxylate (5.6 g) was dissolved in acetic acid (12 ml) and trifluoroacetic acid (12 ml) and cooled in an ice bath. 1,3-Dibromo-5,5-dimethylhydantoin (4.8 g) was added in one portion then concentrated sulphuric acid was added dropwise. The mixture was then stirred at 0° C. for 30 minutes. Sodium acetate (6.12 g) was added and the mixture was partitioned between DCM and water. The organic layer was separated, dried (Na$_2$SO$_4$) and filtered. The filtrate was evaporated to dryness and the residue was purified by chromatography on silica, eluting with a mixture of DCM and pentane with a gradient of 20-70% to give methyl 8-bromo-2-methylnaphthalene-1-carboxylate (3.27 g) as a colourless oil.

NMR (CDCl$_3$) d 7.85 (dd, 1H), 7.8 (m, 2H), 7.35 (d, 1H), 7.3-7.2 (m, 1H), 4.0 (s, 3H), 2.5 (s, 3H).

Intermediate 192

Methyl 6-[2-(3-diethylaminopropylamino)-benzenesulphonyl-methyl]-3-(furan-3-yl)-2-methoxybenzoate

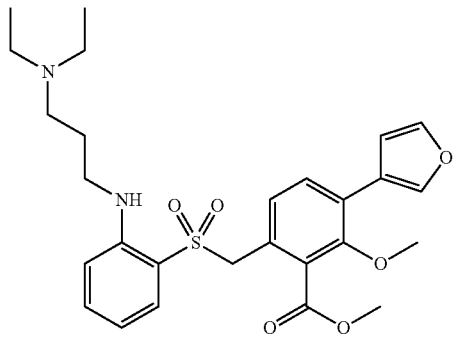 [SMILES: CCN(CC)CCCNc1ccccc1S(=O)(=O)Cc1ccc(-c2ccoc2)c(OC)c1C(=O)OC]

A solution of methyl 6-(2-fluorobenzenesulphonylmethyl)-3-(furan-3-yl)-2-methoxybenzoate (Intermediate 96, 0.07 g) in acetonitrile (2.2 ml) was added to a solution of N,N-diethyl-1,3-propanediamine (0.225 g) in triethylamine (0.07 g) in a microwave vial. The mixture was heated in the microwave at 130° C. for 2 hours. After cooling, DCM and hydrochloric acid (1M) were added and the pH was adjusted to 8 by addition of saturated aqueous sodium hydrogen carbonate. The mixture was extracted with DCM, washed with brine, dried (MgSO$_4$) and filtered. The filtrate was evaporated to dryness and the residue was purified by chromatography on silica, eluting with a mixture of DCM, methanol, acetic acid and water (350:20:3:2) to give methyl 6-[2-(3-diethylaminopropylamino)benzenesulphonylmethyl]-3-(furan-3-yl)-2-methoxybenzoate (0.083 g) as a colourless oil.

(NMR (CDCl$_3$) δ 7.95 (d, 1H), 7.55 (m, 1H), 7.5 (t, 1H), 7.45 (m, 1H), 6.95 (d, 2H), 6.75 (m, 1H), 6.7 (m, 1H), 6.1 (s, 1H), 4.55 (s, 2H), 3.9 (s, 3H), 3.65 (s, 3H), 3.2 (q, 2H), 3.05 (m, 4H), 3.0 (m, 2H), 2.15 (s, 2H), 1.35 (t, 6H).

Intermediate 193

(Z)-tert-Butyl 2-(cyanomethoxy)-6-((2-(3-(diethylamino)prop-1-enyl)-4-fluorobenzenesulfonyl)methyl)-3-(furan-3-yl)benzoate

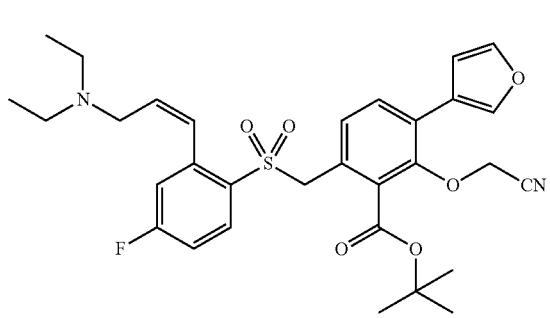 [SMILES: CCN(CC)C/C=C\c1cc(F)ccc1S(=O)(=O)Cc1ccc(-c2ccoc2)c(OCC#N)c1C(=O)OC(C)(C)C]

Prepared by proceeding in a similar manner to Intermediate 10, starting from (Z)-tert-butyl 6-((2-(3-(diethylamino)prop-1-enyl)-4-fluorobenzenesulfonyl)methyl)-3-(furan-3-yl)-2-hydroxybenzoate (Intermediate 194) and bromoacetonitrile.

NMR (CDCl$_3$) δ 7.95 (dd, 1H), 7.9 (s, 1H), 7.55 (t, 1H), 7.4 (d, 1H), 7.15 (m, 3H), 7.05 (m, 1H), 6.75 (d, 1H), 6.2 (m, 1H), 4.6 (s, 2H), 4.55 (s, 2H), 3.4-3.25 (br, 2H), 2.75-2.55 (br, 4H), 1.7 (s, 9H), 1.05 (m, 6H).

Intermediate 194

(Z)-tert-Butyl 6-((2-(3-(diethylamino)prop-1-enyl)-4-fluorobenzenesulfonyl)methyl)-3-(furan-3-yl)-2-hydroxybenzoate

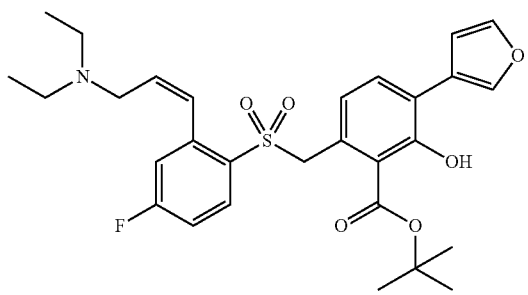 [SMILES: CCN(CC)C/C=C\c1cc(F)ccc1S(=O)(=O)Cc1ccc(-c2ccoc2)c(O)c1C(=O)OC(C)(C)C]

Prepared by proceeding in a similar manner to Intermediate 120, starting from (Z)-6-((2-(3-(diethylamino)prop-1-enyl)-4-fluorobenzenesulfonyl)methyl)-3-(furan-3-yl)-2-hydroxybenzoic acid (Intermediate 195, 0.093 g), as a colourless gum.

NMR (CDCl$_3$) δ 12.3 (s, 1H), 8.15 (dd, 1H), 7.6 (dd, 1H), 7.45 (t, 1H), 7.3 (,d 1H), 7.2 (s, 2H), 6.9 (dt, 1H), 6.7 (dd, 1H), 6.15 (dt, 1H), 6.05 (d, 1H), 4.95 (s, 2H), 3.25 (dd, 2H), 2.55 (q, 4H), 1.7 (s, 9H), 1.0 (t, 6H).

Intermediate 195

(Z)-6-((2-(3-(Diethylamino)prop-1-enyl)-4-fluorobenzenesulfonyl)methyl)-3-(furan-3-yl)-2-hydroxybenzoic acid

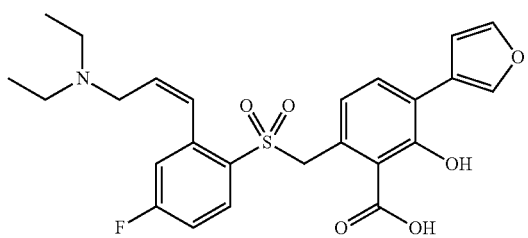 [SMILES: CCN(CC)C/C=C\c1cc(F)ccc1S(=O)(=O)Cc1ccc(-c2ccoc2)c(O)c1C(=O)O]

Prepared by proceeding in a similar manner to Intermediate 121, starting from (Z)-methyl 6-((2-(3-(diethylamino)prop-1-enyl)-4-fluorobenzenesulfonyl)methyl)-3-(furan-3-yl)-2-hydroxybenzoate (Intermediate 196).

LCMS (Method H) r/t 2.97 (M+H) 488.

Intermediate 196

(Z)-Methyl 6-((2-(3-(diethylamino)prop-1-enyl)-4-fluorobenzenesulfonyl)methyl)-3-(furan-3-yl)-2-hydroxybenzoate

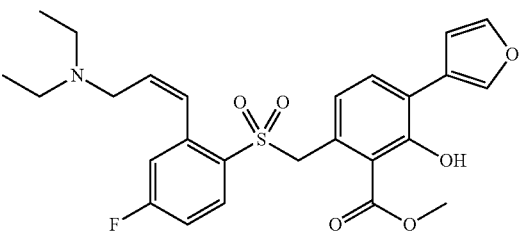 [SMILES: CCN(CC)C/C=C\c1cc(F)ccc1S(=O)(=O)Cc1ccc(-c2ccoc2)c(O)c1C(=O)OC]

Prepared by proceeding in a similar manner to Intermediate 160, starting from (Z)-methyl 3-bromo-6-((2-(3-(diethylamino)prop-1-enyl)-4-fluorobenzenesulfonyl)methyl)-2-hydroxybenzoate (Intermediate 197) and furan-3-boronic acid.

NMR (CDCl$_3$) δ 8.2 (dd, 1H), 7.7 (dd, 1H), 7.5 (t, 1H), 7.4 (d, 1H), 7.25 (dd, 1H), 7.15 (d, 1H), 7.0 (dt, 1H), 6.75 (dd, 1H), 6.35 (d, 1H), 6.15 (dt, 1H), 4.9 (s, 2H), 4.05 (s, 3H), 3.3 (d, 2H), 2.6 (q, 4H), 1.05 (t, 6H).

Intermediate 197

(Z)-Methyl 3-bromo-6-((2-(3-(diethylamino)prop-1-enyl)-4-fluorobenzenesulfonyl)methyl)-2-hydroxybenzoate

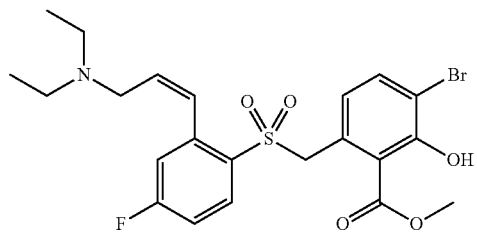 [SMILES: CCN(CC)C/C=C\c1cc(F)ccc1S(=O)(=O)Cc1ccc(Br)c(O)c1C(=O)OC]

Aluminium chloride (0.303 g) was added to a stirred solution of (Z)-methyl 3-bromo-6-((2-(3-(diethylamino)prop-1-enyl)-4-fluorobenzenesulfonyl)methyl)-2-methoxybenzoate (Intermediate 161, 0.528 g) and N,N-dimethylaniline (0.915 g) in DCM (20 ml). The resultant mixture was stirred for 3 hours then a mixture of ice, water and DCM were added. The organic layer was separated, dried (Na$_2$SO$_4$) and filtered. The filtrate was evaporated to dryness and the residue was purified by chromatography on silica, eluting with a mixture of methanol and DCM with a gradient of 0-6% to give (Z)-methyl 3-bromo-6-((2-(3-(diethylamino)prop-1-enyl)-4-fluorobenzenesulfonyl)methyl)-2-hydroxybenzoate (0.514 g) as a pale purple oil.

NMR (CDCl$_3$) δ 7.75 (dd, 1H), 7.5 (d, 1H), 7.15 (br, s, 1H), 7.05 (m, 2H), 6.3 (d, 1H), 6.15 (br, s, 1H), 4.85 (s, 2H), 4.05 (s, 3H), 3.35 (m, 2H), 2.7 (br, s, 4H), 1.1 (s, 6H).

Intermediate 198

(Z)-Methyl 3-(furan-3-yl)-2-methoxy-6-((2-(3-(piperidin-1-yl)prop-1-enyl)benzenesulfonyl)methyl)benzoate

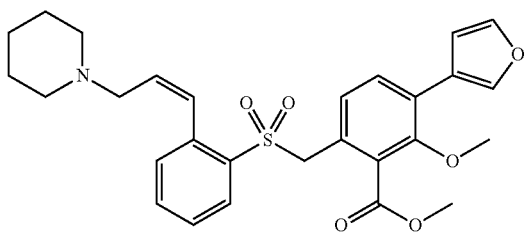 [SMILES: COC(=O)c1c(CS(=O)(=O)c2ccccc2/C=C\CN2CCCCC2)ccc(-c2ccoc2)c1OC]

Prepared by proceeding in a similar manner to Intermediate 160, starting from (Z)-methyl 3-bromo-2-methoxy-6-((2-(3-(piperidin-1-yl)prop-1-enyl)benzenesulfonyl)methyl)benzoate (Intermediate 199).

NMR (CDCl$_3$) δ 7.9 (s, 1H), 7.85 (m, 1H), 7.6 (t, 1H), 7.5 (t, 1H), 7.4 (t, 3H), 7.15 (d, 1H), 6.9 (d, 1H), 6.75 (m, 1H), 6.15 (m, 1H), 4.55 (s, 2H), 3.95 (s, 3H), 3.65 (s, 3H), 3.2 (m, 2H), 2.45 (m, 4H), 1.6 (m, 4H), 1.4 (m, 2H).

Intermediate 199

(Z)-Methyl 3-bromo-2-methoxy-6-((2-(3-(piperidin-1-yl)prop-1-enyl)benzenesulfonyl)methyl)benzoate

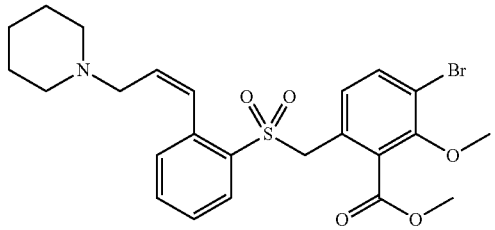 [SMILES: COC(=O)c1c(CS(=O)(=O)c2ccccc2/C=C\CN2CCCCC2)ccc(Br)c1OC]

Carbon tetrabromide (0.291 g) was added to a solution of methyl-(Z) 3-bromo-6-((2-(3-hydroxyprop-1-enyl)benzenesulfonyl)methyl)-2-methoxybenzoate (Intermediate 60, 0.322 g), and triphenyl phosphine (0.229 g) in DCM (12 ml) and the resultant solution was stirred at room temperature for 4 hours. The mixture was evaporated to dryness and piperidine (0.72 ml) and THF (9 ml) were added. The mixture was stirred for 3 hours then was evaporated to dryness. The residue was purified by chromatography on silica, eluting with a mixture of methanol and DCM with a gradient of 0-3% to give (Z)-methyl 3-bromo-2-methoxy-6-((2-(3-(piperidin-1-yl)prop-1-enyl)benzenesulfonyl)methyl)benzoate (0.211 g) as a cloudy oil.

NMR (CDCl$_3$) δ 7.9 (dd, 1H), 7.65 (t, 1H), 7.55-7.3 (m, 3H), 7.15 (d, 1H), 6.8 (d, 1H), 6.2 (m, 1H), 4.55 (s, 2H), 4.0 (s, 3H), 3.95 (s, 2H), 3.9 (s, 3H), 3.2 (d, 2H), 2.5 (s, 4H), 1.65 (m, 2H), 1.45 (m, 2H).

Intermediate 200

Ethyl 6-(benzenesulphonylmethyl)-3-(furan-3-yl)-2,4-dimethoxybenzoate

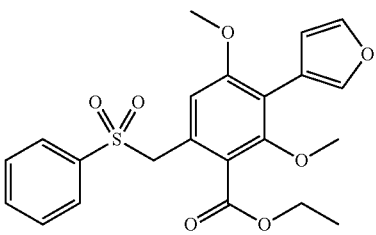 [SMILES: CCOC(=O)c1c(CS(=O)(=O)c2ccccc2)cc(OC)c(-c2ccoc2)c1OC]

Prepared by proceeding in a similar manner to Intermediate 160, starting from ethyl 6-(benzenesulphonylmethyl)-3-iodo-2,4-dimethoxybenzoate (Intermediate 201), using THF instead of dioxane.

NMR (CDCl$_3$) δ 7.85 (dd, 1H), 7.7 (m, 2H), 7.65 (m, 1H), 7.5 (m, 1H), 7.5 (m, 2H), 6.9 (dd, 1H), 6.65 (s, 1H), 4.6 (s, 2H), 4.3 (m, 2H), 3.8 (s, 3H), 3.5 (s, 3H), 1.35 (m, 3H).

Intermediate 201

Ethyl 6-(benzenesulphonylmethyl)-3-iodo-2,4-dimethoxybenzoate

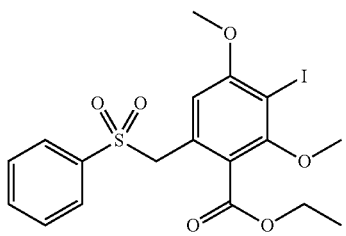 [SMILES: CCOC(=O)c1c(CS(=O)(=O)c2ccccc2)cc(OC)c(I)c1OC]

Prepared by proceeding in a similar manner to Intermediate 85, starting from ethyl 6-bromomethyl-3-iodo-2,4-dimethoxybenzoate (Intermediate 202).

NMR (CDCl$_3$) δ 7.7 (m, 2H), 7.65 (m, 1H), 7.5 (m, 2H), 6.6 (s, 1H), 4.6 (d, 2H), 4.25 (q, 2H), 3.85 (d, 3H), 3.8 (s, 3H), 1.35 (t, 3H).

Intermediate 202

Ethyl 6-bromomethyl-3-iodo-2,4-dimethoxybenzoate

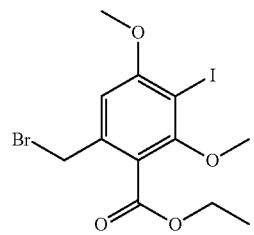 [SMILES: CCOC(=O)c1c(CBr)cc(OC)c(I)c1OC]

Prepared by proceeding in a similar manner to Intermediate 87, starting from ethyl 3-iodo-2,4-dimethoxy-6-methylbenzoate (Intermediate 203).

NMR (CDCl$_3$) δ 6.5 (s, 1H), 4.55 (d, 2H), 4.45 (m, 2H), 3.9 (s, 3H), 3.9 (s, 3H), 1.35 (d, 3H).

Intermediate 203

Ethyl 3-iodo-2,4-dimethoxy-6-methylbenzoate

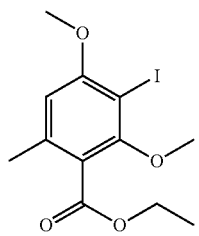 [SMILES: CCOC(=O)c1c(C)cc(OC)c(I)c1OC]

A mixture of ethyl 2,4-dihydroxy-3-iodo-6-methylbenzoate (Intermediate 204, 0.144 g), dimethylsulphate (0.085 ml) and potassium carbonate (0.185 g) in acetone (10 ml) was heated at reflux for 2.5 hours. After cooling, the mixture was filtered and the filtrate was evaporated to dryness. The residue was partitioned between DCM and water and the organic layer was filtered through a phase separator. The filtrate was evaporated to dryness and the residue was purified by chromatography on silica, eluting with a mixture of ethyl acetate and cyclohexane with a gradient of 0-20% to give ethyl 3-iodo-2,4-dimethoxy-6-methylbenzoate (0.158 g).

NMR (CDCl$_3$) δ 6.45 (s, 1H), 4.4 (q, 2H), 3.9 (s, 3H), 3.85 (s, 3H), 2.35 (d, 3H), 1.4 (t, 3H).

Intermediate 204

Ethyl 2,4-dihydroxy-3-iodo-6-methylbenzoate

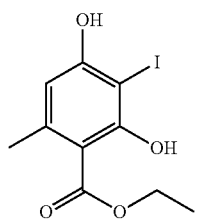

A mixture of ethyl 2,4-dihydroxy-6-methylbenzoate (0.25 g), benzyltrimethylammonium chloride (0.48 g) and potassium hydrogen carbonate (0.825 g) in DCM was stirred at room temperature, for 18 hours. Further DCM was added and the solution was washed with saturated aqueous sodium hydrogen carbonate, dried (MgSO$_4$) and filtered. The filtrate was evaporated to dryness and the residue was purified by chromatography on silica, eluting with a mixture of ethyl acetate and cyclohexane with a gradient of 5-20% to give ethyl 2,4-dihydroxy-3-iodo-6-methylbenzoate (0.16 g) as a white solid.

NMR (DMSO-d$_6$) δ 12.25 (br, s, 1H), 11.1 (br, s, 1H), 6.35 (d, 1H), 4.35 (q, 2H), 2.4 (s, 3H), 1.35 (t, 3H).

Intermediate 205

Methyl 6-[2-(2-diethylaminomethylazetidin-1-yl)-benzenesulphonylmethyl]-3-(furan-3-yl)-2-methoxybenzoate

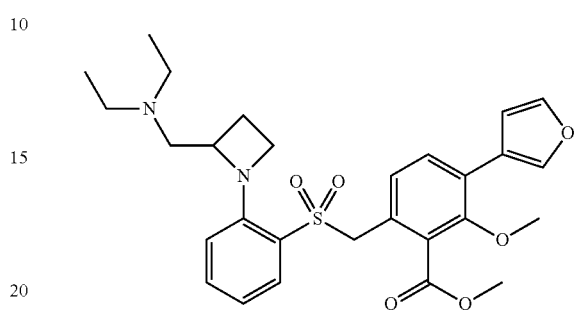

Triethylamine (0.762 ml) was added to a solution of methyl 6-(2-fluorobenzenesulphonylmethyl)-3-(furan-3-yl)-2-methoxybenzoate (Intermediate 96, 0.0657 g) and 2-Diethylaminomethylazetidine dihydrochloride (Intermediate 206, 0.314 g) in acetonitrile (10 ml) and the mixture was sealed in a microwave vial and heated in the microwave for 3 hours at 140° C. The mixture was cooled to room temperature and evaporated to dryness. DCM and water were added to the residue and the pH was adjusted to 6 by addition of 1M HCl. The organic layer was separated, washed with water, dried (Na$_2$SO$_4$) and filtered. The filtrate was evaporated to dryness and the residue was purified by chromatography on silica, eluting with a mixture of DCM: methanol: acetic acid:water (350:20:3:2) to give methyl 6-[2-(2-diethylaminomethylazetidin-1-yl)benzenesulphonylmethyl]-3-(furan-3-yl)-2-methoxybenzoate (0.051 g) as a brown gum.

NMR (CDCl$_3$) δ 7.9 (m, 2H), 7.55 (m, 1H), 7.5 (t, 2H), 7.35 (d, 1H), 7.2 (d, 1H), 6.9 (d, 1H), 6.75 (dd, 1H), 4.9 (q, 2H), 3.95 (s, 3H), 3.65 (s, 3H), 3.55 (m, 1H), 3.5 (m, 2H), 3.35 (m, 2H), 2.85 (m, 4H), 2.05 (s, 2H), 1.15 (m, 6H).

Intermediate 206

2-Diethylaminomethylazetidine dihydrochloride

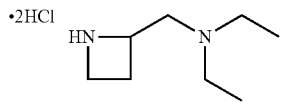

Prepared by proceeding in a similar manner to Example 38, starting from t-butyl 2-diethylaminomethyl-azetidine-1-carboxylate (Intermediate 207).

NMR (DMSO-d$_6$) δ 4.9 (s, 1H), 3.9 (m, 2H), 3.75 (m, 1H), 3.45 (m, 1H), 3.15 (m, 4H), 2.5 (m, 1H), 2.35 (t, 1H), 1.25 (dt, 6H).

Intermediate 207 t-Butyl 2-diethylaminomethylazetidine-1-carboxylate

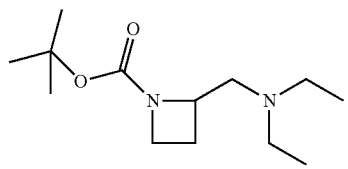 [SMILES: CCN(CC)CC1CCN1C(=O)OC(C)(C)C]

A solution of t-butyl 2-diethylcarbamoylazetidine-1-carboxylate (0.614 g) in THF (15 ml) was cooled in an ice/water bath and borane/THF complex (1M in THF, 7.68 ml) was added dropwise over 15 minutes. The mixture was then warmed to room temperature and stirred for a further 18 hours. The mixture was evaporated to dryness and ethanol and water (9:1, 20 ml) was added. The reaction mixture was then heated to reflux for 3 hours. After cooling, it was evaporated to dryness and the residue was purified by chromatography on silica, eluting with a mixture of DCM:methanol: acetic acid:water with a gradient of 350:20:3:2 to 120:15:3:2 to give t-butyl 2-diethylaminomethylazetidine-1-carboxylate (0.47 g) as a yellow oil.

NMR (CDCl$_3$) δ 4.4 (s, 1H), 3.8 (m, 2H), 3.1 (s, 1H), 2.8 (m, 1H), 2.8 (s, 4H), 2.35 (m, 1H), 2.1 (d, 1H), 1.45 (s, 9H), 1.15 (t, 6H).

Intermediate 208 t-Butyl 2-diethylcarbamoylazetidine-1-carboxylate

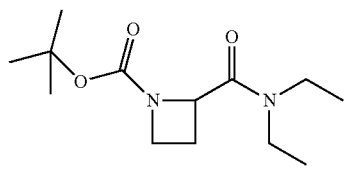 [SMILES: CCN(CC)C(=O)C1CCN1C(=O)OC(C)(C)C]

A solution of diethylamine (0.453 g), azetidine-1,2-dicarboxylic acid-1-t-butyl ester (Intermediate 209, 0.891 g), HATU (2.53 g) and DIPEA (1.72 g) in acetonitrile (20 ml) was stirred at room temperature under argon for 4 hours. The mixture was evaporated to dryness and ethyl acetate was added to the residue. The solution was washed with 1M NaOH, brine and water then dried (Na$_2$SO$_4$) and filtered. The filtrate was evaporated to dryness and the residue was purified by chromatography on silica, eluting with a mixture of methanol and DCM with a gradient of 0-4% to give t-butyl 2-diethylcarbamoylazetidine-1-carboxylate (0.733 g) as light brown oil.

NMR (CDCl$_3$) δ 4.9 (dd, 1H), 4.1 (m, 1H), 3.85 (dt, 1H), 3.4 (m, 4H), 3.2 (dt, 1H), 2.4 (m, 1H), 1.45 (s, 9H), 1.2 (dt, 6H).

Intermediate 209

Azetidine-1,2-dicarboxylic acid-1-t-butyl ester

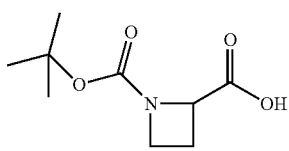

Azetidine-1,2-dicarboxylic acid 1-t-butyl ester 2-methyl ester (1.0 g) was added to a solution of lithium hydroxide monohydrate (0.586 g) in water (6 ml) and dioxane (12 ml) and the resultant mixture was stirred at room temperature for 2.5 hours. The mixture was evaporated to dryness and ice cold 1M HCl was added to the cooled residue. DCM was added and the organic layer was separated and washed with water, brine, dried (Na$_2$SO$_4$) and filtered. The filtrate was evaporated to dryness to give azetidine-1,2-dicarboxylic acid-1-t-butyl ester (0.925 g) as a colourless oil.

NMR (CDCl$_3$) δ 4.8 (s, 1H), 3.9 (q, 1H), 3.85 (s, 1H), 2.55 (s, 1H), 2.4 (s, 1H), 1.45 (s, 9H).

Intermediate 210

5-(Benzenesulphonylmethyl)-8-(furan-3-yl)-1,2-dihydro-benzo[d][1,3]oxazin-4-one

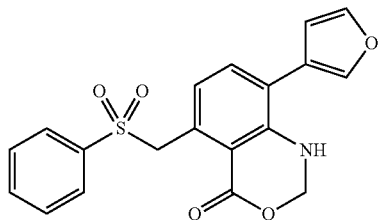 [SMILES: O=C1OCNc2c(-c3ccoc3)ccc(CS(=O)(=O)c3ccccc3)c21]

Formaldehyde (0.138 ml) was added dropwise to a solution of 2-amino-6-(benzenesulphonylmethyl)-3-(furan-3-yl)benzoic acid (Intermediate 211, 0.116 g) in methanol (4 ml) at 60° C. and the resultant mixture was stirred at that temperature for 0.5 hours. After cooling, the mixture was filtered through a phase separator and the filtrate was evaporated to dryness. The residue was triturated with diethyl ether and the solid was collected by filtration to give 5-(benzenesulphonylmethyl)-8-(furan-3-yl)-1,2-dihydro-benzo[d][1,3]oxazin-4-one (0.118 g) as a white solid.

NMR (CDCl$_3$) δ 7.85 (dd, 2H), 7.7 (t, 1H), 7.65 (m, 1H), 7.55 (t, 1H), 7.5 (t, 2H), 7.45 (d, 1H), 7.1 (d, 1H), 6.6 (dd, 1H), 5.25 (s, 2H), 4.95 (s, 2H).

Intermediate 211

2-Amino-6-(benzenesulphonylmethyl)-3-(furan-3-yl) benzoic acid

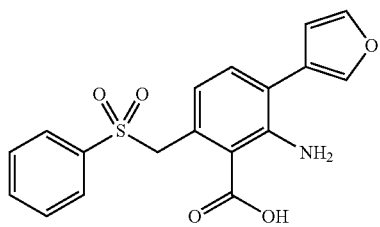 [SMILES: Nc1c(-c2ccoc2)ccc(CS(=O)(=O)c2ccccc2)c1C(=O)O]

Prepared as a yellow foam by proceeding in a similar manner to Intermediate 121, starting from methyl 2-amino-6-(benzenesulphonylmethyl)-3-(furan-3-yl)benzoate (Intermediate 212).

NMR (CDCl$_3$) δ 7.75 (d, 2H), 7.65 (s, 1H), 7.55 (s, 1H), 7.5 (t, 2H), 7.25 (s, 1H), 7.15 (d, 1H), 6.6 (s, 1H), 6.5 (d, 1H), 4.9 (s, 2H).

Intermediate 212

Methyl 2-amino-6-(benzenesulphonylmethyl)-3-(furan-3-yl)benzoate

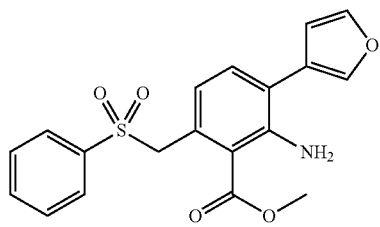 [SMILES: COC(=O)c1c(CS(=O)(=O)c2ccccc2)ccc(-c2ccoc2)c1N]

Prepared by proceeding in a similar manner to Intermediate 131, starting from methyl 6-(benzenesulphonylmethyl)-2-benzylamino-3-(furan-3-yl)benzoate (Intermediate 213)

NMR (CDCl$_3$) δ 7.7 (dd, 2H), 7.6 (m, 2H), 7.55 (t, 1H), 7.5-7.45 (m, 2H), 7.05 (d, 1H), 6.55 (dd, 1H), 6.35 (d, 1H), 4.8 (s, 2H), 3.9 (s, 3H).

Intermediate 213

Methyl 6-(benzenesulphonylmethyl)-2-benzylamino-3-(furan-3-yl)benzoate

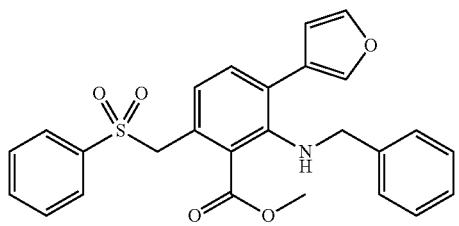 [SMILES: COC(=O)c1c(CS(=O)(=O)c2ccccc2)ccc(-c2ccoc2)c1NCc1ccccc1]

Prepared as a yellow gum by proceeding in a similar manner to Intermediate 122, starting from methyl 6-(benzenesulphonylmethyl)-3-(furan-3-yl)-2-(trifluoromethanesulphonyloxy)benzoate (Intermediate 123) and benzylamine NMR (CDCl$_3$) δ 7.75 (dd, 1H), 7.7 (d, 1H), 7.65 (d, 1H), 7.6 (m, 2H), 7.5 (t, 1H), 7.45 (m, 2H), 7.25 (m, 2H), 7.2 (d, 1H), 7.05 (dd, 2H), 6.7 (dd, 1H), 6.65 (d, 1H), 4.65 (s, 2H), 3.95 (s, 2H), 3.75 (s, 3H).

Intermediate 214

6-(Furan-3-yl)-5-methoxy-2-oxo-2-phenyl-1H-2λ*6*-benzo[d][1,2]thiazin-4-one

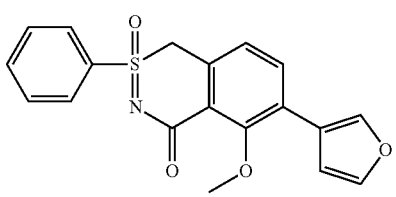 [SMILES: COc1c(-c2ccoc2)ccc2c1C(=O)N=S(=O)(c1ccccc1)C2]

Potassium carbonate (1.38 g) was added to a stirred solution of methyl 3-(furan-3-yl)-2-methoxy-6-{[S-phenyl-N-(trifluoroacetyl)sulphonimidoyl]methyl}benzoate (Intermediate 215) in methanol (20 ml) and the resultant mixture was stirred at room temperature for 1 hour. The mixture was evaporated to dryness and ethyl acetate and water were added to the residue. The organic layer was separated, dried (Na$_2$SO$_4$) and filtered. The filtrate was evaporated to dryness and the residue was purified by chromatography on silica, eluting with a mixture of ethyl acetate and cyclohexane with a gradient of 20-70%. The isolated product was triturated with diethyl ether and the solid was collected by filtration to give 6-(furan-3-yl)-5-methoxy-2-oxo-2-phenyl-1H-2-λ*6*-benzo[d][1,2]thiazin-4-one (0.23 g) as a white solid.

LCMS (Method G) r/t 3.78 (M+H) 354.

Intermediate 215

Methyl 3-(furan-3-yl)-2-methoxy-6-{[S-phenyl-N-(trifluoroacetyl)sulphonimidoyl]methyl}benzoate

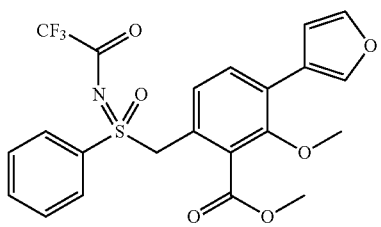 [SMILES: COC(=O)c1c(CS(=O)(=NC(=O)C(F)(F)F)c2ccccc2)ccc(-c2ccoc2)c1OC]

A mixture of methyl 6-(benzenesulphinylmethyl)-3-(furan-3-yl)-2-methoxybenzoate (Intermediate 216, 0.920 g), trifluoroacetamide (0.56 g), magnesium oxide (0.40 g), iodobenzene diacetate (1.20 g) and rhodium (II) acetate dimer (0.030 g) in DCM (20 mL) was stirred at room temperature for 22 hours. The mixture was filtered and the filtrate was evaporated to dryness. The residue was purified by chromatography on silica eluting with ethyl acetate and cyclohexane with a gradient of 10-40% to give methyl 3-(furan-3-yl)-2-methoxy-6-{[S-phenyl-N-(trifluoroacetyl)sulphonimidoyl]methyl}benzoate (0.46 g) as a colourless gum.

NMR (CDCl$_3$) δ 7.95 (dd, 1H), 7.7 (m, 3H), 7.6 (m, 2H), 7.5 (t, 1H), 7.5 (d, 1H), 7.05 (d, 1H), 6.75 (dd, 1H), 5.2 (d, 1H), 4.85 (d, 1H), 3.85 (s, 3H), 3.6 (s, 3H).

Intermediate 216

Methyl 6-(benzenesulphinylmethyl)-3-(furan-3-yl)-2-methoxybenzoate

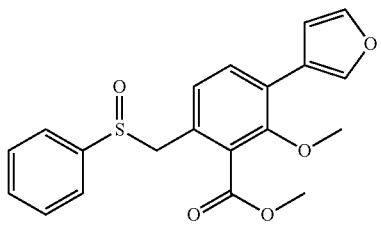 [SMILES: COC(=O)c1c(CS(=O)c2ccccc2)ccc(-c2ccoc2)c1OC]

Prepared by proceeding in a similar manner to Intermediate 2, starting from methyl 3-(furan-3-yl)-2-methoxy-6-phenylthiobenzoate (Intermediate 217).

NMR (CDCl$_3$) δ 7.95 (t, 1H), 7.5 (m, 6H), 7.4 (d, 1H), 6.9 (d, 1H), 6.75 (dd, 1H), 4.1 (m, 2H), 3.95 (s, 3H), 3.65 (s, 3H).

Intermediate 217

Methyl 3-(furan-3-yl)-2-methoxy-6-(phenylthiomethyl)benzoate

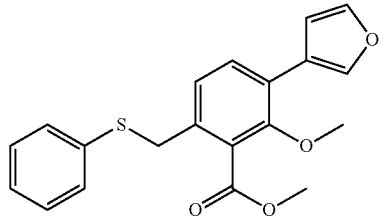 [SMILES: COC(=O)c1c(CSc2ccccc2)ccc(-c2ccoc2)c1OC]

Prepared by proceeding in a similar manner to Intermediate 36, starting from methyl 3-bromo-2-methoxy-6-(phenylthiomethyl)-benzoate (Intermediate 80) and used without further characterization.

Intermediate 218 t-Butyl 3-(furan-3-yl)-2-methoxy-6-[(N-methyl-S-phenylsulphonimidoyl)methyl]benzoate

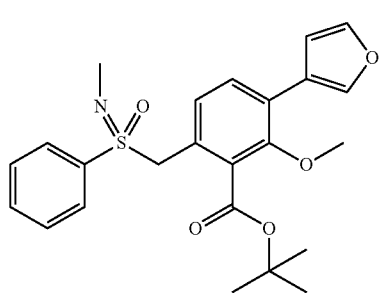 [SMILES: CN=S(=O)(Cc1ccc(-c2ccoc2)c(OC)c1C(=O)OC(C)(C)C)c1ccccc1]

A mixture of t-butyl 3-(furan-3-yl)-2-methoxy-6-[(S-phenylsulphonimidoyl)methyl]benzoate (Intermediate 219, 0.16 g), trimethyloxonium tetrafluoroborate (0.12 g) and potassium carbonate (0.21 g) in DCM (15 ml) was stirred for 2 hours. Water was added to the mixture and the organic layer was separated, dried (NaSO$_4$) and filtered. The filtrate was evaporated to dryness and the residue was purified by chromatography on silica eluting with a mixture of ethyl acetate and cyclohexane with a gradient of 10-80%, to give t-butyl 3-(furan-3-yl)-2-methoxy-6-[(N-methyl-5-phenylsulphonimidoyl)methyl]benzoate (0.11 g) as a colourless gum.

NMR (CDCl$_3$) δ 7.9 (t, 1H), 7.7 (d, 2H), 7.6 (d, 1H), 7.5 (m, 3H), 7.35 (d, 1H), 7.1 (d, 1H), 6.75 (dd, 1H), 4.7-4.6 (m, 1H), 4.55 (m, 1H), 3.6 (s, 3H), 2.75 (s, 3H), 1.6 (s, 9H).

Intermediate 219 t-Butyl 3-(furan-3-yl)-2-methoxy-6-[(S-phenylsulphonimidoyl)methyl]benzoate

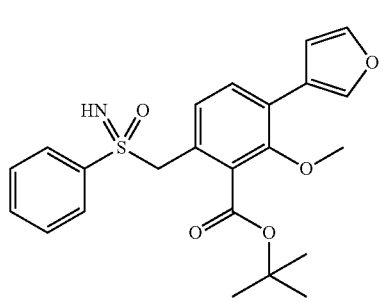 [SMILES: COc1c(-c2ccoc2)ccc(CS(=N)(=O)c2ccccc2)c1C(=O)OC(C)(C)C]

Prepared by proceeding in a similar manner to Intermediate 214, starting from t-butyl 3-(furan-3-yl)-2-methoxy-6-{[S-phenyl-N-(trifluoroacetyl)sulphonimidoyl]methyl}benzoate (Intermediate 220).

NMR (CDCl$_3$) δ 7.95 (s, 2H), 7.9 (s, 1H), 7.65 (t, 1H), 7.55 (d, 2H), 7.5 (t, 1H), 7.4 (d, 1H), 7.0 (d, 1H), 6.75 (m, 1H), 4.5 (m, 2H), 3.65 (s, 3H), 1.65 (s, 9H).

Intermediate 220 t-Butyl 3-(furan-3-yl)-2-methoxy-6-{[S-phenyl-N-(trifluoroacetyl)sulphonimidoyl]methyl}benzoate

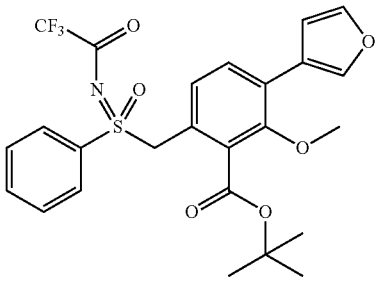 [SMILES: COc1c(-c2ccoc2)ccc(CS(=O)(=NC(=O)C(F)(F)F)c2ccccc2)c1C(=O)OC(C)(C)C]

Prepared by proceeding in a similar manner to Intermediate 215, starting from t-butyl 6-(benzenesulphinylmethyl)-3-(furan-3-yl)-2-methoxybenzoate (Intermediate 221).

LCMS (Method G) r/t 4.87 (M+H) 524.

Intermediate 221 t-Butyl 6-(benzenesulphinylmethyl)-3-(furan-3-yl)-2-methoxy-benzoate

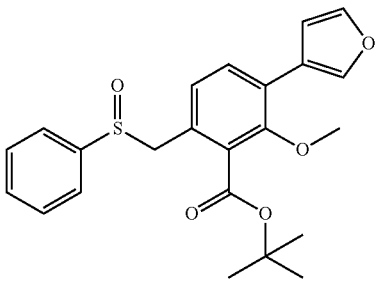 [SMILES: COc1c(-c2ccoc2)ccc(CS(=O)c2ccccc2)c1C(=O)OC(C)(C)C]

Prepared by proceeding in a similar manner to Intermediate 2, starting from t-butyl 3-(furan-3-yl)-2-methoxy-6-(phenylthiomethyl)benzoate (Intermediate 222).

LCMS (Method G) r/t 4.76 (M+H) 413.

Intermediate 222 t-Butyl 3-(furan-3-yl)-2-methoxy-6-(phenylthiomethyl)benzoate

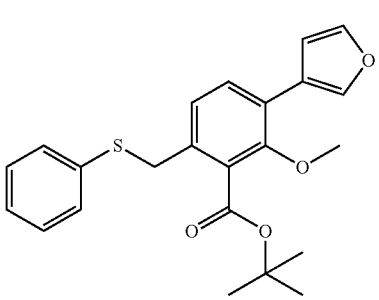 [SMILES: COc1c(-c2ccoc2)ccc(CSc2ccccc2)c1C(=O)OC(C)(C)C]

Concentrated sulphuric acid (0.31 g) was added to a stirred suspension of magnesium sulphate (1.31 g) in DCM (10 ml) in a sealed vial and the mixture was stirred for 5 minutes before addition of a solution of 3-(furan-3-yl)-2-methoxy-6-(phenylthiomethyl)benzoic acid (Intermediate 223, 0.96 g) in DCM (8 ml) and t-butanol (1.03 g). The mixture was stirred in a sealed tube for 48 hours. DCM and saturated aqueous sodium hydrogen carbonate were added to the mixture and the organic layer was separated, dried ($Na_2SO_4$) and filtered. The filtrate was evaporated to dryness and the residue was purified by chromatography on silica, eluting with a mixture of ethyl acetate and cyclohexane with a gradient of 0-100%, to give t-butyl 3-(furan-3-yl)-2-methoxy-6-(phenylthiomethyl)benzoate (0.67 g) as a colourless gum.

LCMS (Method G) r/t 5.32 (M+Na) 419.

Intermediate 223

3-(Furan-3-yl)-2-methoxy-6-(phenylthiomethyl)benzoic acid

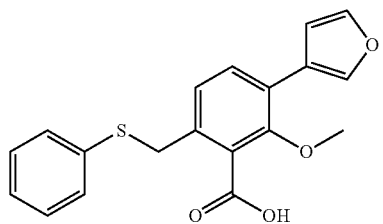 [SMILES: COc1c(-c2ccoc2)ccc(CSc2ccccc2)c1C(=O)O]

Prepared by proceeding in a similar manner to Example 3, starting from methyl 3-(furan-3-yl)-2-methoxy-6-(phenylthiomethyl)benzoate (Intermediate 217) which was used without further characterization.

Intermediate 224

Benzyl 6-[(N-cyano-S-phenylsulphonimidoyl)methyl]-3-(furan-3-yl)-2-methoxybenzoate

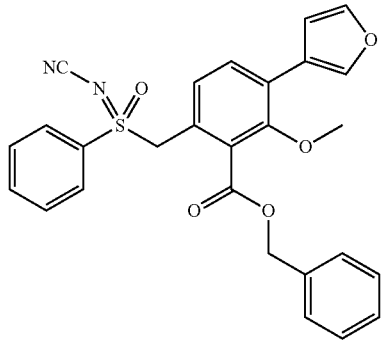 [SMILES: COc1c(-c2ccoc2)ccc(CS(=O)(=NC#N)c2ccccc2)c1C(=O)OCc1ccccc1]

Prepared by proceeding in a similar manner to Intermediate 2, starting from benzyl 6-[(N-cyano-S-phenylsulphinimidoyl)methyl]-3-(furan-3-yl)-2-methoxybenzoate (Intermediate 225).

LCMS (Method G) r/t 4.17 (M+H) 487.

Intermediate 225

Benzyl 6-[(N-cyano-S-phenylsulphinimidoyl)methyl]-3-(furan-3-yl)-2-methoxybenzoate

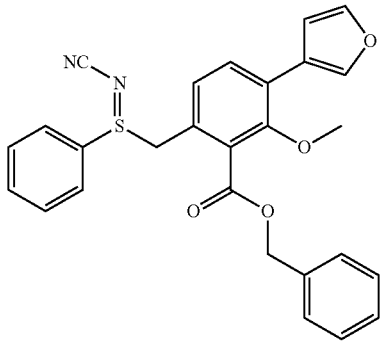 [SMILES: COc1c(-c2ccoc2)ccc(C/S(=N/C#N)c2ccccc2)c1C(=O)OCc1ccccc1]

A solution of benzyl 3-(furan-3-yl)-2-methoxy-6-(phenylthiomethyl)benzoate (Intermediate 226, 0.96 g), cyanamide (0.19 g) and iodobenzene diacetate (0.79 g) in acetonitrile (20 ml) was stirred for 16 hours. The mixture was evaporated to dryness and the residue was purified by chromatography on silica eluting with ethyl acetate and DCM with a gradient of 0-5% to give benzyl 6-[(N-cyano-S-phenylsulphinimidoyl)methyl]-3-(furan-3-yl)-2-methoxybenzoate (0.17 g) as a colourless gum.

NMR ($CDCl_3$) δ 7.95 (dd, 1H), 7.6 (m, 3H), 7.5 (m, 6H), 7.4 (m, 3H), 7.15 (d, 1H), 6.75 (dd, 1H), 5.45 (m, 2H), 4.5 (d, 1H), 4.25 (d, 1H), 3.6 (s, 3H).

Intermediate 226

Benzyl 3-(furan-3-yl)-2-methoxy-6-(phenylthiomethyl)benzoate

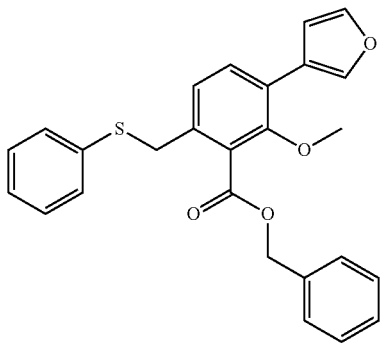 [SMILES: COc1c(-c2ccoc2)ccc(CSc2ccccc2)c1C(=O)OCc1ccccc1]

A solution of 3-(furan-3-yl)-2-methoxy-6-(phenylthiomethyl)benzoic acid (Intermediate 223, 0.83 g), benzyl bromide (0.46 g) and potassium carbonate (0.55 g) in THF (15 ml) was heated to 60° C. for 8 hours. After cooling, the mixture was filtered and the filtrate was evaporated to dryness. The residue was purified by chromatography on silica, eluting with a mixture of ethyl acetate and cyclohexane with a gradient of 0-10% to give benzyl 3-(furan-3-yl)-2-methoxy-6-(phenylthiomethyl)-benzoate (0.96 g) as a white solid.

NMR ($CDCl_3$) δ 7.9 (dd, 1H), 7.5 (d, 1H), 7.45 (m, 2H), 7.35 (m, 5H), 7.25 (dd, 2H), 7.23 (m, 1H), 7.2 (m, 1H), 7.05 (d, 1H), 6.75 (dd, 1H), 5.4 (s, 2H), 4.1 (s, 2H), 3.6 (s, 3H).

Example 97

Biological Activity

Compounds are tested for their capacity to inhibit recombinant human MetAP2 activity using the following assay.

Human recombinant Flag-MetAP2 expressed in Sf9 cells followed by affinity purification and EDTA treatment to remove endogenous active site cation is dialysed against MnCl$_2$ to produce the manganese enzyme used in the assay. The assay is carried out for 30 minutes at 25° C. in 50 mM HEPES buffer containing 100 mM NaCl, pH 7.5 the presence of 0.75 mM Methionine-Alanine-Serine (MAS) substrate and 50 µg/ml amino acid oxidase using a dilution of purified MetAP2 giving approximately 50,000 RFU control activity. Cleavage of the substrate by MetAP2 and oxidation of free methionine by amino acid oxidase is detected and quantified using fluorescence generated by Amplex red (10-acetyl-3,7-dihydroxyphenoxazine) in combination with horseradish peroxidase which detects H$_2$O$_2$ released during the oxidation step. The fluorescent signal is detected using a multiwell fluorimeter. Compounds are diluted in DMSO prior to addition to assay buffer, the final DMSO concentration in the assay being 1%.

The IC$_{50}$ is defined as the concentration at which a given compound achieves 50% inhibition of control. IC$_{50}$ values are calculated using the XLfit software package (version 2.0.5).

Compounds of the invention demonstrated activity in the assay of this Example as indicated in the following table, wherein A represents IC$_{50}$<0.2 µM, B represents IC$_{50}$ between 0.2 µM and 2 µM, and C represents IC$_{50}$>2 µM.

| Compound name | Activity |
| --- | --- |
| 2-(Benzenesulphonylmethyl)-5-ethylbenzoic acid | B |
| 6-(Benzenesulphonylmethyl)-3-ethyl-2-methoxybenzoic acid | B |
| 6-(Benzenesulphonylmethyl)-2-methoxy-3-propylbenzoic acid | C |
| 6-(Benzenesulphinylmethyl)-3-ethyl-2-methoxybenzoic acid | C |
| 6-(Benzenesulphonylmethyl)-3-cyclopropyl-2-methoxybenzoic acid | B |
| 6-(4-Chlorobenzenesulphonylmethyl)-3-ethyl-2-methoxybenzoic acid | C |
| 6-(Benzenesulphonylmethyl)-3-bromo-2-methoxybenzoic acid | B |
| 6-(Benzenesulphonylmethyl)-2-methoxy-3-methylbenzoic acid | B |
| 3-Ethyl-2-methoxy-6-(2-methylbenzenesulphonylmethyl)benzoic acid | B |
| 6-(Benzenesulphonylmethyl)-3-(furan-3-yl)-2-methoxybenzoic acid | A |
| 6-(1-Benzenesulphonylethyl)-3-ethyl-2-methoxybenzoic acid | B |
| 6-(Benzenesulphonylmethyl)-2-methoxy-3-(oxazol-5-yl)benzoic acid | B |
| 6-(Benzenesulphonylmethyl)-3-(isothiazol-5-yl)-2-methoxybenzoic acid | A |
| 6-(Benzenesulphonylmethyl)-2-methoxy-3-phenylbenzoic acid | C |
| 6-(Benzenesulphonylmethyl)-2-methoxy-3-(3-pyridyl)benzoic acid | C |
| 6-(Benzenesulphonylmethyl)-2-methoxy-3-(pyrazol-3-yl)benzoic acid | C |
| 2-(Benzenesulphonylmethyl)-5-(furan-3-yl)benzoic acid | B |
| 2-(Benzenesulphonylmethyl)-5-(oxazol-5-yl)benzoic acid | C |
| 3-(Furan-3-yl)-2-methoxy-6-(2-methylbenzenesulphonylmethyl)-benzoic acid | B |
| 2-Methoxy-6-(2-methylbenzenesulphonylmethyl)benzoic acid | C |
| 6-(3-Chlorobenzenesulphonylmethyl)-3-(furan-3-yl)-2-methoxybenzoic acid | A |
| 6-(Benzenesulphonylmethyl)-3-(oxazol-4-yl)-2-methoxybenzoic acid | C |
| 6-(Benzenesulphonylmethyl)-3-(isothiazol-4-yl)-2-methoxybenzoic acid | B |
| 6-(Benzenesulphonylmethyl)-2-methoxy-3-(thiazol-2-yl)benzoic acid | C |
| (Z)-6-((2-(3-(Diethylamino)prop-1-enyl)benzenesulfonyl)methyl)-3-(furan-3-yl)-2-methoxybenzoic acid | A |
| (E)-6-((2-(3-(diethylamino)prop-1-enyl)benzenesulfonyl)methyl)-3-(furan-3-yl)-2-methoxybenzoic acid | B |
| 6-(Benzenesulphonylmethyl)-2-ethoxy-3-(furan-3-yl)benzoic acid | B |
| 6-(Benzenesulphonylmethyl)-3-(furan-3-yl)-2-hydroxybenzoic acid | C |
| 6-(Benzenesulphonylmethyl)-3-(furan-3-yl)-2-(2-hydroxyethoxy)-benzoic acid | A |
| 6-(Benzenesulphonylmethyl)-3-(furan-3-yl)-2-(2-methoxyethoxy)-benzoic acid | C |
| 6-[2-(3-Diethylaminopropyl)benzenesulphonylmethyl]-3-(furan-3-yl)-2-methoxybenzoic acid | A |
| 3-(Furan-3-yl)-2-methoxy-6-(pyrid-3-ylsulphonyl)methylbenzoic acid | B |
| 6-(Benzenesulphonylmethyl)-3-(isoxazol-3-yl)-2-methoxybenzoic acid | C |
| 3-(Furan-3-yl)-2-methoxy-6-(2-methoxybenzenesulphonylmethyl)benzoic acid | B |
| 3-(Furan-3-yl)-2-methoxy-6-(pyrid-2-ylsulphonylmethyl)benzoic acid | A |
| 3-Ethyl-6-(4-fluorobenzenesulphonylmethyl)-2-methoxybenzoic acid | B |
| 6-(Benzenesulphonylmethyl)-3-cyano-2-methyoxybenzoic acid | C |
| 6-(Benzenesulphonylmethyl)-3-(furan-2-yl)-2-methoxybenzoic acid | C |
| 2-(2-Aminoethoxy)-6-(benzenesulphonylmethyl)-3-(furan-3-yl)benzoic acid hydrochloride | A |
| 2-(2-Aminoethoxy)-6-(3-chlorobenzenesulphonylmethyl)-3-(furan-3-yl)benzoic acid hydrochloride | A |
| 2-(2-Aminoethoxy)-6-(4-fluorobenzenesulphonylmethyl)-3-(furan-3-yl)benzoic acid hydrochloride | A |
| 2-(2-Aminoethoxy)-3-(furan-3-yl)-6-(2-methoxybenzenesulphonyl-methyl)benzoic acid hydrochloride | B |
| 6-(Benzenesulphonylmethyl)-2-(2-dimethylaminoethoxy)-3-(3-furanyl)benzoic acid hydrochloride | C |
| 6-(2-Chlorobenzenesulphonylmethyl)-3-(furan-3-yl)-2-methoxybenzoic acid | B |
| 6-(3-Fluorobenzenesulphonylmethyl)-3-(furan-3-yl)-2-methoxybenzoic acid | A |

| Compound name | Activity |
|---|---|
| 6-(2-Fluorobenzenesulphonylmethyl)-3-(furan-3-yl)-2-methoxybenzoic acid | B |
| 3-(Furan-3-yl)-6-(3-methoxybenzenesulphonylmethyl)-2-methoxybenzoic acid | C |
| 2-(2-Aminoethoxy)-3-ethyl-6-(benzenesulphonylmethyl)benzoic acid hydrochloride | A |
| 2-(3-Aminopropoxy)-6-(benzenesulphonylmethyl)-3-(furan-3-yl)benzoic acid hydrochloride | B |
| 6-(Benzenesulphonylmethyl)-2-methoxy-3-(thien-2-yl)benzoic acid | C |
| 6-(Benzenesulphonylmethyl)-2-methyoxy-3-(thien-3-yl)benzoic acid | C |
| 6-(4-Fluorobenzenesulphonylmethyl)-3-(furan-3-yl)-2-methoxybenzoic acid | A |
| 6-(Benzenesulphonylmethyl)-2-(cyanomethoxy)-3-(furan-3-yl)benzoic acid | A |
| 2-(2-Aminoethylamino)-6-benzenesulphonylmethyl-3-(furan-3-yl)-benzoic acid hydrochloride | C |
| 6-(Benzenesulphonylmethyl)-3-(furan-3-yl)-2-[2-(methylamino)-ethoxy]benzoic acid hydrochloride | C |
| 6-(Benzenesulphonylmethyl)-3-ethyl-2-(2-methyl-2H-pyrazol-3-yl)-benzoic acid | C |
| 2-(2-Aminopropoxy)-6-(benzenesulphonylmethyl)-3-(furan-3-yl)-benzoic acid hydrochloride | C |
| 6-Benzenesulphonylmethyl-3-ethyl-2-(1-methyl-1H-pyrazol-3-yl)-benzoic acid | C |
| 2-(3-Aminopropyl)-6-(benzenesulphonylmethyl)-3-(furan-3-yl)-benzoic acid hydrochloride | C |
| 6-(Benzenesulphonylmethyl)-2-methoxy-3-(pyrazol-1-yl)benzoic acid | C |
| 2-(Benzenesulphonylmethyl)-5-(2-methyl-2H-pyrazol-3-yl)benzoic acid | C |
| 2-(Benzenesulphonylmethyl)naphthalene-1-carboxylic acid | B |
| 3-(Furan-3-yl)-6-(2-hydroxybenzenesulphonylmethyl)-2-methoxybenzoic acid | A |
| 3-(Furan-3-yl)-6-(3-hydroxybenzenesulphonylmethyl)-2-methoxy-benzoic acid. | B |
| 2-(Benzenesulphonylmethyl)-5-(2-methylfuran-3-yl)benzoic acid | B |
| 6-(Benzenesulphonylmethyl)-3-ethyl-2-(1H-pyrazol-3-yl)benzoic acid | B |
| 3-(Furan-3-yl)-2-methoxy-6-(piperidine-1-ylsulphonylmethyl)benzoic acid | A |
| 3-(Furan-3-yl)-2-methoxy-6-(pyrrolidin-1-ylsulphonylmethyl)-benzoic acid | B |
| 6-[2-(2-Diethylaminoethylamino)benzenesulphonylmethyl]-3-(furan-3-yl)-2-methoxybenzoic acid | B |
| 6-(Benzenesulphonylmethyl)-2-ethyl-3-(furan-3-yl)benzoic acid | B |
| 6-[2-(2-Diethylaminoethoxy)benzenesulphonylmethyl]-3-(furan-3-yl)-2-methoxybenzoic acid | C |
| 6-(Benzenesulphonylmethyl)-3-(furan-3-yl)-2-(prop-1-yn-1-yl)benzoic acid | C |
| 2-(Benzenesulphonylmethyl)-6-methoxybenzoic acid | C |
| 6-(Cyclohexanesulphonylmethyl)-3-(furan-3-yl)-2-methoxybenzoic acid | B |
| 6-(Benzenesulphonylmethyl)-2-(carbamoylmethoxy)-3-(furan-3-yl)-benzoic acid | B |
| (Z)-6-((2-(3-(Diethylamino)prop-1-enyl)-4-fluorophenylsulfonyl)methyl)-3-(furan-3-yl)-2-methoxybenzoic acid | A |
| 3-(Furan-3-yl)-6-(3-hydroxypyrrolidine-1-ylsulphonylmethyl)-2-methoxybenzoic acid | B |
| 2-(Azetidin-3-yloxy)-6-(benzenesulphonylmethyl)-3-(furan-3-yl)-benzoic acid hydrochloride | C |
| 6-(Bicyclo[2.2.2]octane-2-ylsulphonylmethyl)-3-(furan-3-yl)-2-methoxybenzoic acid | C |
| 6-(Bicyclo[2.2.2]octane-2-ylsulphonylmethyl)-2-methoxy-3-(tetrahydrofuran-3-yl)benzoic acid | C |
| 6-(7-Azabicyclo[2.2.1]heptane-7-ylsulphonylmethyl)-3-(furan-3-yl)-2-methoxybenzoic acid | B |
| 6-(4,4-Difluoropiperidine-1-ylsulphonylmethyl)-3-(furan-3-yl)-2-methoxybenzoic acid | A |
| 6-(Bicyclo[2.2.1]heptane-7-ylsulphonylmethyl)-3-(furan-3-yl)-2-methoxybenzoic acid | B |
| 6-(Benzenesulphonylmethyl)-3-(furan-3-yl)-2-methylamino benzoic acid | A |
| 6-(8-Azabicyclo[3.2.1]octane-8-ylsulphonylmethyl)-3-(furan-3-yl)-2-methoxybenzoic acid | C |
| 2-(Benzenesulphonylmethyl)-8-methoxynaphthalene-1-carboxylic acid | C |
| 6-[2-(3-Diethylaminopropylamino)benzenesulphonylmethyl]-3-(furan-3-yl)-2-methoxybenzoic acid | A |
| (Z)-2-Cyanomethoxy-6-((2-(3-(Diethylamino)prop-1-enyl)-4-fluorobenzenesulfonyl)methyl)-3-(furan-3-yl)benzoic acid | A |

-continued

| Compound name | Activity |
|---|---|
| (Z)-3-(Furan-3-yl)-2-methoxy-6-((2-(3-(piperidin-1-yl)prop-1-enyl)benzenesulfonyl)methyl)benzoic acid | A |
| 6-(Benzenesulphonylmethyl)-3-(furan-3-yl)-2,4-dimethoxybenzoic acid | B |
| 6-[2-(2-Diethylaminomethylazetidin-1-yl)-benzenesulphonylmethyl]-3-(furan-3-yl)-2-methoxybenzoic acid | C |
| 6-(Benzenesulphonylmethyl)-2-(cyanomethylamino)-3-(furan-3-yl)benzoic acid | A |
| 6-(Benzenesulphonylmethyl)-3-(imidazol-1-yl)-2-methoxybenzoic acid | C |
| 6-(Benzenesulphonylmethyl)-2-methoxy-3-(thiazol-5-yl)benzoic acid | B |
| 3-(Furan-3-yl)-2-methoxy-6-[(S-phenylsulphonimidoyl)methyl]benzoic acid | B |
| 3-(Furan-3-yl)-2-methoxy-6-[(N-methyl-S-phenylsulphonimidoyl)methyl]benzoic acid | B |
| 6-[(N-cyano-S-phenylsulphonimidoyl)methyl]-3-(furan-3-yl)-2-methoxybenzoic acid | A |

Incorporation By Reference

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound represented by:

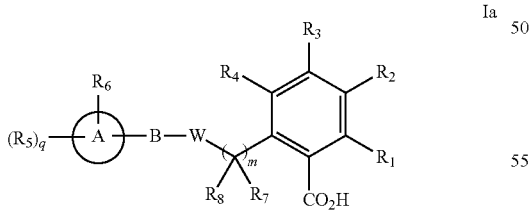

Ia and pharmaceutically acceptable salts, stereoisomers, esters and prodrugs thereof, wherein B is selected from the group consisting of a bond or $(CR_9R_{10})_p$, wherein p is 1 or 2;

A is a ring selected from the group consisting of phenyl, a 5-6 membered heteroaryl having 1, 2 or 3 heteroatoms selected from S, N or O, a $C_{3-6}$cycloalkyl, a 4-7 membered heterocycle, a bridged 6-10 membered heterocycle, and a bridged 6-10 membered cycloalkyl;

$R_1$ is selected from the group consisting of:
hydrogen, halogen, cyano, hydroxyl, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— wherein w is 0, 1 or 2, $C_{1-6}$ alkyl-N(R$^a$)-carbonyl, R$^f$R$^g$N—, R$^f$R$^g$N-carbonyl, R$^f$R$^g$N-carbonyl-N(R$^a$)—, R$^f$R$^g$NSO$_2$—, $C_{1-6}$alkyl-carbonyl-N(R$^a$)—, $C_{1-6}$alkoxy-carbonyl-N(R$^a$)—, phenyl, phenyloxy, phenyl-$C_{1-6}$alkyl-, phenyl-$C_{1-6}$alkoxy, heteroaryl, heteroaryloxy, heteroaryl-$C_{1-6}$alkyl, heteroaryl-$C_{1-6}$ alkoxy, heterocyclyl, heterocyclyloxy, heterocyclyl-$C_{1-6}$alkyl, and heterocyclyl-$C_{1-6}$alkoxy, wherein said heteroaryl is a 5-6 membered ring having one, two or three heteroatoms selected from O, S, or N, and wherein said phenyl or heteroaryl is optionally substituted with one or more substituents selected from R$^b$; wherein said heterocyclyl is a 4-7 membered ring optionally substituted by one or more substituents selected from R$^c$ and wherein if said heterocyclyl contains a —NH moiety that nitrogen may be optionally substituted by one or more groups R$^d$; and wherein $C_{2-6}$alkenyl, $C_{2-6}$alkynyl, $C_{3-6}$alkenyloxy, and $C_{3-6}$alkynyloxy may be optionally substituted by one or more substituents selected from R$^p$, wherein $C_{1-6}$alkyl and $C_{1-6}$alkoxy may be optionally substituted by one or more substituents selected from R$^{p'}$ and wherein $C_{3-6}$cycloalkyl and $C_{3-6}$cycloalkoxy may be optionally substituted by one or more substituents selected from R$^{p''}$;

$R_2$ is selected from the group consisting of:
hydrogen, halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkyloxy, $C_{1-6}$alkyl-S(O)$_2$—, $C_{3-6}$cycloalkylC$_{1-4}$alkyl-, $C_{3-6}$cycloalkylC$_{1-4}$alkoxy- , R$^f$R$^g$N-carbonyl, phenyl-$C_{1-6}$ alkyl-, phenyl, phenyoxy, phenyl-$C_{1-6}$alkoxy-, heteroaryl, heteroaryloxy, heteroaryl-$C_{1-6}$alkyl, heteroaryl-$C_{1-6}$alkoxy, heterocyclylC$_{1-6}$alkyl-, and heterocyclyl-$C_{1-6}$alkoxy, wherein said heteroaryl is a 5-6 membered monocyclic ring having one, two or three heteroatoms selected from O, S, or N, and optionally substituted with one or more substituents selected from R$^b$; wherein said heterocyclyl is a 4-7 membered ring optionally substituted by one or more substituents selected from Re and wherein if said heterocyclyl contains a —NH moiety that nitrogen may be optionally substituted by one or more groups R$^d$, and wherein $C_{1-6}$alkyl, $C_{2-6}$alkenyl, $C_{2-6}$alkynyl, $C_{1-6}$alkoxy, $C_{3-6}$alkenyloxy, or $C_{3-6}$alkynyloxy may be optionally substituted by one or more substituents selected from halogen, hydroxyl, $R^aR^{a'}N-$, or cyano, and $C_{3-6}$cycloalkyl and $C_{3-6}$cycloalkoxy may be optionally substituted by one or more substituents selected from halogen, hydroxyl, $R^aR^{a'}N-$, cyano and $C_{1-6}$alkyl; or $R_1$ and $R_2$ may be joined together with the carbons to which they are attached to form a 5-7 membered saturated, partially unsaturated, or unsaturated ring, optionally having 1, 2 or 3 heteroatoms selected from O, $NR^h$, or $S(O)_r$ where r is 0, 1, or 2, wherein the formed 5-7 membered ring is optionally substituted on a carbon by one or more groups $R^e$, and wherein the formed ring may be optionally bridged by a moiety selected from $-O-$, $CH_2$, $-(CH_2)_2-$, cis-$CH=CH-$, $NR^h$; or $-CH_2NR^h-$;

and wherein if $R_1$ is hydrogen, $R_2$ may not be hydrogen;

$R_3$ is selected from the group consisting of hydrogen, hydroxyl, cyano, halogen, $C_{1-6}$alkyl, or, $C_{1-6}$alkoxy, wherein $C_{1-6}$alkyl, and $C_{1-6}$alkoxy may be optionally substituted by one or more halogens;

$R_4$ is selected from the group consisting of hydrogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O), wherein w is 0, 1 or 2, $R^fR^gN-$, $R^fR^gN$-carbonyl, $R^fR^gN$-carbonyl-$N(R^a)-$, $R^fR^gN-SO_2-$, $C_{1-6}$alkyl-carbonyl-N$(R^a)-$, and $C_{1-6}$alkoxy-carbonyl-N$(R^a)-$, wherein $C_{2-6}$alkenyl, $C_{2-6}$alkynyl, $C_{1-6}$alkoxy, $C_{3-6}$alkenyloxy, or $C_{3-6}$alkynyloxy may be optionally substituted by one or more substituents selected from $R^p$; wherein $C_{1-6}$alkyl and $C_{1-6}$alkoxy may be optionally substituted by one or more substituents selected from $R^{p'}$, and wherein $C_{3-6}$cycloalkyl may be optionally substituted by one or more substituents selected from $R^{p''}$;

m is 1 or 2;

$R_5$ is selected, independently for each occurrence, from the group consisting of hydrogen, hydroxyl, cyano, halogen, $C_{1-6}$alkyl, $C_{2-6}$alkenyl, $C_{3-6}$alkynyl, $C_{3-6}$cycloalkyl, or $C_{1-6}$alkoxy, or $R^fR^gN-$, wherein $C_{1-6}$alkyl, $C_{2-6}$alkenyl, $C_{3-6}$alkynyl, $C_{3-6}$cycloalkyl, or $C_{1-6}$alkoxy may be optionally substituted with one or more halogens;

$R_6$ is selected from the group consisting of hydrogen, hydroxyl, cyano, halogen, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w-$ wherein w is 0, 1 or 2, $R^fR^gN-$, $R^fR^gN$-carbonyl-, $R^fR^gN$-carbonyl-$N(R^a)-$, $R^fR^gN-SO_2-$, $C_{1-6}$alkyl-carbonyl-$N(R^a)-$, $C_{1-6}$alkylsulphonylN$(R^a)-$, $C_{1-6}$alkoxycarbonyl-$N(R^a)-$, phenyl, phenoxy, phenyl-$C_{1-6}$alkoxy, heteroaryl, heteroaryloxy, heterocycloxy, heteroaryl-$C_{1-6}$alkyl, heteroaryl-$C_{1-6}$alkoxy-, heterocyclyl-$C_{1-6}$alkyl-, and heterocyclyl-$C_{1-6}$alkoxy-, wherein said heteroaryl is a 5-6 membered monocyclic ring having one, two or three heteroatoms selected from O, S, or N, and optionally substituted with one or more substituents selected from $R^b$; wherein said heterocyclyl is a 4-7 membered ring optionally substituted by one or more substituents selected from $R^c$ and wherein if said heterocyclyl contains a $-NH$ moiety that nitrogen may be optionally substituted by one or more groups $R^d$, and, wherein $C_{1-6}$alkyl and $C_{1-6}$alkoxy may be optionally substituted by $R^{p'}$, wherein $C_{2-6}$alkenyl, and $C_{2-6}$alkynyl may be optionally substituted by one or more substituents selected from $R^p$; and wherein $C_{3-6}$cycloalkyl or $C_{3-6}$cycloalkoxy may be optionally substituted by one or more substituents selected from $R^{p''}$;

$R_7$ and $R_8$ are independently selected from the group consisting of hydrogen, halogen, $C_{1-6}$alkoxy, $C_{2-6}$alkenyl, $C_{3-6}$alkynyl, and $C_{3-6}$cycloalkyl wherein $C_{2-6}$alkenyl, $C_{3-6}$alkynyl is optionally substituted by $R^p$, wherein $C_{1-6}$alkyl is optionally substituted by $R^{p'}$; and wherein $C_{3-6}$ cycloalkyl is optionally substituted by $R^{p''}$; or $R_7$ and $R_8$ taken together with the carbon to which they are attached form a cyclopropyl ring or 4-6 membered ring which may optionally have one group selected from $N(R^h)$, O or $S(O)_r$ wherein r is 0, 1, or 2;

$R_9$ and $R_{10}$ are independently selected from the group consisting of hydrogen, $C_{1-6}$alkoxy, halogen, $C_{1-6}$alkyl, $C_{2-6}$alkenyl, $C_{3-6}$alkynyl, and $C_{3-6}$cycloalkyl wherein $C_{2-6}$alkenyl, $C_{3-6}$alkynyl is optionally substituted by $R^p$, $C_{1-6}$alkyl and $C_{1-6}$alkoxy is optionally substituted by $R^{p'}$; and $C_{3-6}$cycloalkyl is optionally substituted by $R^{p''}$; or $R_9$ and $R_{10}$ taken together with the carbon to which they are attached form a cyclopropyl ring or 4-6 membered ring which may optionally have one group selected from $N(R^h)$, O or $S(O)_r$ wherein r is 0, 1, or 2;

W is $-S(O)_n-$, or $-S(O)(NR_{11})-$;

n is 1 or 2;

$R_{11}$ is selected from the group consisting of H, $C_{1-3}$alkyl, CN;

q is 0, 1, 2, or 3;

$R^a$ and $R^{a'}$ are independently selected, for each occurrence, from the group consisting of hydrogen and $C_{1-6}$alkyl, or $R^a$ and $R^{a'}$ when they occur together may form a 4-6 membered heterocyclic ring, wherein $C_{1-6}$alkyl may be optionally substituted by one or more substituents selected from the group consisting of halogen, oxo and hydroxyl, and wherein the heterocyclic ring may be optionally substituted by one or more substituents selected from the group consisting of halogen, alkyl, oxo or hydroxyl;

$R^b$ is independently selected, for each occurrence, from the group consisting of halogen, hydroxyl, cyano, $C_{1-6}$alkyl, $C_{2-6}$alkenyl, $C_{3-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w-$ wherein w is 0, 1 or 2, $C_{1-6}$alkylN$(R^a)-$, $C_{1-6}$alkyl-N$(R^a)$carbonyl, $R^aR^{a'}N-$, $R^aR^{a'}N$-carbonyl-, $R^aR^{a'}N$-carbonyl-$N(R^a)-$; $R^aR^{a'}N-SO_2-$, and $C_{1-6}$alkyl-carbonyl-$N(R^a)-$, wherein $C_{2-6}$alkenyl, $C_{3-6}$alkynyl, or $C_{1-6}$alkoxy may be optionally substituted by one or more substituents selected from $R^p$; wherein $C_{3-6}$cycloalkyl and $C_{3-6}$cycloalkoxy may be optionally substituted by one or more substituents selected from $R^{p''}$, and wherein $C_{1-6}$alkyl may be optionally substituted by one or more substituents selected from $R^{p'}$;

$R^c$ for each occurrence is independently selected from the group consisting of, hydroxyl, cyano, oxo, halogen, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w-$, wherein w is 0, 1 or 2, $C_{1-6}$alkyl-$NR^a-$, $C_{1-6}$alkyl$C_{3-6}$cycloalkyl-, $C_{3-6}$cycloalkyl$C_{1-6}$alkyl, $R^aR^{a'}N-$, $C_{1-6}$alkylcarbonyl-N$(R^a)-$; $C_{1-6}$alkoxycarbonyl-$N(R^a)-$, $R^aR^{a'}N-SO_2-$, $R^aR^{a'}N$-carbonyl-, $R^aR^{a'}N$-carbony-$N(R^a)$, wherein $C_{1-6}$alkenyl, $C_{2-6}$alkenyl, $C_{2-6}$alkynyl, $C_{3-6}$cycloalkyl, or $C_{1-6}$alkoxy may be optionally substituted by $R^t$;

$R^d$ is independently selected for each occurrence from the group consisting of $C_{1-6}$alkyl, $C_{1-6}$alkylcarbonyl or $C_{1-6}$alkylsulphonyl, wherein $C_{1-6}$alkyl is optionally substituted by one or more substituents selected from halogen, hydroxyl, and $R^aR^{a'}N-$;

$R^e$ is independently selected for each occurrence from the group consisting of hydroxyl, cyano, halogen, oxo, $C_{1-4}$alkyl, $C_{2-4}$alkenyl, $C_{2-4}$alkynyl, $C_{3-6}$cycloalkyl, $C_{1-4}$alkoxy, $C_{3-6}$alkenyloxy, $C_{3-6}$alkynyloxy, $C_{3-6}$cycloalkoxy, $C_{3-6}$cycloalkyl-$C_{1-4}$alkyloxy-, $C_{1-4}$alkyl-S(O)$_w$—wherein w is 0, 1 or 2, $R^aR^{a\prime}N$—, $R^aR^{a\prime}N$-carbonyl, $R^aR^{a\prime}N$-carbonyl-$N(R^a)$—, $R^aR^{a\prime}N$—SO$_2$—, $C_{1-6}$alkyl-carbonyl-$N(R^a)$—, $C_{1-6}$alkyl-SO$_2$—N$(R^a)$—, $C_{1-6}$alkoxycarbonyl-, $C_{1-4}$alkoxycarbonyl-N$(R^a)$—, wherein $C_{2-4}$alkenyl, and $C_{2-4}$alkynyl may be optionally substituted by one or more substituents selected from $R^p$; wherein $C_{1-4}$alkyl and $C_{1-4}$alkoxy may optionally substituted by one or more substituents selected from $R^{p\prime}$; and wherein $C_{3-6}$cycloalkyl or $C_{3-6}$cycloalkoxy may be optionally substituted by $R^{p\prime\prime}$;

$R^f$ and $R^g$, independently for each occurrence, are selected from group consisting of hydrogen, $C_{1-4}$alkyl optionally substituted by one or more substituents selected from $R^{p\prime}$, and $C_{3-6}$cycloalkyl optionally substituted by one or more substituents selected from $R^{p\prime\prime}$, or $R^f$ and $R^g$ taken together with the nitrogen to which they are attached form a 4-7 membered heterocyclyl, optionally substituted by one or more substituents selected from the group consisting of halogen, hydroxyl, oxo, cyano, $C_{1-6}$alkyl, $C_{1-6}$alkoxy, $R^aR^{a\prime}N$—, $C_{1-6}$alkylcarbonyl-$N(R^a)$—; $C_{1-6}$alkoxycarbonyl-$N(R^a)$—, $R^aR^{a\prime}N$—SO$_2$—, $R^aR^{a\prime}N$-carbonyl-, $R^aR^{a\prime}N$-carbonyl-$N(R^a)$, and wherein $C_{1-6}$alkyl or $C_{1-6}$alkoxy may be optionally substituted by at least one or more substituent selected from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, $C_{1-4}$alkylS(O)$_w$—, wherein w is 0, 1 or 2;

$R_p$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, and $C_{1-4}$alkylS(O)$_w$—, wherein w is 0, 1 or 2;

$R^{p\prime}$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, $C_{1-4}$alkylS(O)$_w$— and $C_{3-6}$cycloalkyl, wherein w is 0, 1 or 2 and wherein $C_{3-6}$cycloalkyl is optionally substituted with $R^{p\prime\prime}$;

$R^{p\prime\prime}$ is independently selected, for each occurrence, from the group consisting of $R^aR^{a\prime}N$—, halogen, hydroxy, cyano, $C_{1-4}$alkoxycarbonyl, $R^aR^{a\prime}N$-carbonyl, $R^aR^{a\prime}N$—SO$_2$—, $C_{1-4}$alkoxy, $C_{1-4}$alkylS(O)$_w$ and $C_{1-6}$alkyl, wherein w is 0, 1 or 2 and $C_{1-6}$alkyl is optionally substituted by one or more substituents selected from $R^p$;

$R^t$ is independently selected from the group consisting of $R^aR^{a\prime}N$—, halogen, cyano, hydroxyl and $C_{1-6}$alkoxy;

$R^h$ is independently selected from the group consisting of hydrogen, $C_{1-6}$alkyl, $C_{3-6}$alkenyl (wherein any unsaturated bond is not directly attached to a nitrogen), $C_{3-6}$alkynyl(wherein any unsaturated bond is not directly attached to a nitrogen), $C_{3-6}$cycloalkyl, $C_{1-6}$alkyl-S(O)$_2$—, and $C_{1-6}$alkyl-N$(R^a)$carbonyl, wherein $C_{1-6}$alkyl is optionally substituted by one or more substituents selected from $R^{p\prime}$; wherein $C_{3-6}$alkenyl and $C_{3-6}$alkynyl are optionally substituted by at least one substituent selected from $R^p$, and wherein $C_{3-6}$cycloalkyl is optionally substituted by at least one substituent selected from $R^{p\prime\prime}$.

2. The compound of claim 1, wherein A is phenyl or pyridinyl.

3. The compound of claim 1, wherein A is phenyl.

4. The compound of claim 1, wherein A is a piperdinyl or a pyrrolidinyl.

5. The compound of claim 1, wherein B is a bond, and m is 1.

6. The compound of claim 1, wherein $R_2$ is selected from the group consisting of halogen, cyano, $C_{1-4}$alkyl, $C_{3-6}$cycloalkyl, a 5-6 membered monocyclic heteroaryl, or a $C_{4-6}$heterocyclyl.

7. The compound of claim 1, wherein $R_2$ is selected from the group consisting of furyl, furazanyl, imidazolyl, thiazolyl; thienyl, pyrrolyl, pyrazolyl, isothiazolyl, isoxazolyl, triazolyl, or oxazolyl.

8. The compound of claim 1, wherein $R_2$ is selected from 3-furyl and 5-isothiazolyl.

9. The compound of claim 1, wherein $R_2$ is selected from the group consisting of methyl, ethyl, propyl, or cyclopropyl.

10. The compound of claim 9, wherein $R_2$ is ethyl.

11. The compound of claim 1, represented by:

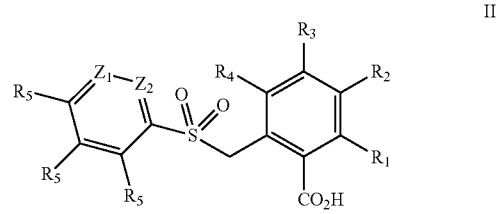

II wherein $Z_1$ is $CR_5$ and $Z_2$ is $CR_6$, or $Z_1$ is N and $Z_2$ is $CR_6$, or $Z_2$ is N and $Z_1$ is $CR_5$;

$R_1$ is selected from the group consisting of hydrogen, halogen, hydroxyl, cyano, $R^fR^gN$—, $C_{1-4}$alkyl, $C_{1-4}$alkoxy and $C_{3-6}$cycloalkyl, wherein $C_{1-4}$alkyl and $C_{1-4}$alkoxy may be optionally substituted by one or more substituents selected from $R^{p\prime}$, and wherein $C_{3-6}$cycloalkyl may be optionally substituted by one or more substituents selected from $R^{p\prime\prime}$;

$R_2$ is selected from the group consisting of hydrogen, halogen, hydroxyl, cyano, $C_{1-4}$alkyl, $C_{1-4}$alkoxy, $C_{3-6}$cycloalkyl, $C_{3-6}$cycloalkyl-$C_{1-4}$alkyl, a five membered monocyclic heteroaryl having one or two heteroatoms selected from O, S, or N, wherein said heteroaryl is optionally substituted by one or more groups $R^b$;

$R_3$ is selected from H or halogen;

$R_4$ is selected from the group consisting of H, hydroxyl, or methyl; and $R_5$ is selected, independently for each occurrence, from the group consisting of hydrogen, hydroxyl, cyano, halogen, $C_{1-4}$alkyl, $C_{3-6}$cycloalkyl, or $C_{1-4}$alkoxy, wherein $C_{1-4}$alkyl $C_{3-6}$cycloalkyl, or $C_{1-4}$alkoxy may be optionally substituted with one or more halogens.

12. The compound of claim 11, wherein $R_1$ is selected from H, hydroxyl, or $C_{1-4}$alkoxy optionally substituted by cyano, NH$_2$ or hydroxyl.

13. The compound of claim 12, wherein $R_1$ is methoxy or ethoxy, optionally substituted by one, two, or three substituents selected from Cl or F.

14. The compound of claim 11, wherein $R_2$ is selected from:

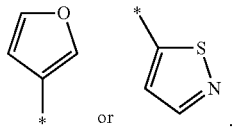 [SMILES: *c1ccoc1 ; *c1ccns1]

15. The compound of claim 11, wherein $Z_2$ is $CR_6$.

16. The compound of claim 11, wherein $R_6$ is $C_{1-4}$alkyl substituted by (N,N di-$C_{1-4}$alkyl)amino), or $C_{3-4}$alkenyl substituted by (N,N-di-$C_{1-4}$ alkylamino)

17. The compound of claim 1, wherein $R_6$ is cis-3-(N,N-diethylamino)-prop-1-en-1-yl.

18. A compound represented by Formula IV:

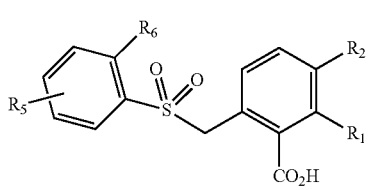

or pharmaceutically acceptable salts, esters, stereoisomers, or prodrugs thereof, wherein $R_1$ is selected from the group consisting of:
hydrogen, halogen, cyano, hydroxyl, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— wherein w is 0, 1 or 2, $C_{1-6}$alkyl-N($R^a$)-carbonyl, $R^fR^gN$—, $R^fR^gN$-carbonyl, $R^fR^gN$-carbonyl-N($R^a$)—, $R^fR^gNSO_2$—, $C_{1-6}$alkyl-carbonyl-N($R^a$)—, $C_{1-6}$ alkoxy-carbonyl-N($R^a$)—, phenyl, phenyloxy, phenyl-$C_{1-6}$alkyl-, phenyl-$C_{1-6}$alkoxy, heteroaryl, heteroaryloxy, heteroaryl-$C_{1-6}$alkyl, heteroaryl-$C_{1-6}$alkoxy, heterocyclyl, heterocyclyloxy, heterocyclyl-$C_{1-6}$alkyl, and heterocyclyl-$C_{1-6}$alkoxy, wherein said heteroaryl is a 5-6 membered ring having one, two or three heteroatoms selected from O, S, or N, and wherein said phenyl or heteroaryl is optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$; and wherein $C_{2-6}$alkenyl, $C_{2-6}$alkynyl, $C_{3-6}$alkenyloxy, and $C_{3-6}$alkynyloxy may be optionally substituted by one or more substituents selected from RP, and wherein $C_{1-6}$alkyl and $C_{1-6}$alkoxy may be optionally substituted by one or more substituents selected from $R^{p'}$ and wherein $C_{3-6}$cycloalkyl and $C_{3-6}$cycloalkoxy may be optionally substituted by one or more substituents selected from $R^{p''}$;

$R_2$ is selected from the group consisting of:
halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{2-6}$alkenyloxy, $C_{3-6}$alkynyloxy, $C_{3-6}$cycloalkyloxy, $C_{1-6}$alkyl-S(O)$_2$—, $C_{3-6}$cycloalkyl$C_{1-4}$alkyl-, $C_{3-6}$cycloalkyl$C_{1-4}$alkoxy- , $R^fR^gN$-carbonyl, phenyl-$C_{1-6}$alkyl-, phenyl, phenyoxy, phenyl-$C_{1-6}$alkoxy-, heteroaryl, heteroaryloxy, heteroaryl-$C_{1-6}$alkyl, heteroaryl-$C_{1-6}$alkoxy, heterocyclyl$C_{1-6}$alkyl-, and heterocyclyl-$C_{1-6}$alkoxy, wherein said heteroaryl is a 5-6 membered monocyclic ring having one, two or three heteroatoms selected from O, S, or N, and optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$, and wherein $C_{1-6}$alkyl, $C_{2-6}$alkenyl, $C_{2-6}$alkynyl, $C_{1-6}$alkoxy, $C_{3-6}$alkenyloxy, or $C_{3-6}$alkynyloxy may be optionally substituted by one or more substituents selected from halogen, hydroxyl, $R^aR^{a'}N$—, or cyano, and wherein $C_{3-6}$cycloalkyl and $C_{3-6}$cycloalkoxy may be optionally substituted by one or more substituents selected from halogen, hydroxyl, $R^aR^{a'}N$—, cyano and $C_{1-6}$alkyl; or $R_1$ and $R_2$ may be joined together with the carbons to which they are attached to form a 5-7 membered saturated, partially unsaturated, or unsaturated ring, optionally having 1, 2 or 3 heteroatom groups selected from O, $NR^h$, or S(O)$_r$, where r is 0, 1, or 2, wherein the formed 5-7 membered ring is optionally substituted on a carbon by one or more groups $R^e$, and wherein the formed ring may be optionally bridged by a moiety selected from CH$_2$, —(CH$_2$)$_2$—, cis-CH=CH—, $NR^h$; or —CH$_2NR^h$—; and wherein if $R_1$ is hydrogen, $R_2$ may not be hydrogen;

$R_5$ is selected, independently for each occurrence, from the group consisting of hydrogen, hydroxyl, cyano, halogen, $C_{1-6}$alkyl, $C_{2-6}$alkenyl, $C_{3-6}$alkynyl, $C_{3-6}$cycloalkyl, or $C_{1-6}$alkoxy, or $R^fR^gN$—, wherein $C_{1-6}$alkyl, $C_{2-6}$alkenyl, $C_{3-6}$ alkynyl, $C_{3-6}$cycloalkyl, or $C_{1-6}$alkoxy may be optionally substituted with one or more halogens;

$R_6$ is selected from the group consisting of hydrogen, hydroxyl, cyano, halogen, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— wherein w is 0, 1 or 2, $R^fR^gN$—, $R^fR^gN$-carbonyl-, $R^fR^gN$—carbonyl-N($R^a$)—, $R^fR^gN$—SO$_2$—, $C_{1-6}$alkyl-carbonyl-N($R^a$)—, $C_{1-6}$alkylsulphonylN($R^a$)—, $C_{1-6}$alkoxycarbonyl-N($R^a$)—, phenyl, phenoxy, phenyl-$C_{1-6}$alkyl-, phenyl-$C_{1-6}$alkyoxy, heteroaryl, heteroaryloxy, heterocycloxy, heteroaryl-$C_{1-6}$alkyl, heteroaryl-$C_{1-6}$alkoxy-, heterocyclyl-$C_{1-6}$alkyl-, and heterocyclyl-$C_{1-6}$alkoxy-, wherein said heteroaryl is a 5-6 membered monocyclic ring having one, two or three heteroatoms selected from O, S, or N, and optionally substituted with one or more substituents selected from $R^b$; wherein said heterocyclyl is a 4-7 membered ring optionally substituted by one or more substituents selected from $R^c$ and wherein if said heterocyclyl contains a —NH moiety that nitrogen may be optionally substituted by one or more groups $R^d$, and, wherein $C_{1-6}$alkyl and $C_{1-6}$alkoxy may be optionally substituted by $R^{p'}$, wherein $C_{2-6}$alkenyl, and $C_{2-6}$ alkynyl may be optionally substituted by one or more substituents selected from $R^p$; and wherein $C_{3-6}$cycloalkyl or $C_{3-6}$ cycloalkoxy may be optionally substituted by one or more substituents selected from $R^{p''}$;

$R^a$ and $R^{a'}$ are independently selected, for each occurrence, from the group consisting of hydrogen and $C_{1-6}$alkyl, or $R^a$ and $R^{a'}$ when they occur together may form a 4-6 membered heterocyclic ring, wherein $C_{1-6}$alkyl may be optionally substituted by one or more substituents selected from the group consisting of halogen, oxo and hydroxyl, and wherein the heterocyclic ring may be optionally substituted by one or more substituents selected from the group consisting of halogen, alkyl, oxo or hydroxyl;

$R^b$ is independently selected, for each occurrence, from the group consisting of halogen, hydroxyl, cyano, $C_{1-6}$alkyl, $C_{2-6}$alkenyl, $C_{3-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkoxy, $C_{3-6}$cycloalkyl, $C_{1-6}$alkyl-S(O)$_w$—wherein w is 0, 1 or 2, $C_{1-6}$alkylN($R^a$)—, $C_{1-6}$alkyl-N($R^a$)carbonyl, $R^aR^{a'}$N—, $R^aR^{a'}$N-carbonyl-, $R^aR^{a'}$N-carbonyl-N($R^a$)—; $R^aR^{a'}$N—SO$_2$—, and $C_{1-6}$alkyl-carbonyl-N($R^a$)—, wherein $C_{2-6}$alkenyl, $C_{2-6}$alkynyl, or $C_{1-6}$alkoxy may be optionally substituted by one or more substituents selected from $R^p$; wherein $C_{3-6}$cycloalkyl may be optionally substituted by one or more substituents selected from $R^{p''}$, and wherein $C_{1-6}$alkyl may be optionally substituted by one or more substituents selected from $R^{p'}$;

$R^c$ for each occurrence is independently selected from the group consisting of, hydroxyl, cyano, oxo, halogen, $C_{1-6}$alkyl, $C_{2-6}$alkenyl, $C_{3-6}$ alkynyl, $C_{3-6}$cycloalkyl, $C_{1-6}$alkoxy, $C_{1-6}$alkyl-S(O)$_w$—, wherein w is 0, 1 or 2, $C_{1-6}$alkyl-N$R^a$—, $C_{1-6}$alkylC$_{3-6}$cycloalkyl-, $C_{3-6}$cycloalkylC$_{1-6}$alkyl, $R^aR^{a'}$N—, $C_{1-6}$alkylcarbonyl-N($R^a$)—; $C_{1-6}$alkoxycarbonyl-N($R^a$)—, $R^aR^{a'}$N—SO$_2$—, $R^aR^{a'}$N-carbonyl-, $R^aR^{a'}$N—carbonyl-N($R^a$)—, wherein $C_{1-6}$alkyl, $C_{2-6}$alkenyl, $C_{3-6}$alkynyl, $C_{3-6}$cycloalkyl, or $C_{1-6}$alkoxy may be optionally substituted by $R^t$;

$R^d$ is independently selected for each occurrence from the group consisting of $C_{1-6}$alkyl, $C_{1-6}$alkylcarbonyl or $C_{1-6}$alkylsulphonyl, wherein $C_{1-6}$alkyl is optionally substituted by one or more substituents selected from halogen, hydroxyl, and $R^aR^{a'}$N—;

$R^e$ is independently selected for each occurrence from the group consisting of hydroxyl, cyano, halogen, oxo, $C_{1-4}$alkyl, $C_{2-4}$alkenyl, $C_{2-4}$alkynyl, $C_{3-6}$cycloalkyl, $C_{1-4}$alkoxy, $C_{3-6}$alkenyloxy, $C_{3-6}$alkynyloxy, $C_{3-6}$cycloalkoxy, $C_{3-6}$cycloalkyl-$C_{1-4}$alkoxy-, $C_{1-4}$alkyl-S(O)$_w$—wherein w is 0, 1 or 2, $R^aR^{a'}$N—, $R^aR^{a'}$N-carbonyl, $R^aR^{a'}$N-carbonyl-N($R^a$)—, $R^aR^{a'}$N—SO$_2$—, $C_{1-6}$alkyl-carbonyl-N($R^a$)—, $C_{1-6}$alkyl-SO$_2$—N($R^a$)—, $C_{1-6}$alkoxycarbonyl-, $C_{1-4}$alkoxycarbonyl-N($R^a$)—, wherein $C_{2-4}$alkenyl, and $C_{2-4}$alkynyl may be optionally substituted by one or more substituents selected from $R^p$; wherein $C_{1-4}$alkyl and $C_{1-4}$alkoxy may optionally substituted by one or more substituents selected from $R^{p'}$; and wherein $C_{3-6}$cycloalkyl or $C_{3-6}$cycloalkoxy may be optionally substituted by $R^{p''}$;

$R^f$ and $R^g$, independently for each occurrence, are selected from group consisting of hydrogen, $C_{1-4}$alkyl optionally substituted by one or more substituents selected from $R^{p'}$, and $C_{3-6}$cycloalkyl optionally substituted by one or more substituents selected from $R^{p''}$, or $R^f$ and $R^g$ taken together with the nitrogen to which they are attached form a 4-7 membered heterocyclyl, optionally substituted by one or more substituents selected from the group consisting of halogen, hydroxyl, oxo, cyano, $C_{1-6}$alkyl, $C_{1-6}$alkoxy, $R^aR^{a'}$N—, $C_{1-6}$alkylcarbonyl-N($R^a$)—; $C_{1-6}$alkoxycarbonyl-N($R^a$)—, $R^aR^{a'}$N—SO$_2$—, $R^aR^{a'}$N-carbonyl-, $R^aR^{a'}$N-carbonyl-N($R^a$), and wherein $C_{1-6}$alkyl or $C_{1-6}$alkoxy may be optionally substituted by at least one or more substituent selected from the group consisting of $R^aR^{a'}$N, halogen, hydroxy, and cyano, $C_{1-4}$alkoxycarbonyl, $R^aR^{a'}$N-carbonyl, $R^aR^{a'}$N—SO$_2$—, $C_{1-4}$alkoxy, $C_{1-4}$alkylS(O)$_w$—, wherein w is 0, 1 or 2;

$R^p$ is independently selected, for each occurrence, from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, and $C_{1-4}$alkylS(O)$_w$—, wherein w is 0, 1 or 2;

$R^{p'}$ is independently selected, for each occurrence, from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, $C_{1-4}$alkylS(O)$_w$— and $C_{3-6}$cycloalkyl, wherein w is 0, 1 or 2 and wherein $C_{3-6}$cycloalkyl is optionally substituted with $R^{p''}$;

$R^{p''}$ is independently selected, for each occurrence, from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, $C_{1-4}$alkylS(O)$_w$ and $C_{1-6}$alkyl, wherein w is 0, 1 or 2 and wherein $C_{1-6}$alkyl is optionally substituted by one or more substituents selected from $R^p$;

$R^t$ is independently selected from the group consisting of $R^fR^gN$—, halogen, cyano, hydroxyl and $C_{1-6}$alkoxy;

$R^h$ is independently selected from the group consisting of hydrogen, $C_{1-6}$alkyl, $C_{3-6}$alkenyl (wherein any unsaturated bond is not directly attached to a nitrogen), $C_{3-6}$alkynyl(wherein any unsaturated bond is not directly attached to a nitrogen), $C_{3-6}$cycloalkyl, $C_{1-6}$alkyl-S(O)$_2$—, and $C_{1-6}$alkyl-N($R^a$)carbonyl, wherein $C_{1-6}$alkyl is optionally substituted by one or more substituents selected from $R^{p'}$; wherein $C_{3-6}$alkenyl and $C_{3-6}$alkynyl are optionally substituted by at least one substituent selected from $R^p$, and wherein $C_{3-6}$cycloalkyl is optionally substituted by at least one substituent selected from $R^{p''}$.

19. A compound selected from the group consisting of: 2-(Benzenesulphonylmethyl)-5-ethylbenzoic acid; 6-(Benzenesulphonylmethyl)-3-ethyl-2-methoxy-benzoic acid; 6-(Benzenesulphonylmethyl)-2-methoxy-3-propyl-benzoic acid; 6-(Benzenesulphinylmethyl)-3-ethyl-2-methoxy-benzoic acid; 6-(Benzenesulphonylmethyl)-3-cyclopropyl-2-methoxy-benzoic acid; 6-(4-Chlorobenzenesulphonylmethyl)-3-ethyl-2-methoxy-benzoic acid; 6-(Benzenesulphonylmethyl)-3-bromo-2-methoxy-benzoic acid; 6-(Benzenesulphonylmethyl)-2-methoxy-3-methyl-benzoic acid; 3-Ethyl-2-methoxy-6-(2-methylbenzenesulphonyl-methyl)benzoic acid; 6-(Benzenesulphonylmethyl)-3-(furan-3-yl)-2-methoxy-benzoic acid; 6-(1-Benzenesulphonylethyl)-3-ethyl-2-methoxy-benzoic acid; 6-(Benzenesulphonylmethyl)-2-methoxy-3-(oxazol-5-yl) benzoic acid; 6-(Benzenesulphonylmethyl)-3-(isothiazol-5-yl)-2-methoxy-benzoic acid; 2-(Benzenesulphonylmethyl)-5-furan-3-yl)benzoic acid; 2-(Benzenesulphonylmethyl)-5-(oxazol-5-yl)benzoic acid; 3-(Furan-3-yl)-2-methoxy-6-(2-methyl-benzenesulphonylmethyl)benzoic acid; 6-(3-Chlorobenzenesulphonylmethyl)-3-(furan-3-yl)-2-methoxybenzoic acid; 6-(Benzenesulphonylmethyl)-3-(oxazol-4-yl)-2-methoxybenzoic acid; 6-(Benzenesulphonylmethyl-3-(isothiazol-4-yl)-2-methoxybenzoic acid; (Z)-6-((2-(3-(Diethylamino)prop-1-enyl)benzenesulfonyl)methyl)-3-(furan-3-yl)-2-methoxybenzoic acid; (E)-6-((2-(3-(diethylamino)prop-1-enyl)benzenesulfonyl)methyl)-3-(furan-3-yl)-2-methoxybenzoic acid; 6-(Benzenesulphonylmethyl)-2-ethoxy-3-(furan-3-yl)benzoic acid; 6-(Benzenesulphonylmethyl)-3-(furan-3-yl)-2-hydroxy-benzoic acid; 6-(Benzenesulphonylmethyl)-3-(furan-3-yl)-2-(2-hydroxyethoxy)benzoic acid; 6-(2-(3-Diethylaminopropyl)benzenesulphonylmethyl)-3-(furan-3-yl)-2-methoxybenzoic acid; 3-(3-Furan-3-yl)-2-methoxy-6-(pyridin-3-ylsulphonylmethyl)benzoic acid; 6-(Benzenesulphonylmethyl)-3-(isoxazol-3-yl)-2-methoxy-benzoic acid; 3-(Furan-3-yl)-2-methoxy-6-(2-methoxybenzenesulphonylmethyl) benzoic acid; 3-(Furan-3-yl)-2-methoxy-6-(pyridin-2-ylsulphonylmethyl)benzoic acid; 3-Ethyl-6-(4-fluorobenzenesulphonylmethyl)-2-methoxybenzoic acid; 6-(Benzenesulphonylmethyl)-3-cyano-2-methoxybenzoic acid; 6-(Benzenesulphonylmethyl)-3-(furan-2-yl)-2-methoxy-benzoic acid; 2-(2-Aminoethoxy)-6-(benzenesulphonylmethyl)-3-(furan-3-yl)benzoic acid hydrochloride; 2-(2-Aminoethoxy)-6-(3-chlorobenzenesulphonylmethyl)-3-(furan-3-yl)benzoic acid hydrochloride; 2-(2-Aminoethoxy)-6-(4-fluorobenzenesulphonylmethyl)-3-(furan-3-yl) benzoic acid hydrochloride; 2-(2-Aminoethoxy)-3-(furan-3-yl)-6-(2-methoxybenzenesulphonylmethyl)benzoic acid hydrochloride; 6-(2-Chlorobenzenesulphonylmethyl)-3-(furan-3-yl)-2-methoxybenzoic acid; 6-(3-Fluorobenzenesulphonylmethyl)-3-(furan-3-yl)-2-methoxybenzoic acid; 6-(2-Fluorobenzenesulphonylmethyl)-3-(furan-3-yl)-2-methoxybenzoic acid; 3-(Furan-3-yl)-6-(3-methoxybenzenesulphonylmethyl)-2-methoxybenzoic acid; 2-(2-Aminoethoxy)-3-ethyl-6-benzenesulphonylmethylbenzoic acid hydrochloride; 2-(3-Aminopropoxy)-6-benzenesulphonylmethyl-3-(furan-3-yl)benzoic acid hydrochloride; 6-(Benzenesulphonylmethyl)-2-methoxy-3-(thien-2-yl)benzoic acid; 6-(4-Fluorobenzenesulphonylmethyl)-3-(furan-3-yl)-2-methoxybenzoic acid; 6-(Benzenesulphonylmethyl)-2-methoxy-3-phenylbenzoic acid; 6-(Benzenesulphonylmethyl)-2-methoxy-3-(3-pyridyl)benzoic acid; 6-(Benzenesulphonylmethyl)-2-methoxy-3-(pyrazol-3-yl) benzoic acid; 2-Methoxy-6-(2-methylbenzenesulphonylmethyl)benzoic acid; 6-(Benzenesulphonylmethyl)-2-methoxy-3-(thiazol-2-yl)benzoic acid; 6-(Benzenesulphonylmethyl)-3-(furan-3-yl)-2-(2-methoxyethoxy)-benzoic acid; 6-Benzenesulphonylmethyl-2-(2-dimethylaminoethoxy)-3-(furan-3-yl)benzoic acid hydrochloride; 6-(Benzenesulphonylmethyl)-2-methyoxy-3-(thien-3-yl)benzoic acid; 6-(Benzenesulphonylmethyl)-2-(cyanomethoxy)-3-(furan-3-yl)benzoic acid; 2-(2-Aminoethylamino)-6-benzenesulphonylmethyl-3-(furan-3-yl)-benzoic acid hydrochloride; 6-(Benzenesulphonylmethyl)-3-(furan-3-yl)-2-[2-(methylamino)-ethoxy]benzoic acid hydrochloride; 6-(Benzenesulphonylmethyl)-3-ethyl-2-(2-methyl-2H-pyrazol-3-yl)-benzoic acid; 2-(2-Aminopropoxy)-6-(benzenesulphonylmethyl)-3-(furan-3-yl)-benzoic acid hydrochloride; 6-Benzenesulphonylmethyl-3-ethyl-2-(1-methyl-1H-pyrazol-3-yl)-benzoic acid; 2-(3-Aminopropyl)-6-(benzenesulphonylmethyl)-3-(furan-3-yl)-benzoic acid hydrochloride; 6-(Benzenesulphonylmethyl)-2-methoxy-3-(pyrazol-1-yl)benzoic acid; 2-(Benzenesulphonylmethyl)-5-(2-methyl-2H-pyrazol-3-yl)-benzoic acid; 2-(Benzenesulphonylmethyl)naphthalene-1-carboxylic acid; 3-(Furan-3-yl)-6-(2-hydroxybenzenesulphonylmethyl)-2-methoxybenzoic acid; 3-(Furan-3-yl)-6-(3-hydroxybenzenesulphonylmethyl)-2-methoxy-benzoic acid; 2-(Benzenesulphonylmethyl)-5-(2-methylfuran-3-yl)benzoic acid; 6-(Benzenesulphonylmethyl)-3-ethyl-2-(1H-pyrazol-3-yl)benzoic acid; 3-(Furan-3-yl)-2-methoxy-6-(piperidine-1-ylsulphonylmethyl)benzoic acid; 3-(Furan-3-yl)-2-methoxy-6-(pyrrolidin-1-ylsulphonylmethyl)-benzoic acid; 6-[2-(2-Diethylaminoethylamino)benzenesulphonylmethyl]-3-(furan-3-yl)-2-methoxybenzoic acid; 6-(Benzenesulphonylmethyl)-2-ethyl-3-(furan-3-yl)benzoic acid; 6-[2-(2-Diethylaminoethoxy)benzenesulphonylmethyl]-3-(furan-3-yl)-2-methoxybenzoic acid; 6-(Benzenesulphonylmethyl)-3-(furan-3-yl)-2-(prop-1-yn-1-yl)benzoic acid; 2-(Benzenesulphonylmethyl)-6-methoxybenzoic acid; 6-(Cyclohexanesulphonylmethyl)-3-(furan-3-yl)-2-methoxybenzoic acid; 6-(Benzenesulphonylmethyl)-2-(carbamoylmethoxy)-3-(furan-3-yl)-benzoic acid; (Z)-6-((2-(3-(Diethylamino)prop-1-enyl)-4-fluorobenzenesulfonyl)methyl)-3-(furan-3-yl)-2-methoxybenzoic acid; 3-(Furan-3-yl)-6-(3-hydroxypyrrolidine-1-ylsulphonylmethyl)-2-methoxybenzoic acid; 2-(Azetidin-3-yloxy)-6-(benzenesulphonylmethyl)-3-(furan-3-yl)-benzoic acid hydrochloride; 6-(Bicyclo[2.2.2]octane-2-ylsulphonylmethyl)-3-(furan-3-yl)-2-methoxybenzoic acid; 6-(Bicyclo[2.2.2]octane-2-ylsulphonylmethyl)-2-methoxy-3-(tetrahydrofuran-3-yl)benzoic acid; 6-(7-Azabicyclo[2.2.1]heptane-7-ylsulphonylmethyl)-3-(furan-3-yl)-2-methoxybenzoic acid; 6-(4,4-Difluoropiperidine-1-ylsulphonylmethyl)-3-(furan-3-yl)-2-methoxybenzoic acid; 6-(Bicyclo[2.2.1]heptane-7-ylsulphonylmethyl)-3-(furan-3-yl)-2-methoxybenzoic acid; 6-(Benzenesulphonylmethyl)-3-(furan-3-yl)-2-methylamino benzoic acid; 6-(8-Azabicyclo[3.2.1]octane-8-ylsulphonylmethyl)-3-(furan-3-yl)-2-methoxybenzoic acid; 2-(Benzenesulphonylmethyl)-8-methoxynaphthalene-1-carboxylic acid; 6-[2-(3-Diethylaminopropylamino)benzenesulphonylmethyl]-3-(furan-3-yl)-2-methoxybenzoic acid; (Z)-2-(Cyanomethoxy)-6-((2-(3-(diethylamino)prop-1-enyl)-4-fluorobenzenesulfonyl)methyl)-3-(furan-3-yl)benzoic acid; (Z)-3-(Furan-3-yl)-2-methoxy-6-((2-(3-(piperidin-1-yl)prop-1-enyl)benzenesulfonyl)methyl)benzoic acid ; 6-(Benzenesulphonylmethyl)-3-(furan-3-yl)-2,4-dimethoxybenzoic acid; 6-[2-(2-Diethylaminomethylazetidin-1-yl)-benzenesulphonylmethyl]-3-(furan-3-yl)-2-methoxybenzoic acid; 6-(Benzenesulphonylmethyl)-2-(cyanomethylamino)-3-(furan-3-yl)benzoic acid; 6-(Benzenesulphonylmethyl)-3-(imidazol-1-yl)-2-methoxybenzoic acid; 6-(Benzenesulphonylmethyl)-2-methoxy-3-(thiazol-5-yl)benzoic acid; 3-(Furan-3-yl)-2-methoxy-6-[(S-phenylsulphonimidoyl)methyl]benzoic acid; 3-(Furan-3-yl)-2-methoxy-6-[(N-methyl-S-phenylsulphonimidoyl)methyl] benzoic acid; and 6-[(N-cyano-S-phenylsulphonimidoyl) methyl]-3-(furan-3-yl)-2-methoxybenzoic acid; and pharmaceutically acceptable salts and stereoisomers thereof.

20. A compound selected from the group consisting of 6-(Benzenesulphonylmethyl)-3-(furan-3-yl)-2-methoxybenzoic acid, 2-(2-Aminoethoxy)-6-(benzenesulphonylmethyl)-3-(furan-3-yl)benzoic acid hydrochloride, 6-(4-Fluorobenzenesulphonylmethyl)-3-(furan-3-yl)-2-methoxybenzoic acid, 6-(3-Fluorobenzenesulphonylmethyl)-3-(furan-3-yl)-2-methoxybenzoic acid, 6-(Benzenesulphonylmethyl)-2-(cyanomethoxy)-3-(furan-3-yl)benzoic acid, 6-(Benzenesulphonylmethyl)-3-(furan-3-yl)-2-methylamino benzoic acid, 6-(Benzenesulphonylmethyl)-2-(cyanomethylamino)-3-(furan-3-yl)benzoic acid, and 6-(Benzenesulphonylmethyl)-3-(isothiazol-5-yl)-2-methoxy-benzoic acid.

21. A compound selected from the group consisting of (Z)-6-((2-(3-(Diethylamino)prop-1-enyl)benzenesulfonyl) methyl)-3-(furan-3-yl)-2-methoxybenzoic acid 6-[2-(3-Diethylaminopropyl)benzenesulphonylmethyl]-3-(furan-3-yl)-2-methoxybenzoic acid, (Z)-6-((2-(3-(Diethylamino)prop-1-enyl)-4-fluorobenzenesulfonyl)methyl)-3-(furan-3-yl)-2-methoxybenzoic acid, 6-[2-(3-Diethylaminopropylamino) benzenesulphonylmethyl]-3-(furan-3-yl)-2-methoxybenzoic acid, (Z)-2-(Cyanomethoxy)-6-((2-(3-(diethylamino)prop-1-enyl)-4-fluorobenzenesulfonyl)methyl)-3-(furan-3-yl) benzoic acid, and (Z)-3-(Furan-3-yl)-2-methoxy-6-((2-(3-(piperidin-1-yl)prop-1-enyl)benzenesulfonyl)methyl) benzoic acid.

22. A method of treating and/or controlling obesity, comprising administering to a patient in need thereof an effective amount of a compound of claim 1.

23. The method of claim 22, wherein the compound is administered orally.

24. A pharmaceutical composition comprising a compound of claim 1, and a pharmaceutically acceptable carrier.

* * * * *